US012616395B2

(12) United States Patent
Rao et al.

(10) Patent No.: US 12,616,395 B2
(45) Date of Patent: May 5, 2026

(54) SYSTEMS, DEVICES, AND METHODS FOR ASSEMBLING AN APPLICATOR AND SENSOR CONTROL DEVICE

(71) Applicant: ABBOTT DIABETES CARE INC., Alameda, CA (US)

(72) Inventors: Vivek Rao, Alameda, CA (US); Tuan Nguyen, Dublin, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 704 days.

(21) Appl. No.: 16/239,121

(22) Filed: Jan. 3, 2019

(65) Prior Publication Data

US 2019/0133501 A1     May 9, 2019

Related U.S. Application Data

(63) Continuation of application No. 15/154,329, filed on May 13, 2016, now Pat. No. 10,213,139.

(60) Provisional application No. 62/203,565, filed on Aug. 11, 2015, provisional application No. 62/199,912, filed on Jul. 31, 2015, provisional application No. 62/161,778, filed on May 14, 2015.

(51) Int. Cl.
*A61B 5/15*      (2006.01)
*A61B 5/145*     (2006.01)

(52) U.S. Cl.
CPC ........ *A61B 5/14503* (2013.01); *A61B 5/1451* (2013.01); *A61B 5/14532* (2013.01); *A61B 2505/07* (2013.01); *A61B 2562/12* (2013.01)

(58) Field of Classification Search
None
See application file for complete search history.

(56) References Cited

U.S. PATENT DOCUMENTS

| | | | |
|---|---|---|---|
| 2,402,306 A | 6/1946 | Turkel | |
| 2,752,918 A | 7/1956 | Uytenbogaart | |
| 3,123,790 A | 3/1964 | Tyler | |
| 3,132,123 A | 5/1964 | Harris, Jr. et al. | |
| 3,173,200 A | 3/1965 | Dunmire et al. | |
| 3,211,001 A | 10/1965 | Petit | |

(Continued)

FOREIGN PATENT DOCUMENTS

| | | |
|---|---|---|
| AU | 2003259741 | 2/2004 |
| CA | 2291105 | 12/1998 |

(Continued)

OTHER PUBLICATIONS

Alcock, S. J., et al., "Continuous Analyte Monitoring to Aid Clinical Practice", IEEE Engineering in Medicine and Biology Magazine, 1994, pp. 319-325.

(Continued)

*Primary Examiner* — Etsub D Berhanu
(74) *Attorney, Agent, or Firm* — ONE LLP

(57) ABSTRACT

Systems, devices, and methods are provided for the assembly and subsequent delivery of an in vivo analyte sensor. An applicator with sensor electronics is inserted into a tray containing an assembly that includes a sharp and an analyte sensor. The insertion causes the assembly to couple with the sensor electronics and form a deliverable sensor control device retained within the applicator, which can then be placed in position on a body of a user to monitor that user's analyte levels.

15 Claims, 46 Drawing Sheets

(56)                    References Cited

U.S. PATENT DOCUMENTS

| | | | |
|---|---|---|---|
| 3,260,656 A | 7/1966 | Ross, Jr. |
| 3,517,670 A | 6/1970 | Speelman |
| 3,522,807 A | 8/1970 | Millenbach |
| 3,581,062 A | 5/1971 | Aston |
| 3,653,841 A | 4/1972 | Klein |
| 3,670,727 A | 6/1972 | Reiterman |
| 3,719,564 A | 3/1973 | Lilly, Jr. et al. |
| 3,776,832 A | 12/1973 | Oswin et al. |
| 3,837,339 A | 9/1974 | Aisenberg et al. |
| 3,926,760 A | 12/1975 | Allen et al. |
| 3,949,388 A | 4/1976 | Fuller |
| 3,960,497 A | 6/1976 | Acord et al. |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,033,330 A | 7/1977 | Willis et al. |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,120,292 A | 10/1978 | LeBlanc, Jr. et al. |
| 4,129,128 A | 12/1978 | McFarlane |
| 4,151,845 A | 5/1979 | Clemens |
| 4,168,205 A | 9/1979 | Danniger et al. |
| 4,172,770 A | 10/1979 | Semersky et al. |
| 4,178,916 A | 12/1979 | McNamara |
| 4,203,446 A | 5/1980 | Hofert et al. |
| 4,206,755 A | 6/1980 | Klein |
| 4,224,125 A | 9/1980 | Nakamura et al. |
| 4,240,438 A | 12/1980 | Updike et al. |
| 4,240,889 A | 12/1980 | Yoda et al. |
| 4,245,634 A | 1/1981 | Albisser et al. |
| 4,247,297 A | 1/1981 | Berti et al. |
| 4,294,258 A | 10/1981 | Bernard |
| 4,305,401 A | 12/1981 | Reissmueller et al. |
| 4,308,981 A | 1/1982 | Miura |
| 4,327,725 A | 5/1982 | Cortese et al. |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,353,888 A | 10/1982 | Sefton |
| 4,356,074 A | 10/1982 | Johnson |
| 4,365,637 A | 12/1982 | Johnson |
| 4,366,033 A | 12/1982 | Richter et al. |
| 4,373,527 A | 2/1983 | Fischell |
| 4,375,399 A | 3/1983 | Havas et al. |
| 4,384,586 A | 5/1983 | Christiansen |
| 4,390,621 A | 6/1983 | Bauer |
| 4,392,849 A | 7/1983 | Petre et al. |
| 4,401,122 A | 8/1983 | Clark, Jr. |
| 4,404,066 A | 9/1983 | Johnson |
| 4,418,148 A | 11/1983 | Oberhardt |
| 4,425,920 A | 1/1984 | Bourland et al. |
| 4,427,004 A | 1/1984 | Miller et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,441,968 A | 4/1984 | Emmer et al. |
| 4,450,842 A | 5/1984 | Zick et al. |
| 4,458,686 A | 7/1984 | Clark, Jr. |
| 4,461,691 A | 7/1984 | Frank |
| 4,464,170 A | 8/1984 | Clemens et al. |
| 4,469,110 A | 9/1984 | Slama |
| 4,477,314 A | 10/1984 | Richter et al. |
| 4,478,976 A | 10/1984 | Goertz et al. |
| 4,484,987 A | 11/1984 | Gough |
| 4,494,950 A | 1/1985 | Fischell |
| 4,509,531 A | 4/1985 | Ward |
| 4,522,690 A | 6/1985 | Venkatsetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,553,541 A | 11/1985 | Burns |
| 4,560,534 A | 12/1985 | Kung et al. |
| 4,571,292 A | 2/1986 | Liu et al. |
| 4,573,994 A | 3/1986 | Fischell et al. |
| 4,581,336 A | 4/1986 | Malloy et al. |
| 4,592,745 A | 6/1986 | Rex et al. |
| 4,595,011 A | 6/1986 | Phillips |
| 4,619,754 A | 10/1986 | Niki et al. |
| 4,619,793 A | 10/1986 | Lee |
| 4,622,966 A | 11/1986 | Beard |
| 4,627,445 A | 12/1986 | Garcia et al. |
| 4,627,842 A | 12/1986 | Katz |
| 4,627,908 A | 12/1986 | Miller |
| 4,633,878 A | 1/1987 | Bombardien |
| 4,637,403 A | 1/1987 | Garcia et al. |
| 4,639,062 A | 1/1987 | Taniguchi et al. |
| 4,650,547 A | 3/1987 | Gough |
| 4,654,197 A | 3/1987 | Lilja et al. |
| 4,655,880 A | 4/1987 | Liu |
| 4,655,885 A | 4/1987 | Hill et al. |
| 4,663,824 A | 5/1987 | Kenmochi |
| 4,665,906 A | 5/1987 | Jervis |
| 4,671,288 A | 6/1987 | Gough |
| 4,675,346 A | 6/1987 | Lin et al. |
| 4,679,562 A | 7/1987 | Luksha |
| 4,680,268 A | 7/1987 | Clark, Jr. |
| 4,682,602 A | 7/1987 | Prohaska |
| 4,684,245 A | 8/1987 | Goldring |
| 4,684,537 A | 8/1987 | Graetzel et al. |
| 4,685,463 A | 8/1987 | Williams |
| 4,685,466 A | 8/1987 | Rau |
| 4,690,675 A | 9/1987 | Katz |
| 4,698,057 A | 10/1987 | Joishy |
| 4,703,324 A | 10/1987 | White |
| 4,703,756 A | 11/1987 | Gough et al. |
| 4,711,245 A | 12/1987 | Higgins et al. |
| 4,711,247 A | 12/1987 | Fishman |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,729,672 A | 3/1988 | Takagi |
| 4,731,726 A | 3/1988 | Allen, III |
| 4,749,985 A | 6/1988 | Corsberg |
| 4,755,173 A | 7/1988 | Konopka |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Gough |
| 4,781,683 A | 11/1988 | Wozniak et al. |
| 4,781,798 A | 11/1988 | Gough |
| 4,784,736 A | 11/1988 | Lonsdale et al. |
| 4,785,868 A | 11/1988 | Koenig, Jr. |
| 4,795,707 A | 1/1989 | Niiyama et al. |
| 4,796,634 A | 1/1989 | Huntsman et al. |
| 4,805,624 A | 2/1989 | Yao et al. |
| 4,813,424 A | 3/1989 | Wilkins |
| 4,815,469 A | 3/1989 | Cohen et al. |
| 4,817,603 A | 4/1989 | Turner et al. |
| 4,818,994 A | 4/1989 | Orth et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| RE32,947 E | 6/1989 | Dormer et al. |
| 4,840,893 A | 6/1989 | Hill et al. |
| 4,847,785 A | 7/1989 | Stephens |
| 4,848,351 A | 7/1989 | Finch |

(56)                    References Cited

U.S. PATENT DOCUMENTS

| | | | |
|---|---|---|---|
| 4,852,025 A | 7/1989 | Herpichböhm |
| 4,854,322 A | 8/1989 | Ash et al. |
| 4,856,648 A | 8/1989 | Krueger |
| 4,865,038 A | 9/1989 | Rich et al. |
| 4,871,351 A | 10/1989 | Feingold |
| 4,871,440 A | 10/1989 | Nagata et al. |
| 4,874,500 A | 10/1989 | Madou et al. |
| 4,890,622 A | 1/1990 | Gough |
| 4,894,137 A | 1/1990 | Takizawa et al. |
| 4,895,147 A | 1/1990 | Bodicky et al. |
| 4,897,162 A | 1/1990 | Lewandowski et al. |
| 4,897,173 A | 1/1990 | Nankai et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,921,199 A | 5/1990 | Villavecs |
| 4,923,586 A | 5/1990 | Katayama et al. |
| 4,924,879 A | 5/1990 | O'Brien |
| 4,925,268 A | 5/1990 | Iyer et al. |
| 4,927,516 A | 5/1990 | Yamaguchi et al. |
| 4,934,369 A | 6/1990 | Maxwell |
| 4,935,105 A | 6/1990 | Churchouse |
| 4,935,345 A | 6/1990 | Guibeau et al. |
| 4,938,860 A | 7/1990 | Wogoman |
| 4,944,299 A | 7/1990 | Silvian |
| 4,950,378 A | 8/1990 | Nagara |
| 4,953,552 A | 9/1990 | DeMarzo |
| 4,954,129 A | 9/1990 | Giuliani et al. |
| 4,969,468 A | 11/1990 | Byers et al. |
| 4,970,145 A | 11/1990 | Bennetto et al. |
| 4,974,929 A | 12/1990 | Cuny |
| 4,985,142 A | 1/1991 | Laycock et al. |
| 4,986,271 A | 1/1991 | Wilkins |
| 4,988,341 A | 1/1991 | Columbus et al. |
| 4,994,167 A | 2/1991 | Shults et al. |
| 4,995,402 A | 2/1991 | Smith et al. |
| 5,000,180 A | 3/1991 | Kuypers et al. |
| 5,001,054 A | 3/1991 | Wagner |
| 5,002,054 A | 3/1991 | Ash et al. |
| 5,006,110 A | 4/1991 | Garrison et al. |
| 5,013,161 A | 5/1991 | Zaragoza et al. |
| 5,019,974 A | 5/1991 | Beckers |
| 5,035,860 A | 7/1991 | Kleingeld et al. |
| 5,036,860 A | 8/1991 | Leigh et al. |
| 5,047,044 A | 9/1991 | Smith et al. |
| 5,050,612 A | 9/1991 | Matsumura |
| 5,051,688 A | 9/1991 | Murase et al. |
| 5,055,171 A | 10/1991 | Peck |
| 5,058,592 A | 10/1991 | Whisler |
| 5,067,957 A | 11/1991 | Jervis |
| 5,068,536 A | 11/1991 | Rosenthal |
| 5,070,535 A | 12/1991 | Hochmair et al. |
| 5,082,550 A | 1/1992 | Rishpon et al. |
| 5,082,786 A | 1/1992 | Nakamoto |
| 5,086,246 A | 2/1992 | Dymond et al. |
| 5,089,112 A | 2/1992 | Skotheim et al. |
| 5,095,904 A | 3/1992 | Seligman et al. |
| 5,101,814 A | 4/1992 | Palti |
| 5,106,365 A | 4/1992 | Hernandez |
| 5,108,564 A | 4/1992 | Szuminsky et al. |
| 5,108,889 A | 4/1992 | Smith et al. |
| 5,109,850 A | 5/1992 | Blanco et al. |
| 5,120,420 A | 6/1992 | Nankai et al. |
| 5,122,925 A | 6/1992 | Inpyn |
| 5,124,661 A | 6/1992 | Zelin et al. |
| 5,126,034 A | 6/1992 | Carter et al. |
| 5,133,856 A | 7/1992 | Yamaguchi et al. |
| 5,135,003 A | 8/1992 | Souma |
| 5,135,004 A | 8/1992 | Adams et al. |
| 5,140,985 A | 8/1992 | Schroeder et al. |
| 5,141,868 A | 8/1992 | Shanks et al. |
| 5,161,532 A | 11/1992 | Joseph |
| 5,162,407 A | 11/1992 | Turner |
| 5,165,407 A | 11/1992 | Wilson et al. |
| 5,173,165 A | 12/1992 | Schmid et al. |
| 5,174,291 A | 12/1992 | Schoonen et al. |
| 5,190,041 A | 3/1993 | Palti |
| 5,190,546 A | 3/1993 | Jervis |
| 5,192,416 A | 3/1993 | Wang et al. |
| 5,193,545 A | 3/1993 | Marsoner et al. |
| 5,198,367 A | 3/1993 | Aizawa et al. |
| 5,202,261 A | 4/1993 | Musho et al. |
| 5,204,264 A | 4/1993 | Kaminer et al. |
| 5,205,297 A | 4/1993 | Montecalvo et al. |
| 5,205,920 A | 4/1993 | Oyama et al. |
| 5,208,154 A | 5/1993 | Weaver et al. |
| 5,209,229 A | 5/1993 | Gilli |
| 5,217,595 A | 6/1993 | Smith et al. |
| 5,228,449 A | 7/1993 | Christ et al. |
| 5,229,282 A | 7/1993 | Yoshioka et al. |
| 5,231,988 A | 8/1993 | Wernicke et al. |
| 5,234,835 A | 8/1993 | Nestor et al. |
| 5,238,729 A | 8/1993 | Debe |
| 5,243,696 A | 9/1993 | Carr et al. |
| 5,245,314 A | 9/1993 | Kah et al. |
| 5,246,867 A | 9/1993 | Lakowicz et al. |
| 5,250,439 A | 10/1993 | Musho et al. |
| 5,251,126 A | 10/1993 | Kahn et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,267,963 A | 12/1993 | Bachynsky |
| 5,271,815 A | 12/1993 | Wong |
| 5,279,294 A | 1/1994 | Anderson |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,289,497 A | 2/1994 | Jackobson et al. |
| 5,293,546 A | 3/1994 | Tadros et al. |
| 5,293,877 A | 3/1994 | O'Hara et al. |
| 5,299,571 A | 4/1994 | Mastrototaro |
| 5,305,008 A | 4/1994 | Turner et al. |
| 5,318,583 A | 6/1994 | Rabenau et al. |
| 5,320,098 A | 6/1994 | Davidson |
| 5,320,715 A | 6/1994 | Berg |
| 5,320,725 A | 6/1994 | Gregg et al. |
| 5,322,063 A | 6/1994 | Allen et al. |
| 5,333,615 A | 8/1994 | Craelius et al. |
| 5,337,747 A | 8/1994 | Neftei |
| 5,340,722 A | 8/1994 | Wolfbeis et al. |
| 5,342,789 A | 8/1994 | Chick et al. |
| 5,352,348 A | 10/1994 | Young et al. |
| 5,356,420 A | 10/1994 | Czernecki et al. |
| 5,356,786 A | 10/1994 | Heller et al. |
| 5,360,404 A | 11/1994 | Novacek et al. |
| 5,368,028 A | 11/1994 | Palti |
| 5,372,133 A | 12/1994 | Hogen Esch |
| 5,372,427 A | 12/1994 | Padovani et al. |
| 5,376,251 A | 12/1994 | Kaneko et al. |
| 5,378,628 A | 1/1995 | Gratzel et al. |
| 5,379,238 A | 1/1995 | Stark |
| 5,384,547 A | 1/1995 | Lynk et al. |
| 5,387,327 A | 2/1995 | Khan |
| 5,390,670 A | 2/1995 | Centa et al. |
| 5,390,671 A | 2/1995 | Lord et al. |
| 5,391,250 A | 2/1995 | Cheney, II et al. |
| 5,394,877 A | 3/1995 | Orr et al. |
| 5,395,504 A | 3/1995 | Saurer et al. |
| 5,400,782 A | 3/1995 | Beaubiah |
| 5,400,794 A | 3/1995 | Gorman |
| 5,402,780 A | 4/1995 | Faasse, Jr. |
| 5,407,431 A | 4/1995 | Botich et al. |
| 5,408,999 A | 4/1995 | Singh et al. |
| 5,410,326 A | 4/1995 | Goldstein |
| 5,411,647 A | 5/1995 | Johnson et al. |
| 5,425,361 A | 6/1995 | Fenzlein et al. |
| 5,425,868 A | 6/1995 | Pedersen |

(56)                    References Cited

U.S. PATENT DOCUMENTS

| | | |
|---|---|---|
| 5,431,160 A | 7/1995 | Wilkins |
| 5,431,921 A | 7/1995 | Thombre |
| 5,437,999 A | 8/1995 | Dieboid et al. |
| 5,438,983 A | 8/1995 | Falcone |
| 5,462,051 A | 10/1995 | Oka et al. |
| 5,462,645 A | 10/1995 | Albery et al. |
| 5,469,846 A | 11/1995 | Khan |
| 5,472,317 A | 12/1995 | Field et al. |
| 5,482,473 A | 1/1996 | Lord et al. |
| 5,484,403 A | 1/1996 | Yoakum et al. |
| 5,489,414 A | 2/1996 | Schreiber et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,499,243 A | 3/1996 | Hall |
| 5,507,288 A | 4/1996 | Bocker et al. |
| 5,509,410 A | 4/1996 | Hill et al. |
| 5,514,718 A | 5/1996 | Lewis et al. |
| 5,516,832 A | 5/1996 | Kennan et al. |
| 5,527,288 A | 6/1996 | Gross et al. |
| 5,531,878 A | 7/1996 | Vadgama et al. |
| 5,532,686 A | 7/1996 | Urbas et al. |
| 5,533,977 A | 7/1996 | Metcalf et al. |
| 5,536,259 A | 7/1996 | Utterberg |
| 5,543,326 A | 8/1996 | Heller et al. |
| 5,544,196 A | 8/1996 | Tiedmann, Jr. et al. |
| 5,545,191 A | 8/1996 | Mann et al. |
| 5,549,368 A | 8/1996 | Shields |
| 5,551,427 A | 9/1996 | Altman |
| 5,555,190 A | 9/1996 | Derby et al. |
| 5,558,638 A | 9/1996 | Evers et al. |
| 5,560,357 A | 10/1996 | Faupei et al. |
| 5,562,713 A | 10/1996 | Silvian |
| 5,564,434 A | 10/1996 | Halperin et al. |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,571,022 A | 11/1996 | Schaarschmidt |
| 5,575,563 A | 11/1996 | Chiu et al. |
| 5,581,206 A | 12/1996 | Chevallier et al. |
| 5,582,184 A | 12/1996 | Erickson et al. |
| 5,582,697 A | 12/1996 | Ikeda et al. |
| 5,582,698 A | 12/1996 | Flaherty et al. |
| 5,584,813 A | 12/1996 | Livingston et al. |
| 5,586,553 A | 12/1996 | Halili et al. |
| 5,589,326 A | 12/1996 | Deng et al. |
| 5,593,852 A | 1/1997 | Heller et al. |
| 5,596,150 A | 1/1997 | Arndt et al. |
| 5,597,378 A | 1/1997 | Jervis |
| 5,600,301 A | 2/1997 | Robinson, III |
| 5,601,435 A | 2/1997 | Quy |
| 5,609,575 A | 3/1997 | Larson et al. |
| 5,613,978 A | 3/1997 | Harding |
| 5,617,851 A | 4/1997 | Lipkovker |
| 5,623,933 A | 4/1997 | Amano et al. |
| 5,626,566 A | 5/1997 | Petersen et al. |
| 5,628,310 A | 5/1997 | Rao et al. |
| 5,628,324 A | 5/1997 | Sarbach |
| 5,628,890 A | 5/1997 | Carter et al. |
| 5,632,557 A | 5/1997 | Simons |
| 5,634,468 A | 6/1997 | Platt et al. |
| 5,636,640 A | 6/1997 | Staehlin |
| 5,638,832 A | 6/1997 | Singer et al. |
| 5,640,954 A | 6/1997 | Pfeiffer et al. |
| 5,651,869 A | 7/1997 | Yoshioka et al. |
| 5,653,239 A | 8/1997 | Pompei et al. |
| 5,659,454 A | 8/1997 | Vermesse |
| 5,660,163 A | 8/1997 | Schulman et al. |
| 5,665,071 A | 9/1997 | Wyrick |
| 5,665,222 A | 9/1997 | Heller et al. |
| 5,669,543 A | 9/1997 | Ueno |
| 5,669,890 A | 9/1997 | Grimm |
| 5,670,031 A | 9/1997 | Hintsche et al. |
| 5,673,322 A | 9/1997 | Pepe et al. |
| 5,680,858 A | 10/1997 | Hansen et al. |
| 5,682,233 A | 10/1997 | Brinda |
| 5,695,623 A | 12/1997 | Michel et al. |
| 5,707,502 A | 1/1998 | McCaffrey et al. |
| 5,708,247 A | 1/1998 | McAleer et al. |
| 5,711,001 A | 1/1998 | Bussan et al. |
| 5,711,297 A | 1/1998 | Iliff et al. |
| 5,711,861 A | 1/1998 | Ward et al. |
| 5,711,862 A | 1/1998 | Sakoda et al. |
| 5,724,030 A | 3/1998 | Urbas et al. |
| 5,726,646 A | 3/1998 | Bane et al. |
| 5,733,044 A | 3/1998 | Rose et al. |
| 5,733,259 A | 3/1998 | Valcke et al. |
| 5,733,262 A | 3/1998 | Paul |
| 5,733,313 A | 3/1998 | Barreras, Sr. et al. |
| 5,735,285 A | 4/1998 | Albert et al. |
| 5,738,220 A | 4/1998 | Geszler |
| 5,741,211 A | 4/1998 | Renirie et al. |
| 5,743,262 A | 4/1998 | Lepper, Jr. et al. |
| 5,746,217 A | 5/1998 | Erickson et al. |
| 5,746,697 A | 5/1998 | Swedlow et al. |
| 5,748,103 A | 5/1998 | Flach et al. |
| 5,749,656 A | 5/1998 | Boehm et al. |
| 5,749,907 A | 5/1998 | Mann |
| 5,758,290 A | 5/1998 | Nealon et al. |
| 5,766,131 A | 6/1998 | Kondo et al. |
| 5,770,028 A | 6/1998 | Maley et al. |
| 5,771,001 A | 6/1998 | Cobb |
| 5,771,891 A | 6/1998 | Gozani |
| 5,772,586 A | 6/1998 | Heinonen et al. |
| 5,778,879 A | 7/1998 | Ota et al. |
| 5,779,665 A | 7/1998 | Mastrototaro et al. |
| 5,786,439 A | 7/1998 | Van Antwerp et al. |
| 5,791,344 A | 8/1998 | Schulman et al. |
| 5,798,961 A | 8/1998 | Heyden et al. |
| 5,800,420 A | 9/1998 | Gross et al. |
| 5,804,047 A | 9/1998 | Karube et al. |
| 5,807,375 A | 9/1998 | Gross et al. |
| 5,814,020 A | 9/1998 | Gross |
| 5,820,551 A | 10/1998 | Hill et al. |
| 5,820,570 A | 10/1998 | Erickson et al. |
| 5,820,622 A | 10/1998 | Gross et al. |
| 5,822,715 A | 10/1998 | Worthington et al. |
| 5,823,802 A | 10/1998 | Bartley |
| 5,827,184 A | 10/1998 | Netherly et al. |
| 5,830,064 A | 11/1998 | Bradish et al. |
| 5,833,603 A | 11/1998 | Kovacs et al. |
| 5,840,020 A | 11/1998 | Heinonen et al. |
| 5,842,983 A | 12/1998 | Abel et al. |
| 5,851,197 A | 12/1998 | Marano et al. |
| 5,856,758 A | 1/1999 | Joffe et al. |
| 5,858,001 A | 1/1999 | Tsals et al. |
| 5,865,804 A | 2/1999 | Bachynsky |
| 5,871,494 A | 2/1999 | Simons et al. |
| 5,875,186 A | 2/1999 | Belanger et al. |
| 5,879,311 A | 3/1999 | Duchon et al. |
| 5,885,211 A | 3/1999 | Eppstein et al. |
| 5,891,049 A | 4/1999 | Cyrus et al. |
| 5,899,855 A | 5/1999 | Brown |
| 5,899,856 A | 5/1999 | Schoendorfer et al. |
| 5,914,026 A | 6/1999 | Blubaugh, Jr. et al. |
| 5,918,603 A | 7/1999 | Brown |
| 5,919,141 A | 7/1999 | Money et al. |
| 5,921,963 A | 7/1999 | Erez et al. |
| 5,924,979 A | 7/1999 | Sedlow et al. |
| 5,925,021 A | 7/1999 | Castellano et al. |
| 5,931,814 A | 8/1999 | Alex et al. |
| 5,931,868 A | 8/1999 | Gross |
| 5,935,224 A | 8/1999 | Svancarek et al. |
| 5,938,679 A | 8/1999 | Freeman et al. |
| 5,942,979 A | 8/1999 | Luppino |
| 5,948,006 A | 9/1999 | Mann |
| 5,951,485 A | 9/1999 | Cyrus et al. |
| 5,951,492 A | 9/1999 | Douglas et al. |
| 5,951,521 A | 9/1999 | Mastrototaro et al. |
| 5,951,582 A | 9/1999 | Thorne et al. |
| 5,954,643 A | 9/1999 | Van Antwerp |
| 5,954,685 A | 9/1999 | Tiemy |

(56)                    References Cited

U.S. PATENT DOCUMENTS

| | | | |
|---|---|---|---|
| 5,957,854 A | 9/1999 | Besson et al. |
| 5,961,451 A | 10/1999 | Reber et al. |
| 5,964,718 A | 10/1999 | Duchon et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,971,941 A | 10/1999 | Simons et al. |
| 5,972,199 A | 10/1999 | Heller et al. |
| 5,987,353 A | 11/1999 | Khatchatrian et al. |
| 5,993,411 A | 11/1999 | Choi |
| 5,995,860 A | 11/1999 | Sun et al. |
| 5,997,501 A | 12/1999 | Gross et al. |
| 6,001,067 A | 12/1999 | Shults et al. |
| 6,004,278 A | 12/1999 | Botich et al. |
| 6,017,335 A | 1/2000 | Burnham |
| 6,022,315 A | 2/2000 | Iliff |
| 6,022,368 A | 2/2000 | Gavronsky et al. |
| 6,024,699 A | 2/2000 | Surwit et al. |
| 6,026,321 A | 2/2000 | Miyata et al. |
| 6,027,459 A | 2/2000 | Shain et al. |
| 6,028,413 A | 2/2000 | Brockmann |
| 6,032,064 A | 2/2000 | Devlin et al. |
| 6,036,924 A | 3/2000 | Simons et al. |
| 6,048,352 A | 4/2000 | Douglas et al. |
| 6,049,727 A | 4/2000 | Crothall |
| 6,052,565 A | 4/2000 | Ishikura et al. |
| 6,054,194 A | 4/2000 | Kane |
| 6,056,718 A | 5/2000 | Funderburk et al. |
| 6,059,946 A | 5/2000 | Yukawa et al. |
| 6,066,243 A | 5/2000 | Anderson et al. |
| 6,068,399 A | 5/2000 | Tseng |
| 6,071,294 A | 6/2000 | Simons et al. |
| 6,071,391 A | 6/2000 | Gotoh et al. |
| 6,083,710 A | 7/2000 | Heller et al. |
| 6,085,342 A | 7/2000 | Marholev et al. |
| 6,088,605 A | 7/2000 | Griffith et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,091,987 A | 7/2000 | Thompson |
| 6,093,172 A | 7/2000 | Funderbunk et al. |
| 6,096,364 A | 8/2000 | Bok et al. |
| 6,097,480 A | 8/2000 | Kaplan |
| 6,099,484 A | 8/2000 | Douglas et al. |
| 6,102,896 A | 8/2000 | Roser |
| 6,103,033 A | 8/2000 | Say et al. |
| 6,106,484 A | 8/2000 | Terwilliger |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,129,666 A | 10/2000 | DeLuca et al. |
| 6,130,623 A | 10/2000 | MacLellan et al. |
| 6,132,449 A | 10/2000 | Lum et al. |
| 6,134,461 A | 10/2000 | Say et al. |
| 6,141,573 A | 10/2000 | Kurnik et al. |
| 6,143,164 A | 11/2000 | Heller et al. |
| 6,144,837 A | 11/2000 | Quy |
| 6,144,871 A | 11/2000 | Saito et al. |
| 6,144,922 A | 11/2000 | Douglas et al. |
| 6,149,626 A | 11/2000 | Bachynsky et al. |
| 6,157,850 A | 12/2000 | Diab et al. |
| 6,159,147 A | 12/2000 | Lichter et al. |
| 6,159,181 A | 12/2000 | Crossman et al. |
| 6,161,095 A | 12/2000 | Brown |
| 6,162,611 A | 12/2000 | Heller et al. |
| 6,168,606 B1 | 1/2001 | Levin et al. |
| 6,175,752 B1 | 1/2001 | Say et al. |
| 6,186,982 B1 | 2/2001 | Gross et al. |
| 6,192,891 B1 | 2/2001 | Gravel et al. |
| 6,197,040 B1 | 3/2001 | LeVaughn et al. |
| 6,198,946 B1 | 3/2001 | Shin et al. |
| 6,200,265 B1 | 3/2001 | Walsh et al. |
| 6,203,495 B1 | 3/2001 | Bardy et al. |
| 6,212,416 B1 | 4/2001 | Ward et al. |
| 6,213,972 B1 | 4/2001 | Butterfield et al. |
| 6,219,574 B1 | 4/2001 | Cormier et al. |
| 6,223,283 B1 | 4/2001 | Chaiken et al. |
| 6,231,531 B1 | 5/2001 | Lum et al. |
| 6,233,471 B1 | 5/2001 | Berner et al. |
| 6,237,394 B1 | 5/2001 | Harris et al. |
| 6,248,067 B1 | 6/2001 | Causey, III et al. |
| 6,254,536 B1 | 7/2001 | DeVito |
| 6,254,586 B1 | 7/2001 | Mann et al. |
| 6,264,810 B1 | 7/2001 | Stol et al. |
| 6,270,455 B1 | 8/2001 | Brown |
| 6,275,717 B1 | 8/2001 | Gross et al. |
| 6,283,761 B1 | 9/2001 | Joao |
| 6,283,982 B1 | 9/2001 | Levaughn et al. |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,298,255 B1 | 10/2001 | Cordero et al. |
| 6,299,347 B1 | 10/2001 | Pompei |
| 6,299,757 B1 | 10/2001 | Feldman et al. |
| 6,302,866 B1 | 10/2001 | Marggi |
| 6,304,766 B1 | 10/2001 | Colvin, Jr. |
| 6,306,104 B1 | 10/2001 | Cunningham et al. |
| 6,306,141 B1 | 10/2001 | Jervis |
| 6,309,884 B1 | 10/2001 | Cooper et al. |
| 6,314,317 B1 | 11/2001 | Willis |
| 6,329,161 B1 | 12/2001 | Heller et al. |
| 6,331,244 B1 | 12/2001 | Lewis et al. |
| 6,336,269 B1 | 1/2002 | Eldridge et al. |
| 6,338,790 B1 | 1/2002 | Feldman et al. |
| 6,341,232 B1 | 1/2002 | Conn et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,364,890 B1 | 4/2002 | Lum et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,368,339 B1 | 4/2002 | Amplatz |
| 6,377,828 B1 | 4/2002 | Chaiken et al. |
| 6,377,829 B1 | 4/2002 | Al-Ali |
| 6,377,894 B1 | 4/2002 | Deweese et al. |
| 6,379,301 B1 | 4/2002 | Worthington et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,409,740 B1 | 6/2002 | Kuhr et al. |
| 6,413,393 B1 | 7/2002 | Van Antwerp et al. |
| 6,416,471 B1 | 7/2002 | Kumar et al. |
| 6,418,332 B1 | 7/2002 | Mastrototaro et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,433,743 B1 | 8/2002 | Massy et al. |
| 6,435,017 B1 | 8/2002 | Nowicki, Jr. et al. |
| 6,437,679 B1 | 8/2002 | Roques |
| 6,438,414 B1 | 8/2002 | Conn et al. |
| 6,440,068 B1 | 8/2002 | Brown et al. |
| 6,442,413 B1 | 8/2002 | Silver |
| 6,445,374 B2 | 9/2002 | Albert et al. |
| 6,451,025 B1 | 9/2002 | Jervis |
| 6,458,109 B1 | 10/2002 | Henley et al. |
| 6,461,496 B1 | 10/2002 | Feldman et al. |
| 6,471,689 B1 | 10/2002 | Joseph et al. |
| 6,472,220 B1 | 10/2002 | Simons et al. |
| 6,478,736 B1 | 11/2002 | Mault |
| 6,482,176 B1 | 11/2002 | Wich |
| 6,484,045 B1 | 11/2002 | Holker et al. |
| 6,484,046 B1 | 11/2002 | Say et al. |
| 6,493,069 B1 | 12/2002 | Nagashimada et al. |
| 6,494,830 B1 | 12/2002 | Wessel |
| 6,496,729 B2 | 12/2002 | Thompson |
| 6,497,655 B1 | 12/2002 | Linberg et al. |
| 6,503,381 B1 | 1/2003 | Gotoh et al. |

(56)                References Cited

U.S. PATENT DOCUMENTS

| | | | |
|---|---|---|---|
| 6,510,344 B1 | 1/2003 | Halpern |
| 6,514,460 B1 | 2/2003 | Fendrock |
| 6,514,689 B2 | 2/2003 | Han et al. |
| 6,514,718 B2 | 2/2003 | Heller et al. |
| 6,520,326 B2 | 2/2003 | McIvor et al. |
| 6,522,927 B1 | 2/2003 | Bishay et al. |
| 6,533,805 B1 | 3/2003 | Jervis |
| 6,537,242 B1 | 3/2003 | Palmer |
| 6,540,891 B1 | 4/2003 | Stewart et al. |
| 6,544,212 B2 | 4/2003 | Galley et al. |
| 6,546,268 B1 | 4/2003 | Ishikawa et al. |
| 6,549,796 B2 | 4/2003 | Sohrab |
| 6,551,494 B1 | 4/2003 | Heller et al. |
| 6,551,496 B1 | 4/2003 | Moles et al. |
| 6,554,795 B2 | 4/2003 | Bagaoisan et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,572,566 B2 | 6/2003 | Effenhauser |
| 6,574,490 B2 | 6/2003 | Abbink et al. |
| 6,574,510 B2 | 6/2003 | Von Arx et al. |
| 6,575,895 B1 | 6/2003 | Blair |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,584,335 B1 | 6/2003 | Haar et al. |
| 6,585,644 B2 | 7/2003 | Lebel et al. |
| 6,589,229 B1 | 7/2003 | Connelly et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,602,268 B2 | 8/2003 | Kuhr et al. |
| 6,603,995 B1 | 8/2003 | Carter |
| 6,604,050 B2 | 8/2003 | Trippel et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,607,543 B2 | 8/2003 | Purcell et al. |
| 6,608,562 B1 | 8/2003 | Kimura et al. |
| 6,610,012 B2 | 8/2003 | Mault |
| 6,611,206 B2 | 8/2003 | Eshelman et al. |
| 6,613,015 B2 | 9/2003 | Sandstrom et al. |
| 6,616,819 B1 | 9/2003 | Liamos et al. |
| 6,618,934 B1 | 9/2003 | Feldman et al. |
| 6,627,154 B1 | 9/2003 | Goodman et al. |
| 6,631,281 B1 | 10/2003 | Kastle |
| 6,633,772 B2 | 10/2003 | Ford et al. |
| 6,635,014 B2 | 10/2003 | Starkweather et al. |
| 6,635,167 B1 | 10/2003 | Batman et al. |
| 6,637,611 B2 | 10/2003 | Luch |
| 6,641,533 B2 | 11/2003 | Causey, III et al. |
| 6,645,359 B1 | 11/2003 | Bhullar et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,662,439 B1 | 12/2003 | Bhullar |
| 6,666,849 B1 | 12/2003 | Marshall et al. |
| 6,668,196 B1 | 12/2003 | Villegas et al. |
| 6,671,534 B2 | 12/2003 | Putz |
| 6,675,030 B2 | 1/2004 | Ciurczak et al. |
| 6,676,290 B1 | 1/2004 | Lu |
| 6,676,816 B2 | 1/2004 | Mao et al. |
| 6,682,546 B2 | 1/2004 | Amplatz |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,699,188 B2 | 3/2004 | Wessel |
| 6,702,857 B2 | 3/2004 | Brauker et al. |
| 6,706,159 B2 | 3/2004 | Moerman et al. |
| 6,721,582 B2 | 4/2004 | Trepagnier et al. |
| 6,730,025 B1 | 5/2004 | Platt |
| 6,730,072 B2 | 5/2004 | Shawgo et al. |
| 6,730,200 B1 | 5/2004 | Stewart et al. |
| 6,731,976 B2 | 5/2004 | Penn et al. |
| 6,733,446 B2 | 5/2004 | Lebel et al. |
| 6,735,183 B2 | 5/2004 | O'Toole et al. |
| 6,735,479 B2 | 5/2004 | Fabian et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,743,635 B2 | 6/2004 | Neel et al. |
| 6,746,582 B2 | 6/2004 | Heller et al. |
| 6,748,445 B1 | 6/2004 | Darcey et al. |
| 6,749,740 B2 | 6/2004 | Liamos et al. |
| 6,758,810 B2 | 7/2004 | Lebel et al. |
| 6,758,835 B2 | 7/2004 | Close et al. |
| 6,764,581 B1 | 7/2004 | Forrow et al. |
| 6,767,440 B1 | 7/2004 | Bhullar et al. |
| 6,770,030 B1 | 8/2004 | Schaupp et al. |
| 6,773,671 B1 | 8/2004 | Lewis et al. |
| 6,781,522 B2 | 8/2004 | Sleva et al. |
| 6,790,178 B1 | 9/2004 | Mault et al. |
| 6,804,558 B2 | 10/2004 | Haller et al. |
| 6,804,561 B2 | 10/2004 | Stover |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,814,844 B2 | 11/2004 | Bhullar et al. |
| 6,830,551 B1 | 12/2004 | Uchigaki et al. |
| 6,837,858 B2 | 1/2005 | Cunningham et al. |
| 6,837,885 B2 | 1/2005 | Koblish et al. |
| 6,837,988 B2 | 1/2005 | Leong et al. |
| 6,849,052 B2 | 2/2005 | Uchigaki et al. |
| 6,850,790 B2 | 2/2005 | Berner et al. |
| 6,850,859 B1 | 2/2005 | Schuh |
| 6,854,882 B2 | 2/2005 | Chen |
| 6,862,465 B2 | 3/2005 | Shults et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,923,764 B2 | 8/2005 | Aceti et al. |
| 6,925,393 B1 | 8/2005 | Kalatz et al. |
| 6,931,327 B2 | 8/2005 | Goode, Jr. et al. |
| 6,932,892 B2 | 8/2005 | Chen |
| 6,932,894 B2 | 8/2005 | Mao et al. |
| 6,936,006 B2 | 8/2005 | Sabra |
| 6,937,222 B2 | 8/2005 | Numao |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman IV et al. |
| 6,954,662 B2 | 10/2005 | Freger et al. |
| 6,958,705 B2 | 10/2005 | Lebel et al. |
| 6,959,211 B2 | 10/2005 | Rule et al. |
| 6,960,192 B1 | 11/2005 | Flaherty et al. |
| 6,968,294 B2 | 11/2005 | Gutta et al. |
| 6,971,274 B2 | 12/2005 | Olin |
| 6,971,999 B2 | 12/2005 | Py et al. |
| 6,973,706 B2 | 12/2005 | Say et al. |
| 6,974,437 B2 | 12/2005 | Lebel et al. |
| 6,975,893 B2 | 12/2005 | Say et al. |

(56)                    References Cited

U.S. PATENT DOCUMENTS

| | | | |
|---|---|---|---|
| 6,983,867 B1 | 1/2006 | Fugere |
| 6,990,366 B2 | 1/2006 | Say et al. |
| 6,997,907 B2 | 2/2006 | Safabash et al. |
| 6,998,247 B2 | 2/2006 | Monfre et al. |
| 6,999,854 B2 | 2/2006 | Roth |
| 7,003,336 B2 | 2/2006 | Holker et al. |
| 7,003,340 B2 | 2/2006 | Say et al. |
| 7,003,341 B2 | 2/2006 | Say et al. |
| 7,005,857 B2 | 2/2006 | Stiene et al. |
| 7,009,511 B2 | 3/2006 | Mazar et al. |
| 7,010,356 B2 | 3/2006 | Jog et al. |
| 7,015,817 B2 | 3/2006 | Copley et al. |
| 7,016,713 B2 | 3/2006 | Gardner et al. |
| 7,020,508 B2 | 3/2006 | Stivoric et al. |
| 7,022,072 B2 | 4/2006 | Fox et al. |
| 7,022,219 B2 | 4/2006 | Mansouri et al. |
| 7,024,236 B2 | 4/2006 | Ford et al. |
| 7,024,245 B2 | 4/2006 | Lebel et al. |
| 7,025,743 B2 | 4/2006 | Mann et al. |
| 7,025,774 B2 | 4/2006 | Freeman et al. |
| 7,027,848 B2 | 4/2006 | Robinson et al. |
| 7,027,859 B1 | 4/2006 | McNichols et al. |
| 7,027,931 B1 | 4/2006 | Jones et al. |
| 7,029,444 B2 | 4/2006 | Shin et al. |
| 7,041,057 B1 | 5/2006 | Faupel et al. |
| 7,041,068 B2 | 5/2006 | Freeman et al. |
| 7,041,468 B2 | 5/2006 | Drucker et al. |
| 7,043,305 B2 | 5/2006 | Kenknight et al. |
| 7,046,153 B2 | 5/2006 | Oja et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,073,246 B2 | 7/2006 | Bhullar et al. |
| 7,074,307 B2 | 7/2006 | Simpson et al. |
| 7,081,195 B2 | 7/2006 | Simpson et al. |
| 7,082,334 B2 | 7/2006 | Boute et al. |
| 7,097,637 B2 | 8/2006 | Triplett et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,120,483 B2 | 10/2006 | Russel et al. |
| 7,123,950 B2 | 10/2006 | Mannheimer |
| 7,124,027 B1 | 10/2006 | Ernst et al. |
| 7,125,382 B2 | 10/2006 | Zhou et al. |
| 7,131,984 B2 | 11/2006 | Sato et al. |
| 7,134,999 B2 | 11/2006 | Brauker et al. |
| 7,136,689 B2 | 11/2006 | Shults et al. |
| 7,144,384 B2 | 12/2006 | Gorman et al. |
| 7,154,398 B2 | 12/2006 | Chen et al. |
| 7,155,290 B2 | 12/2006 | Von Arx et al. |
| 7,167,818 B2 | 1/2007 | Brown |
| 7,169,600 B2 | 1/2007 | Hoss et al. |
| 7,171,274 B2 | 1/2007 | Starkweather et al. |
| 7,174,199 B2 | 2/2007 | Berner et al. |
| 7,179,226 B2 | 2/2007 | Crothall et al. |
| 7,183,102 B2 | 2/2007 | Monfre et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,207,974 B2 | 4/2007 | Safabash et al. |
| 7,220,387 B2 | 5/2007 | Flaherty et al. |
| 7,223,276 B2 | 5/2007 | List et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,228,162 B2 | 6/2007 | Ward et al. |
| 7,228,182 B2 | 6/2007 | Healy et al. |
| 7,237,712 B2 | 7/2007 | DeRocco et al. |
| 7,267,665 B2 | 9/2007 | Steil et al. |
| 7,276,029 B2 | 10/2007 | Goode, Jr. et al. |
| 7,276,146 B2 | 10/2007 | Wilsey |
| 7,276,147 B2 | 10/2007 | Wilsey |
| 7,278,983 B2 | 10/2007 | Ireland et al. |
| 7,286,894 B1 | 10/2007 | Grant et al. |
| 7,287,318 B2 | 10/2007 | Bhullar et al. |
| 7,291,497 B2 | 11/2007 | Holmes et al. |
| 7,295,867 B2 | 11/2007 | Berner et al. |
| 7,297,151 B2 | 11/2007 | Boecker et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,324,012 B2 | 1/2008 | Mann et al. |
| 7,324,850 B2 | 1/2008 | Persen et al. |
| 7,329,239 B2 | 2/2008 | Safabash et al. |
| 7,335,294 B2 | 2/2008 | Heller et al. |
| 7,340,287 B2 | 3/2008 | Mason et al. |
| 7,340,309 B2 | 3/2008 | Miazga et al. |
| 7,344,500 B2 | 3/2008 | Talbot et al. |
| 7,347,819 B2 | 3/2008 | Lebel et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,384,397 B2 | 6/2008 | Zhang et al. |
| 7,386,937 B2 | 6/2008 | Bhullar et al. |
| 7,387,010 B2 | 6/2008 | Sunshine et al. |
| 7,399,277 B2 | 7/2008 | Saidara et al. |
| 7,400,111 B2 | 7/2008 | Batman et al. |
| 7,401,111 B1 | 7/2008 | Batman et al. |
| 7,402,153 B2 | 7/2008 | Steil et al. |
| 7,404,796 B2 | 7/2008 | Ginsberg |
| 7,407,493 B2 | 8/2008 | Cane |
| 7,408,132 B2 | 8/2008 | Wambsganss et al. |
| 7,416,541 B2 | 8/2008 | Yuzhakov et al. |
| 7,419,573 B2 | 9/2008 | Gundel |
| 7,424,318 B2 | 9/2008 | Brister et al. |
| 7,429,255 B2 | 9/2008 | Thompson |
| 7,433,727 B2 | 10/2008 | Ward |
| 7,448,996 B2 | 11/2008 | Khanuja et al. |
| 7,455,663 B2 | 11/2008 | Bikovsky |
| 7,460,898 B2 | 12/2008 | Brister et al. |
| 7,462,264 B2 | 12/2008 | Heller et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,476,827 B1 | 1/2009 | Bhullar et al. |
| 7,481,819 B2 | 1/2009 | Koeppel et al. |
| 7,492,254 B2 | 2/2009 | Bandy et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,519,408 B2 | 4/2009 | Rasdal et al. |
| 7,545,272 B2 | 6/2009 | Goodnow et al. |
| 7,547,281 B2 | 6/2009 | Hayes et al. |
| 7,565,197 B2 | 7/2009 | Haubrich et al. |
| 7,568,619 B2 | 8/2009 | Todd et al. |
| 7,569,030 B2 | 8/2009 | Lebel et al. |
| 7,574,266 B2 | 8/2009 | Dudding et al. |
| 7,582,059 B2 | 9/2009 | Funderburk et al. |
| 7,583,990 B2 | 9/2009 | Goode, Jr. et al. |
| 7,585,287 B2 | 9/2009 | Bresina et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,604,592 B2 | 10/2009 | Freeman et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,643,798 B2 | 1/2010 | Ljung |
| 7,651,596 B2 | 1/2010 | Petisce et al. |
| 7,651,845 B2 | 1/2010 | Doyle, III et al. |
| 7,653,425 B2 | 1/2010 | Hayter et al. |
| 7,654,956 B2 | 2/2010 | Brister et al. |
| 7,657,297 B2 | 2/2010 | Simpson et al. |

(56) References Cited

U.S. PATENT DOCUMENTS

| | | |
|---|---|---|
| 7,659,823 B1 | 2/2010 | Killian et al. |
| 7,660,615 B2 | 2/2010 | VanAntwerp et al. |
| 7,666,149 B2 | 2/2010 | Simons et al. |
| 7,668,596 B2 | 2/2010 | Von Arx et al. |
| 7,682,338 B2 | 3/2010 | Griffin |
| 7,697,967 B2 | 4/2010 | Stafford |
| 7,699,775 B2 | 4/2010 | Desai et al. |
| 7,699,807 B2 | 4/2010 | Faust et al. |
| 7,701,052 B2 | 4/2010 | Borland et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,729,737 B2 | 6/2010 | Ward |
| 7,731,657 B2 | 6/2010 | Stafford |
| 7,731,691 B2 | 6/2010 | Cote et al. |
| 7,736,310 B2 | 6/2010 | Taub et al. |
| 7,736,344 B2 | 6/2010 | Moberg et al. |
| 7,741,734 B2 | 6/2010 | Joannopoulos et al. |
| 7,757,022 B2 | 7/2010 | Kato et al. |
| 7,763,042 B2 | 7/2010 | Iio et al. |
| 7,766,829 B2 | 8/2010 | Sloan et al. |
| 7,768,387 B2 | 8/2010 | Fennell et al. |
| 7,771,352 B2 | 8/2010 | Shults et al. |
| 7,774,145 B2 | 8/2010 | Brauker et al. |
| 7,775,444 B2 | 8/2010 | DeRocco et al. |
| 7,778,680 B2 | 8/2010 | Goode, Jr. et al. |
| 7,779,332 B2 | 8/2010 | Karr et al. |
| 7,780,827 B1 | 8/2010 | Bhullar et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,811,231 B2 | 10/2010 | Jin et al. |
| 7,813,809 B2 | 10/2010 | Strother et al. |
| 7,822,454 B1 | 10/2010 | Alden et al. |
| 7,826,981 B2 | 11/2010 | Goode, Jr. et al. |
| 7,831,310 B2 | 11/2010 | Lebel et al. |
| 7,833,151 B2 | 11/2010 | Khait et al. |
| 7,833,170 B2 | 11/2010 | Matsumoto et al. |
| 7,837,633 B2 | 11/2010 | Conway et al. |
| 7,842,046 B1 | 11/2010 | Nakao |
| 7,846,132 B2 | 12/2010 | Gravesen et al. |
| 7,850,652 B2 | 12/2010 | Lingier et al. |
| 7,860,574 B2 | 12/2010 | Von Arx et al. |
| 7,866,026 B1 | 1/2011 | Wang et al. |
| 7,867,244 B2 | 1/2011 | Lathrop et al. |
| 7,873,299 B2 | 1/2011 | Berner et al. |
| 7,882,611 B2 | 2/2011 | Shah et al. |
| 7,883,464 B2 | 2/2011 | Stafford |
| 7,883,473 B2 | 2/2011 | LeVaughn et al. |
| 7,885,697 B2 | 2/2011 | Brister et al. |
| 7,889,069 B2 | 2/2011 | Fifolt et al. |
| 7,896,844 B2 | 3/2011 | Thalmann et al. |
| 7,899,511 B2 | 3/2011 | Shults et al. |
| 7,899,545 B2 | 3/2011 | John |
| 7,905,833 B2 | 3/2011 | Brister et al. |
| 7,912,655 B2 | 3/2011 | Power et al. |
| 7,912,674 B2 | 3/2011 | Killoren Clark et al. |
| 7,914,450 B2 | 3/2011 | Goode, Jr. et al. |
| 7,914,460 B2 | 3/2011 | Melker et al. |
| 7,916,013 B2 | 3/2011 | Stevenson |
| 7,920,906 B2 | 4/2011 | Goode, Jr. et al. |
| 7,920,907 B2 | 4/2011 | McGarraugh et al. |
| 7,938,797 B2 | 5/2011 | Estes |
| 7,941,200 B2 | 5/2011 | Weinart et al. |
| 7,946,984 B2 | 5/2011 | Brister et al. |
| 7,946,985 B2 | 5/2011 | Mastrototaro et al. |
| 7,955,258 B2 | 6/2011 | Goscha et al. |
| 7,955,297 B2 | 6/2011 | Radmer et al. |
| 7,970,448 B2 | 6/2011 | Shults et al. |
| 7,970,449 B2 | 6/2011 | Ward |
| 7,972,296 B2 | 7/2011 | Braig et al. |
| 7,974,672 B2 | 7/2011 | Shults et al. |
| 7,976,467 B2 | 7/2011 | Young et al. |
| 7,978,063 B2 | 7/2011 | Baldus et al. |
| 7,985,203 B2 | 7/2011 | Haueter et al. |
| 7,985,222 B2 | 7/2011 | Gall et al. |
| 7,996,158 B2 | 8/2011 | Hayter et al. |
| 7,999,674 B2 | 8/2011 | Kamen |
| 8,000,918 B2 | 8/2011 | Fjield et al. |
| 8,005,524 B2 | 8/2011 | Brauker et al. |
| 8,010,174 B2 | 8/2011 | Goode, Jr. et al. |
| 8,010,256 B2 | 8/2011 | Oowada |
| 8,016,774 B2 | 9/2011 | Freeman et al. |
| 8,028,837 B2 | 10/2011 | Gerstle et al. |
| 8,029,441 B2 | 10/2011 | Mazza et al. |
| 8,029,442 B2 | 10/2011 | Funderburk et al. |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,103,471 B2 | 1/2012 | Hayter |
| 8,111,042 B2 | 2/2012 | Bennett |
| 8,112,240 B2 | 2/2012 | Fennell |
| 8,115,488 B2 | 2/2012 | McDowell |
| 8,116,681 B2 | 2/2012 | Baarman |
| 8,116,683 B2 | 2/2012 | Baarman |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Docks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,140,312 B2 | 3/2012 | Hayter et al. |
| 8,150,321 B2 | 4/2012 | Winter et al. |
| 8,150,516 B2 | 4/2012 | Levine et al. |
| 8,160,670 B2 | 4/2012 | Quyang et al. |
| 8,160,900 B2 | 4/2012 | Taub et al. |
| 8,172,805 B2 | 5/2012 | Mogensen et al. |
| 8,175,673 B2 | 5/2012 | Say et al. |
| 8,179,266 B2 | 5/2012 | Hermle |
| 8,180,423 B2 | 5/2012 | Mang et al. |
| 8,192,394 B2 | 6/2012 | Estes et al. |
| 8,216,138 B1 | 7/2012 | McGaraugh et al. |
| 8,221,332 B2 | 7/2012 | Robbins et al. |
| 8,224,410 B2 | 7/2012 | Hadvary et al. |
| 8,239,166 B2 | 8/2012 | Hayter et al. |
| 8,255,026 B1 | 8/2012 | Al-Ali |
| 8,260,558 B2 | 9/2012 | Hayter et al. |
| 8,262,618 B2 | 9/2012 | Scheurer |
| 8,282,549 B2 | 10/2012 | Brauker et al. |
| 8,333,714 B2 | 12/2012 | Stafford |
| 8,346,335 B2 | 1/2013 | Harper et al. |
| 8,346,337 B2 | 1/2013 | Heller et al. |
| 8,373,544 B2 | 2/2013 | Pitt-Plady |
| 8,374,668 B1 | 2/2013 | Hayter et al. |
| 8,376,945 B2 | 2/2013 | Hayter et al. |
| 8,377,271 B2 | 2/2013 | Mao et al. |
| 8,382,671 B2 | 2/2013 | Anthony et al. |
| 8,398,664 B2 | 3/2013 | Lamps et al. |
| 8,409,093 B2 | 4/2013 | Bugler |
| 8,409,145 B2 | 4/2013 | Raymond et al. |
| 8,439,838 B2 | 5/2013 | Mogensen et al. |
| 8,444,560 B2 | 5/2013 | Hayter et al. |

(56) References Cited

U.S. PATENT DOCUMENTS

| | | |
|---|---|---|
| 8,461,985 B2 | 6/2013 | Fennell et al. |
| 8,469,986 B2 | 6/2013 | Schraga |
| 8,512,243 B2 | 8/2013 | Stafford |
| 8,515,518 B2 | 8/2013 | Ouyang et al. |
| 8,515,519 B2 | 8/2013 | Brister et al. |
| 8,538,512 B1 | 9/2013 | Bibian et al. |
| 8,545,403 B2 | 10/2013 | Peyser et al. |
| 8,560,038 B2 | 10/2013 | Hayter et al. |
| 8,562,567 B2 | 10/2013 | Gundberg |
| 8,571,808 B2 | 10/2013 | Hayter |
| 8,583,205 B2 | 11/2013 | Budiman et al. |
| 8,585,591 B2 | 11/2013 | Sloan et al. |
| 8,597,570 B2 | 12/2013 | Terashima et al. |
| 8,600,681 B2 | 12/2013 | Hayter et al. |
| 8,602,991 B2 | 12/2013 | Stafford |
| 8,612,163 B2 | 12/2013 | Hayter et al. |
| 8,615,282 B2 | 12/2013 | Brister et al. |
| 8,617,069 B2 | 12/2013 | Bernstein et al. |
| 8,617,071 B2 | 12/2013 | Say et al. |
| 8,622,903 B2 | 1/2014 | Jin et al. |
| 8,628,498 B2 | 1/2014 | Safabach et al. |
| 8,641,674 B2 | 2/2014 | Bobroff et al. |
| 8,652,043 B2 | 2/2014 | Drucker et al. |
| 8,682,408 B2 | 3/2014 | Boock et al. |
| 8,682,615 B2 | 3/2014 | Hayter et al. |
| 8,684,930 B2 | 4/2014 | Feldman et al. |
| 8,692,655 B2 | 4/2014 | Zimman et al. |
| 8,710,993 B2 | 4/2014 | Hayter et al. |
| 8,747,363 B2 | 6/2014 | Nielsen et al. |
| 8,750,955 B2 | 6/2014 | Brister et al. |
| 8,771,183 B2 | 7/2014 | Sloan |
| 8,797,163 B2 | 8/2014 | Finkenzeller |
| 8,808,515 B2 | 8/2014 | Feldman et al. |
| 8,834,366 B2 | 9/2014 | Hayter et al. |
| 8,845,536 B2 | 9/2014 | Brauker et al. |
| 8,870,822 B2 | 10/2014 | Thalmann et al. |
| 8,880,138 B2 | 11/2014 | Cho |
| 8,945,056 B2 | 2/2015 | Lio et al. |
| 8,961,413 B2 | 2/2015 | Teller et al. |
| 9,007,781 B2 | 4/2015 | Moein et al. |
| 9,014,774 B2 | 4/2015 | Mao et al. |
| 9,031,630 B2 | 5/2015 | Hoss et al. |
| 9,060,719 B2 | 6/2015 | Hayter et al. |
| 9,060,805 B2 | 6/2015 | Goodnow et al. |
| 9,066,697 B2 | 6/2015 | Peyser et al. |
| 9,101,302 B2 | 8/2015 | Mace et al. |
| 9,186,098 B2 | 11/2015 | Lee et al. |
| 9,215,992 B2 | 12/2015 | Donnay et al. |
| 9,241,631 B2 | 1/2016 | Valdes et al. |
| 9,259,175 B2 | 2/2016 | Stafford |
| 9,265,453 B2 | 2/2016 | Curry et al. |
| 9,289,179 B2 | 3/2016 | Hayter et al. |
| 9,295,786 B2 | 3/2016 | Gottlieb et al. |
| 9,357,951 B2 | 6/2016 | Simpson et al. |
| 9,398,872 B2 | 7/2016 | Hayter et al. |
| 9,402,544 B2 | 8/2016 | Yee et al. |
| 9,402,570 B2 | 8/2016 | Pace et al. |
| 9,439,586 B2 | 9/2016 | Bugler |
| 9,451,910 B2 | 9/2016 | Brister et al. |
| 9,474,479 B2 | 10/2016 | Pusey et al. |
| 9,480,421 B2 | 11/2016 | Stafford |
| 9,483,608 B2 | 11/2016 | Hayter et al. |
| 9,504,471 B2 | 11/2016 | Vaitekunas et al. |
| 9,558,325 B2 | 1/2017 | Hayter et al. |
| 9,566,384 B2 | 2/2017 | Gyrn et al. |
| 9,636,068 B2 | 5/2017 | Yee et al. |
| 9,668,682 B2 | 6/2017 | Brister et al. |
| 9,743,876 B2 | 8/2017 | Gelfand et al. |
| 9,808,574 B2 | 11/2017 | Yodfat et al. |
| 9,814,414 B2 | 11/2017 | Brister et al. |
| 10,213,139 B2 | 2/2019 | Rao et al. |
| 10,292,632 B2 | 5/2019 | Lee et al. |
| 10,342,489 B2 | 7/2019 | Stafford |
| 10,772,547 B1 | 9/2020 | Lee et al. |
| 10,820,842 B2 | 11/2020 | Harper |
| 10,827,954 B2 | 11/2020 | Hoss et al. |
| 10,874,338 B2 | 12/2020 | Stafford |
| 10,881,340 B2 | 1/2021 | Curry et al. |
| 10,881,341 B1 | 1/2021 | Curry et al. |
| 10,945,647 B2 | 3/2021 | Mazza et al. |
| 10,945,649 B2 | 3/2021 | Lee et al. |
| 10,952,653 B2 | 3/2021 | Harper |
| 10,959,654 B2 | 3/2021 | Curry et al. |
| 10,966,644 B2 | 4/2021 | Stafford |
| 10,973,443 B2 | 4/2021 | Funderburk et al. |
| 10,980,461 B2 | 4/2021 | Bohm et al. |
| 11,000,213 B2 | 5/2021 | Kamath et al. |
| 11,000,216 B2 | 5/2021 | Curry et al. |
| 11,006,870 B2 | 5/2021 | Yee et al. |
| 11,006,871 B2 | 5/2021 | Yee et al. |
| 11,013,440 B2 | 5/2021 | Lee et al. |
| 11,051,724 B2 | 7/2021 | Pace et al. |
| 11,064,917 B2 | 7/2021 | Simpson et al. |
| 11,116,430 B2 | 9/2021 | Funderburk et al. |
| 11,141,084 B2 | 10/2021 | Funderburk et al. |
| 11,166,656 B2 | 11/2021 | Yee et al. |
| 11,179,068 B2 | 11/2021 | Pace et al. |
| 11,197,625 B1 | 12/2021 | Schleicher et al. |
| 11,202,591 B2 | 12/2021 | Yee et al. |
| 11,213,229 B2 | 1/2022 | Yee et al. |
| 11,246,519 B2 | 2/2022 | Donnay et al. |
| 11,266,335 B2 | 3/2022 | Donnay et al. |
| 11,298,056 B2 | 4/2022 | Harper |
| 11,298,058 B2 | 4/2022 | Stafford |
| 11,510,625 B2 | 11/2022 | Gray et al. |
| 2001/0016682 A1 | 8/2001 | Berner et al. |
| 2001/0034479 A1 | 10/2001 | Ring et al. |
| 2001/0037060 A1 | 11/2001 | Thompson et al. |
| 2001/0037366 A1 | 11/2001 | Webb et al. |
| 2001/0039387 A1 | 11/2001 | Rutynowski et al. |
| 2001/0044608 A1 | 11/2001 | Odell et al. |
| 2001/0047127 A1 | 11/2001 | New et al. |
| 2001/0056262 A1 | 12/2001 | Cabin et al. |
| 2002/0002344 A1 | 1/2002 | Douglas et al. |
| 2002/0010390 A1 | 1/2002 | Guice et al. |
| 2002/0013522 A1 | 1/2002 | Lav et al. |
| 2002/0013538 A1 | 1/2002 | Teller |
| 2002/0016534 A1 | 2/2002 | Trepagnier et al. |
| 2002/0016568 A1 | 2/2002 | Lebel et al. |
| 2002/0019022 A1 | 2/2002 | Dunn et al. |
| 2002/0019584 A1 | 2/2002 | Schulze et al. |
| 2002/0019586 A1 | 2/2002 | Teller et al. |
| 2002/0019606 A1 | 2/2002 | Lebel et al. |
| 2002/0022855 A1 | 2/2002 | Bobroff et al. |
| 2002/0023852 A1 | 2/2002 | McIvor et al. |
| 2002/0029058 A1 | 3/2002 | LeVaughn et al. |
| 2002/0032386 A1 | 3/2002 | Sackner et al. |
| 2002/0039026 A1 | 4/2002 | Stroth et al. |
| 2002/0042090 A1 | 4/2002 | Heller et al. |
| 2002/0045808 A1 | 4/2002 | Ford et al. |
| 2002/0049482 A1 | 4/2002 | Fabian et al. |
| 2002/0050250 A1 | 5/2002 | Peterson et al. |
| 2002/0055711 A1 | 5/2002 | Lavi et al. |
| 2002/0057993 A1 | 5/2002 | Maisey et al. |
| 2002/0065454 A1 | 5/2002 | Lebel et al. |
| 2002/0066764 A1 | 6/2002 | Perry et al. |
| 2002/0072720 A1 | 6/2002 | Hague et al. |
| 2002/0072784 A1 | 6/2002 | Sheppard et al. |
| 2002/0074162 A1 | 6/2002 | Su et al. |
| 2002/0076966 A1 | 6/2002 | Carron et al. |
| 2002/0077599 A1 | 6/2002 | Wojcik |
| 2002/0082487 A1 | 6/2002 | Kollias et al. |
| 2002/0084196 A1 | 7/2002 | Liamos et al. |
| 2002/0091796 A1 | 7/2002 | Higginson et al. |
| 2002/0093969 A1 | 7/2002 | Lin et al. |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0111832 A1 | 8/2002 | Judge |
| 2002/0117639 A1 | 8/2002 | Paolini et al. |
| 2002/0118528 A1 | 8/2002 | Su et al. |
| 2002/0119711 A1 | 8/2002 | Van Antwerp et al. |
| 2002/0120186 A1 | 8/2002 | Keimel |
| 2002/0124017 A1 | 9/2002 | Mault |

(56)  References Cited

U.S. PATENT DOCUMENTS

| | | |
|---|---|---|
| 2002/0128594 A1 | 9/2002 | Das et al. |
| 2002/0130042 A1 | 9/2002 | Moerman et al. |
| 2002/0133066 A1 | 9/2002 | Miller et al. |
| 2002/0147135 A1 | 10/2002 | Schnell |
| 2002/0150959 A1 | 10/2002 | Lejeune et al. |
| 2002/0151770 A1 | 10/2002 | Noll et al. |
| 2002/0151796 A1 | 10/2002 | Koulik |
| 2002/0151816 A1 | 10/2002 | Rich et al. |
| 2002/0154050 A1 | 10/2002 | Krupp et al. |
| 2002/0161288 A1 | 10/2002 | Shin et al. |
| 2002/0161290 A1 | 10/2002 | Chance |
| 2002/0161338 A1 | 10/2002 | Peterson |
| 2002/0164836 A1 | 11/2002 | Ho |
| 2002/0165462 A1 | 11/2002 | Westbrook et al. |
| 2002/0169369 A1 | 11/2002 | Ward et al. |
| 2002/0169439 A1 | 11/2002 | Flaherty et al. |
| 2002/0169635 A1 | 11/2002 | Shillingburg |
| 2002/0183604 A1 | 12/2002 | Gowda et al. |
| 2002/0185128 A1 | 12/2002 | Theobald |
| 2002/0185130 A1 | 12/2002 | Wright et al. |
| 2002/0188748 A1 | 12/2002 | Blackwell et al. |
| 2002/0197522 A1 | 12/2002 | Lawrence et al. |
| 2002/0198444 A1 | 12/2002 | Ughigaki et al. |
| 2002/0198543 A1 | 12/2002 | Burdulis et al. |
| 2003/0004403 A1 | 1/2003 | Drinan et al. |
| 2003/0020477 A1 | 1/2003 | Goldstein |
| 2003/0023189 A1 | 1/2003 | Kuo |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0028184 A1 | 2/2003 | Lebel et al. |
| 2003/0032077 A1 | 2/2003 | Itoh et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0054428 A1 | 3/2003 | Monfre et al. |
| 2003/0055380 A1 | 3/2003 | Flaherty |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0069509 A1 | 4/2003 | Matzinger et al. |
| 2003/0069510 A1 | 4/2003 | Semler |
| 2003/0076792 A1 | 4/2003 | Theimer |
| 2003/0077642 A1 | 4/2003 | Fritsch et al. |
| 2003/0078481 A1 | 4/2003 | McIvor et al. |
| 2003/0078560 A1 | 4/2003 | Miller et al. |
| 2003/0083686 A1 | 5/2003 | Freeman et al. |
| 2003/0088166 A1 | 5/2003 | Say et al. |
| 2003/0097092 A1 | 5/2003 | Flaherty |
| 2003/0100040 A1 | 5/2003 | Bonnecaze et al. |
| 2003/0100821 A1 | 5/2003 | Heller et al. |
| 2003/0109775 A1 | 6/2003 | O'Neil et al. |
| 2003/0114897 A1 | 6/2003 | Von Arx et al. |
| 2003/0114898 A1 | 6/2003 | Von Arx et al. |
| 2003/0119457 A1 | 6/2003 | Standke |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0135127 A1 | 7/2003 | Sackner et al. |
| 2003/0135333 A1 | 7/2003 | Aceti et al. |
| 2003/0144579 A1 | 7/2003 | Buss |
| 2003/0144581 A1 | 7/2003 | Conn et al. |
| 2003/0144608 A1 | 7/2003 | Kojima et al. |
| 2003/0153900 A1 | 8/2003 | Aceti et al. |
| 2003/0155656 A1 | 8/2003 | Chiu et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0188427 A1 | 10/2003 | Say et al. |
| 2003/0199744 A1 | 10/2003 | Buse et al. |
| 2003/0199790 A1 | 10/2003 | Boecker et al. |
| 2003/0199910 A1 | 10/2003 | Boecker et al. |
| 2003/0204290 A1 | 10/2003 | Sadler et al. |
| 2003/0208113 A1 | 11/2003 | Mault et al. |
| 2003/0208114 A1 | 11/2003 | Ackerman |
| 2003/0212317 A1 | 11/2003 | Kovatchev et al. |
| 2003/0212379 A1 | 11/2003 | Bylund et al. |
| 2003/0212579 A1 | 11/2003 | Brown et al. |
| 2003/0216621 A1 | 11/2003 | Alpert et al. |
| 2003/0216630 A1 | 11/2003 | Jersey-Willuhn et al. |
| 2003/0217966 A1 | 11/2003 | Tapsak et al. |
| 2003/0225361 A1 | 12/2003 | Sabra |
| 2003/0225373 A1 | 12/2003 | Bobroff et al. |
| 2003/0236489 A1 | 12/2003 | Jacobson et al. |
| 2004/0002382 A1 | 1/2004 | Kovelman et al. |
| 2004/0010207 A1 | 1/2004 | Flaherty et al. |
| 2004/0011671 A1 | 1/2004 | Shults et al. |
| 2004/0015131 A1 | 1/2004 | Flaherty et al. |
| 2004/0017300 A1 | 1/2004 | Kotzin et al. |
| 2004/0030226 A1 | 2/2004 | Quy |
| 2004/0030531 A1 | 2/2004 | Miller et al. |
| 2004/0030581 A1 | 2/2004 | Levin et al. |
| 2004/0034289 A1 | 2/2004 | Teller et al. |
| 2004/0039255 A1 | 2/2004 | Simonsen et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0060818 A1 | 4/2004 | Feldman et al. |
| 2004/0061232 A1 | 4/2004 | Shah et al. |
| 2004/0063435 A1 | 4/2004 | Sakamoto et al. |
| 2004/0064068 A1 | 4/2004 | DeNuzzio et al. |
| 2004/0064133 A1 | 4/2004 | Miller et al. |
| 2004/0072357 A1 | 4/2004 | Steine et al. |
| 2004/0073266 A1 | 4/2004 | Haefner et al. |
| 2004/0078215 A1 | 4/2004 | Dahlin et al. |
| 2004/0096959 A1 | 5/2004 | Stiene et al. |
| 2004/0100376 A1 | 5/2004 | Lye et al. |
| 2004/0105411 A1 | 6/2004 | Boatwright et al. |
| 2004/0106858 A1 | 6/2004 | Say et al. |
| 2004/0106859 A1 | 6/2004 | Say et al. |
| 2004/0106860 A1 | 6/2004 | Say et al. |
| 2004/0111017 A1 | 6/2004 | Say et al. |
| 2004/0116847 A1 | 6/2004 | Wall |
| 2004/0116865 A1 | 6/2004 | Bengtsson |
| 2004/0116866 A1 | 6/2004 | Gorman et al. |
| 2004/0117204 A1 | 6/2004 | Mazar et al. |
| 2004/0119169 A1 | 6/2004 | Hanawa |
| 2004/0122353 A1 | 6/2004 | Shahmirian et al. |
| 2004/0122489 A1 | 6/2004 | Mazar et al. |
| 2004/0133089 A1 | 7/2004 | Kilcoyne et al. |
| 2004/0133164 A1 | 7/2004 | Funderburk et al. |
| 2004/0133390 A1 | 7/2004 | Osorio et al. |
| 2004/0135571 A1 | 7/2004 | Uutela et al. |
| 2004/0135684 A1 | 7/2004 | Steinthal et al. |
| 2004/0138544 A1 | 7/2004 | Ward et al. |
| 2004/0138588 A1 | 7/2004 | Saikley et al. |
| 2004/0138688 A1 | 7/2004 | Giraud |
| 2004/0140211 A1 | 7/2004 | Broy et al. |
| 2004/0142403 A1 | 7/2004 | Hetzel et al. |
| 2004/0146909 A1 | 7/2004 | Duong et al. |
| 2004/0147872 A1 | 7/2004 | Thompson |
| 2004/0147996 A1 | 7/2004 | Miazga et al. |
| 2004/0152366 A1 | 8/2004 | Schultz et al. |
| 2004/0152622 A1 | 8/2004 | Keith et al. |
| 2004/0158207 A1 | 8/2004 | Hunn et al. |
| 2004/0162521 A1 | 8/2004 | Bengtsson et al. |
| 2004/0162678 A1 | 8/2004 | Hetzel et al. |
| 2004/0167801 A1 | 8/2004 | Say et al. |
| 2004/0171910 A1 | 9/2004 | Moore-Steele |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204673 A1 | 10/2004 | Flaherty |
| 2004/0204687 A1 | 10/2004 | Mogensen et al. |
| 2004/0204744 A1 | 10/2004 | Penner et al. |

(56)                References Cited

U.S. PATENT DOCUMENTS

| 2004/0204868 A1 | 10/2004 | Maynard et al. |
| 2004/0206625 A1 | 10/2004 | Bhullar et al. |
| 2004/0206916 A1 | 10/2004 | Colvin, Jr. et al. |
| 2004/0210122 A1 | 10/2004 | Sleburg |
| 2004/0221057 A1 | 11/2004 | Darcey et al. |
| 2004/0223876 A1 | 11/2004 | Kirollos et al. |
| 2004/0223985 A1 | 11/2004 | Dunfield et al. |
| 2004/0225199 A1 | 11/2004 | Evanyk et al. |
| 2004/0225262 A1 | 11/2004 | Fathallah et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0240426 A1 | 12/2004 | Wu et al. |
| 2004/0249253 A1 | 12/2004 | Racchini et al. |
| 2004/0249999 A1 | 12/2004 | Connolly et al. |
| 2004/0254433 A1 | 12/2004 | Bandis et al. |
| 2004/0254434 A1 | 12/2004 | Goodnow et al. |
| 2004/0258564 A1 | 12/2004 | Charlton |
| 2004/0260224 A1 | 12/2004 | Binder et al. |
| 2004/0267300 A1 | 12/2004 | Mace et al. |
| 2005/0001024 A1 | 1/2005 | Kusaka et al. |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0006122 A1 | 1/2005 | Burnette |
| 2005/0010269 A1 | 1/2005 | Lebel et al. |
| 2005/0017864 A1 | 1/2005 | Tsoukalis |
| 2005/0027177 A1 | 2/2005 | Shin et al. |
| 2005/0027180 A1 | 2/2005 | Goode, Jr. et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0038465 A1 | 2/2005 | Shraga |
| 2005/0038680 A1 | 2/2005 | McMahon |
| 2005/0043598 A1 | 2/2005 | Goode, Jr. et al. |
| 2005/0049179 A1 | 3/2005 | Davidson et al. |
| 2005/0051427 A1 | 3/2005 | Brauker et al. |
| 2005/0051440 A1 | 3/2005 | Simpson et al. |
| 2005/0056552 A1 | 3/2005 | Simpson et al. |
| 2005/0065464 A1 | 3/2005 | Talbot et al. |
| 2005/0070774 A1 | 3/2005 | Addison et al. |
| 2005/0070819 A1 | 3/2005 | Poux et al. |
| 2005/0085872 A1 | 4/2005 | Yanagihara et al. |
| 2005/0090607 A1 | 4/2005 | Tapsak et al. |
| 2005/0090850 A1 | 4/2005 | Thoes et al. |
| 2005/0096511 A1 | 5/2005 | Fox et al. |
| 2005/0096512 A1 | 5/2005 | Fox et al. |
| 2005/0096516 A1 | 5/2005 | Soykan et al. |
| 2005/0096520 A1 | 5/2005 | Maekawa et al. |
| 2005/0096587 A1 | 5/2005 | Santini, Jr. et al. |
| 2005/0101912 A1 | 5/2005 | Faust et al. |
| 2005/0101932 A1 | 5/2005 | Cote et al. |
| 2005/0103624 A1 | 5/2005 | Bhullar et al. |
| 2005/0104457 A1 | 5/2005 | Jordan et al. |
| 2005/0106713 A1 | 5/2005 | Phan et al. |
| 2005/0112169 A1 | 5/2005 | Brauker et al. |
| 2005/0112544 A1 | 5/2005 | Xu et al. |
| 2005/0113648 A1 | 5/2005 | Yang et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0115832 A1 | 6/2005 | Simpson et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0131347 A1 | 6/2005 | Marano-Ford et al. |
| 2005/0134731 A1 | 6/2005 | Lee et al. |
| 2005/0137488 A1 | 6/2005 | Henry et al. |
| 2005/0137530 A1 | 6/2005 | Campbell et al. |
| 2005/0143635 A1 | 6/2005 | Kamath et al. |
| 2005/0149066 A1 | 7/2005 | Stafford |
| 2005/0151976 A1 | 7/2005 | Toma |
| 2005/0154271 A1 | 7/2005 | Rasdal et al. |
| 2005/0154410 A1 | 7/2005 | Conway et al. |
| 2005/0159678 A1 | 7/2005 | Taniike et al. |
| 2005/0161346 A1 | 7/2005 | Simpson et al. |
| 2005/0165404 A1 | 7/2005 | Miller |
| 2005/0171442 A1 | 8/2005 | Shirasaki et al. |
| 2005/0173245 A1 | 8/2005 | Feldman et al. |
| 2005/0176136 A1 | 8/2005 | Burd et al. |
| 2005/0177398 A1 | 8/2005 | Watanabe et al. |
| 2005/0181010 A1 | 8/2005 | Hunter et al. |
| 2005/0182306 A1 | 8/2005 | Sloan |
| 2005/0182358 A1 | 8/2005 | Heit et al. |
| 2005/0187442 A1 | 8/2005 | Cho et al. |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0197554 A1 | 9/2005 | Polcha |
| 2005/0197793 A1 | 9/2005 | Baker, Jr. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0214892 A1 | 9/2005 | Kovatchev et al. |
| 2005/0215871 A1 | 9/2005 | Feldman et al. |
| 2005/0221504 A1 | 10/2005 | Petruno et al. |
| 2005/0222518 A1 | 10/2005 | Dib |
| 2005/0222599 A1 | 10/2005 | Czernecki et al. |
| 2005/0235156 A1 | 10/2005 | Drucker et al. |
| 2005/0236277 A9 | 10/2005 | Imran et al. |
| 2005/0236361 A1 | 10/2005 | Ufer et al. |
| 2005/0239154 A1 | 10/2005 | Feldman et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245844 A1 | 11/2005 | Mace et al. |
| 2005/0245904 A1 | 11/2005 | Estes et al. |
| 2005/0247319 A1 | 11/2005 | Berger |
| 2005/0251033 A1 | 11/2005 | Scarantino et al. |
| 2005/0261563 A1 | 11/2005 | Zhou et al. |
| 2005/0267325 A1 | 12/2005 | Bouchier et al. |
| 2005/0267327 A1 | 12/2005 | Lizuka et al. |
| 2005/0269214 A1 | 12/2005 | Lee |
| 2005/0277164 A1 | 12/2005 | Dmcker et al. |
| 2005/0277912 A1 | 12/2005 | John |
| 2005/0281234 A1 | 12/2005 | Kawamura et al. |
| 2005/0283114 A1 | 12/2005 | Bresina et al. |
| 2005/0283208 A1 | 12/2005 | Von Arx et al. |
| 2005/0283209 A1 | 12/2005 | Katoozi et al. |
| 2005/0284758 A1 | 12/2005 | Funke et al. |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0004270 A1 | 1/2006 | Bedard et al. |
| 2006/0004272 A1 | 1/2006 | Shah et al. |
| 2006/0004303 A1 | 1/2006 | Weidenhaupt et al. |
| 2006/0006141 A1 | 1/2006 | Ufer et al. |
| 2006/0009727 A1 | 1/2006 | O'Mahony et al. |
| 2006/0010098 A1 | 1/2006 | Goodnow et al. |
| 2006/0012464 A1 | 1/2006 | Nitzan et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025662 A1 | 2/2006 | Buse et al. |
| 2006/0025663 A1 | 2/2006 | Talbot et al. |
| 2006/0029177 A1 | 2/2006 | Cranford et al. |
| 2006/0030789 A1 | 2/2006 | Allen |
| 2006/0031094 A1 | 2/2006 | Cohen et al. |
| 2006/0036139 A1 | 2/2006 | Brister et al. |
| 2006/0036140 A1 | 2/2006 | Brister et al. |

(56)                    References Cited

U.S. PATENT DOCUMENTS

| | | |
|---|---|---|
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0040402 A1 | 2/2006 | Brauker et al. |
| 2006/0040793 A1 | 2/2006 | Martens et al. |
| 2006/0041276 A1 | 2/2006 | Chan |
| 2006/0042080 A1 | 3/2006 | Say et al. |
| 2006/0047220 A1 | 3/2006 | Sakata et al. |
| 2006/0049359 A1 | 3/2006 | Busta et al. |
| 2006/0058588 A1 | 3/2006 | Zdeblick |
| 2006/0064035 A1 | 3/2006 | Wang et al. |
| 2006/0068208 A1 | 3/2006 | Tapsak et al. |
| 2006/0079740 A1 | 4/2006 | Silver et al. |
| 2006/0081469 A1 | 4/2006 | Lee |
| 2006/0086624 A1 | 4/2006 | Tapsak et al. |
| 2006/0091006 A1 | 5/2006 | Wang et al. |
| 2006/0094944 A1 | 5/2006 | Chuang |
| 2006/0095014 A1 | 5/2006 | Ethelfeld |
| 2006/0116607 A1 | 6/2006 | Nakamura et al. |
| 2006/0129173 A1 | 6/2006 | Wilkinson |
| 2006/0129733 A1 | 6/2006 | Solbelman |
| 2006/0135908 A1 | 6/2006 | Liniger et al. |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0155210 A1 | 7/2006 | Beckman et al. |
| 2006/0155317 A1 | 7/2006 | List et al. |
| 2006/0161194 A1 | 7/2006 | Freeman et al. |
| 2006/0161664 A1 | 7/2006 | Motoyama |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0181695 A1 | 8/2006 | Sage, Jr. |
| 2006/0183984 A1 | 8/2006 | Dobbles et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0189939 A1 | 8/2006 | Gonnelli et al. |
| 2006/0193375 A1 | 8/2006 | Lee et al. |
| 2006/0195029 A1 | 8/2006 | Shults et al. |
| 2006/0195133 A1 | 8/2006 | Freeman et al. |
| 2006/0200020 A1 | 9/2006 | Brister et al. |
| 2006/0200022 A1 | 9/2006 | Brauker et al. |
| 2006/0200181 A1 | 9/2006 | Fukuzawa et al. |
| 2006/0200970 A1 | 9/2006 | Brister et al. |
| 2006/0200981 A1 | 9/2006 | Bhullar et al. |
| 2006/0200982 A1 | 9/2006 | Bhullar et al. |
| 2006/0202805 A1 | 9/2006 | Schulman et al. |
| 2006/0202859 A1 | 9/2006 | Mastrototaro et al. |
| 2006/0211921 A1 | 9/2006 | Brauker et al. |
| 2006/0220839 A1 | 10/2006 | Fifolt et al. |
| 2006/0222566 A1 | 10/2006 | Brauker et al. |
| 2006/0222866 A1 | 10/2006 | Nakamura et al. |
| 2006/0224108 A1 | 10/2006 | Brauker et al. |
| 2006/0224109 A1 | 10/2006 | Steil et al. |
| 2006/0224141 A1 | 10/2006 | Rush et al. |
| 2006/0224171 A1 | 10/2006 | Sakata et al. |
| 2006/0226985 A1 | 10/2006 | Goodnow et al. |
| 2006/0229512 A1 | 10/2006 | Petisce et al. |
| 2006/0233839 A1 | 10/2006 | Jacquet |
| 2006/0247508 A1 | 11/2006 | Fennell |
| 2006/0247710 A1 | 11/2006 | Goetz et al. |
| 2006/0247895 A1 | 11/2006 | Liamos et al. |
| 2006/0248398 A1 | 11/2006 | Neel et al. |
| 2006/0253085 A1 | 11/2006 | Geismar et al. |
| 2006/0253086 A1 | 11/2006 | Moberg et al. |
| 2006/0258929 A1 | 11/2006 | Goode, Jr. et al. |
| 2006/0258939 A1 | 11/2006 | Pesach et al. |
| 2006/0258959 A1 | 11/2006 | Sode |
| 2006/0264785 A1 | 11/2006 | Dring et al. |
| 2006/0264888 A1 | 11/2006 | Moberg et al. |
| 2006/0270922 A1 | 11/2006 | Brauker et al. |
| 2006/0270923 A1 | 11/2006 | Brauker et al. |
| 2006/0271013 A1 | 11/2006 | Triplett et al. |
| 2006/0272652 A1 | 12/2006 | Stocker et al. |
| 2006/0273759 A1 | 12/2006 | Reggiardo |
| 2006/0276714 A1 | 12/2006 | Holt et al. |
| 2006/0276724 A1 | 12/2006 | Freeman et al. |
| 2006/0276771 A1 | 12/2006 | Galley et al. |
| 2006/0281985 A1 | 12/2006 | Ward et al. |
| 2006/0282042 A1 | 12/2006 | Walters et al. |
| 2006/0287591 A1 | 12/2006 | Ocvirk et al. |
| 2006/0287691 A1 | 12/2006 | Drew |
| 2006/0290496 A1 | 12/2006 | Peeters et al. |
| 2006/0293607 A1 | 12/2006 | Alt et al. |
| 2007/0007133 A1 | 1/2007 | Mang et al. |
| 2007/0010950 A1 | 1/2007 | Abensour et al. |
| 2007/0016129 A1 | 1/2007 | Liniger et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0027384 A1 | 2/2007 | Brister et al. |
| 2007/0027385 A1 | 2/2007 | Brister et al. |
| 2007/0027507 A1 | 2/2007 | Burdett et al. |
| 2007/0030154 A1 | 2/2007 | Aiki et al. |
| 2007/0032706 A1 | 2/2007 | Kamath et al. |
| 2007/0032717 A1 | 2/2007 | Brister et al. |
| 2007/0032718 A1 | 2/2007 | Shults et al. |
| 2007/0033074 A1 | 2/2007 | Nitzan et al. |
| 2007/0038044 A1 | 2/2007 | Dobbies et al. |
| 2007/0045902 A1 | 3/2007 | Brauker et al. |
| 2007/0049865 A1 | 3/2007 | Radmer et al. |
| 2007/0055799 A1 | 3/2007 | Koehler et al. |
| 2007/0056858 A1 | 3/2007 | Chen et al. |
| 2007/0059196 A1 | 3/2007 | Brister et al. |
| 2007/0060801 A1 | 3/2007 | Neinast |
| 2007/0060814 A1 | 3/2007 | Stafford |
| 2007/0060869 A1 | 3/2007 | Tolle et al. |
| 2007/0066873 A1 | 3/2007 | Kamath et al. |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0088377 A1 | 4/2007 | Levaughn et al. |
| 2007/0090511 A1 | 4/2007 | Borland et al. |
| 2007/0093704 A1 | 4/2007 | Brister et al. |
| 2007/0093754 A1 | 4/2007 | Mogensen et al. |
| 2007/0093786 A1 | 4/2007 | Goldsmith et al. |
| 2007/0095661 A1 | 5/2007 | Wang et al. |
| 2007/0100218 A1 | 5/2007 | Sweitzer et al. |
| 2007/0100222 A1 | 5/2007 | Mastrototaro et al. |
| 2007/0106133 A1 | 5/2007 | Satchwell et al. |
| 2007/0106135 A1 | 5/2007 | Sloan et al. |
| 2007/0108048 A1 | 5/2007 | Wang et al. |
| 2007/0110124 A1 | 5/2007 | Shiraki et al. |
| 2007/0111196 A1 | 5/2007 | Alarcon et al. |
| 2007/0123819 A1 | 5/2007 | Mernoe et al. |
| 2007/0124002 A1 | 5/2007 | Estes et al. |
| 2007/0129621 A1 | 6/2007 | Kellogg et al. |
| 2007/0135696 A1 | 6/2007 | Ward |
| 2007/0135774 A1 | 6/2007 | Turner et al. |
| 2007/0149873 A1 | 6/2007 | Say et al. |
| 2007/0149875 A1 | 6/2007 | Ouyang et al. |
| 2007/0153705 A1 | 7/2007 | Rosar et al. |
| 2007/0156033 A1 | 7/2007 | Causey, III et al. |
| 2007/0156094 A1 | 7/2007 | Safabash et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173741 A1 | 7/2007 | Deshmukh et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179406 A1 | 8/2007 | DeNuzzio et al. |
| 2007/0191701 A1 | 8/2007 | Feldman et al. |
| 2007/0191702 A1 | 8/2007 | Yodfat et al. |

(56)          References Cited

U.S. PATENT DOCUMENTS

| | | |
|---|---|---|
| 2007/0197889 A1 | 8/2007 | Brister et al. |
| 2007/0199818 A1 | 8/2007 | Petyt et al. |
| 2007/0202562 A1 | 8/2007 | Curry et al. |
| 2007/0203407 A1 | 8/2007 | Hoss et al. |
| 2007/0203539 A1 | 8/2007 | Stone et al. |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0213611 A1 | 9/2007 | Simpson et al. |
| 2007/0219480 A1 | 9/2007 | Kamen et al. |
| 2007/0219496 A1 | 9/2007 | Kamen et al. |
| 2007/0222609 A1 | 9/2007 | Duron et al. |
| 2007/0227911 A1 | 10/2007 | Wang et al. |
| 2007/0228071 A1 | 10/2007 | Kamen et al. |
| 2007/0231846 A1 | 10/2007 | Cosentino et al. |
| 2007/0232877 A1 | 10/2007 | He |
| 2007/0232878 A1 | 10/2007 | Kovatchev et al. |
| 2007/0232879 A1 | 10/2007 | Brister et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0244368 A1 | 10/2007 | Bayloff et al. |
| 2007/0244379 A1 | 10/2007 | Boock et al. |
| 2007/0244383 A1 | 10/2007 | Talbot et al. |
| 2007/0244398 A1 | 10/2007 | Lo et al. |
| 2007/0249922 A1 | 10/2007 | Peyser et al. |
| 2007/0253021 A1 | 11/2007 | Mehta et al. |
| 2007/0255116 A1 | 11/2007 | Mehta et al. |
| 2007/0255125 A1 | 11/2007 | Moberg et al. |
| 2007/0255302 A1 | 11/2007 | Koeppel et al. |
| 2007/0255321 A1 | 11/2007 | Gerber et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0270672 A1 | 11/2007 | Hayter |
| 2007/0282299 A1 | 12/2007 | Hellwig |
| 2007/0285238 A1 | 12/2007 | Batra |
| 2008/0004512 A1 | 1/2008 | Funderburk et al. |
| 2008/0004515 A1 | 1/2008 | Jennewine et al. |
| 2008/0004573 A1 | 1/2008 | Kaufmann et al. |
| 2008/0004601 A1 | 1/2008 | Jennewine et al. |
| 2008/0004904 A1 | 1/2008 | Tran |
| 2008/0009304 A1 | 1/2008 | Fry |
| 2008/0009692 A1 | 1/2008 | Stafford |
| 2008/0009805 A1 | 1/2008 | Ethelfeld |
| 2008/0017522 A1 | 1/2008 | Heller et al. |
| 2008/0018433 A1 | 1/2008 | Pitt-Pladdy |
| 2008/0021543 A1 | 1/2008 | Shrivastava |
| 2008/0021666 A1 | 1/2008 | Goode, Jr. et al. |
| 2008/0027296 A1 | 1/2008 | Hadvary et al. |
| 2008/0027474 A1 | 1/2008 | Curry et al. |
| 2008/0029391 A1 | 2/2008 | Mao et al. |
| 2008/0030369 A1 | 2/2008 | Mann et al. |
| 2008/0031941 A1 | 2/2008 | Pettersson |
| 2008/0033254 A1 | 2/2008 | Kamath et al. |
| 2008/0033268 A1 | 2/2008 | Stafford |
| 2008/0033273 A1 | 2/2008 | Zhou et al. |
| 2008/0033318 A1 | 2/2008 | Mace et al. |
| 2008/0039702 A1 | 2/2008 | Hayter et al. |
| 2008/0045824 A1 | 2/2008 | Tapsak et al. |
| 2008/0046038 A1 | 2/2008 | Hill et al. |
| 2008/0055070 A1 | 3/2008 | Bange et al. |
| 2008/0057484 A1 | 3/2008 | Miyata et al. |
| 2008/0058625 A1 | 3/2008 | McGarraugh et al. |
| 2008/0058626 A1 | 3/2008 | Miyata et al. |
| 2008/0058678 A1 | 3/2008 | Miyata et al. |
| 2008/0058773 A1 | 3/2008 | John |
| 2008/0058830 A1 | 3/2008 | Cole et al. |
| 2008/0059227 A1 | 3/2008 | Clapp |
| 2008/0060955 A1 | 3/2008 | Goodnow |
| 2008/0061961 A1 | 3/2008 | John |
| 2008/0062055 A1 | 3/2008 | Cunningham et al. |
| 2008/0064437 A1 | 3/2008 | Chambers et al. |
| 2008/0064937 A1 | 3/2008 | McGarraugh et al. |
| 2008/0064941 A1 | 3/2008 | Funderburk et al. |
| 2008/0064943 A1 | 3/2008 | Talbot et al. |
| 2008/0064944 A1 | 3/2008 | VanAntwerp et al. |
| 2008/0065646 A1 | 3/2008 | Zhang et al. |
| 2008/0066305 A1 | 3/2008 | Wang et al. |
| 2008/0067627 A1 | 3/2008 | Boeck et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0071580 A1 | 3/2008 | Marcus |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0092911 A1 | 4/2008 | Schulman et al. |
| 2008/0097246 A1 | 4/2008 | Stafford |
| 2008/0097289 A1 | 4/2008 | Steil et al. |
| 2008/0097908 A1 | 4/2008 | Dicks et al. |
| 2008/0099332 A1 | 5/2008 | Scott et al. |
| 2008/0102441 A1 | 5/2008 | Chen et al. |
| 2008/0108942 A1 | 5/2008 | Brister et al. |
| 2008/0112848 A1 | 5/2008 | Huffstodt et al. |
| 2008/0114228 A1 | 5/2008 | McCluskey et al. |
| 2008/0114280 A1 | 5/2008 | Stafford |
| 2008/0119705 A1 | 5/2008 | Patel et al. |
| 2008/0119707 A1 | 5/2008 | Stafford |
| 2008/0119710 A1 | 5/2008 | Reggiardo et al. |
| 2008/0125636 A1 | 5/2008 | Ward et al. |
| 2008/0127052 A1 | 5/2008 | Rostoker |
| 2008/0129486 A1 | 6/2008 | Jeckelmann et al. |
| 2008/0133059 A1 | 6/2008 | Trippel et al. |
| 2008/0133702 A1 | 6/2008 | Sharma et al. |
| 2008/0139910 A1 | 6/2008 | Mastrototaro et al. |
| 2008/0146904 A1 | 6/2008 | Hunn |
| 2008/0148873 A1 | 6/2008 | Wang |
| 2008/0154205 A1 | 6/2008 | Wojcik |
| 2008/0154286 A1 | 6/2008 | Abbott et al. |
| 2008/0154513 A1 | 6/2008 | Kovatchev et al. |
| 2008/0161664 A1 | 7/2008 | Mastrototaro et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0167578 A1 | 7/2008 | Bryer et al. |
| 2008/0172205 A1 | 7/2008 | Breton et al. |
| 2008/0177149 A1 | 7/2008 | Weinart et al. |
| 2008/0177165 A1 | 7/2008 | Blomquist et al. |
| 2008/0179187 A1 | 7/2008 | Ouyang |
| 2008/0182537 A1 | 7/2008 | Manku et al. |
| 2008/0183060 A1 | 7/2008 | Steil et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0188796 A1 | 8/2008 | Steil et al. |
| 2008/0189051 A1 | 8/2008 | Goode, Jr. et al. |
| 2008/0194926 A1 | 8/2008 | Goh et al. |
| 2008/0194934 A1 | 8/2008 | Ray et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0201325 A1 | 8/2008 | Doniger et al. |
| 2008/0208025 A1 | 8/2008 | Shults et al. |
| 2008/0208026 A1 | 8/2008 | Noujaim et al. |
| 2008/0208113 A1 | 8/2008 | Damiano et al. |
| 2008/0214481 A1 | 9/2008 | Challoner et al. |
| 2008/0214900 A1 | 9/2008 | Fennell et al. |
| 2008/0214910 A1 | 9/2008 | Buck |
| 2008/0214915 A1 | 9/2008 | Brister et al. |

(56)                    References Cited

U.S. PATENT DOCUMENTS

| | | |
|---|---|---|
| 2008/0214918 A1 | 9/2008 | Brister et al. |
| 2008/0215035 A1 | 9/2008 | Yodfat et al. |
| 2008/0228051 A1 | 9/2008 | Shults et al. |
| 2008/0228054 A1 | 9/2008 | Shults et al. |
| 2008/0234561 A1 | 9/2008 | Roesicke et al. |
| 2008/0234992 A1 | 9/2008 | Ray et al. |
| 2008/0235469 A1 | 9/2008 | Drew |
| 2008/0242961 A1 | 10/2008 | Brister et al. |
| 2008/0242962 A1 | 10/2008 | Roesicke et al. |
| 2008/0242963 A1 | 10/2008 | Essenpreis et al. |
| 2008/0243051 A1 | 10/2008 | DeStefano |
| 2008/0252459 A1 | 10/2008 | Butler et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255440 A1 | 10/2008 | Eilerson et al. |
| 2008/0255808 A1 | 10/2008 | Hayter |
| 2008/0256048 A1 | 10/2008 | Hayter |
| 2008/0262300 A1 | 10/2008 | Reynolds et al. |
| 2008/0262469 A1 | 10/2008 | Brister et al. |
| 2008/0267823 A1 | 10/2008 | Wang et al. |
| 2008/0269584 A1 | 10/2008 | Shekalim |
| 2008/0269673 A1 | 10/2008 | Butoi et al. |
| 2008/0269683 A1 | 10/2008 | Bikovsky |
| 2008/0269687 A1 | 10/2008 | Chong et al. |
| 2008/0269714 A1 | 10/2008 | Mastrototaro et al. |
| 2008/0275313 A1 | 11/2008 | Brister et al. |
| 2008/0275327 A1 | 11/2008 | Faarbaek et al. |
| 2008/0278333 A1 | 11/2008 | Fennell et al. |
| 2008/0281178 A1 | 11/2008 | Chuang et al. |
| 2008/0281179 A1 | 11/2008 | Fennell et al. |
| 2008/0283396 A1 | 11/2008 | Wang et al. |
| 2008/0287755 A1 | 11/2008 | Sass et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0294024 A1 | 11/2008 | Cosentino et al. |
| 2008/0294096 A1 | 11/2008 | Uber et al. |
| 2008/0296155 A1 | 12/2008 | Shults et al. |
| 2008/0300476 A1 | 12/2008 | Stafford |
| 2008/0300572 A1 | 12/2008 | Rankers et al. |
| 2008/0306368 A1 | 12/2008 | Goode, Jr. et al. |
| 2008/0306434 A1 | 12/2008 | Dobbies et al. |
| 2008/0306435 A1 | 12/2008 | Kamath et al. |
| 2008/0306444 A1 | 12/2008 | Brister et al. |
| 2008/0308523 A1 | 12/2008 | Krulevitch et al. |
| 2008/0312518 A1 | 12/2008 | Jina et al. |
| 2008/0312601 A1 | 12/2008 | Cane |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0312859 A1 | 12/2008 | Skyggebjerg et al. |
| 2008/0319085 A1 | 12/2008 | Wright et al. |
| 2008/0319295 A1 | 12/2008 | Bernstein et al. |
| 2008/0319296 A1 | 12/2008 | Bernstein et al. |
| 2008/0319414 A1 | 12/2008 | Yodfat et al. |
| 2008/0319416 A1 | 12/2008 | Yodfat et al. |
| 2009/0005659 A1 | 1/2009 | Kollias et al. |
| 2009/0005665 A1 | 1/2009 | Hayter et al. |
| 2009/0005666 A1 | 1/2009 | Shin et al. |
| 2009/0005729 A1 | 1/2009 | Hendrixson et al. |
| 2009/0006034 A1 | 1/2009 | Hayter et al. |
| 2009/0006061 A1 | 1/2009 | Thukral et al. |
| 2009/0006133 A1 | 1/2009 | Weinart et al. |
| 2009/0012376 A1 | 1/2009 | Agus |
| 2009/0012377 A1 | 1/2009 | Jennewine et al. |
| 2009/0012379 A1 | 1/2009 | Goode, Jr. et al. |
| 2009/0018424 A1 | 1/2009 | Kamath et al. |
| 2009/0018425 A1 | 1/2009 | Ouyang et al. |
| 2009/0020502 A1 | 1/2009 | Bhullar et al. |
| 2009/0028824 A1 | 1/2009 | Chiang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0036915 A1 | 2/2009 | Karbowniczek et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048499 A1 | 2/2009 | Glejbol |
| 2009/0048503 A1 | 2/2009 | Dalal et al. |
| 2009/0048563 A1 | 2/2009 | Ethelfeld et al. |
| 2009/0054737 A1 | 2/2009 | Magar et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0054753 A1 | 2/2009 | Robinson et al. |
| 2009/0054866 A1 | 2/2009 | Teisen-Simony et al. |
| 2009/0055149 A1 | 2/2009 | Hayter et al. |
| 2009/0058635 A1 | 3/2009 | LaLonde et al. |
| 2009/0062633 A1 | 3/2009 | Brauker et al. |
| 2009/0062635 A1 | 3/2009 | Brauker et al. |
| 2009/0062767 A1 | 3/2009 | Van Antwerp et al. |
| 2009/0063187 A1 | 3/2009 | Johnson et al. |
| 2009/0063402 A1 | 3/2009 | Hayter |
| 2009/0069658 A1 | 3/2009 | Say et al. |
| 2009/0069750 A1 | 3/2009 | Schraga |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0088614 A1 | 4/2009 | Taub |
| 2009/0088787 A1 | 4/2009 | Koike et al. |
| 2009/0093687 A1 | 4/2009 | Telfort et al. |
| 2009/0099436 A1 | 4/2009 | Brister et al. |
| 2009/0099521 A1 | 4/2009 | Gravesen et al. |
| 2009/0102678 A1 | 4/2009 | Mazza et al. |
| 2009/0105554 A1 | 4/2009 | Stahmann et al. |
| 2009/0105560 A1 | 4/2009 | Solomon |
| 2009/0105568 A1 | 4/2009 | Bugler |
| 2009/0105569 A1 | 4/2009 | Stafford |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0108992 A1 | 4/2009 | Shafer |
| 2009/0112123 A1 | 4/2009 | Freeman et al. |
| 2009/0112478 A1 | 4/2009 | Mueller, Jr. et al. |
| 2009/0118592 A1 | 5/2009 | Klitgaard |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0124979 A1 | 5/2009 | Raymond et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielson |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0149728 A1 | 6/2009 | Van Antwerp et al. |
| 2009/0150186 A1 | 6/2009 | Cohen et al. |
| 2009/0150454 A1 | 6/2009 | Gejdos et al. |
| 2009/0156919 A1 | 6/2009 | Brister et al. |
| 2009/0156924 A1 | 6/2009 | Shariati et al. |

(56)                    References Cited

U.S. PATENT DOCUMENTS

| | | |
|---|---|---|
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0171182 A1 | 7/2009 | Stafford |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0198186 A1 | 8/2009 | Mernoe et al. |
| 2009/0198215 A1 | 8/2009 | Chong et al. |
| 2009/0203981 A1 | 8/2009 | Brauker et al. |
| 2009/0204340 A1 | 8/2009 | Feldman et al. |
| 2009/0204341 A1 | 8/2009 | Brauker et al. |
| 2009/0210249 A1 | 8/2009 | Rasch-Menges et al. |
| 2009/0212766 A1 | 8/2009 | Olson et al. |
| 2009/0216100 A1 | 8/2009 | Ebner et al. |
| 2009/0216103 A1 | 8/2009 | Brister et al. |
| 2009/0216215 A1 | 8/2009 | Thalmann et al. |
| 2009/0234200 A1 | 9/2009 | Husheer |
| 2009/0240120 A1 | 9/2009 | Mensinger et al. |
| 2009/0240121 A1 | 9/2009 | Bickoff |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorenson |
| 2009/0253973 A1 | 10/2009 | Bashan et al. |
| 2009/0259118 A1 | 10/2009 | Feldman et al. |
| 2009/0259201 A1 | 10/2009 | Hwang et al. |
| 2009/0259202 A1 | 10/2009 | Leeflang et al. |
| 2009/0267765 A1 | 10/2009 | Greene et al. |
| 2009/0270765 A1 | 10/2009 | Ghesquire et al. |
| 2009/0277242 A1 | 11/2009 | Crane et al. |
| 2009/0281406 A1 | 11/2009 | McGarraugh et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0292184 A1 | 11/2009 | Funderburk et al. |
| 2009/0292185 A1 | 11/2009 | Funderburk et al. |
| 2009/0294277 A1 | 12/2009 | Thomas et al. |
| 2009/0298182 A1 | 12/2009 | Schulat et al. |
| 2009/0299152 A1 | 12/2009 | Taub et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299167 A1 | 12/2009 | Seymour |
| 2009/0299276 A1 | 12/2009 | Brauker et al. |
| 2009/0299301 A1 | 12/2009 | Gottleib et al. |
| 2010/0004597 A1 | 1/2010 | Gryn et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0014626 A1 | 1/2010 | Fennell et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022863 A1 | 1/2010 | Mogensen et al. |
| 2010/0022988 A1 | 1/2010 | Wochner et al. |
| 2010/0025238 A1 | 2/2010 | Gottlieb et al. |
| 2010/0030038 A1 | 2/2010 | Brauker et al. |
| 2010/0030053 A1 | 2/2010 | Goode, Jr. et al. |
| 2010/0030111 A1 | 2/2010 | Perriere |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0036281 A1 | 2/2010 | Doi |
| 2010/0041971 A1 | 2/2010 | Goode, Jr. et al. |
| 2010/0045465 A1 | 2/2010 | Brauker et al. |
| 2010/0049014 A1 | 2/2010 | Funderburk et al. |
| 2010/0049024 A1 | 2/2010 | Saint et al. |
| 2010/0049129 A1 | 2/2010 | Yokoi et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0069728 A1 | 3/2010 | Funderburk et al. |
| 2010/0076283 A1 | 3/2010 | Simpson et al. |
| 2010/0076379 A1 | 3/2010 | Matusch |
| 2010/0081905 A1 | 4/2010 | Bommakanti et al. |
| 2010/0081906 A1 | 4/2010 | Hayter et al. |
| 2010/0081908 A1 | 4/2010 | Dobbies et al. |
| 2010/0081910 A1 | 4/2010 | Brister et al. |
| 2010/0081953 A1 | 4/2010 | Syeda-Mahmood et al. |
| 2010/0087724 A1 | 4/2010 | Brauker et al. |
| 2010/0094251 A1 | 4/2010 | Estes et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0100113 A1 | 4/2010 | Lio et al. |
| 2010/0105999 A1 | 4/2010 | Dixon et al. |
| 2010/0106088 A1 | 4/2010 | Yodfat et al. |
| 2010/0113894 A1 | 5/2010 | Brenneman et al. |
| 2010/0119693 A1 | 5/2010 | Tapsak et al. |
| 2010/0119881 A1 | 5/2010 | Patel et al. |
| 2010/0121167 A1 | 5/2010 | McGarraugh et al. |
| 2010/0121169 A1 | 5/2010 | Petisce et al. |
| 2010/0137695 A1 | 6/2010 | Yodfat et al. |
| 2010/0141656 A1 | 6/2010 | Krieftewirth |
| 2010/0145229 A1 | 6/2010 | Perez et al. |
| 2010/0145377 A1 | 6/2010 | Lai et al. |
| 2010/0146300 A1 | 6/2010 | Brown |
| 2010/0151987 A1 | 6/2010 | Notsu |
| 2010/0152548 A1 | 6/2010 | Koski |
| 2010/0152554 A1 | 6/2010 | Steine et al. |
| 2010/0152674 A1 | 6/2010 | Kavazov et al. |
| 2010/0160757 A1 | 6/2010 | Weinart et al. |
| 2010/0160759 A1 | 6/2010 | Celentano et al. |
| 2010/0160760 A1 | 6/2010 | Shults et al. |
| 2010/0161269 A1 | 6/2010 | Kamath et al. |
| 2010/0168538 A1 | 7/2010 | Keenan et al. |
| 2010/0168540 A1 | 7/2010 | Kamath et al. |
| 2010/0168541 A1 | 7/2010 | Kamath et al. |
| 2010/0168542 A1 | 7/2010 | Kamath et al. |
| 2010/0168543 A1 | 7/2010 | Kamath et al. |
| 2010/0168544 A1 | 7/2010 | Kamath et al. |
| 2010/0168545 A1 | 7/2010 | Kamath et al. |
| 2010/0168546 A1 | 7/2010 | Kamath et al. |
| 2010/0168547 A1 | 7/2010 | Kamath et al. |
| 2010/0168660 A1 | 7/2010 | Galley et al. |
| 2010/0168677 A1 | 7/2010 | Gabriel et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode, Jr. et al. |
| 2010/0174266 A1 | 7/2010 | Estes |
| 2010/0179399 A1 | 7/2010 | Goode, Jr. et al. |
| 2010/0179400 A1 | 7/2010 | Brauker et al. |
| 2010/0179401 A1 | 7/2010 | Rasdal et al. |
| 2010/0179402 A1 | 7/2010 | Goode, Jr. et al. |
| 2010/0179404 A1 | 7/2010 | Kamath et al. |

(56)  References Cited

U.S. PATENT DOCUMENTS

| | | | |
|---|---|---|---|
| 2010/0179405 A1 | 7/2010 | Goode, Jr. et al. |
| 2010/0179407 A1 | 7/2010 | Goode, Jr. et al. |
| 2010/0179408 A1 | 7/2010 | Kamath et al. |
| 2010/0179409 A1 | 7/2010 | Kamath et al. |
| 2010/0185065 A1 | 7/2010 | Goode, Jr. et al. |
| 2010/0185073 A1 | 7/2010 | Goode, Jr. et al. |
| 2010/0185074 A1 | 7/2010 | Goode, Jr. et al. |
| 2010/0186069 A1 | 7/2010 | Brister et al. |
| 2010/0186070 A1 | 7/2010 | Brister et al. |
| 2010/0186071 A1 | 7/2010 | Simpson et al. |
| 2010/0186072 A1 | 7/2010 | Goode, Jr. et al. |
| 2010/0186075 A1 | 7/2010 | Brister et al. |
| 2010/0190435 A1 | 7/2010 | Cook et al. |
| 2010/0191082 A1 | 7/2010 | Brister et al. |
| 2010/0191087 A1 | 7/2010 | Talbot et al. |
| 2010/0191472 A1 | 7/2010 | Doniger et al. |
| 2010/0198033 A1 | 8/2010 | Krulevitch et al. |
| 2010/0198034 A1 | 8/2010 | Thomas et al. |
| 2010/0198035 A1 | 8/2010 | Kamath et al. |
| 2010/0198036 A1 | 8/2010 | Kamath et al. |
| 2010/0198042 A1 | 8/2010 | Sloan et al. |
| 2010/0198142 A1 | 8/2010 | Sloan et al. |
| 2010/0198314 A1 | 8/2010 | Wei |
| 2010/0204557 A1 | 8/2010 | Kiaie et al. |
| 2010/0204653 A1 | 8/2010 | Gryn et al. |
| 2010/0212583 A1 | 8/2010 | Brister et al. |
| 2010/0213057 A1 | 8/2010 | Feldman et al. |
| 2010/0213080 A1 | 8/2010 | Celentano et al. |
| 2010/0214104 A1 | 8/2010 | Goode, Jr. et al. |
| 2010/0217105 A1 | 8/2010 | Yodfat et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228111 A1 | 9/2010 | Friman et al. |
| 2010/0228497 A1 | 9/2010 | Kamath et al. |
| 2010/0230285 A1 | 9/2010 | Hoss et al. |
| 2010/0235439 A1 | 9/2010 | Goodnow et al. |
| 2010/0240975 A1 | 9/2010 | Goode, Jr. et al. |
| 2010/0240976 A1 | 9/2010 | Goode, Jr. et al. |
| 2010/0256471 A1 | 10/2010 | Say et al. |
| 2010/0259543 A1 | 10/2010 | Tarassenko et al. |
| 2010/0262183 A1 | 10/2010 | Abbott et al. |
| 2010/0262201 A1 | 10/2010 | He et al. |
| 2010/0267161 A1 | 10/2010 | Wu et al. |
| 2010/0274107 A1 | 10/2010 | Boock et al. |
| 2010/0274111 A1 | 10/2010 | Say et al. |
| 2010/0274515 A1 | 10/2010 | Hoss et al. |
| 2010/0275108 A1 | 10/2010 | Sloan et al. |
| 2010/0280341 A1 | 11/2010 | Boock et al. |
| 2010/0286496 A1 | 11/2010 | Simpson et al. |
| 2010/0298684 A1 | 11/2010 | Leach et al. |
| 2010/0312176 A1 | 12/2010 | Lauer et al. |
| 2010/0313105 A1 | 12/2010 | Nekoomaram et al. |
| 2010/0317952 A1 | 12/2010 | Budiman et al. |
| 2010/0324392 A1 | 12/2010 | Yee et al. |
| 2010/0324403 A1 | 12/2010 | Brister et al. |
| 2010/0325868 A1 | 12/2010 | Wang et al. |
| 2010/0326842 A1 | 12/2010 | Mazza et al. |
| 2010/0331642 A1 | 12/2010 | Bruce et al. |
| 2010/0331644 A1 | 12/2010 | Neale et al. |
| 2010/0331647 A1 | 12/2010 | Shah et al. |
| 2010/0331648 A1 | 12/2010 | Kamath et al. |
| 2010/0331651 A1 | 12/2010 | Groll |
| 2010/0331653 A1 | 12/2010 | Stafford |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0004276 A1 | 1/2011 | Blair et al. |
| 2011/0009727 A1 | 1/2011 | Mensinger et al. |
| 2011/0015509 A1 | 1/2011 | Peyser |
| 2011/0016691 A1 | 1/2011 | Alden et al. |
| 2011/0021889 A1 | 1/2011 | Hoss et al. |
| 2011/0022411 A1 | 1/2011 | Hjelm et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0031986 A1 | 2/2011 | Bhat et al. |
| 2011/0040163 A1 | 2/2011 | Telson et al. |
| 2011/0046456 A1 | 2/2011 | Hordum et al. |
| 2011/0046467 A1 | 2/2011 | Simpson et al. |
| 2011/0046977 A1 | 2/2011 | Goodnow et al. |
| 2011/0054275 A1 | 3/2011 | Stafford |
| 2011/0054282 A1 | 3/2011 | Nekoomaram et al. |
| 2011/0060196 A1 | 3/2011 | Stafford |
| 2011/0060530 A1 | 3/2011 | Fennell |
| 2011/0070633 A1 | 3/2011 | Matsumoto et al. |
| 2011/0073475 A1 | 3/2011 | Kastanos et al. |
| 2011/0077469 A1 | 3/2011 | Blocker et al. |
| 2011/0077490 A1 | 3/2011 | Simpson et al. |
| 2011/0077494 A1 | 3/2011 | Doniger et al. |
| 2011/0077659 A1 | 3/2011 | Mandecki et al. |
| 2011/0081726 A1 | 4/2011 | Berman et al. |
| 2011/0082484 A1 | 4/2011 | Saravia et al. |
| 2011/0087196 A1 | 4/2011 | Hunn et al. |
| 2011/0097090 A1 | 4/2011 | Cao |
| 2011/0106126 A1 | 5/2011 | Love et al. |
| 2011/0112696 A1 | 5/2011 | Yodfat et al. |
| 2011/0118579 A1 | 5/2011 | Goode, Jr. et al. |
| 2011/0118580 A1 | 5/2011 | Goode, Jr. et al. |
| 2011/0123971 A1 | 5/2011 | Berkowitz et al. |
| 2011/0124992 A1 | 5/2011 | Brauker et al. |
| 2011/0124997 A1 | 5/2011 | Goode, Jr. et al. |
| 2011/0125040 A1 | 5/2011 | Crawford et al. |
| 2011/0125410 A1 | 5/2011 | Goode, Jr. et al. |
| 2011/0130970 A1 | 6/2011 | Goode, Jr. et al. |
| 2011/0130971 A1 | 6/2011 | Goode, Jr. et al. |
| 2011/0130998 A1 | 6/2011 | Goode, Jr. et al. |
| 2011/0137257 A1 | 6/2011 | Gyrn et al. |
| 2011/0137571 A1 | 6/2011 | Power et al. |
| 2011/0144465 A1 | 6/2011 | Shults et al. |
| 2011/0148905 A1 | 6/2011 | Simmons et al. |
| 2011/0152637 A1 | 6/2011 | Kateraas et al. |
| 2011/0172510 A1 | 7/2011 | Chickering, III et al. |
| 2011/0178378 A1 | 7/2011 | Brister et al. |
| 2011/0178461 A1 | 7/2011 | Chong et al. |
| 2011/0184258 A1 | 7/2011 | Stafford |
| 2011/0184482 A1 | 7/2011 | Eberman et al. |
| 2011/0184752 A1 | 7/2011 | Ray et al. |
| 2011/0190603 A1 | 8/2011 | Stafford |
| 2011/0190614 A1 | 8/2011 | Brister et al. |
| 2011/0191044 A1 | 8/2011 | Stafford |
| 2011/0193704 A1 | 8/2011 | Harper et al. |
| 2011/0201910 A1 | 8/2011 | Rasdal et al. |
| 2011/0201911 A1 | 8/2011 | Johnson et al. |
| 2011/0208027 A1 | 8/2011 | Wagner et al. |
| 2011/0213225 A1 | 9/2011 | Bernstein et al. |
| 2011/0218414 A1 | 9/2011 | Kamath et al. |
| 2011/0218490 A1 | 9/2011 | Ocvirk et al. |
| 2011/0230741 A1 | 9/2011 | Liang et al. |
| 2011/0231107 A1 | 9/2011 | Brauker et al. |
| 2011/0231140 A1 | 9/2011 | Goode, Jr. et al. |
| 2011/0231141 A1 | 9/2011 | Goode, Jr. et al. |
| 2011/0231142 A1 | 9/2011 | Goode, Jr. et al. |
| 2011/0240256 A1 | 10/2011 | Huang et al. |
| 2011/0240263 A1 | 10/2011 | Yu et al. |
| 2011/0253533 A1 | 10/2011 | Shults et al. |
| 2011/0257495 A1 | 10/2011 | Hoss et al. |
| 2011/0257521 A1 | 10/2011 | Fraden |
| 2011/0257895 A1 | 10/2011 | Brauker et al. |
| 2011/0263958 A1 | 10/2011 | Brauker et al. |
| 2011/0263959 A1 | 10/2011 | Young et al. |
| 2011/0264378 A1 | 10/2011 | Breton et al. |
| 2011/0270062 A1 | 11/2011 | Goode, Jr. et al. |
| 2011/0270158 A1 | 11/2011 | Brauker et al. |
| 2011/0275919 A1 | 11/2011 | Petisce et al. |
| 2011/0282327 A1 | 11/2011 | Kellogg et al. |
| 2011/0287528 A1 | 11/2011 | Fern et al. |
| 2011/0288574 A1 | 11/2011 | Curry et al. |

(56)                    References Cited

U.S. PATENT DOCUMENTS

| | | |
|---|---|---|
| 2011/0289497 A1 | 11/2011 | Kiaie et al. |
| 2011/0290645 A1 | 12/2011 | Brister et al. |
| 2011/0313543 A1 | 12/2011 | Brauker et al. |
| 2011/0319729 A1 | 12/2011 | Donnay et al. |
| 2011/0319733 A1 | 12/2011 | Stafford |
| 2011/0319738 A1 | 12/2011 | Woodruff et al. |
| 2011/0319739 A1 | 12/2011 | Kamath et al. |
| 2011/0320130 A1 | 12/2011 | Valdes et al. |
| 2012/0010642 A1 | 1/2012 | Lee et al. |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0078071 A1 | 3/2012 | Bohm et al. |
| 2012/0088995 A1 | 4/2012 | Fennell et al. |
| 2012/0095406 A1 | 4/2012 | Gyrn et al. |
| 2012/0108934 A1 | 5/2012 | Valdes et al. |
| 2012/0108983 A1 | 5/2012 | Banet et al. |
| 2012/0116322 A1 | 5/2012 | Brink et al. |
| 2012/0123385 A1 | 5/2012 | Edwards et al. |
| 2012/0143135 A1 | 6/2012 | Cole et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0179113 A1 | 7/2012 | Yokota et al. |
| 2012/0184909 A1 | 7/2012 | Gyrn et al. |
| 2012/0190989 A1 | 7/2012 | Kaiser et al. |
| 2012/0197098 A1 | 8/2012 | Donnay et al. |
| 2012/0197222 A1 | 8/2012 | Donnay et al. |
| 2012/0245447 A1 | 9/2012 | Karan et al. |
| 2012/0265042 A1 | 10/2012 | Neinast et al. |
| 2012/0296327 A1 | 11/2012 | Hutchins et al. |
| 2012/0303043 A1 | 11/2012 | Donnay et al. |
| 2013/0035575 A1 | 2/2013 | Mayou et al. |
| 2013/0047981 A1 | 2/2013 | Bacon |
| 2013/0109940 A1 | 5/2013 | Yang et al. |
| 2013/0111248 A1 | 5/2013 | Ghesquiere et al. |
| 2013/0150691 A1 | 6/2013 | Pace et al. |
| 2013/0184547 A1 | 7/2013 | Taub et al. |
| 2013/0199312 A1 | 8/2013 | Wilmer et al. |
| 2013/0225959 A1 | 8/2013 | Bugler |
| 2013/0235166 A1 | 9/2013 | Jones et al. |
| 2013/0253289 A1 | 9/2013 | Hadvary et al. |
| 2013/0267811 A1 | 10/2013 | Pryor et al. |
| 2013/0317323 A1 | 11/2013 | Fujiwara et al. |
| 2014/0031655 A1* | 1/2014 | Stafford ............... A61B 5/6832 |
| | | 600/347 |
| 2014/0121480 A1 | 5/2014 | Budiman et al. |
| 2014/0148667 A1 | 5/2014 | Boock et al. |
| 2014/0171771 A1 | 6/2014 | Feldman et al. |
| 2014/0188053 A1 | 7/2014 | Lundquist |
| 2014/0228760 A1 | 8/2014 | Ethelfeld |
| 2014/0275907 A1 | 9/2014 | Feldman et al. |
| 2015/0005601 A1 | 1/2015 | Hoss et al. |
| 2015/0018643 A1 | 1/2015 | Cole et al. |
| 2015/0025338 A1 | 1/2015 | Lee et al. |
| 2015/0073238 A1 | 3/2015 | Matsumoto et al. |
| 2015/0105644 A1 | 4/2015 | Yang et al. |
| 2015/0141776 A1 | 5/2015 | Hadvary et al. |
| 2015/0164545 A1 | 6/2015 | Gyrn |
| 2015/0173661 A1 | 6/2015 | Myles |
| 2015/0241407 A1 | 8/2015 | Ou et al. |
| 2015/0326072 A1 | 11/2015 | Petras et al. |
| 2016/0058342 A1 | 3/2016 | Maiz-Aguinaga et al. |
| 2016/0058470 A1 | 3/2016 | Peterson et al. |
| 2016/0058474 A1 | 3/2016 | Peterson et al. |
| 2016/0128615 A1 | 5/2016 | Curry et al. |
| 2016/0157759 A1 | 6/2016 | Yang |
| 2016/0256106 A1 | 9/2016 | Krasnow et al. |
| 2016/0331283 A1 | 11/2016 | Rao et al. |
| 2016/0331284 A1 | 11/2016 | Pace |
| 2016/0338733 A1 | 11/2016 | Shah et al. |
| 2016/0338734 A1 | 11/2016 | Shah et al. |
| 2016/0354555 A1 | 12/2016 | Gibson et al. |
| 2017/0112531 A1 | 4/2017 | Schoonmaker et al. |
| 2017/0112533 A1 | 4/2017 | Schoonmaker et al. |
| 2017/0112534 A1 | 4/2017 | Schoonmaker et al. |
| 2017/0127985 A1 | 5/2017 | Thompson et al. |
| 2017/0128011 A1 | 5/2017 | Frey et al. |
| 2017/0188908 A1 | 7/2017 | Hoss et al. |
| 2017/0188910 A1 | 7/2017 | Halac et al. |
| 2017/0188912 A1 | 7/2017 | Halac et al. |
| 2017/0216536 A1 | 8/2017 | Scott |
| 2017/0265791 A1 | 9/2017 | Pace et al. |
| 2017/0290533 A1 | 10/2017 | Antonio et al. |
| 2017/0290534 A1 | 10/2017 | Antonio et al. |
| 2017/0290535 A1 | 10/2017 | Rao et al. |
| 2017/0290546 A1 | 10/2017 | Antonio et al. |
| 2017/0319137 A1 | 11/2017 | Tsubouchi et al. |
| 2017/0367630 A1 | 12/2017 | Arita et al. |
| 2017/0368268 A1 | 12/2017 | Chopra |
| 2018/0116572 A1 | 5/2018 | Simpson et al. |
| 2018/0125464 A1 | 5/2018 | Kolb et al. |
| 2018/0235520 A1 | 8/2018 | Rao et al. |
| 2018/0360493 A1 | 12/2018 | Baker et al. |
| 2018/0368771 A1 | 12/2018 | Gray et al. |
| 2019/0133501 A1 | 5/2019 | Rao et al. |
| 2019/0133638 A1 | 5/2019 | Il et al. |
| 2019/0298240 A1 | 10/2019 | Lee et al. |
| 2020/0077928 A1 | 3/2020 | Brister et al. |
| 2020/0100712 A1 | 4/2020 | Stafford |
| 2020/0113494 A1 | 4/2020 | Akiyama |
| 2020/0178899 A1 | 6/2020 | Chae et al. |
| 2020/0196919 A1 | 6/2020 | Rao et al. |
| 2020/0397356 A1 | 12/2020 | Yee et al. |
| 2021/0030969 A1 | 2/2021 | Huang et al. |
| 2021/0113124 A1 | 4/2021 | Yee et al. |
| 2021/0161437 A1 | 6/2021 | Thomas et al. |
| 2021/0177315 A1 | 6/2021 | Thomas et al. |
| 2021/0204841 A1 | 7/2021 | Thomas et al. |
| 2021/0204843 A1 | 7/2021 | Mazza et al. |
| 2021/0378592 A1 | 12/2021 | Rodriguez et al. |
| 2022/0007973 A1 | 1/2022 | Rao et al. |
| 2022/0079475 A1 | 3/2022 | Cole et al. |
| 2022/0125480 A1 | 4/2022 | Rao et al. |
| 2023/0108476 A1 | 4/2023 | Rao |
| 2024/0293615 A1 | 9/2024 | Lanigan |

FOREIGN PATENT DOCUMENTS

| | | |
|---|---|---|
| CA | 2468577 | 6/2003 |
| CA | 2495648 | 2/2004 |
| CA | 2143172 | 7/2005 |
| CA | 2498682 | 9/2005 |
| CA | 2555749 | 9/2005 |
| CA | 2632709 | 6/2007 |
| CA | 2396613 | 3/2008 |
| CA | 2678336 | 5/2008 |
| CA | 2615575 | 6/2008 |
| CA | 2626349 | 9/2008 |
| CA | 2701374 | 4/2009 |
| CA | 2413148 | 8/2010 |
| CA | 2728831 | 7/2011 |
| CA | 2766693 A1 | 9/2011 |
| CA | 2617965 | 10/2011 |
| CA | 2766685 A1 | 12/2011 |
| CA | 3050721 | 7/2018 |
| CN | 1202872 | 5/2005 |
| CN | 101163440 | 4/2008 |
| CN | 101268932 | 9/2008 |
| CN | 101296650 | 10/2008 |
| CN | 201370857 | 12/2009 |
| DE | 44 01 400 | 7/1995 |
| DE | 201 10 059 | 8/2002 |
| DE | 101 17 285 | 11/2002 |
| DE | 10 2008 053 216 | 5/2010 |
| EP | 0 010 375 | 4/1980 |
| EP | 0 026 995 | 4/1981 |
| EP | 0 048 090 | 3/1982 |
| EP | 0 078 636 | 5/1983 |
| EP | 0 096 288 | 12/1983 |
| EP | 0 098 592 | 1/1984 |
| EP | 0 125 139 | 11/1984 |
| EP | 0 127 958 | 12/1984 |
| EP | 0 136 362 | 4/1985 |

(56)                    References Cited

FOREIGN PATENT DOCUMENTS

| | | |
|----|----|----|
| EP | 0 170 375 | 2/1986 |
| EP | 0 177 743 | 4/1986 |
| EP | 0 080 304 | 5/1986 |
| EP | 0 184 909 | 6/1986 |
| EP | 0 206 218 | 12/1986 |
| EP | 0 230 472 | 8/1987 |
| EP | 0 241 309 | 10/1987 |
| EP | 0 245 073 | 11/1987 |
| EP | 0 255 291 | 2/1988 |
| EP | 0 278 647 | 8/1988 |
| EP | 0 319 277 A1 | 6/1989 |
| EP | 0320109 | 6/1989 |
| EP | 0 353 328 | 2/1990 |
| EP | 0 359 831 | 3/1990 |
| EP | 0 368 209 | 5/1990 |
| EP | 0390390 | 10/1990 |
| EP | 0396788 | 11/1990 |
| EP | 0 400 918 | 12/1990 |
| EP | 0 453 283 | 10/1991 |
| EP | 0 470 290 | 2/1992 |
| EP | 0 567 725 | 11/1993 |
| EP | 0 286 118 | 1/1995 |
| EP | 0 680 727 | 11/1995 |
| EP | 0 724 859 | 8/1996 |
| EP | 0 805 574 | 11/1997 |
| EP | 1 897 488 | 12/1999 |
| EP | 0 973 289 | 1/2000 |
| EP | 0 678 308 | 5/2000 |
| EP | 1 048 264 | 11/2000 |
| EP | 1 177 802 | 2/2002 |
| EP | 0 729 366 | 7/2002 |
| EP | 1 292 218 | 3/2003 |
| EP | 1 077 634 | 7/2003 |
| EP | 1 092 390 | 7/2004 |
| EP | 1 568 309 | 8/2005 |
| EP | 1 630 898 | 3/2006 |
| EP | 1 666 091 | 6/2006 |
| EP | 1 669 020 | 6/2006 |
| EP | 1 703 697 | 9/2006 |
| EP | 1 704 889 | 9/2006 |
| EP | 1 704 893 | 9/2006 |
| EP | 1 729 128 | 12/2006 |
| EP | 0 987 982 | 1/2007 |
| EP | 1 956 371 | 8/2008 |
| EP | 1 972 270 A1 | 9/2008 |
| EP | 2 031 534 | 3/2009 |
| EP | 2060284 | 5/2009 |
| EP | 1 897 487 | 11/2009 |
| EP | 1 897 492 | 11/2009 |
| EP | 2 113 864 | 11/2009 |
| EP | 1 681 992 | 4/2010 |
| EP | 2201969 | 6/2010 |
| EP | 1 448 489 | 8/2010 |
| EP | 1 971 396 | 8/2010 |
| EP | 1 725 163 | 12/2010 |
| EP | 2 260 757 | 12/2010 |
| EP | 1 413 245 | 6/2011 |
| EP | 2 327 362 | 6/2011 |
| EP | 2 327 984 | 6/2011 |
| EP | 2335587 | 6/2011 |
| EP | 2 153 382 | 2/2012 |
| EP | 2 284 773 | 2/2012 |
| EP | 1 789 116 B1 | 5/2013 |
| EP | 3 251 597 B1 | 11/2019 |
| EP | 3 632 314 | 4/2020 |
| EP | 3 632 315 A1 | 4/2020 |
| EP | 3 851 045 A1 | 7/2021 |
| EP | 3 730 044 B1 | 12/2021 |
| EP | 3 730 045 B1 | 3/2022 |
| EP | 3 766 408 B1 | 4/2022 |
| EP | 3 928 688 B1 | 6/2022 |
| EP | 4 111 949 B1 | 7/2023 |
| EP | 3 300 658 B1 | 1/2024 |
| EP | 4 344 633 | 4/2024 |
| EP | 4 203 819 | 7/2024 |
| GB | 1 394 171 | 5/1975 |
| GB | 1 599 241 | 9/1981 |
| GB | 2 073 891 | 10/1981 |
| GB | 2 067 764 | 1/1984 |
| GB | 2 154 003 | 8/1985 |
| GB | 2 204 408 | 11/1988 |
| GB | 2 254 436 | 10/1992 |
| GB | 2 409 951 | 7/2005 |
| JP | 54-041191 | 4/1979 |
| JP | 55-010581 | 1/1980 |
| JP | 55-010583 | 1/1980 |
| JP | 55-010584 | 1/1980 |
| JP | 55-012406 | 1/1980 |
| JP | 56-163447 | 1/1981 |
| JP | 57-070448 | 4/1982 |
| JP | 60-173457 | 9/1985 |
| JP | 60-173458 | 9/1985 |
| JP | 60-173459 | 9/1985 |
| JP | 62-085855 | 4/1987 |
| JP | 62-114747 | 5/1987 |
| JP | 63-058149 | 3/1988 |
| JP | 63-128252 | 5/1988 |
| JP | 63-139246 | 6/1988 |
| JP | 63-294799 | 12/1988 |
| JP | 63-317757 | 12/1988 |
| JP | 63-317758 | 12/1988 |
| JP | 01-114746 | 5/1989 |
| JP | 01-114747 | 5/1989 |
| JP | 01-124060 | 5/1989 |
| JP | 01-134244 | 5/1989 |
| JP | 01-156658 | 6/1989 |
| JP | 02-062958 | 3/1990 |
| JP | 02-120655 | 5/1990 |
| JP | 02-287145 | 11/1990 |
| JP | 02-310457 | 12/1990 |
| JP | 03-020752 | 1/1991 |
| JP | 03-026956 | 2/1991 |
| JP | 03-028752 | 2/1991 |
| JP | 03-500940 | 2/1991 |
| JP | 03-194458 | 8/1991 |
| JP | 03-202764 | 9/1991 |
| JP | 05-072171 | 3/1993 |
| JP | 05-196595 | 8/1993 |
| JP | 06-190050 | 7/1994 |
| JP | 07-055757 | 3/1995 |
| JP | 07-072585 | 3/1995 |
| JP | 07-182462 | 7/1995 |
| JP | 07-311196 | 11/1995 |
| JP | 08-285814 | 11/1996 |
| JP | 08-285815 | 11/1996 |
| JP | 09-021778 | 1/1997 |
| JP | 09-101280 | 4/1997 |
| JP | 09-285459 | 4/1997 |
| JP | 10-170471 | 6/1998 |
| JP | 10-305016 | 11/1998 |
| JP | 11-506629 | 6/1999 |
| JP | 11-225359 | 8/1999 |
| JP | 2003-144417 | 5/2003 |
| JP | 2004-033438 | 2/2004 |
| JP | 2004-214014 | 7/2004 |
| JP | 2004-520103 | 7/2004 |
| JP | 2004-520898 | 7/2004 |
| JP | 2004-358016 | 12/2004 |
| JP | 2006-021031 | 1/2006 |
| JP | 2006-280464 | 10/2006 |
| JP | 2006-527036 | 11/2006 |
| JP | 2007-510499 | 4/2007 |
| JP | 2007-152037 | 6/2007 |
| JP | 2008-506468 | 3/2008 |
| KR | 10-2017-0068694 | 6/2017 |
| SU | 1281988 | 1/1987 |
| WO | WO 89/05119 | 6/1989 |
| WO | WO 89/08713 | 9/1989 |
| WO | WO 90/05300 | 5/1990 |
| WO | WO 90/05910 | 5/1990 |
| WO | WO 91/01680 | 2/1991 |
| WO | WO 91/04704 | 4/1991 |
| WO | WO 91/15993 | 10/1991 |
| WO | WO-1992/013271 | 8/1992 |

(56)　　　　　References Cited

FOREIGN PATENT DOCUMENTS

| | | |
|---|---|---|
| WO | WO-1994/020602 | 9/1994 |
| WO | WO 95/28878 | 2/1995 |
| WO | WO 96/25089 | 8/1996 |
| WO | WO 96/35370 | 11/1996 |
| WO | WO 96/39977 | 12/1996 |
| WO | WO 97/02847 | 1/1997 |
| WO | WO 97/19344 | 5/1997 |
| WO | WO 97/21457 | 6/1997 |
| WO | WO 97/33513 | 9/1997 |
| WO | WO 97/42882 | 11/1997 |
| WO | WO 97/42883 | 11/1997 |
| WO | WO 97/42886 | 11/1997 |
| WO | WO 97/42888 | 11/1997 |
| WO | WO 97/43962 | 11/1997 |
| WO | WO 98/04902 | 2/1998 |
| WO | WO 98/35053 | 8/1998 |
| WO | WO 98/56293 | 12/1998 |
| WO | WO 99/27849 | 6/1999 |
| WO | WO 99/28736 | 6/1999 |
| WO | WO 99/33504 | 7/1999 |
| WO | WO 99/56613 | 11/1999 |
| WO | WO 00/40159 | 7/2000 |
| WO | WO 00/49940 | 8/2000 |
| WO | WO 00/60350 | 10/2000 |
| WO | WO-2000/059370 | 10/2000 |
| WO | WO 00/74753 | 12/2000 |
| WO | WO 00/78992 | 12/2000 |
| WO | WO 01/17875 A1 | 3/2001 |
| WO | WO 01/52727 A1 | 7/2001 |
| WO | WO-2001/052935 | 7/2001 |
| WO | WO 01/58348 | 8/2001 |
| WO | WO-2001/054753 | 8/2001 |
| WO | WO 02/15778 | 2/2002 |
| WO | WO 02/16905 | 2/2002 |
| WO | WO 02/50534 | 6/2002 |
| WO | WO 02/058537 | 8/2002 |
| WO | WO 02/100457 | 12/2002 |
| WO | WO 03/026728 | 4/2003 |
| WO | WO 03/028784 | 4/2003 |
| WO | WO 03/056319 | 7/2003 |
| WO | WO 03/057027 | 7/2003 |
| WO | WO 03/072164 | 9/2003 |
| WO | WO 03/073936 | 9/2003 |
| WO | WO 03/076893 | 9/2003 |
| WO | WO 03/085372 | 10/2003 |
| WO | WO-2003/082091 | 10/2003 |
| WO | WO 2004/006982 | 1/2004 |
| WO | WO 2004/015539 | 2/2004 |
| WO | WO 2004/028337 | 4/2004 |
| WO | WO 2004/030726 | 4/2004 |
| WO | WO 2004/034024 | 4/2004 |
| WO | WO 2004/047445 | 6/2004 |
| WO | WO 2004/049237 | 6/2004 |
| WO | WO 2004/054445 | 7/2004 |
| WO | WO 2004/060436 | 7/2004 |
| WO | WO 2004/061420 | 7/2004 |
| WO | WO 2004/090503 | 10/2004 |
| WO | WO 2004/098405 | 11/2004 |
| WO | WO 2004/098682 A2 | 11/2004 |
| WO | WO 2004/098683 | 11/2004 |
| WO | WO 2004/098684 | 11/2004 |
| WO | WO 2004/098685 | 11/2004 |
| WO | WO 2004/107971 | 12/2004 |
| WO | WO 2004/112602 | 12/2004 |
| WO | WO 2005/011779 A1 | 2/2005 |
| WO | WO 2005/018450 | 3/2005 |
| WO | WO 2005/037184 | 4/2005 |
| WO | WO 2005/041766 | 5/2005 |
| WO | WO 2005/044116 | 5/2005 |
| WO | WO 2005/045744 | 5/2005 |
| WO | WO 2005/046780 | 5/2005 |
| WO | WO 2005/051170 | 6/2005 |
| WO | WO 2005/057175 | 6/2005 |
| WO | WO 2005/065538 | 7/2005 |
| WO | WO 2005/084534 | 9/2005 |
| WO | WO 2005/089103 | 9/2005 |
| WO | WO 2005/092177 | 10/2005 |
| WO | WO 2005/121785 | 12/2005 |
| WO | WO 2005/123186 | 12/2005 |
| WO | WO 2006/001024 | 1/2006 |
| WO | WO 2006/015922 | 2/2006 |
| WO | WO 2006/017358 | 2/2006 |
| WO | WO 2006/020212 | 2/2006 |
| WO | WO 2006/024671 | 3/2006 |
| WO | WO 2006/026741 | 3/2006 |
| WO | WO 2006/036145 | 4/2006 |
| WO | WO 2006/040083 | 4/2006 |
| WO | WO 2006/042811 | 4/2006 |
| WO | WO 2006/061354 | 6/2006 |
| WO | WO 2006/064397 | 6/2006 |
| WO | WO 2006/072035 | 7/2006 |
| WO | WO 2006/079114 | 7/2006 |
| WO | WO 2006/086423 | 8/2006 |
| WO | WO 2006/094513 | 9/2006 |
| WO | WO 2006/108809 | 10/2006 |
| WO | WO 2006/110742 | 10/2006 |
| WO | WO 2006/114297 | 11/2006 |
| WO | WO 2006/118947 | 11/2006 |
| WO | WO 2006/121921 | 11/2006 |
| WO | WO 2006/124099 | 11/2006 |
| WO | WO 2007/002189 | 1/2007 |
| WO | WO 2007/007459 | 1/2007 |
| WO | WO 2007/016399 | 2/2007 |
| WO | WO 2007/019289 | 2/2007 |
| WO | WO 2007/027788 | 3/2007 |
| WO | WO 2007/041069 | 4/2007 |
| WO | WO 2007/041070 | 4/2007 |
| WO | WO 2007/041248 | 4/2007 |
| WO | WO 2007/053832 | 5/2007 |
| WO | WO 2007/056638 | 5/2007 |
| WO | WO 2007/065285 | 6/2007 |
| WO | WO 2007/089738 | 8/2007 |
| WO | WO 2007/092618 | 8/2007 |
| WO | WO 2007/097754 | 8/2007 |
| WO | WO 2007/101223 | 9/2007 |
| WO | WO 2007/120363 | 10/2007 |
| WO | WO 2007/126444 | 11/2007 |
| WO | WO 2007/140783 | 12/2007 |
| WO | WO 2007/143225 | 12/2007 |
| WO | WO 2007/149319 | 12/2007 |
| WO | WO 2008/001366 | 1/2008 |
| WO | WO 2008/014792 | 2/2008 |
| WO | WO 2008/021913 | 2/2008 |
| WO | WO 2008/031106 | 3/2008 |
| WO | WO 2008/031110 | 3/2008 |
| WO | WO 2008/039944 | 4/2008 |
| WO | WO 2008/042760 | 4/2008 |
| WO | WO 2008/048452 | 4/2008 |
| WO | WO 2008/051920 | 5/2008 |
| WO | WO 2008/051924 | 5/2008 |
| WO | WO 2008/052374 | 5/2008 |
| WO | WO 2008/061552 A1 | 5/2008 |
| WO | WO 2008/062099 | 5/2008 |
| WO | WO 2008/065646 | 6/2008 |
| WO | WO 2008/073813 | 6/2008 |
| WO | WO 2008/086541 | 7/2008 |
| WO | WO 2008/103620 | 8/2008 |
| WO | WO 2008/114223 | 9/2008 |
| WO | WO 2008/115409 | 9/2008 |
| WO | WO 2008/128210 | 10/2008 |
| WO | WO 2008/129532 | 10/2008 |
| WO | WO 2008/130896 | 10/2008 |
| WO | WO 2008/130897 | 10/2008 |
| WO | WO 2008/130898 | 10/2008 |
| WO | WO 2008/133702 | 11/2008 |
| WO | WO 2008/138006 | 11/2008 |
| WO | WO 2008/143943 | 11/2008 |
| WO | WO 2008/144445 | 11/2008 |
| WO | WO 2008/147921 | 12/2008 |
| WO | WO 2008/150917 | 12/2008 |
| WO | WO 2008/153693 | 12/2008 |
| WO | WO 2008/155377 | 12/2008 |
| WO | WO 2008/157821 | 12/2008 |
| WO | WO 2009/007287 | 1/2009 |

(56)                    References Cited

FOREIGN PATENT DOCUMENTS

| WO | WO 2009/010396 | | 1/2009 |
|---|---|---|---|
| WO | WO 2009/016635 | | 2/2009 |
| WO | WO 2009/016638 | | 2/2009 |
| WO | WO 2009/018058 | | 2/2009 |
| WO | WO 2006/032653 | | 3/2009 |
| WO | WO 2009/035773 | | 3/2009 |
| WO | WO 2009/039013 | | 3/2009 |
| WO | WO 2009/062674 | | 5/2009 |
| WO | WO 2009/062675 | | 5/2009 |
| WO | WO 2009/066288 | A1 | 5/2009 |
| WO | WO-2009/068661 | | 6/2009 |
| WO | WO 2009/086216 | | 7/2009 |
| WO | WO 2009/096992 | | 8/2009 |
| WO | WO 2009/097594 | | 8/2009 |
| WO | WO 2010/062898 | | 6/2010 |
| WO | WO 2010/077329 | | 7/2010 |
| WO | WO 2010/091005 | | 8/2010 |
| WO | WO 2010/099507 | A1 | 9/2010 |
| WO | WO 2010/112521 | | 10/2010 |
| WO | WO 2010/141922 | | 12/2010 |
| WO | WO 2011/000528 | | 1/2011 |
| WO | WO 2011/002815 | | 1/2011 |
| WO | WO 2011/015659 | | 2/2011 |
| WO | WO 2011/022418 | | 2/2011 |
| WO | WO 2011/025549 | | 3/2011 |
| WO | WO 2011/025549 | A1 | 3/2011 |
| WO | WO 2011/104616 | | 9/2011 |
| WO | WO 2011/119896 | | 9/2011 |
| WO | WO 2011/119898 | A1 | 9/2011 |
| WO | WO 2012/103429 | | 8/2012 |
| WO | WO 2013/090215 | | 6/2013 |
| WO | WO 2016/183493 | | 11/2016 |
| WO | WO 2017/027749 | | 2/2017 |
| WO | WO 2017/116915 | | 7/2017 |
| WO | WO 2017/134227 | | 8/2017 |
| WO | WO 2018/136898 | | 7/2018 |
| WO | WO 2018/166963 | | 9/2018 |
| WO | WO 2019/005627 | A1 | 1/2019 |
| WO | WO 2019/236850 | | 12/2019 |
| WO | WO 2019/236859 | | 12/2019 |
| WO | WO 2019/236876 | | 12/2019 |
| WO | WO 2022/046416 | | 3/2022 |
| WO | WO 2022/060677 | | 3/2022 |

OTHER PUBLICATIONS

Armour, J. C., et al., "Application of Chronic Intravascular Blood Glucose Sensor in Dogs", Diabetes, vol. 39, 1990, pp. 1519-1526.

Aussedat, B., et al., "A User-Friendly Method for Calibrating a Subcutaneous Glucose Sensor-Based Hypoglycaemic Alarm", Biosensors & Bioelectronics, vol. 12, No. 11, 1997, pp. 1061-1071.

Bennion, N., et al., "Alternate Site Glucose Testing: A Crossover Design", Diabetes Technology & Therapeutics, vol. 4, No. 1, 2002, pp. 25-33.

Bindra, D. S., et al., "Design and in Vitro Studies of a Needle-Type Glucose Sensor for Subcutaneous Monitoring", Analytical Chemistry, vol. 63, No. 17, 1991, pp. 1692-1696.

Bindra, D. S., et al., "Pulsed Amperometric Detection of Glucose in Biological Fluids at a Surface-Modified Gold Electrode", Analytical Chemistry, vol. 61, No. 22, 1989, pp. 2566-2570.

Bobbioni-Harsch, E., et al., "Lifespan of Subcutaneous Glucose Sensors and Their Performances During Dynamic Glycaemia Changes in Rats", Journal of Biomedical Engineering, vol. 15, 1993, pp. 457-463.

Cass, A. E., et al., "Ferrocene-Medicated Enzyme Electrode for Amperometric Determination of Glucose", Analytical Chemistry, vol. 56, No. 4, 1984, pp. 667-671.

Claremont, D. J., et al., "Biosensors for Continuous In Vivo Glucose Monitoring", Proceedings of the Annual International Conference of the IEEE Engineering in Medicine and Biology Society, vol. 10, 1988.

Clark Jr., L. C., et al., "Electrode Systems for Continuous Monitoring in Cardiovascular Surgery", Annals New York Academy of Sciences, 1962, pp. 29-43.

Clark Jr., L. C., et al., "Long-term Stability of Electroenzymatic Glucose Sensors Implanted in Mice", American Society of Artificial Internal Organs Transactions, vol. XXXIV, 1988, pp. 259-265.

Csöregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.

Csöregi, E., et al., "Design, Characterization, and One-Point in Vivo Calibration of a Subcutaneously Implanted Glucose Electrode", Analytical Chemistry, vol. 66, No. 19, 1994, pp. 3131-3138.

Feldman, B., et al., "A Continuous Glucose Sensor Based on Wired Enzyme™ Technology—Results from a 3-Day Trial in Patients with Type 1 Diabetes", Diabetes Technology & Therapeutics, vol. 5, No. 5, 2003, pp. 769-779.

Feldman, B., et al., "Correlation of Glucose Concentrations in Interstitial Fluid and Venous Blood During Periods of Rapid Glucose Change", Abbott Diabetes Care Inc. Freestyle Navigator Continuous Glucose Monitor Pamphlet, 2004.

Gregg, B. A., et al., "Cross-Linked Redox Gels Containing Glucose Oxidase for Amperometric Biosensor Applications", Analytical Chemistry, vol. 62, No. 3, 1990, pp. 258-263.

Gunasingham, et al., "Electrochemically Modulated Optrode for Glucose", Biosensors & Bioelectronics, vol. 7, 1992, pp. 353-359.

Harrison, D. J., et al., "Characterization of Perfluorosulfonic Acid Polymer Coated Enzyme Electrodes and a Miniaturized Integrated Potentiostat for Glucose Analysis in Whole Blood", Analytical Chemistry, vol. 60, No. 19, 1988, pp. 2002-2007.

Heller, A., "Electrical Connection Enzyme Redox Centers to Electrodes", Journal of Physical Chemistry, vol. 96, No. 9, 1990, pp. 3579-3587.

Heller, A., "Electrical Wiring of Redox Enzymes", Accounts of Chemical Research, 1990, vol. 23, No. 5, pp. 128-134.

Ikeda, T., et al., "Artificial Pancreas—Investigation of the Stability of Glucose Sensors Using a Telemetry System" (English translation of abstract), Jpn. J. Artif. Organs, vol. 19, No. 2, 1990, pp. 889-892.

Isermann, R., "Supervision, Fault-Detection and Fault-Diagnosis Methods—An Introduction", Control Engineering Practice, vol. 5, No. 5, 1997, pp. 639-652.

Isermann, R., et al., "Trends in the Application of Model-Based Fault Detection and Diagnosis of Technical Processes", Control Engineering Practice, vol. 5, No. 5, 1997, pp. 709-719.

Johnson, K. W., "Peripheral Circulation", John Wiley & Sons, 1978, pp. 1989.

Johnson, K. W., et al., "In vivo evaluation of an electroenzymatic glucose sensor implanted in subcutaneous tissue", Biosensors & Bioelectronics, vol. 7, 1992, pp. 709-714.

Jungheim, K., et al., "How Rapid Does Glucose Concentration Change in Daily Life of Patients with Type 1 Diabetes?", Diabetologia, 2002, pp. 250.

Jungheim, K., et al., "Risky Delay of Hypoglycemia Detection by Glucose Monitoring at the Arm", Diabetes Care, vol. 24, No. 7, 2001, pp. 1303-1304.

Koudelka, M., et al., "In-Vivo Behaviour of Hypodermically Implanted Microfabricated Glucose Sensors", Biosensors & Bioelectronics, vol. 6, 1991, pp. 31-36.

Lager, W., et al., "Implantable Electrocatalytic Glucose Sensor", Hormone Metabolic Research, vol. 26, 1994, pp. 526-530.

Maidan, R., et al., "Elimination of Electrooxidizable Interferant-Produced Currents in Amperometric Biosensors", Analytical Chemistry, vol. 64, No. 23, 1992, pp. 2889-2896.

Mastrototaro, J. J., et al., "An Electroenzymatic Glucose Sensor Fabricated on a Flexible Substrate", Sensors and Actuators B, vol. 5, 1991, pp. 139-144.

McKean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.

Minimed Technologies, "Tape Tips and Other Infusion Site Information", 1995, pp. 1-10.

(56)                    References Cited

OTHER PUBLICATIONS

Moatti-Sirat, D., et al., "Evaluating In Vitro and In Vivo the Interference of Ascorbate and Acetaminophen on Glucose Detection by a Needle-Type Glucose Sensor", Biosensors & Bioelectronics, vol. 7, 1992, pp. 345-352.

Moatti-Sirat, D., et al., "Reduction of acetaminophen interference in glucose sensors by a composite Nafion membrane: demonstration in rats and man", Diabetologia, vol. 37, 1994, pp. 610-616.

Moatti-Sirat, D., et al., "Towards continuous glucose monitoring: in vivo evaluation of a miniaturized glucose sensoriImplanted for several days in rat subcutaneous tissue", Diabetologia, vol. 35, 1992, pp. 224-230.

Ohara, T. J., et al., "Glucose Electrodes Based on Cross-Linked $[Os(bpy)_2Cl]^{30/2+}$ Complexed Poly(1-vinylimidazole) Films", Analytical Chemistry, vol. 65, No. 23, 1993, pp. 3512-3517.

Olievier, C. N., et al., "In vivo Measurement of Carbon Dioxide Tension with a Miniature Electrode", Pflügers Archiv: European Journal of Physiology, vol. 373, 1978, pp. 269-272.

Pickup, J., et al., "Implantable Glucose Sensors: Choosing the Appropriate Sensing Strategy", Biosensors, vol. 3, 1987/88, pp. 335-346.

Pickup, J., "Developing glucose sensors for in vivo use", Tibtech, vol. 11, 1993, pp. 285-291.

Pickup, J., et al., "Potentially-Implantable, Amperometric Glucose Sensors with Mediated Electron Transfer: Improving the Operating Stability", Biosensors, vol. 4, 1989, pp. 109-119.

Pickup, J., et al., "In vivo molecular sensing in diabetes mellitus: an implantable glucose sensor with direct electron transfer", Diabetologia, vol. 32, 1989, pp. 213-217.

Pishko, M. V., et al., "Amperometric Glucose Microelectrodes Prepared through Immobilization of Glucose Oxidase in Redox Hydrogels", Analytical Chemistry, vol. 63, No. 20, 1991, pp. 2268-2272.

Poitout, V., et al., "A glucose monitoring system for on line estimation in man of blood glucose concentration using a miniaturized glucose sensor implanted in the subcutaneous tissue and a wearable control unit", Diabetolgia, vol. 36, 1993, pp. 658-663.

Poitout, V., et al., "Calibration in dogs of a subcutaneous miniaturized glucose sensor using a glucose meter for blood glucose determination", Biosensors & Bioelectronics, vol. 7, 1992, pp. 587-592.

Poitout, V., et al., "In Vitro and In Vivo Evaluation in Dogs of a Miniaturized Glucose Sensor", ASAIO Transactions, vol. 37, No. 3, 1991, pp. M298-M300.

Quinn, C. P., et al., "Kinetics of glucose delivery to subcutaneous tissue in rats measured with 0.3-mm amperometric microsensors", The American Physiological Society, 1995, pp. E155-E161.

Ratner, B. D., "Reducing capsular thickness and enhancing angiogenesis around implant drug release systems", Journal of Controlled Release, vol. 78, 2002, pp. 211-218.

Reach, G., et al., "Can Continuous Glucose Monitoring Be Used for the Treatment of Diabetes?", Analytical Chemistry, vol. 64, No. 6, 1992, pp. 381-386.

Rebrin, K., et al., "Automated feedback control of subcutaneous glucose concentration in diabetic dogs", Diabetologia, vol. 32, 1989, pp. 573-576.

Roe, J. N., et al., "Bloodless Glucose Measurements", Critical Review in Therapeutic Drug Carrier Systems, vol. 15, No. 3, 1998, pp. 199-241.

Sakakida, M., et al., "Development of ferrocene-mediated needle-type glucose sensor as a measure of true subcutaneous tissue glucose concentrations," Artificial Organs Today, vol. 2, No. 2, 1992, pp. 145-158.

Sakakida, M., et al., "Ferrocene-mediated needle-type glucose sensor covered with newly designed biocompatible membrane", Sensors and Actuators B, vol. 13-14, 1993, pp. 319-322.

Salehi, C., et al., "A Telemetry-Instrumentation System for Long-Term Implantable Glucose and Oxygen Sensors", Analytical Letters, vol. 29, No. 13, 1996, pp. 2289-2308.

Scheller, F., et al., "Enzyme electrodes and their application", Philosophical Transactions of the Royal Society of London B, vol. 316, 1987, pp. 85-94.

Schmidt, F. J., et al., "Calibration of a wearable glucose sensor", The International Journal of Artificial Organs, vol. 15, No. 1, 1992, pp. 55-61.

Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.

Shaw, G. W., et al., "In vitro testing of a simply constructed, highly stable glucose sensor suitable for implantation in diabetic patients", Biosensors & Bioelectronics, vol. 6, 1991, pp. 401-406.

Shichiri, M., et al., "Glycaemic Control in Pancreatectomized Dogs with a Wearable Artificial Endocrine Pancreas", Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers", Hormone and Metabolic Research Supplement Series, vol. 20, 1988, pp. 17-20.

Shichiri, M., et al., "Membrane design for extending the long-life of an implantable glucose sensor", Diabetes Nutrition and Metabolism, vol. 2, 1989, pp. 309-313.

Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", Diabetes Care, vol. 9, No. 3, 1986, pp. 298-301.

Shichiri, M., et al., "Wearable Artificial Endocrine Pancreas With Needle-Type Glucose Sensor", The Lancet, 1982, pp. 1129-1131.

Shults, M. C., et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.

Sternberg, R., et al., "Study and Development of Multilayer Needle-type Enzyme-based Glucose Microsensors", Biosensors, vol. 4, 1988, pp. 27-40.

Thompson, M., et al., "In Vivo Probes: Problems and Perspectives", Clinical Biochemistry, vol. 19, 1986, pp. 255-261.

Turner, A.P.F., et al., "Diabetes Mellitus: Biosensors for Research and Management", Biosensors, vol. 1, 1985, pp. 85-115.

Updike, S. J., et al., "Principles of Long-term Fully Implanted Sensors with Emphasis on Radiotelemetric Monitoring of Blood Glucose from inside a Subcutaneous Foreign Body Capsule (FBC)", Biosensors in the Body: Continuous in vivo Monitoring, Chapter 4, 1997, pp. 117-137.

Updike, S. J., et al., "A Subcutaneous Glucose Sensor With Improved Longevity, Dynamic Range, and Stability of Calibration", Diabetes Care, 2000, vol. 23, pp. 208-214.

Velho, G., et al., "Strategies for calibrating a subcutaneous glucose sensor", Biomedica Biochimica Acta, vol. 48, 1989, pp. 957-964.

Velho, G., et al., "In Vitro and In Vivo Stability of Electrode Potentials in Needle-Type Glucose Sensors", Diabetes, vol. 38, No. 2, 1989, pp. 164-171.

Von Woedtke, T., et al., "In situ calibration of implanted electro-chemical glucose sensors", Biomedica Biochimica Acta, vol. 48, 1989, pp. 943-952.

Wilson, G. S., et al., "Progress toward the Development of an Implantable Sensor for Glucose", Clinical Chemistry, vol. 38, No. 9, 1992, pp. 1613-1617.

Ye, L., et al., "High Current Density 'Wired' Quinoprotein Glucose Dehydrogenase Electrode", Analytical Chemistry, vol. 65, No. 3, 1993, pp. 238-241.

PCT/US2012/068839 ISR and Written Opinion dated Feb. 22, 2013.

NL 2009963 Search Report and Written Opinion dated Aug. 12, 2013.

AU 2011269796 Examination Report dated Apr. 3, 2014.

EP 11760268.0 Extended Search Report dated Apr. 14, 2014.

EP 10739015.5 Extended Search Report dated May 10, 2013.

AU, 2007309066 Examiner's Recort, Jul. 12, 2012.

AU, 2007309066, Examiner's Report, Aug. 16, 2013.

(56) References Cited

OTHER PUBLICATIONS

AU, 2008265541, Examiner's Report, Oct. 15, 2012.
AU, 2008265541, Examiner's Report, Nov. 29, 2013.
AU, 2010286917, Examiner's Report, Sep. 8, 2014.
AU, 2011230596, Examiner's Repor,t Feb. 28, 2014.
AU, 2017254903, Examiner's Report, Dec. 11, 2018.
AU, 2018200899, Examiner's Report, Dec. 6, 2018.
CA, 2,765,712, Examiner's Report, Apr. 10, 2017.
CA, 2,765,712, Examiner's Report, Mar. 27, 2018.
CN, 200780045373.9, Notice of Allowance, May 18, 2011.
CN, 200780045373.9, Office Action, Apr. 14, 2010.
CN, 201080077344.1, Office Action, Jun. 5, 2014.
CN, 201080027344.1, Office Action, Feb. 6, 2015.
CN, 201080006480.2, Office Action, May 6, 2013.
CN, 201080006480.2, Office Action, Dec. 11, 2013.
CN, 201080006481.7, Office Action, Dec. 2, 2014.
CN, 201180002616.7, Office Action, Apr. 24, 2014.
CN, 201180002617.1, Office Action, Jul. 3, 2014.
CN, 20160144860.1, Office Action, Mar. 23, 2018.
CN, 20160144860.1, Office Action, Dec. 10, 2018.
CN, 20160144860.1, Office Action, May 23, 2019.
EP, 06804122.7 Decision to Refuse the Application, Feb. 25, 2013.
EP, 06804122.7 Examination Report, Nov. 30, 2011.
EP, 06804122.7 Examination Report, Jan. 25, 2011.
EP, 06815715.5 Extended Search Report, Oct. 30, 2009.
EP, 07842173.2 Examination Report, Mar. 21, 2013.
EP, 07842173.2 Extended Search Report, Dec. 29, 2010.
EP, 07842180.7 Examination Report, Oct. 23, 2012.
EP, 07842180.7 Examination Report, Dec. 14, 2011.
EP, 07842180.7 Examination Report, Feb. 23, 2011.
EP, 07842180.7 Extended Search Report, Sep. 28, 2009.
EP, 10739031.2 Extended Search Report, May 7, 2013.
EP, 10739031.2 Examination Report, Oct. 28, 2016.
EP, 10739031.2 Notice of Opposition, Dec. 20, 2018.
EP, 0739031.2 Reply to Notice of Opposition, May 21, 2019.
EP, 10739031.2 Reply to Notice of Opposition Reply, Aug. 8, 2019.
EP, 10739031.2 Summons to Attend Oral Proceedings, Sep. 17, 2019.
EP, 10739031.2 Written Submissions, Dec. 3, 2019.
EP, 10739031.2 Response to Written Submissions, Jan. 24, 2020.
EP 10739031.2 Summons to Attend Oral Proceedings, May 20, 2020.
EP, 10739031.2 Written Submissions, Nov. 20, 2020.
EP, 10739031.2 Response to Written Submissions, Jan. 7, 2021.
EP, 10739031.2 Decision and Grounds for Revoking Patent, Jun. 9, 2021.
EP, 10739031.2 Grounds of Appeal, Oct. 19, 2021.
EP, 10739031.2 Response to Grounds of Appeal, Mar. 1, 2022.
EP, 10739031.2 Response to Response to Grounds of Appeal, Jul. 29, 2022.
EP, 10812438.9 Extended Search Report, Dec. 10, 2013.
EP, 11760268.0 Communication from Board of Appeals, Mar. 31, 2022.
EP, 11760268.0 Response to Written Submissions, Jan. 14, 2020.
EP, 11760268.0 Statement of Grounds of Appeal, Apr. 23, 2019.
EP, 11760268.0 Grounds of Appeal, Apr. 18, 2019.
EP, 11760268.0 Notice of Appeal ADC, Feb. 25, 2019.
EP, 11760268.0 Notice of Appeal Dexcom, Feb. 22, 2019.
11760268.0 Interlocutory Decision, Dec. 13, 2018.
EP, 11760268.0 Response to Summons to Attend Oral Proceeding, Sep. 13, 2018.
EP, 11760268.0 Letter Regarding the Opposition Procedure, Sep. 12, 2018.
EP, 11760268.0 Summons to Attend Oral Proceedings, Mar. 22, 2018.
EP, 11760268.0 Comments on Reply to Notice of Opposition, Dec. 27, 2017.
EP, 11760268.0 Reply to Notice of Opposition, Sep. 4, 2017.
EP, 11760268.0 Notice of Opposition, Mar. 29, 2017.
EP, 13000105.0 Examination Report, Oct. 18, 2016.

EP, 13000105.0 Minutes of the Oral Proceedings, Oct. 18, 2016.
EP, 13000105.0 Notice of Opposition, Jan. 4, 2019.
EP, 15184320.8 Examination Report, Apr. 18, 2017.
EP, 16176370.1 Extended Search Report, Dec. 7, 2016.
EP, 16793637.6 Extended Search Report, Oct. 9, 2018.
EP, 17182379.2 Extended Search Report, Feb. 21, 2018.
EP, 17201183.5 Extended Search Report, May 7, 2018.
EP, 17201183.5 Examination Report, May 7, 2019.
EP, 18192278.2 Extended Search Report, Mar. 13, 2018
EP, 18208224.8 Extended Search Report, Oct. 11, 2019.
EP, 18741791.0 Extended Search Report, Sep. 23, 2020.
EP, 19151577.4 Extended Search Report, Aug. 16, 2019.
EP, 19151577.4 Examination Report, May 27, 2022.
EP, 19184881.1 Extended Search Report, Nov. 21, 2019.
EP, 20177703.4 Extended Search Report, Sep. 25, 2020.
EP, 20177712.5 Extended Search Report, Sep. 30, 2020.
EP, 20195922.8 Extended Search Report, Dec. 16, 2020.
EP, 21152231.3 Extended Search Report, May 11, 2021.
EP, 21192910.4 Extended Search Report, Mar. 31, 2022.
EP, 21211041.5 Extended Search Report, Mar. 3, 2022.
IL, 198329 Office Action, Mar. 5, 2012.
JP, 2009-534798 Office Action, Sep. 25, 2012.
JP, 2012-526736 Office Action, Apr. 15, 2014.
JP, 2012-526736 Office Action, Dec. 16, 2014.
JP, 2013-501503 Office Action, Mar. 3, 2015.
EP, 2015-159805 Office Action, Aug. 9, 2016.
JP, 2016-44196 Office Action, Apr. 11, 2017.
MX, MX/a/2009/004398 Office Action, Sep. 24, 2012.
US, Institution Decision, IPR No. 2022-00605, Jul. 27, 2022.
US, Patent Owner's Preliminary Sur-Reply, IPR No. 2022-00605, Jun. 28, 2022.
US, Petitioner's Preliminary Reply to Patent Owner's Preliminary Response, IPR No. 2022-00605, Jun. 21, 2022.
US, Patent Owner's Preliminary Response, IPR No. 2022-00605, May 24, 2022.
US, Petition For Inter Partes Review Of U.S. Pat. No. 10,945,649, IPR No. 2022-00605, Feb. 15, 2022.
US, Institution Decision, IPR No. 2022-00637, Jul. 27, 2022.
US, Patent Owner's Preliminary Sur-Reply, IPR No. 2022-00637, Jun. 28, 2022.
US, Petitioner's Preliminary Reply to Patent Owner's Preliminary Response, IPR No. 2022-00637, Jun. 21, 2022.
US, Patent Owner's Preliminary Response, IPR No. 2022-00637, Jun. 9, 2022.
US, Petition For Inter Partes Review Of U.S. Pat. No. 11,013,440, IPR No. 2022-00637, Feb. 8, 2022.
US, Reexamination U.S. Appl. No. 95/002,162 Request to Review Order Denying Request for Reexamination, Dec. 13, 2012.
US, Reexamination U.S. Appl. No. 95/002,162 Order Denying Request for Reexamination, Nov. 13, 2012.
US, Request for Reexamination U.S. Appl. No. 95/002,162 of U.S. Pat. No. 8,175,673, Sep. 9, 2012.
US, Reexamination U.S. Appl. No. 95/002,113 Request to Review Order Denying Request for Reexamination, Dec. 13, 2012.
US, Reexamination U.S. Appl. No. 95/002,113 Order Denying Request for Reexamination, Nov. 13, 2012.
US, Request for Reexamination U.S. Appl. No. 95/002,113 of U.S. Pat. No. 6,990,366, Aug. 30, 2012.
US, Reexamination U.S. Appl. No. 90/011,730 Notice of Intent to Issue Ex Parte Reexamination Certificate, Apr. 5, 2012.
US, Reexamination U.S. Appl. No. 90/011,730 Office Action, Jan. 11, 2012.
US, Reexamination U.S. Appl. No. 90/011,730 Order Granting Request for Reexamination, Aug. 24, 2011.
US, Request for Reexamination U.S. Appl. No. 90/011,730 of U.S. Pat. No. 6,990,366, Jun. 3, 2011.
US, Reexamination U.S. Appl. No. 90/010,791 Ex Parte Reexamination Certificate, May 17, 2011.
US, Reexamination U.S. Appl. No. 90/010,791 Office Action, Dec. 17, 2010.
US, Reexamination U.S. Appl. No. 90/010,791 Office Action, May 28, 2010.

(56)                    References Cited

OTHER PUBLICATIONS

US, Reexamination U.S. Appl. No. 90/010,791 Order Granting Request for Reexamination, Feb. 22, 2010.
US, Request for Reexamination U.S. Appl. No. 90/010,791 of U.S. Pat. No. 6,990,366, Dec. 22, 2009.
US, Reexamination U.S. Appl. No. 90/009,328 Notice of Intent to Issue Ex Parte Reexamination Certificate, Nov. 20, 2009.
US, Reexamination U.S. Appl. No. 90/009,328 Office Action, Sep. 30, 2009.
US, Reexamination U.S. Appl. No. 90/009,328 Office Action, Aug. 4, 2009.
US, Reexamination U.S. Appl. No. 90/009,328 Order Granting Request for Reexamination, Dec. 9, 2008.
US, Request for Reexamination U.S. Appl. No. 90/009,328 of U.S. Pat. No. 6,990,366, Nov. 10, 2008.
US, Reexamination U.S. Appl. No. 90/009,104 Notice of Intent to Issue Ex Parte Reexamination Certificate, Nov. 20, 2009.
US, Reexamination U.S. Appl. No. 90/009,104 Office Action, Sep. 30, 2009.
US, Reexamination U.S. Appl. No. 90/009,104 Office Action, Aug. 4, 2009.
US, Reexamination U.S. Appl. No. 90/009,104 Office Action, Oct. 16, 2008.
US, Reexamination U.S. Appl. No. 90/009,104 Order Granting Request for Reexamination, Jun. 5, 2008.
US, Request for Reexamination U.S. Appl. No. 90/009,104 of U.S. Pat. No. 6,990,366, Apr. 8, 2008.
US, Reexamination U.S. Appl. No. 90/008,457 Notice of Intent to Issue Ex Parte Reexamination Certificate, Mar. 13, 2008.
US, Reexamination U.S. Appl. No. 90/008,457 Order Granting Request for Reexamination, Feb. 23, 2007.
US, Request for Reexamination U.S. Appl. No. 90/008,457 of U.S. Pat. No. 6,990,366, Jan. 23, 2007.
US, Request for Reexamination U.S. Appl. No. 90/008,172 of U.S. Pat. No. 6,990,366, Aug. 16, 2006.
US, Reexamination U.S. Appl. No. 90/007,910 Patent Board Decision, May 17, 2013.
US, Reexamination U.S. Appl. No. 90/007,910 Decision on Appeal, Jan. 18, 2011.
US, Reexamination U.S. Appl. No. 90/007,910 Advisory Action, Jul. 30, 2009.
US, Reexamination U.S. Appl. No. 90/007,910 Advisory Action, Feb. 6, 2009.
US, Reexamination U.S. Appl. No. 90/007,910 Examiner's Answer to Appeal Brief, Nov. 19, 2009.
US, Reexamination U.S. Appl. No. 90/007,910 Office Action, Oct. 2, 2008.
US, Reexamination U.S. Appl. No. 90/007,910 Office Action, Feb. 13, 2008.
US, Reexamination U.S. Appl. No. 90/007,910 Order Granting Request for Reexamination, Mar. 27, 2006.
US, Request for Reexamination U.S. Appl. No. 90/007,910 of U.S. Pat. No. 6,175,752, Feb. 1, 2006.
US, Reexamination U.S. Appl. No. 90/009,270 Order Denying Request for Reexamination, Dec. 1, 2008.
US, Request for Reexamination U.S. Appl. No. 90/009,270 of U.S. Pat. No. 6,175,752, Sep. 8, 2008.
US, Reexamination U.S. Appl. No. 90/009,497 Notice of Intent to Issue Reexamination Certificate, Aug. 23, 2010.
US, Reexamination U.S. Appl. No. 90/009,497 Order Granting Request, Jul. 30, 2009.
US, Request for Reexamination U.S. Appl. No. 90/009,497 of U.S. Pat. No. 6,175,752, Jun. 17, 2009.
WO, PCT/US2006/037312 ISR and Written Opinion, Apr. 17, 2007.
WO, PCT/US2006/037928 ISR and Written Opinion, Jul. 11, 2008.
WO, PCT/US2007/078065 ISR and Written Opinion, Apr. 11, 2008.
WO, PCT/US2007/078073 ISR and Written Opinion, Apr. 11, 2008.
WO, PCT/US2007/082114 ISR and Written Opinion, May 9, 2008.
WO, PCT/US2010/002401 ISR and Written Opinion, Nov. 12, 2010.

WO, PCT/US2010/022860 ISR and Written Opinion, Mar. 23, 2010.
WO, PCT/US2010/022928 ISR and Written Opinion, Mar. 21, 2010.
WO, PCT/US2010/047381 ISR and Written Opinion, Oct. 15, 2010.
WO, PCT/US2010/050772 ISR and Written Opinion, Dec. 3, 2010.
WO, PCT/US2010/050888 ISR and Written Opinion, Nov. 29, 2010.
WO, PCT/US2010/051861 ISR and Written Opinion, Nov. 30, 2010.
WO PCT/US2011/029881 ISR and Written Opinion, May 20, 2010.
WO, PCT/US2011/029883 ISR and Written Opinion, Jun. 2, 2010.
WO, PCT/US2011/029884 ISR and Written Opinion, Jun. 1, 2011.
WO, PCT/US2013/052397 ISR and Written Opinion, Dec. 2, 2013.
WO, PCT/US2016/032485 ISR and Written Opinion, Sep. 12, 2016.
WO, PCT/US2018/014745 ISR and Written Opinion, Jun. 4, 2018.
WO, PCT/US2019/035843 ISR and Written Opinion, Sep. 18, 2019.
WO, PCT/US2021/040541 ISR and Written Opinion, Dec. 20, 2021.
WO, PCT/US2021/045576 ISR and Written Opinion, Jan. 27, 2022.
WO, PCT/US2021/048086 ISR and Written Opinion, Feb. 28, 2022.
WO, PCT/US2021/050672 ISR and Written Opinion, Jan. 5, 2022.
Abruna, H. D., et al., "Rectifying Interfaces Using Two-Layer Films of Electrochemically Polymerized Vinylpyridine and Vinylbipyridine Complexes of Ruthenium and Iron on Electrodes", Journal of the American Chemical Society, 1981, vol. 103, No. 1, pp. 1-5.
ACCU-CHEK Compact Plus Owner's Booklet, 2008, pp. 1-100.
ACCU-CHEK Softclix Plus Lancet Device retrieved from https://web.archive.org/web/20061018055737/http://www.accu-check.com/us/rewrite/content/en_US/2.1.7.1:10/article/ACCM_general_article_3303.htm, 2006, pp. 1-2.
Ahson, S., et al., "RFID Handbook: Applications, Technology, Security, and Privacy", 2008, Chapter 4, Far-Field Tag Antenna Design Methodology, and Chapter 13, RFID Tags for Metallic Object Identification, pp. 71 and 253-254.
Albery, W.J., et al., "Amperometric Enzyme Electrodes Part II: Conducting Salts as Electrode Materials for the Oxidation of Glucose Oxidase", Journal of ElectroAnalytical Chemistry, 1985, vol. 194, pp. 223-235.
Albery, W.J., et al., "Amperometric Enzyme Electrodes", Philosophical Transactions of the Royal Society of London, 1987, vol. 316, pp. 107-119.
Ambade, V. N., et al., "Methods for Estimation of Blood Glucose: A Comparative Evaluation", Medical Journal Armed Forces India, 1998, vol. 54, No. 2, pp. 131-133.
Anderson, L. B., et al., "Thin-Layer Electrochemistry: Steady-State Methods of Studying Rate Processes", Journal of ElectroAnalytical Chemistry, 1965, vol. 10, pp. 295-305.
Application Note AN048, Antenna Part No. FR05-S1-N-0-102, Compact Reach Xtend™Bluetooth®, 802.11b/g WLAN Chip Antenna, 2008, pp. 1-13.
Application Note AVR2023 - AT86RF231 Pcb reference design for antenna diversity, Atmel Corporation, 2008, pp. 1-15.
Application Note nRF9E5 RF and antenna layout, Nordic Semiconductor, 2006, pp. 1-13.
ASTM International, Designation D2240-05, 2010, pp. 1-13.
Bartlett, P. N., et al., "Covalent Binding of Electron Relays to Glucose Oxidase", Journal of the Chemical Society, Chemical Communications, 1987, pp. 1603-1604.
Bartlett, P. N., et al., "Modification of Glucose Oxidase by Tetrathiafulvalene", Journal of the Chemical Society, Chemical Communications, 1990, pp. 1135-1136.
Benkiĉ, K., et al., "Using RSSI value for distance estimation in Wireless sensor networks based on ZigBee", 15th International Conference on Systems, Signals and Image Processing, Bratislava, Slovakia, 2008, pp. 1-4.
Biosensors: Fundamentals and Applications, Turner et al., Eds., 1987, pp. 1-786.
Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, 2002, vol. 4624, pp. 1-10.

(56)　　　　　　References Cited

OTHER PUBLICATIONS

"Bluetooth Antenna Design", National Semiconductor Application Note, 2005, pp. 1-16.

Bluetooth Core Specification 4.0, Jun. 30, 2010, Master Table of Contents & Compliance Requirements, pp. 1-89.

Bonnett, A. H., et al., "Squirrel-Cage Rotor Options for AC Induction Motors", IEEE Transactions on Industry Applications, 2001, vol. 37, No. 4, pp. 1197-1209.

Brandt, J., et al., "Covalent Attachment of Proteins to Polysaccharide Carriers by Means of Benzoquinone", Biochimica et Biophysica Acta, 1975, vol. 386, pp. 196-202.

Brooks, S. L., et al., "Development of an On-Line Glucose Sensor for Fermentation Monitoring", Biosensors, 1987/88, vol. 3, pp. 45-56.

Brownlee, M., et al., "A Glucose-Controlled Insulin-Delivery System: Semisynthetic Insulin Bound to Lectin", Science, 1979, vol. 206, pp. 1190-1191.

Bühling, K. J., et al., "Optimal timing for postprandial glucose measurement in pregnant women with diabetes and a non-diabetic pregnant population evaluated by the Continuous Glucose Monitoring System (CGMS®)", Journal of Perinatal Medicine, 2005, vol. 33, No. 2, pp. 125-131.

Cass, A.E.G et al., "Ferricinium Ion as an Electron Acceptor for Oxido-Reductases", Journal of ElectroAnalytical Chemistry, 1985, vol. 190, pp. 117-127.

Castner, J. F., et al., "Mass Transport and Reaction Kinetic Parameters Determined Electrochemically for Immobilized Glucose Oxidase", Biochemistry, 1984, vol. 23, No. 10, pp. 2203-2210.

Cheyne, E.H., et al., "Performance of a Continuous Glucose Monitoring System During Controlled Hypoglycaemia in Healthy Volunteers", Diabetes Technology & Therapeutics, 2002, vol. 4, No. 5, pp. 607-613.

Clark Jr., L. C., et al., "Differential Anodic Enzyme Polarography for the Measurement of Glucose", Oxygen Transport to Tissue: Instrumentation, Methods, and Physiology, 1973, pp. 127-133.

Clarke, W. L., et al., "Evaluating Clinical Accuracy of Systems for Self-Monitoring of Blood Glucose", Diabetes Care, 1987, vol. 10, No. 5, pp. 622-628.

Clarke, W., et al., "Statistical Tools to Analyze Continuous Glucose Monitor Data", Diabetes Technology & Therapeutics, 2009, vol. 11, Suppl. 1, pp. S-45-S-54.

Compact Plus Blood Glucose Meter retrieved from https://web.archive.org/web/20090316065810/http://www.accu-check.com/us/rewrite/content/en_US/2.1.9:0/article/ACCM_general_article_5136.htm, 2009, pp. 1-3.

Complaint *Abbott Diabetes Care Inc.* v. *Dexcom, Inc.* U.S. District Court Delaware C.A. No. 05-590 filed Aug. 11, 2005.

Complaint, Amended, *Abbott Diabetes Care Inc.* v. *Dexcom, Inc.* U.S. District Court Delaware C.A. No. 05-590 filed Jun. 27, 2006.

Complaint *Abbott Diabetes Care Inc.* v. *Dexcom, Inc.* U.S. District Court Delaware C.A. No. 06-514 filed Aug. 17, 2006.

Cox, M., "An Overview of Continuous Glucose Monitoring Systems", Journal of Pediatric Health Care, 2009, vol. 23, No. 5, pp. 344-347.

Cullen, M.T., et al., "The Changing Presentations of Diabetic Ketoacidosis During Pregnancy", Amer. J. Perinatol, 1996, vol. 13, No. 7, pp. 449-451 (abstract only).

In Vivo Glucose Sensing, Cunningham et al., Eds., 2010, Chemical Analysis, vol. 174, pp. 1-466.

Darley, J., "Is your user experience as good as your technology?", 2019, retrieved from https://www.massdevice.com/is-your-user-experience-as-good-as-your-technology/, p. 1-16.

Davis, G., "Electromechanical Techniques for the Development of Amperometric Biosensors", Biosensors, 1985, vol. 1, pp. 161-178.

IPR2022-00605 (Ex. 2001) Declaration of Michael Cima, Ph.D dated May 24, 2022, pp. 1-70.

IPR2022-00637 (Ex. 2001) Declaration of Michael Cima, Ph.D dated Jun. 9, 2022, pp. 1-79.

IPR2022-00605 (Ex. 1003) Declaration of Gary D. Fletcher, Ph.D dated Feb. 15, 2022, pp. 1-122.

IPR2022-00605 (Ex. 1003) Corrected Declaration of Gary D. Fletcher, Ph.D dated Feb. 18, 2022, pp. 1-124.

IPR2022-00637 (Ex. 1035) Second Declaration of Gary D. Fletcher, Ph.D dated Feb. 28, 2022, pp. 1-136.

Decuir, J., "Bluetooth 4.0: Low Energy", IEEE SCV Consultants' Network of Silicon Valley, 2012, pp. 1-68.

Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", The Journal of Physical Chemistry, 1987, vol. 91, No. 6, pp. 1285-1289.

Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", Journal of the American Chemical Society, 1988, vol. 110, No. 8, pp. 2615-2620.

Degani, Y., et al., "Electrical Communication Between Redox Centers of Glucose Oxidase and Electrodes via Electrostatically and Covalently Bound Redox Polymers", Journal of the American Chemical Society, 1989, vol. 111, pp. 2357-2358.

Dehez, B., et al., "Development of a Spherical Induction Motor With Two Degrees of Freedom", IEEE Transactions on Magnetics, 2006, vol. 42, No. 8, pp. 2077-2089.

Delve Talks: Jake Leach, Dexcom, retrieved from https://www.delve.com/podcasts/delve-talks-jake-leach-dexcom, pp. 1-9.

Dementyev, A., et al., "Power Consumption Analysis of Bluetooth Low Energy, ZigBee and ANT Sensor Nodes in a Cyclic Sleep Scenario", IEEE International Wireless Symposium (IWS), 2013, Beijing, China, pp. 1-4.

Denisevich, P., et al., "Unidirectional Current Flow and Charge State Trapping at Redox Polymer Interfaces on Bilayer Electrodes: Principles, Experimental Demonstration, and Theory", Journal of the American Chemical Society, 1981, vol. 103, pp. 4727-4737.

"Dexcom CEO tells investors not to fear new competition from Abbott's Freestyle Libre", 2017, retrieved from https://www.mobihealthnews.com/content/dexcom-ceo-tells-investors-not-fear-new-competition-abbotts-freestyle-libre, pp. 1-3.

Dexcom G5 Mobile System User Guide, 2020, pp. 1-410.

Dexcom G6, Winner Health & Wellness Award, Core77 Design Awards, 2019, retrieved from https://designawards.core77.com/health-wellness/85111/Dexcom-G6, pp. 1-8.

DexCom™ STS™M Continuous Glucose Monitoring System User's Guide, 2006, pp. 1-57.

Dicks, J.M., et al., "Ferrocene Modified Polypyrrole with Immobilised Glucose Oxidase and its Application in Amperometric Glucose Microbiosensors", Annales de Biologie Clinique, 1989, vol. 47, pp. 607-619.

Diem, P., et al., "Clinical Performance of a Continuous Viscometric Affinity Sensor for Glucose", Diabetes Technology & Therapeutics, 2004, vol. 6, pp. 790-799.

ECMA International Standard ECMA-340, Near Field Communication Interface and Protocol (NFCIP-1), 2nd Edition, 2004, pp. 1-65.

El-Khatib, F. H, et al., "Adaptive Closed-Loop Control Provides Blood-Glucose Regulation Using Subcutaneous Insulin and Glucagon Infusion in Diabetic Swine", Journal of Diabetes Science and Technology, 2007, vol. 1, No. 2, pp. 181-192.

Ellis, C. D., et al., "Selectivity and Directed Charge Transfer through an Electroactive Metallopolymer Film", Journal of the American Chemical Society, 1981, vol. 103, No. 25, pp. 7480-7483.

Engstrom, R. C., "Electrochemical Pretreatment of Glassy Carbon Electrodes", Analytical Chemistry, 1982, vol. 54, No. 13, pp. 2310-2314.

Engstrom, R. C., et al., "Characterization of Electrochemically Pretreated Glassy Carbon Electrodes", Analytical Chemistry, 1984, vol. 56, No. 2, pp. 136-141.

Facchinetti, A., et al., "A New Index to Optimally Design and Compare Continuous Glucose Monitoring Glucose Prediction Algorithms", Diabetes Technology & Therapeutics, 2011, vol. 13, No. 2, pp. 111-119.

(56)         References Cited

OTHER PUBLICATIONS

Feldman, B., et al., "Electron Transfer Kinetics at Redox Polymer/ Solution Interfaces Using Microelectrodes and Twin Electrode Thin Layer Cells", Journal of ElectroAnalytical Chemistry, 1985, vol. 194, pp. 63-81.

Fischer, H., et al., "Intramolecular Electron Transfer Medicated by 4,4'-Bypyridine and Related Bridging Groups", Journal of the American Chemical Society, 1976, vol. 98, No. 18, pp. 5512-5517.

Foulds, N. C., et al., "Enzyme Entrapment in Electrically Conducting Polymers: Immobilisation of Glucose Oxidase in Polypyrrole and its Application in Amperometric Glucose Sensors", Journal of the Chemical Society, Faraday Transactions 1, 1986, vol. 82, pp. 1259-1264.

Foulds, N. C., et al., "Immobilization of Glucose Oxidase in Ferrocene-Modified Pyrrole Polymers", Analytical Chemistry, 1988, vol. 60, No. 22, pp. 2473-2478.

Freedman, D., et al., Statistics: Second Edition, 1991, Chapter 5, p. 74.

Freestyle Navigator Continuous Glucose Monitor FDA Premarket Approval (PMA), May 2022, pp. 1-6.

Freestyle Navigator Summary of Safety and Effectiveness Data, 2008, pp. 1-27.

Freestyle Navigator User's Guide, 2008, pp. 1-195.

Frenzel, L. E., "Printed-Circuit-Board Antennas", retrieved from https://www.electronicdesign.com/technologies/boards/article/ 21751417/printedcircuitboard-antennasprint/3266, Electronic Design, 2005, pp. 1-4.

Frew, J. E., et al., "Electron-Transfer Biosensors", Philosophical Transactions of the Royal Society of London, 1987, vol. 316, pp. 95-106.

Fujipoly Silver ZEBRAR Connector Data Sheet FSDS 01-34, Version 5, 2006, pp. 1-7.

Garg, S., et al., "Improvement in Glycemic Excursions with a Transcutaneous, Real-Time Continuous Glucose Sensor", Diabetes Care, 2006, vol. 29, No. 1, pp. 44-50.

Garibotto, J., et al., "An Innovative Application of Shape Memory Alloy Technology Yields a Novel Therapeutic Approach to Diabetes Management", Insulet Corporation, p. A41.

Gilligan, B. J., et al., "Evaluation of a Subcutaneous Glucose Sensor out to 3 Months in a Dog Model", Diabetes Care, 1994, vol. 17, No. 8, pp. 882-887.

Gonzales, W. V., et al., "The Progress of Glucose Monitoring-A Review of Invasive to Minimally and Non-Invasive Techniques, Devices and Sensors", Sensors, 2019, vol. 19, No. 800, pp. 1-45.

Gonzalez, O. L., et al., "Low-Cost Wireless Sensors - Designer Reference Manual", Freescale Semiconductor, 2007, pp. 1-146.

Gorton, L., et al., "Selective Detection in Flow Analysis Based on the Combination of Immobilized Enzymes and Chemically Modified Electrodes", Analytica Chimica Acta, 1991, vol. 250, pp. 203-248.

Gregg, B. A., et al., "Redox Polymer Films Containing Enzymes. 1. A Redox-Conducting Epoxy Cement: Synthesis, Characterization, and Electrocatalytic Oxidation of Hydroquinone", Journal of Physical Chemistry, 1991, vol. 95, No. 15, pp. 5970-5975.

Gregg, T. H., "How Continuous Glucose Monitoring is Transforming Diabetes Treatment", Qualcomm Life Connect, 2013, pp. 1-33.

Guardian® RT Continuous Glucose Monitoring System REF MMT-7900 User Guide, 2005, pp. 1-128.

Guerra, S., et al., "A Dynamic Risk Measure from Continuous Glucose Monitoring Data", Diabetes Technology & Therapeutics, 2011, vol. 13, No. 8, pp. 843-852.

Güler, N. F., et al., "Theory and Applications of Biotelemetry", Journal of Medical Systems, 2002, vol. 26, No. 2, pp. 159-178.

Hale, p. D., et al., "A New Class of Amperometric Biosensor Incorporating a Polymeric Electron-Transfer Mediator", Journal of the American Chemical Society, 1989, vol. 111, No. 9, pp. 3482-3484.

Hao, Y., "Wireless body sensor networks for health-monitoring applications", Physiol. Meas., 2008, vol. 29, R27-R56.

Hawkridge, F. M., et al., "Indirect Coulometric Titration of Biological Electron Transport Components", Analytical Chemistry, 1973, vol. 45, No. 7, pp. 1021-1027.

Heftman, G., "Chip Antenna Reduces Cell-Phone Dimensions", Microwaves & RF, 1999, p. 182.

Heise, T., et al., "Hypoglycemia Warning Signal and Glucose Sensors: Requirements and Concepts", Diabetes Technology & Therapeutics, 2003, vol. 5, No. 4, pp. 563-571.

Heller, A., et al., "Amperometric Biosensors Based on Three-Dimensional Hydrogel-Forming Epoxy Networks", Sensors and Actuators B, 1993, vol. 13-14, pp. 180-183.

Heller, A., "Implanted Electrochemical Glucose Sensors for the Management of Diabetes", Annnu. Rev. Biomed. Eng., 1999, vol. 1, pp. 153-175.

Hirsch, I. B., "Introduction: History of Glucose Monitoring", Clinical Compendia, 2018, vol. 2018, No. 1, 1 page.

Hoel, P. G., Elementary Statistics: Fourth Edition, 1976, Chapter 5, pp. 113-114.

Howe, D., "Comparing the Dexcom G6 To the G5", 2018, retrieved from https://beyondtype1.org/comparing-the-dexcom-g6-to-the-g5/, pp. 1-10.

Huang, Y., et al., "Antennas from Theory to Practice", 2008, Chapter 8, Antenna Diversity, pp. 322-325.

Ianniello, R. M., et al., "Immobilized Enzyme Chemically Modified Electrode as an Amperometric Sensor", Analytical Chemistry, 1981, vol. 53, No. 13, pp. 2090-2095.

Ianniello, R. M., et al., "Differential Pulse Voltammetric Study of Direct Electron Transfer in Glucose Oxidase Chemically Modified Graphite Electrodes", Analytical Chemistry, 1982, vol. 54, No. 7, pp. 1098-1101.

Ikeda, T., et al., "Kinetics of Outer-Sphere Electron Transfers Between Metal Complexes in Solutions and Polymeric Films on Modified Electrodes", Journal of the American Chemical Society, 1981, vol. 103, No. 25, pp. 7422-7425.

Ikeda, T., et al., "Glucose Oxidase—Immobilized Benzoquinone-Carbon Paste Electrode as a Glucose Sensor", Agricultural and Biological Chemistry, 1985, vol. 49, No. 2, pp. 541-543.

"In Vitro Diagnostic Products for Human Use", Federal Register, 1974, vol. 39, No. 126, pp. 24136-24147.

Jain, A.K., et al., "Wound Rotor Induction Generator With Sensorless Control and Integrated Active Filter for Feeding Nonlinear Loads in a Stand-Alone Grid", IEEE Transactions on Industrial Electronics, 2008, vol. 55, No. 1, pp. 218-228.

James, Jr., et al., "Handbook of Microstrip Antennas", 1969, pp. 1038-1047.

Johnson, J. M., et al., "Potential-Dependent Enzymatic Activity in an Enzyme Thin-Layer Cell", Analytical Chemistry, 1982, vol. 54, No. 8, pp. 1377-1383.

Johnson, K. W., "Reproducible Electrodeposition of Biomolecules for the Fabrication of Miniature Electroenzymatic Biosensors", Sensors and Actuators B, 1991, vol. 5, pp. 85-89.

Jonsson, G., et al., "An Amperometric Glucose Sensor Made by Modification of a Graphite Electrode Surface With Immobilized Glucose Oxidase and Adsorbed Mediator", Biosensors, 1985, vol. 1, pp. 355-368.

Josowicz, M., et al., "Electrochemical Pretreatment of Thin Film Platinum Electrodes", Journal of the Electrochemical Society, 1988, vol. 135, No. 1, pp. 112-115.

Jovanovic, L., "The Role of Continuous Glucose Monitoring in Gestational Diabetes Mellitus", Diabetes Technology & Therapeutics, 2000, vol. 2, Supplement 1, pp. S-67-S-71.

Kaplan, S. M., "Wiley Electrical and Electronics Engineering Dictionary", IEEE Press, 2004, pp. 141, 142, 548, 549.

Katakis, I., et al., "L-$\alpha$-Glycerophosphate and $_L$-Lactate Electrodes Based on the Electrochemical 'Wiring' of Oxidases", Analytical Chemistry, 1992, vol. 64, No. 9, pp. 1008-1013.

Katakis, I., et al., "Electrostatic Control of the Electron Transfer Enabling Binding of Recombinant Glucose Oxidase and Redox Polyelectrolytes", Journal of the American Chemical Society, 1994, vol. 116, No. 8, pp. 3617-3618.

Kenausis, G., et al., "Wiring' of Glucose Oxidase and Lactate Oxidase Within a Hydrogel Made with Poly(vinyl pyridine) complexed

(56)　　　　　References Cited

OTHER PUBLICATIONS with [Os(4,4'-dimethoxy-2,2'-bipyridine) 2Cl] +/2+", Journal of the Chemical Society, Faraday Transactions, 1996, vol. 92, No. 20, pp. 4131-4136.

Klonoff, D. C., "A Review of Continuous Glucose Monitoring Technology", Diabetes Technology & Therapeutics, 2005, vol. 7, No. 5, pp. 770-775.

Kondepati, V., et al., "Recent Progress in Analytical Instrumentation for Glycemic Control in Diabetic and Critically Ill Patients", Analytical Bioanalytical Chemistry, 2007, vol. 388, pp. 545-563.

Kulys, J., et al., "Mediatorless Peroxidase Electrode and Preparation of Bienzyme Sensors", Bioelectrochemistry and Bioenergetics, 1990, vol. 24, pp. 305-311.

Leon, L. P., et al., "Continuous-Flow Analysis for Glucose in Serum, with Use of Hexokinase and Glucose-6-Phosphate Dehydrogenase Co-Immobilized in Tubular Form", Clinical Chemistry, 1980, vol. 26, No. 1, pp. 123-129.

Lindner, E., et al., "Flexible (Kapton-Based) Microsensor Arrays of High Stability for Cardiovascular Applications", Journal of the Chemical Society, Faraday Transactions, 1993, vol. 89, No. 2, pp. 361-367.

Lo, B., et al., "Key Technical Challenges and Current Implementations of Body Sensor Networks", Body Sensor Networks, 2005, pp. 1-5.

Lodwig, V., et al., "Continuous Glucose Monitoring with Glucose Sensors: Calibration and Assessment Criteria", Diabetes Technology & Therapeutics, 2003, vol. 5, No. 4, pp. 573-587.

Lortz, J., et al., "What is Bluetooth? We Explain The Newest Short-Range Connectivity Technology", Smart Computing Learning Series, Wireless Computing, 2002, vol. 8, Issue 5, pp. 72-74.

Loy, M., et al., "ISM-Band and Short Range Device Antennas", Texas Instruments Application Report, 2005, pp. 1-38.

Malin, S. F., et al., "Noninvasive Prediction of Glucose by Near-Infrared Diffuse Reflectance Spectoscopy", Clinical Chemistry, 1999, vol. 45, No. 9, pp. 1651-1658.

McGarraugh, G., et al., "Glucose Measurements Using Blood Extracted from the Forearm and the Finger", TheraSense, Inc., 2001, 16 Pages.

McGarraugh, G., et al., "Physiological Influences on Off-Finger Glucose Testing", Diabetes Technology & Therapeutics, 2001, vol. 3, No. 3, pp. 367-376.

McNeil, C. J., et al., "Thermostable Reduced Nicotinamide Adenine Dinucleotide Oxidase: Application to Amperometric Enzyme Assay", Analytical Chemistry, 1989, vol. 61, No. 1, pp. 25-29.

Medtronic Guardian® REAL-Time Continuous Glucose Monitoring System User Guide, 2006, pp. 1-184.

IPR2022-00605 (Ex. 1027) The Merriam-Webster Dictionary, Merriam Webster, Incorporated (2005), pp. 66, 403, and 415.

Microchip Technology Inc., MRF24J40MA Data Sheet, 2008, pp. 1-30.

IPR2022-00605 (Ex. 2008) MiniMed® Glucose Sensor, Ref MMT-7002, Instructions for Use, pp. 1-4.

Miyawaki, O., et al., "Electrochemical and Glucose Oxidase Coenzyme Activity of Flavin Adenine Dinucleotide Covalently Attached to Glassy Carbon at the Adenine Amino Group", Biochimica et Biophysica Acta, 1985, vol. 838, pp. 60-68.

IPR2022-00605 (Ex. 2003) "Monitoring Your Blood Sugar", retrieved from https://www.cdc.gov/diabetes/managing/managing-blood-sugar/bloodglucosemonitoring.html, pp. 1-3.

Moore, B., "The Potential Use of Radio Frequency Identification Devices for Active Monitoring of Blood Glucose Levels", Journal of Diabetes Science and Technology, 2009, vol. 3, No. 1, pp. 180-183.

Morak, J., et al., "Design and Evaluation of a Telemonitoring Concept Based on NFC- Enabled Mobile Phones and Sensor Devices", IEEE Transactions on Information Technology in Biomedicine, 2012, vol. 16, No. 1, pp. 17-23.

Morbiducci, U., et al., "Improved Usability of the Minimal Model of Insulin Sensitivity Based on an Automated Approach and Genetic algorithms for Parameter Estimation", Clinical Science, vol. 112, 2007, pp. 257-263.

Mougiakakou, S. G., et al., "A Real Time Simulation Model of Glucose-Insulin Metabolism for Type 1 Diabetes Patients", Proceedings of the 2005 IEEE, 2005, pp. 298-301.

Movassaghi, S., et al., "Wireless Technologies for Body Area Networks: Characteristics and Challenges", 2012 International Symposium on Communications and Information Technologies (ISCIT), 2012, Gold Coast, QLD, Australia, pp. 42-47.

"Murata Puts Antenna on a Chip", Passives, 1999, vol. 44, 1 page.

Nagy, G., et al., "A New Type of Enzyme Electrode: The Ascorbic Acid Eliminator Electrode", Life Sciences, 1982, vol. 31, No. 23, pp. 2611-2616.

Nakamura, S., et al., "Effect of Periodate Oxidation on the Structure and Properties of Glucose Oxidase", Biochimica et Biophysica Acta., 1976, vol. 445, pp. 294-308.

Narasimham, K., et al., "p. Benzoquinone Activation of Metal Oxide Electrodes for Attachment of Enzymes", Enzyme and Microbial Technology, 1985, vol. 7, pp. 283-286.

Ohara, T. J., et al., "Wired' Enzyme Electrodes for Amperometric Determination of Glucose or Lactate in the Presence of Interfering Substances", Analytical Chemistry, 1994, vol. 66, No. 15, pp. 2451-2457.

Ohara, T. J., "Osmium Bipyridyl Redox Polymers Used in Enzyme Electrodes", Platinum Metals Review, 1995, vol. 39, No. 2, pp. 54-62.

OmniPod Insulet UST400 User Manual, 2011, pp. 1-190.

Opinion of the Court, Supreme Court of the United States, No. 04-1350, KSR International co., Petitioner v. Teleflex Inc et al., Apr. 30, 2007.

Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", Journal of ElectroAnalytical Chemistry, 1989, vol. 260, pp. 487-494.

Palleschi, G., et al., "A Study of Interferences in Glucose Measurements in Blood by Hydrogen Peroxide Based Glucose Probes", Analytical Biochemistry, 1986, vol. 159, pp. 114-121.

Pankratov, I., et al., "Sol-Gel Derived Renewable-Surface Biosensors", Journal of ElectroAnalytical Chemistry, 1995, vol. 393, pp. 35-41.

Parker, R., et al., "Robust Ho Glucose Control in Diabetes Using a Physiological Model", AIChE Journal, 2000, vol. 46, No. 12, 2000, pp. 2537-2549.

Passey, R. B., et al., "Evaluation and Comparison of 10 Glucose Methods and the Reference Method Recommendation in the Proposed Product Class Standard (1974)", Clinical Chemistry, 1977, vol. 23, No. 1, pp. 131-139.

Pathak, C., et al., "Rapid Photopolymerization of Immunoprotective Gels in Contact with Cells and Tissue", Journal of the American Chemical Society, 1992, vol. 114, No. 21, pp. 8311-8312.

Patton, S. R., et al., "Continuous Glucose Monitoring Versus Self-monitoring of Blood Glucose in Children with Type 1 Diabetes- Are there Pros and Cons for Both?", US Endocrinol., 2012, vol. 8, No. 1, pp. 27-29.

Pollak, A., et al., "Enzyme Immobilization by Condensation Copolymerization into Cross- Linked Polyacrylamide Gels", Journal of the American Chemical Society, 1980, vol. 102, No. 20, pp. 6324-6336.

Rodriguez, N., et al., "Flexible Communication and Control Protocol for Injectable Neuromuscular Interfaces", IEEE Transactions on Biomedical Circuits and Systems, 2007, vol. 1, No. 1, pp. 19-27.

IPR2022-00605 (Ex. 1024) "Rotor," Dictionary of Mechanical Engineering, Fourth Ed., G.H.F. Nayler, Society of Automotive Engineers, Inc., 1996, p. 328.

IPR2022-00605 (Ex. 1025) "Rotor," Random House Kernerman Webster's College Dictionary, K Dictionaries Ltd. (2010), available at https://www.thefreedictionary.com/rotor.

IPR2022-00605 (Ex. 1026) "Rotate," Random House Kernerman Webster's College Dictionary, K Dictionaries Ltd. (2010), available at https://www.thefreedictionary.com/rotate.

(56)         References Cited

OTHER PUBLICATIONS

Salditt, P., "Trends in Medical Device Design and Manufacturing", SMTA News and Journal of Surface Mount Technology, 2004, vol. 17, pp. 19-24.

Samuels, G. J., et al., "An Electrode-Supported Oxidation Catalyst Based on Ruthenium (IV). pH "Encapsulation" in a Polymer Film", Journal of the American Chemical Society, 1981, vol. 103, No. 2, pp. 307-312.

Sandham, W., et al., "Blood Glucose Prediction for Diabetes Therapy Using a Recurrent Artificial Neural Network", 9th European Signal Processing Conference, 1998, Rhodes, Greece, pp. 1-4.

Sasso, S. V., et al., "Electropolymerized 1,2-Diaminobenzene as a Means to Prevent Interferences and Fouling and to Stabilize Immobilized Enzyme in Electrochemical Biosensors", Analytical Chemistry, 1990, vol. 62, No. 11, pp. 1111-1117.

Schmehl, R. H., et al., "The Effect of Redox Site Concentration on the Rate of Mediated Oxidation of Solution Substrates by a Redox Copolymer Film", Journal of ElectroAnalytical Chemistry, 1983, vol. 152, pp. 97-109.

Schoepke, E., "Chip Antenna Layout Considerations for 802.11 Applications", Johanson Technology, 2006, retrieved from https://www.johansontechnology.com/chip-antenna-layout-considerations-for-802-11-applications, pp. 1-7.

Sharawi, M. S., "Use of low-cost patch antennas in modern wireless technology", IEEE Potentials, 2006, pp. 35-38 and 47.

Sittampalam, G., et al., "Surface-Modified Electrochemical Detector for Liquid Chromatography", Analytical Chemistry, 1983, vol. 55, No. 9, pp. 1608-1610.

Soegijoko, S., et al., "External Artificial Pancreas: A New Control Unit Using Microprocessor", Hormone and Metabolic Research Supplement Series, 1982, vol. 12, pp. 165-169.

Sparacino, G., et al., "Glucose Concentration Can Be Predicted Ahead in Time from Continuous Glucose Monitoring Sensor Time-Series", IEEE Transactions on Biomedical Engineering, 2007, vol. 54, No. 5, pp. 931-937.

Sprules, S. D., et al., "Evaluation of a New Disposable Screen-Printed Sensor Strip for the Measurement of NADH and Its Modification to Produce a Lactate Biosensor Employing Microliter Volumes", Electroanalysis, 1996, vol. 8, No. 6, pp. 539-543.

Sternberg, F., et al., "Calibration Problems of Subcutaneous Glucosensors when Applied "In-Situ" in Man", Hormone and Metabolic Research, 1994, vol. 26, pp. 523-526.

Sternberg, R., et al., "Covalent Enzyme Coupling on Cellulose Acetate Membranes for Glucose Sensor Development", Analytical Chemistry, 1988, vol. 60, No. 24, pp. 2781-2786.

Suekane, M., et al., "Immobilization of Glucose Isomerase", Zettschrift fur Allgemeine Mikrobiologie, 1982, vol. 22, No. 8, pp. 565-576.

Tajima, S., et al., "Simultaneous Determination of Glucose and 1,5-Anydroglucitol", Chemical Abstracts, 1989, vol. 111, No. 25, p. 394.

Tarasevich, M. R., "Bioelectrocatalysis", Comprehensive Treatise of Electrochemistry, 1985, vol. 10, pp. 231-295.

Tatsuma, T., et al., "Enzyme Monolayer- and Bilayer-Modified Tin Oxide Electrodes for the Determination of Hydrogen Peroxide and Glucose", Analytical Chemistry, 1989, vol. 61, No. 21, pp. 2352-2355.

Taylor, C., et al., "Wiring" of Glucose Oxidase Within a Hydrogel Made with Polyvinyl Imidazole Complexed with [(Os-4,4'-dimethoxy-2,2'-bipyridine)CI]$^{+/2+}$, Journal of ElectroAnalytical Chemistry, 1995, vol. 396, pp. 511-515.

Townsend, K., et al., "Getting Started with Bluetooth Low Energy—Chapter 1", 2014, pp. 1-26.

Trojanowicz, M., et al., "Enzyme Entrapped Polypyrrole Modified Electrode for Flow- Injection Determination of Glucose", Biosensors & Bioelectronics, 1990, vol. 5, pp. 149-156.

Tung, S., "Layers of Security for Active RFID Tags", RFID Handbook: Applications, Technology, Security, and Privacy, Edited by Ehson, et al., Chapter 33, 2008, pp. 1-28.

Turner, R.F.B., et al., "A Biocompatible Enzyme Electrode for Continuous in vivo Glucose Monitoring in Whole Blood", Sensors and Actuators B, 1990, vol. 1, pp. 561-564.

Tuzhi, P., et al., "Constant Potential Pretreatment of Carbon Fiber Electrodes for in Vivo Electrochemistry", Analytical Letters, 1991, vol. 24, No. 6, pp. 935-945.

Umana, M., "Protein-Modified Electrochemically Active Biomaterial Surface", U.S. Army Research Office, Analytical and Chemical Sciences Research Triangle Institute, 1988, pp. 1-9.

United States Court of Appeals for the Federal Circuit, No. 06-1402, *Leapfrog Enterprises, Inc. v. Fisher-Price, Inc. and Mattel, Inc.*, May 9, 2007.

Urban, G., et al., "Miniaturized Thin-Film Biosensors Using Covalently Immobilized Glucose Oxidase", Biosensors & Bioelectronics, 1991, vol. 6, pp. 555-562.

Vreeke, M. S., et al., "Hydrogen Peroxide Electrodes Based on Electrical Connection of Redox Centers of Various Peroxidases to Electrodes through a Three-Dimensional Electron-Relaying Polymer Network", Diagnostic Biosensors Polymers, Chapter 15, 1993, pp. 180-193.

Vreeke, M., et al., "Hydrogen Peroxide and B-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", Analytical Chemistry, 1992, vol. 64, No. 24, pp. 3084-3090.

Wang, D. L., et al., "Miniaturized Flexible Amperometric Lactate Probe", Analytical Chemistry, 1993, vol. 65, No. 8, pp. 1069-1073.

Wang, J., et al., "Activation of Glassy Carbon Electrodes by Alternating Current Electrochemical Treatment", Analytica Chimica Acta, 1985, vol. 167, pp. 325-334.

Wang, J., et al., "Amperometric Biosensing of Organic Peroxides with Peroxidase-Modified Electrodes", Analytica Chimica Acta, 1991, vol. 254, pp. 81-88.

Wang, J., et al., "Screen-Printable Sol-Gel Enzyme-Containing Carbon Inks", Analytical Chemistry, 1996, vol. 68, No. 15, pp. 2705-2708.

Wang, J., et al., "Sol-Gel-Derived Metal-Dispersed Carbon Composite Amperometric Biosensors", Electroanalysis, 1997, vol. 9, No. 1, pp. 52-55.

Wang, X.H., et al., "Bluetooth: Opening a blue sky for healthcare", Mobile Information Systems, 2006, vol. 2, pp. 151-167.

Waterhouse, R., "Printed Antennas for Wireless Communications," 2007, pp. 116-129 and 284-289.

Williams, D. L., et al., "Electrochemical-Enzymatic Analysis of Blood Glucose and Lactate", Analytical Chemistry, 1970, vol. 42, No. 1, pp. 118-121.

Wong, KL, "Planar Antennas for Wireless Communications," 2003, Chapter 1, Introduction and Overview, pp. 4-17, 38-45, and 218-221.

Yabuki, S., et al., "Electro-Conductive Enzyme Membrane", Journal of the Chemical Society, Chemical Communications, 1989, pp. 945-946.

Yang, L., et al., "Determination of Oxidase Enzyme Substrates Using Cross-Flow Thin-Layer Amperometry", Electroanalysis, 1996, vol. 8, No. 8-9, pp. 716-721.

Yao, S. J., et al., "The Interference of Ascorbate and Urea in Low-Potential Electrochemical Glucose Sensing", Proceedings of the Twelfth Annual International Conference of the IEEE Engineering in Medicine and Biology Society, 1990, vol. 12, Part 2, pp. 487-489.

Yao, T., "A Chemically-Modified Enzyme Membrane Electrode as an Amperometric Glucose Sensor", Analytica Chimica Acta, 1983, vol. 148, pp. 27-33.

Yildiz, A., et al., "Evaluation of an Improved Thin-Layer Electrode", Analytical Chemistry, 1968, vol. 40, No. 7, pp. 1018-1024.

Zamzow, K., et al., "New Wearable Continuous Blood Glucose Monitor (BGM) and Artificial Pancreas (AP)", Diabetes, 1990, vol. 39, p. 5A-20.

Z-Carbon Connector, retrieved from http://www.zaxisconnector.com/SS_zc.shtml, 2004, 2 pages.

Zhang, Y., et al., "Application of Cell Culture Toxicity Tests to the Development of Implantable Biosensors", Biosensors & Bioelectronics, 1991, vol. 6, pp. 653-661.

(56)References Cited

OTHER PUBLICATIONS

Zhang, Y., et al., "Elimination of the Acetaminophen Interference in an Implantable Glucose Sensor", Analytical Chemistry, 1994, vol. 66, No. 7, pp. 1183-1188.
Zhu, J., et al., "Fabrication and Characterization of Glucose Sensors Based on a Microarray $H_2 O_2$ electrode", Biosensors & Bioelectronics, 1994, vol. 9, pp. 295-300.
Zisser, H. C., "The OmniPod Insulin Management System: the Latest Innovation in Insulin Pump Therapy", Diabetes Ther, 2010, vol. 1, No. 1, pp. 10-24.
Z-Silver Connector, retrieved from http://www.zaxisconnector.com/SS_zs.shtml, 2004, 2 pages.
AU, 2016201703 Examiner's Report, Mar. 22, 2017.
Callaway, Jr., E. H., "Wireless Sensor Networks: Architectures and Protocols", 2004, Chapter 8, Antennas and the Definition of RF Performance, pp. 201-202.
Cleo® 90 Infusion Set Training Guide, 2011, 1 page.
Darley, J., "Is your user experience as good as your technology?", 2019, retrieved from https://www.massdevice.com/is-your-user-experience-as-good-as-your-technology/, pp. 1-16.
MINIMED Quick-set™ retrieved from https://web.archive.org/web/20010412224824/http://www.minimed.com/patientfam/pf_ipt_pumpinfusion_quickset.shtml, Apr. 12, 2001, pp. 1-2.
MINIMED Sof-set Micro QR® Sof-set Ultimate QR® retrieved from https://web.archive.org/web/20010412225617/http://www.minimed.com/patientfam/pf_ipt_pumpinfusion_sofset.shtml, Apr. 12, 2001, pp. 1-2.
Osmonics, Poretics® Polycarbonate Membrane; Product Leaflet; Engineering Purity, 2002, pp. 1-2.
Repas, R., "Sensor Sense: RFID for smart position sensing", retrieved from https://www/machinedesign/com/automation-iiot/article/21818777/sensor-sense-rfid-for-smart-position-sensing, 2010, pp. 1-2.
IPR2022-00605 (Ex. 1013) Scheduling Order in Abbott Diabetes Care Inc., et al. v. Dexcom, Inc., 1:21-cv-00977 (D. Del.), dated Dec. 2, 2021.
EP 11760268.0 Response to Notice of Appeal, Sep. 5, 2019.
Cleo™ 90 Infusion Set, 510(k) Summary of Safety and Effectiveness, Aug. 10, 2004, pp. 1-618.
Csöregi, E., et al., "On-Line Glucose Monitoring by Using Microdialysis Sampling and Amperometric Detection Based on 'Wired' Glucose Oxidase in Carbon Paste", Mikrochimica Acta, 1995, vol. 121, pp. 31-40.
EP, 11760268.0 Decision of the Oral Proceedings, Sep. 27, 2022.
EP, 11760268.0 Minutes of Oral Proceedings, Aug. 11, 2022.
EP, 19900891.3 Extended Search Report, Sep. 26, 2002.
EP, 20177703.4 Grounds of Opposition, Sep. 28, 2022.
EP 20177703.4 Notice of Opposition, Sep. 28, 2022.
EP, 20177703.4 Examination Report, Jun. 25, 2021.
EP, 22168031.7 Extended Search Report, Aug. 17, 2022
EP, 22169853.3 Extended Search Report, Sep. 2, 2022.
MY, PI2021004760 Examination Report, Mar. 30, 2022.
MY, PI2021005830 Examination Report, Sep. 30, 2022.
MY, PI2021005830 Examination Report, Aug. 29, 2022.
WO, PCT/US2022/037291 Invitation to Pay Additional Fees, Sep. 29, 2022.
WO, PCT/US2022/037291 ISR and Written Opinion, Nov. 22, 2022.
Affidavit of Richard Paragas signed on May 18, 2016, pp. 1-4.
Affidavit of Paul Neale signed on May 18, 2016, pp. 1-2.
Certified U.S. Appl. No. 60/424,099, filed Nov. 5, 2002.
Choleau, C., et al., "Calibration of a Subcutaneous Amperometric Glucose Sensor Implanted for 7 Days in Diabetic Patients Part 2. Superiority of the One-Point Calibration Method", Biosensor & Bioelectronics, 2002, vol. 17, No. 8, pp. 647-654.
Choleau, C., et al., "Calibration of a Subcutaneous Amperometric Glucose Sensor Part 1. Effect of Measurement Uncertainties on the Determination of Sensor Sensitivity and Background Current", Biosensor & Bioelectronics, 2002, vol. 17, No. 8, pp. 641-646.

De Block, C., et al., "Minimally-Invasive and Non-Invasive Continuous Glucose Monitoring Systems: Indications, Advantages, Limitations and Clinical Aspects", Current Diabetes Reviews, 2008, vol. 4, No. 3, pp. 159-168.
Guerci, B., et al., "Clinical Performance of CGMS in Type 1 Diabetic Patients Treated by Continuous Subcutaneous Insulin Infusion Using Insulin Analogs", Diabetes Care, 2003, vol. 26, No. 3, pp. 582-589.
Kovatchev, B. P., et al., "Evaluating the Accuracy of Continuous Glucose-Monitoring Sensors", Diabetes Care, 2004, vol. 27, No. 8, pp. 1922-1928.
Mauras, N., et al., "Lack of Accuracy of Continuous Sensors in Healthy, Nondiabetic Children: Results of the Diabetes Research in Children Network (DirecNet) Accuracy Study", Journal of Pediatrics, 2004, pp. 770-775.
Medtronic MiniMed Sen-Serter® User Guide, 2006, pp. 1-96.
Schmidtke, D. W., et al., "Accuracy of the One-Point In Vivo Calibration of "Wired" Glucose Oxidase Electrodes Implanted in Jugular Veins of Rats in Periods of Rapid Rise and Decline of the Glucose Concentration", Analytical Chemistry, 1998, vol. 70, No. 10, pp. 2149-2155.
Tierney, M. J., et al., "Effect of Acetaminophen on the Accuracy of Glucose Measurements Obtained with the GlucoWatch Biographer", Diabetes Technology & Therapeutics, 2000, vol. 2, No. 2, pp. 199-207.
Tsalikian, e., et al., "Accuracy of the GlucoWatch G2® Biographer and the Continuous Glucose Monintoring System During Hypoglycemia: Experience of the Diabetes Research in Children Network", Diabetes Care, 2004, vol. 27, No. 3, pp. 722-726.
Ward, W. K., et al., "Rise in Background Current Over Time in a Subcutaneous Glucose Sensor in the Rabbit: Relevance to Calibration and Accuracy", Biosensors & Bioelectronics, 2000, vol. 15, pp. 53-61.
CA, 2,872,576 Examiner's Report, Feb. 17, 2015.
CA, 2,872,576 Examiner's Report, Feb. 19, 2016.
CN, 201980082748.1 First Office Action, Jan. 10, 2023.
EP, 06851063.5 Extended Search Report, Sep. 21, 2009.
EP, 07843396.8 Extended Search Report, Dec. 22, 2010.
EP, 10739031.2 Response to Response to Response to Grounds of Appeal, Jan. 18, 2023.
EP, 13000104.3 Extended Search Report, Mar. 12, 2013.
EP, 14179905.6 Summons to Attend Oral Proceedings, Apr. 10, 2017.
EP, 14179905.6 Notice of Opposition, May 19, 2016.
EP, 14179905.6 Extended Search Report, Dec. 23, 2014.
EP, 15002441.2 Extended Search Report, Dec. 18, 2015.
EP, 20177703.4 Reply to Opposition, Feb. 22, 2023.
EP, 201777712.5 Grounds of Opposition Guide & Partner Patent, Dec. 22, 2022.
EP, 20177712.5 Grounds of Opposition Dexcom, Dec. 22, 2022.
EP, 20195922.8 Grounds of Opposition Dexcom, Jan. 26, 2023.
JP, 2021-531135 Office Action, Feb. 22, 2023.
WO, PCT/US2006/062690 ISR and Written Opinion, Jan. 2, 2008.
WO, PCT/US2007/079774 ISR and Written Opinion, Apr. 1, 2008.
CA, 3,120,335 Examiner's Report, Mar. 31, 2023.
CA, 3,182,961 Examiner's Report, Mar. 29, 2023.
EP, 20177703.4 Response to Notice of Opposition, Jun. 29, 2023.
EP, 20177703.4 Notice of Intervention, Jun. 23, 2023.
EP, 20177712.5 Notice of Intervention, Jun. 23, 2023.
EP, 20177712.5 Reply to Opposition, May 23, 2023.
EP, 20177712.5 Notice of Opposition Gulde & Partner Patent, Dec. 22, 2022.
EP, 20177712.5 Notice of Opposition Dexcom, Dec. 22, 2022.
EP, 20195922.8 Notice of Intervention, Jun. 13, 2023.
EP, 20195922.8 Notice of Opposition Dexcom, Jan. 26, 2023.
MY, PI2022007295 Examination Report, Jul. 11, 2023.
US, Final Written Decision, IPR No. 2022-00605, Jul. 10, 2023.
WO, PCT/US2012/062551 ISR and Written Opinion, Jan. 2, 2013.
WO, PCT/US2023/010054 ISR and Written Opinion, May 15, 2023.
WO, PCT/US2023/010054 Invitation to Pay Additional Fees, Mar. 24, 2023.

(56) References Cited

OTHER PUBLICATIONS

Anderson, A. J., "Foundations of Computer Technology", 1994, pp. 55-57.
Kal, S., "Basic Electronics—Devices, Circuits and IT Fundamentals", 2006, Chapter 13, Microcomputers and Microprocessors, p. 412.
"Abbott Receives CE Mark for Freestyle® Libre, A Revolutionary Glucose Monitoring System for People With Diabetes", 2014, 7 pages.
"Alcove", Webster's New College Dictionary, 2001, p. 26.
Boise, M., "Dexcom CEO Kevin Sayer Explains G6", 2018, retrieved from https://beyondtype1.org/dexcom-ceo-kevin-sayer-explains-g6/, 9 pages.
Breton, M. D., et al., "Optimum Subcutaneous Glucose Sampling and Fourier Analysis of Continuous Glucose Monitors", Journal of Diabetes Science and Technology, 2008, vol. 2, No. 3, pp. 495-500.
Certified True Preliminary Amendment filed on Apr. 20, 2018 for U.S. Pat. No. 10,827,954, 7 pages.
CGMs Changing Diabetes Management: Kevin Sayer, DIC Interview Transcript, 2019, retrieved from https://www.diabetesincontrol.com/cgms-changing-diabetes-management-kevin-sayer-dic-interview-transcript/, 10 pages.
"Deciding When to Submit a 510(k) for a Change to an Existing Device, Guidance for Industry and Food and Drug Administration Staff", 2017, pp. 1-77.
"Deciding When to Submit a 510(k) for a Software Change to an Existing Device, Guidance for Industry and Food and Drug Administration Staff", 2017, pp. 1-31.
Dexcom CEO—Prime Position in Our Market—Mad Money—CNBC.mp4, Transcript 2023 by Sonix, 2 pages.
DexCom (DXCM) 2017 Q4 Earnings Call Transcript, 2017, retrieved from https://docoh.com/transcript/1093557/2017Q4/DXCM, 11 pages.
DexCom (Dxcm) Q1 2018 Results—Earnings Call Transcript, 2018, retrieved from https://seekingalpha.com/article/4168949-dexcom-dxcm-q1-2018-results-earnings-call-transcript, 4 pages.
Dexcom, Inc. NasdaqGS:DXCM Company Conference Presentation, 2019, 10 pages.
Dexcom, Inc. NasdaqGS:DXCM Company Conference Presentation, 2020, 9 pages.
Dexcom, Inc. NasdaqGS:DXCM Company Conference Presentation, 2021, 16 pages.
Dexcom G6 Continuous Glucose Monitoring System User Guide, 2019, pp. 1-27.
Dexcom G6 Start Here Set up Guide, 2019, pp. 1-8.
Dexcom G6 Using Your G6 Guide, Mar. 2020, pp. 1-7.
Dexcom G7 Inserting Sensor Instructions for Use, 2021, pp. 1-2.
Dexcom G7, Start Here, Operational Manual, 2022, pp. 1-9 (English Abstract).
Dexcom G7, User Guide, 2022, p. 1-179 (English Abstract).
Dexcom Seven® Plus Continuous Glucose Monitoring System User's Guide, 2011, pp. 1-144.
DexCom™ STSTM Continuous Glucose Monitoring System FDA Premarket Approval (PMA), 2006, pp. 1-7.
DexCom™M STS™M Continuous Glucose Monitoring System Summary of Safety and Effectiveness Data, 2006, 20 pages.
DexCom™M STSTM Sensor Instructions for Use, 2006, pp. 1-6.
Dexcom STS-7 Continuous Glucose Monitoring System FDA Premarket Approval (PMA), 2007, pp. 1-7.
Dexcom STS®-7 Continuous Glucose Monitoring System Summary of Safety and Effectiveness Data, 2007, 14 pages.
Dexcom STS®-7 Continuous Glucose Monitoring System User's Guide, 2007, pp. 1-74.
Diglas, J., et al., "Reduced pain perception with Pen Mate™M, an automatic needle insertion device for use with an insulin pen", Practical Diabetes International, 1999, vol. 16, No. 2, pp. 39-41.
"Does Dexcom Really Have a Future If It Can't Match Abbott's Scale", 2019, retrieved from https://www.sprucepointcap.com/reports/dxcm_research_thesis_3-21-2019.pdf, p. 46.
Email from John Shaw of Shaw & Keller dated May 16, 2023, 2 pages.

Email chain from Sophie Hood, oldest email dated Jan. 24, 2023, 5 pages.
European Standard, ISO 11607-1, Packaging for terminally sterilized medical devices—Part 1: Requirements for materials, sterile barrier systems and packaging systems, 2006, 32 pages.
European Standard, ISO 13485, Medical devices—Quality management systems—Requirement for regulatory purposes, 2003, 69 pages.
European Standard, ISO 15197, In vitro diagnostic test systems—Requirements for blood glucose monitoring systems for self-testing in managing diabetes mellitus, 2003, 43 pages.
"FDA authorizes first fully interoperable continuous glucose monitoring system, streamlines review pathway for similar devices", FDA News Release, 2018, retrieved from https://www.fda.gov/news-events/press-announcements/fda-authorizes-first-fully-interoperable-continuous-glucose-monitoring-system-streamlines-review, 3 pages.
Food and Drug Administration, HHS, 2009, Code of Federal Regulation § 820.30, Subpart C-Design Controls, pp. 147-148.
Freestyle Libre Pro Flash Glucose Monitoring System Summary of Safety and Effectiveness Data, 2016, 31 pages.
FreeStyle Lite Blood Glucose Monitoring System Owner's Booklet, 2006, 15 pages.
FreeStyle Navigator Continuous Glucose Monitoring System FDA Premarket Approval (PMA), 2008, pp. 1-7.
Hemmerich, K. J., et al., "Sterilization Methods Stand the Test of Time", 2004, retrieved from https://www.mddionline.com/sterilization/sterilization-methods-stand-test-time, pp. 1-8.
Hirsch, I. B., "Realistic Expectations and Practical Use of Continuous Glucose Monitoring for the Endocrinologist", The Journal of Clinical Endocrinology & Metabolism, 2009, VI. 94, No. 7, pp. 2232-2238.
Hoss, U., et al., "Continuous glucose monitoring in the tissue: Do we really need to calibrate in-vivo?", Feb. 28, 2009, pp. 1-21.
Hoss, U., et al., "Continuous Glucose Monitoring in Subcutaneous Tissue Using Factory-Calibrated Sensors: A Pilot Study", Diabetes Technology & Therapeutics, 2010, vol. 12, No. 8, pp. 591-597.
Hoss, U., et al., "Feasibility of Factory Calibration for Subcutaneous Glucose Sensors in Subjects With Diabetes", Journal of Diabetes Science and Technology, 2014, vol. 8, No. 1, pp. 89-94.
"Housing", "recess", "release", and "retain", Merriam-Webster's Collegiate Dictionary, Tenth Edition, 1999, pp. 563, 975, 987, and 999.
"Housing" and "recess", The New Penguin English Dictionary, 2000, pp. 678 and 1167.
Hughes, M. D., "The Business of Self-Monitoring of Blood Glucose: A Market Profile", Journal of Diabetes Science and Technology, 2009, vol. 3, No. 5, pp. 1219-1223.
IEEE 100 The Authoritative Dictionary of IEEE Standards Terms, Seventh Edition, 2000, 3 pages.
International Standard, ISO 14971, Medical devices—Application of risk management to medical devices, 2007, 90 pages.
"An Interview with Kevin Sayer, President and CEO of Dexcom, About The New G6", 2021, 5 pages.
Klueh, U., et al., "Inflammation and Glucose Sensors: Use of Dexamethasone to Extend Glucose Sensor Function and Life Span in Vivo", Journal of Diabetes Science and Technology, 2007, vol. 1, No. 4, pp. 496-504.
Klueh, U., et al., "Blood-Induced Interference of Glucose Sensor Function in Vitro: Implications for in Vivo Sensor Function", Journal of Diabetes Science and Technology, 2007, vol. 1, No. 6, pp. 842-849.
Medtronic Guardian® REAL-Time Continuous Glucose Monitoring System User Guide, 2006, pp. 1-181.
Medtronic MiniMed Guardian RT FDA Premarket Approval (PMA), 2005, pp. 1-6.
Medtronic MiniMed Guardian RT Summary of Safety and Effectiveness Data, 2005, 13 pages.
Medtronic MiniMed Paradigm® REAL-Time 522 and 722 Insulin Pumps User Guide, 2008, pp. 1-262.
Occupational Safety and Health Admin., Labor, 2003, 29 CFR § 1910.1030 Bloodborne pathogens, pp. 260-273.
Omnipod image, Exhibit 182 of ADC Reply Brief SJ, Daubert, Sep. 22, 2022, 2 pages.

(56) References Cited

OTHER PUBLICATIONS

One Touch® Ultra™ Blood Glucose Monitoring System Owner's Booklet, 2000, 23 pages.
One Touch Ultra2 Blood Glucose Monitoring System Owner's Booklet, 2005, 34 pages.
Order, Federal Communications Commission, 2006, pp. 1-8.
Panteleon, A. E., et al., "The Role of the Independent Variable to Glucose Sensor Calibration", Diabetes Technology & Therapeutics, 2003, vol. 5, No. 3, pp. 401-410.
Parker, S. P., ed., McGraw-Hill Dictionary of Mechanical and Design Engineering, 1984 (excerpted), pp. 1-4.
Program, 2nd International Conference on Advanced Technologies & Treatments for Diabetes, Athens, Greece, 2009, 3 pages.
"Recess", Cambridge Dictionary of American English, 2000, pp. 710-711.
"Retract", The Chambers Dictionary, 1998, p. 1410.
"Retract", The New Oxford American Dictionary, 2001, p. 1455.
"Retract", Webster's Third New International Dictionary, 1993, pp. 1939-1940.
Shenoi, B. A., ed., Introduction to Digital Signal Processing and Filter Design, 2006, "Introduction", Chapter 1, pp. 1-30.
Smith, S. S., ed., The Scientist and Engineer's Guide to Digital Signal Processing, Second Edition, 1997-1999, "Digital Signal Processors", Chapter 28, pp. 503-534.
"Submission and Review of Sterility Information in Premarket Notification (510(k)) Submissions for Devices Labeled as Sterile, Guidance for Industry and Food and Drug Administration Staff", 2016, pp. 1-11.
Tegnestedt, C., et al., "Levels and sources of sound in the intensive care unit—an observational study of three room types", Acta Anaesthiesiologica Scandinavica, 2013, pp. 1-10.
CA, 2,617,192 Examiner's Report, Oct. 22, 2012.
CA, 2,984,939 Examiner's Report, Nov. 15, 2023.
CA, 3,182,961 Examiner's Report, Dec. 6, 2023.
CN, 200780039416.2 Second Office Action, Apr. 25, 2012.
CN, 200780039416.2 First Office Action, Mar. 30, 2011.
CN, 200880005388.7 Second Office Action, May 16, 2012.
CN, 200880005388.7 First Office Action, Jul. 25, 2011.
CN, 201980082748.1 Final Office Action, Nov. 27, 2023.
CN, 201980082748.1 Second Office Action, Jul. 10, 2023.
EP, 06788869.3 Examination Report, Sep. 25, 2012.
EP, 06788869.3 Extended Search Report, Mar. 18, 2010.
EP, 06813967.4 Extended Search Report, Mar. 4, 2010.
EP, 07854298.2 Extended Search Report, Mar. 29, 2010.
EP, 08730066.1 Extended Search Report, Oct. 5, 2012.
EP, 10739031.2 Communication from Board of Appeals, Feb. 21, 2024.
EP, 18741791.0 Examination Report, Dec. 15, 2023.
EP, 20177703.4 Reply to Reply to Reply to Notice of Opposition ADC, Dec. 18, 2023.
EP, 20177703.4 Reply to Notice of Intervention, Nov. 17, 2023.
EP, 20177712.5 Reply to Reply to Reply to Notice of Opposition ADC, Dec. 18, 2023.
EP, 20177712.5 Reply to Notice of Intervention, Nov. 17, 2023.
EP, 20177712.5 Reply to Reply to Notice of Opposition Dexcom, Sep. 27, 2023.
EP, 20177712.5 Reply to Reply to Notice of Opposition Gulde & Partner Patent, Aug. 30, 2023.
EP, 20195922.8 Response to Summons to Attend Oral Proceedings, Feb. 15, 2024.
EP, 20195922.8 Written Submissions Dexcom, Dec. 12, 2023.
EP, 20195922.8 Written Submissions ADC, Oct. 23, 2023.
EP, 20195922.8 Summons to Attend Oral Proceedings, Sep. 21, 2023.
EP, 20195922.8 Reply to Notice of Intervention, Aug. 29, 2023.
EP, 20195922.8 Reply to Reply to Notice of Opposition, Aug. 21, 2023.
EP, 20195922.8 Reply to Notice of Opposition, Jun. 20, 2023.
EP, 23166498.8 Extended Search Report, Nov. 17, 2023.
EP, 23190032.5 Extended Search Report, Nov. 17, 2023.

JP, 2009-534799 Final Office Action, Feb. 19, 2013.
JP, 2009-534799 Office Action, Sep. 27, 2011.
JP, 2021-531135 Office Action, Aug. 9, 2023.
MX, MX/a/2009/004322 Office Action, Mar. 11, 2013.
MX, MX/a/2009/004322 Office Action, Sep. 19, 2012.
MY, PI2023005466 Examination Report, Dec. 28, 2023.
RU, 2009119430 Office Action, Jun. 5, 2011.
RU, 2009135048 Office Action, Dec. 20, 2011.
US, Third Declaration of Gary Fletcher, Ph.D., IPR No. 2024-00520, Jan. 31, 2024.
US, Petition For Inter Partes Review Of U.S. Pat. No. 11,266,335, IPR No. 2024-00520, Jan. 31, 2024.
US, Petition For Inter Partes Review Of U.S. Pat. No. 11,202,591, IPR No. 2023-01409, Oct. 11, 2023.
US, Petitioner's Explanation of Material Differences Between Petitions, IPR No. 2023-01397, Oct. 6, 2023.
US, Declaration of Gary D. Fletcher, Ph.D, IPR No. 2023-01396 and IPR No. 2023-01397, Oct. 6, 2023.
US, Petition For Inter Partes Review Of U.S. Pat. No. 11,266,335, IPR No. 2023-01397, Oct. 6, 2023.
US, Petitioner's Explanation of Material Differences Between Petitions, IPR No. 2023-01396, Oct. 6, 2023.
US, Petition For Inter Partes Review Of U.S. Pat. No. 11,266,335, IPR No. 2023-01396, Oct. 6, 2023.
US, Notice of Final Written Decision re Inter Partes Review of the '649 Patent, IPR No. 2022-00605, Jul. 13, 2023.
US, Record of Oral Hearing, IPR No. 2022-00605, Apr. 26, 2023.
US, Petitioner's Reply to Patent Owner's Response to Petition, IPR No. 2022-00605, Jan. 11, 2023.
US, Supplemental Declaration of Gary D. Fletcher, Ph.D, IPR No. 2022-00605, Jan. 11, 2023.
US, Second Declaration by Dr. Michael Cima in Support of Patent Owner's Response, IPR No. 2022-00605, Oct. 19, 2022.
US, Patent Owner's Response, IPR No. 2022-00605, Oct. 19, 2022.
US, Reexamination U.S. Appl. No. 90/019,331 Order Granting Request for Reexamination of U.S. Pat. No. 11,013,440, Jan. 23, 2024.
US, Request for Ex Parte Reexamination Under 35.U.S.C. §§ 302-307 and 37 C.F.R. § 1.510 of U.S. Pat. No. 11,013,440., Dec. 11, 2023.
US, Request for Ex Parte Reexamination Under 35.U.S.C. §§ 302-307 and 37 C.F.R. § 1.510 of U.S. Pat. No. 11,000,216, Dec. 11, 2023.
US, Reexamination U.S. Appl. No. 90/019,307 Order Granting Request for Reexamination of U.S. Pat. No. 10,973,443, Dec. 22, 2023.
US, Request for Ex Parte Reexamination Under 35.U.S.C. §§ 302-307 and 37 C.F.R. § 1.510 of U.S. Pat. No. 10,973,443, Nov. 27, 2023.
US, Request for Ex Parte Reexamination Under 35.U.S.C. §§ 302-307 and 37 C.F.R. § 1.510 of U.S. Pat. No. 10,959,654, Dec. 11, 2023.
WO, PCT/US2006/029541 ISR and Written Opinion, Apr. 24, 2007.
WO, PCT/US2006/033885 ISR and Written Opinion, Aug. 3, 2007.
WO, PCT/US2007/082121 ISR and Written Opinion, May 9, 2008.
WO, PCT/US2008/054186 ISR and Written Opinion, Aug. 8, 2008.
WO, PCT/US2008/065154 ISR and Written Opinion, Sep. 3, 2008.
WO, PCT/US2010/047065 ISR and Written Opinion, Dec. 21, 2010.
WO, PCT/US2010/047414 ISR and Written Opinion, Dec. 27, 2010.
WO, PCT/US2010/047415 ISR and Written Opinion, Oct. 25, 2010.
CA, 2,984,939 Examiner's Report, Aug. 7, 2024.
CA, 3,120,335 Examiner's Report, May 27, 2024.
CN, 200880005149.1 Notice of Allowance, Jun. 21, 2013.
CN, 200880005149.1 Fourth Office Action, Dec. 3, 2012.
CN, 200880005149.1 Third Office Action, Feb. 16 2012.
CN, 200880005149.1 Second Office Action, Aug. 17, 2011.
CN, 200880005149.1 First Office Action, Jul. 29, 2010.
DE, Complaint in Litigation of EP 3300658, Mar. 20, 2024.
EP, 10739031.2 Decision of Oral Proceedings, Jun. 11, 2024.
EP, 10739031.2 Minutes of Oral Proceedings, May 10, 2024.
EP, 17182379.2 Grounds of Opposition, Jul. 12, 2024.

(56) References Cited

OTHER PUBLICATIONS

EP, 17182379.2 Notice of Opposition, Jul. 12, 2024.
EP, 17182379.2 Reply to Examination Report, Apr. 9, 2021.
EP, 17182379.2 Reply to Search Report, Oct. 3, 2018.
EP, 20177703.4 Summons to Attend Oral Proceedings, Apr. 29, 2024.
EP, 20177712.5 Summons to Attend Oral Proceedings, Jul. 2, 2024.
EP, 20177712.5 Response to Written Submissions Dexcom, Feb. 26, 2024.
EP, 20177712.5 Written Submissions ADC, Jan. 26, 2024.
EP, 20195922.8 Notice of Appeal, Jul. 4, 2024.
EP, 20195922.8 Written Submissions Dexcom, May 9, 2024.
EP, 20195922.8 Decision Revoking the European Patent, May 8, 2024.
EP 20195922.8 Minutes of the Oral Proceedings, May 8, 2024.
EP, 20195922.8 Written Submissions Dexcom, Mar. 15, 2024.
EP, 21211041.5 Reply to Notice of Opposition, Jul. 17, 2024.
EP, 21211041.5 Grounds of Opposition Dexcom, Mar. 28, 2024.
EP, 21211041.5 Notice of Opposition Dexcom, Mar. 28, 2024.
EP, 24152079.0 Partial Search Report, Jun. 14, 2024.
GB, Claim No. HP-2021-000025 Approved Judgement, Oct. 18, 2023.
RU, 2009134334 Office Action, Feb. 7, 2012.
UP, First Expert Opinion of Dr Michael Schoemaker of Litigation of EP 3977921, Jun. 11, 2024.
US, Notice of Filing Date Accorded to Petition and Time for Filing Patent Owner Preliminary Response, IPR No. 2024-00860, May 23, 2024.
US, Declaration of Dr. Cameron Riviere, Ph.D., IPR No. 2024-00860, May 9, 2024.
US, Petition For Inter Partes Review Of U.S. Pat. No. 11,510,625, IPR No. 2024-00860, May 9, 2024.
US, Decision Denying Institution of Inter Partes Review, IPR No. 2024-00520, Aug. 8, 2024.
US, Patent Owner's Authorized Sur-Reply to Petitioner's Reply to Patent Owner's Preliminary Response, IPR No. 2024-00520, Jun. 11, 2024.
US, Petitioner's Authorized Reply to Patent Owner's Preliminary Response, IPR No. 2024-00520, May 31, 2024.
US, Patent Owner's Preliminary Response, IPR No. 2024-00520, May 8, 2024.
US, Patent Owner's Exhibit List, IPR2024-00520, Mar. 25, 2024.
US, Telephonic Hearing, IPR2024-00520, Mar. 13, 2024.
US, Petitioner's Explanation of Material Differences Between the Petition in IPR2024-00520 and Previously Filed Petitions in IPR2023-01396 and IPR2023-01397, IPR No. 2024-00520, Jan. 31, 2024.
US, Order, IPR No. 2023-01409, May 30, 2024.
US, Notice of Stipulation, IPR No. 2023-01409, May 29, 2024.
US, Patent Owner's Objections to Petitioner's Exhibits to the Petition, IPR No. 2023-01409, Apr. 29, 2024.
US, Patent Owner's Request for Rehearing by the Director, IPR 2023-01409, Apr. 29, 2024.
US, Email of Peter McAndrews, IPR 2023-01409, Apr. 29, 2024.
US, Decision Granting Institution of Inter Partes Review, IPR No. 2023-01409, Apr. 15, 2024.
US, Scheduling Order, IPR 2023-01409, Apr. 15, 2024.
US, Order Conduct of the Proceeding 37 C.F.R. § 42.5, IPR No. 2023-01409, Feb. 6, 2024.
US, Telephonic Conference Call, IPR No. 2023-01409, Feb. 6, 2024.
US, Petitioner's Updated Exhibit List, IPR No. 2023-01409, Feb. 5, 2024.
US, Patent Owner's Updated Mandatory Notices, IPR No. 2023-01409, Feb. 2, 2024.
US, Email of Andrew M. Mason, IPR 2023-01409, Jan. 30, 2024.
US, Patent Owner's Preliminary Response, IPR No. 2023-01409, Jan. 18, 2024.
US, Notice of Filing Date Accorded to Petition and Time for Filing Patent Owner Preliminary Response, IPR No. 2023-01409, Oct. 18, 2023.

US, Decision Denying Institution of Inter Partes Review, IPR No. 2023-01397, Apr. 16, 2024.
US, Patent Owner's Updated Exhibit List, IPR2023-01397, Mar. 25, 2024.
US, Telephonic Hearing, IPR2023-01397, Mar. 13, 2024.
US, Petitioner's Updated Mandatory Notices Pursuant to 37 C.F.R. § 42.8(a)(3), IPR No. 2023-01397, Feb. 19, 2024.
US, Patent Owner's Updated Mandatory Notices, IPR No. 2023-01397, Feb. 2, 2024.
US, Patent Owner's Preliminary Response, IPR No. 2023-01397, Jan. 18, 2024.
US, Patent Owner's Response to Petitioner's Explanation of Material Differences Between Petitions, IPR Nos. 2023-01396 and 2023-01397, Jan. 18, 2024.
US, Petitioner's Request for Rehearing of Decision Denying Institution, IPR No. 2023-01396, May 16, 2024.
US, Decision Denying Institution of Inter Partes Review, IPR No. 2023-01396, Apr. 16, 2024.
US, Patent Owner's Updated Exhibit List, IPR No. 2023-01396, Mar. 25, 2024.
US, Telephonic Hearing, IPR2023-01396, Mar. 13, 2024.
US, Petitioner's Updated Mandatory Notices Pursuant to 37 C.F.R. § 42.8(a)(3), IPR No. 2023-01396, Feb. 19, 2024.
US, Patent Owner's Preliminary Response, IPR No. 2023-01396, Jan. 18, 2024.
US, Notice of Filing Date Accorded to Petition and Time for Filing Patent Owner Preliminary Response, IPR No. 2023-01396, Oct. 18, 2023.
US, Reexamination U.S. Appl. No. 90/019,329 Notification of Concurrent Proceedings, May 15 2024.
US, Petition Under 37 CFR § 1.181 and/or § 1.182 to Terminate Reexamination No. U.S. Appl. No. 90/019,329, Apr. 26, 2024.
US, Reexamination U.S. Appl. No. 90/019,329 Order Granting Request for Reexamination of U.S. Pat. No. 11,013,440, Jan. 30, 2024.
US, Reexamination U.S. Appl. No. 90/019,329 Declaration of Gary D. Fletcher, Ph.D., Dec. 11, 2023.
US, Reexamination U.S. Appl. No. 90/019,331 Notice of Intent to Issue Ex Parte Reexamination Certificate, Jul. 10, 2024.
US,Reexamination U.S. Appl. No. 90/019,331 Notification of Concurrent Proceedings, May 15, 2024.
US, Reexamination U.S. Appl. No. 90/019,331 Order Granting Request for Reexamination of U.S. Pat. No. 11,000,216, Jan. 23, 2024.
US, Reexamination U.S. Appl. No. 90/019,330 Notification of Concurrent Proceedings, May 15, 2024.
US, Reexamination U.S. Appl. No. 90/019,330 Order Granting Request for Reexamination of U.S. Pat. No. 10,959,654, Jan. 23, 2024.
US, Reexamination U.S. Appl. No. 90/019,330 Declaration of John Mastrototaro, Ph.D., Dec. 11, 2023.
WO, PCT/US2008/054165 ISR and Written Opinion, Jun. 5, 2008.
WO, PCT/US2008/067791 ISR and Written Opinion, Sep. 30, 2008.
WO, PCT/US24/11756 ISR and Written Opinion, Jun. 28, 2024.
WO, PCT/US24/11756 Invitation to Pay Additional Fees, May 7, 2024.
WO, PCT/US24/16127 Invitation to Pay Additional Fees, Jun. 4, 2024.
WO, PCT/US24/18665 ISR and Written Opinion, Jun. 21, 2024.
"27 Winners Announced at the 19th Annual Medical Design Excellence Awards (MDEA) Award Ceremony", UBM Americas, 2017, 4 pages.
"55 Chosen as Winners in Annual BIG Innovation Awards", 2018, retrieved from https://www.bintelligence.com/posts/55-chosen-as-winners-in-annual-big-innovation-awards, 2 pages.
2017 Good Design Award, retrieved from https://www.g-mark.org/gallery/winners/9dda01a3-803d-11ed-af7e-0242ac130002, 9 pages.
"2019 Top 10 Innovations", The Scientist, retrieved from https://www.the-scientist.com/2019-top-10-innovations-66738, 7 pages.
Abbott 2023 Annual Report, retrieved from https://www.abbottinvestor.com/static-files/6cb09c09-2422-40e0-a24b-6545ffcf5267, pp. 1-82.
Abbott Clinical Trials Competitor and Ecosystem Players, 2020, 28 pages.

(56)  References Cited

OTHER PUBLICATIONS

"Abbott's Freestyle Libre® Is Named Best Medical Technology In Last 50 Years By The Galien Foundation", 2022, PRNewswire, 1 page.
"Abbott's Freestyle® Libre 2 ICGM Cleared in U.S. for Adults and Children With Diabetes, Achieving Highest Level of Accuracy and Performance Standards", retrieved from https://abbott.mediaroom.com/2020-06-15-Abbotts-FreeStyle-R-Libre-2-iCGM-Cleared-in-U-S-for-Adults-and-Children-with-Diabetes-Achieving-Highest-Level-of-Accuracy-and-Performance-tandards#:~:text=FDA%20clears%20Abbott's%20FreeStyle%20Libre,high%20or%20low%20without%20scanning, on Jul. 7, 2024, 3 pages.
"Abbott's Freestyle LibreR 3 Receives U.S. FDA Clearance—Features World's Smallest, Thinnest and Most Accurate 14-Day Glucose Sensor", 2022, PRNewswire, 3 pages.
"Abbott's Freestyle Libre Flash Glucose Monitoring System Wins the IMSTA Most Innovative Product Multi-National Award 2017", retrieved from https://www.ie.abbott/media-center/news/abbotts-freestyle-libre-flash-glucose-monitoring-system-wins-the-imsta-award-2017.html, 2 pages.
"Abbott's Freestyle® Libre 14 Day Flash Glucose Monitoring System Now Approved in U.S.", 2018, PRNewswire, 2 pages.
About the Edison Awards retrieved from https://edisonawards.com/about/, 2024, 3 pages.
Ahn, D., "Abbott's Euro approved wearable glucose monitor is different than anything on the market", 2014, retrieved from https://www.imedicalapps.com/2014/09/abbotts-wearable-glucose-monitor/, 6 pages.
"BinaxNOW, FreeStyle Libre 2 win BIG innovation honors", 2021, retrieved from https://www.abbott.com/corpnewsroom/strategy-and-strength/binaxnow-freestyle-libre-win-big-innovation-honors.html, 6 pages.
Blum, A., "Freestyle Libre Glucose Monitoring System", Clinical Pharmacology Update, 2018, vol. 36, No. 2, pp. 203-204.
Cather, D. E., "CGM Frustrations Survey", 2020, 36 pages.
Certified U.S. Appl. No. 61/149,639, filed Feb. 3, 2009.
CES 2022 Innovation Award Honorees, retrieved from https://www.ces.tech/innovation-awards/honorees/2022/best-of/f/freestyle-libre-3-system.aspx, 1 page.
2019 Chicago Innovation Award Winner Abbott Laboratories, retrieved from https://chicagoinnovation.com/winners/abbott-laboratories/, 4 pages.
Continuous Glucose Monitoring Systems Product Reference Guide, Diabetes Health, 2006-2007, pp. 50-51.
Das, S. D., et al., "Review—Electrochemistry and Other Emerging Technologies for Continuous Glucose Monitoring Devices", ECS Sensors Plus, 2022, 19 pages.
Design Concepts Project Status Update, Glucose Sensor Applicator Dexcom (project #2554), 2014, 5 pages.
Dexcom G5 Quick Start Guide, 2020, pp. 1-31.
Dexcom G6 Continuous Glucose Monitoring System User Guide, 2022, 346 pages.
Dexcom G6 Start Here Set up Guide, 2022, pp. 18 pages.
"The Dexcom G7. The most accurate CGM system.1" retrieved from https://www.dexcom.com/g7-cgm-system on Jun. 27, 2024, 20 pages.
Dexcom G7 Continuous Glucose Monitoring (CGM) System Section 510(k) Approval, 2022, 10 pages.
Dexcom G7 User Guide, 2024, p. i-186.
Edison Awards Announces 2016 Gold, Silver, and Bronze Awards Winners, Edison Awards, 9 pages.
Edison Best New Product Awards™ 2021 Winners retrieved from https://edisonawards.com/2021-winners/, 19 pages.
Edison Best New Product Awards™ 2022 Winners retrieved from https://edisonawards.com/2022-winners/, 52 pages.
Email from Christopher M Dougherty dated Dec. 17, 2019, 68 pages.
Englert, K., et al., "Skin and Adhesive Issues With Continuous Glucose Monitors: A Sticky Situation", Journal of Diabetes Science and Technology, 2014, vol. 8, No. 4, pp. 745-751.

Explore The Monroe Street Market Community, retrieved from https://www.monroestreetmarket.com/floor-plans/apartment/B-231 on May 10, 2023, 2 pages.
Freestyle Libre Brochure, 2016, 10 pages.
Freestyle Libre Fact Sheet, 2016, retrieved from www.FreeStyleLibre.de, 2 pages.
Freestyle Libre FAQ, 2024, retrieved from https://www.freestyle.abbott/uk-en/support/faq/question-answer.html?q=UKFaqquestion-55#, 2 pages.
"FreeStyle Libre Honored by Prix Galien", 2019, 4 pages.
FreeStyle Libre In-Service Guide, 2021, 28 pages.
FreeStyle Libre 2 Get Started Guide, 2023, pp. 1-28.
FreeStyle Libre 3 Get Started Guide, 2023, pp. 1-20.
FreeStyle Libre 3 User's Manual, 2022-2023, pp. iv-241.
The Galien Foundation is proud to announce the laureates of the best-of-the-best from the half century 1970-2020, The 2022 Galien Golden Jubilee Winners, retrieved from https://www.galienfoundation.org/galien-golden-jubilee, 3 pages.
Gough, D. A., et al., "Development of the Implantable Glucose Sensor: What Are the Prospects and Why Is It Taking So Long?", Diabetes, 1995, vol. 44, pp. 1005-1009.
Harris, J. M., et al., "Common Causes of Glucose Oxidase Instability in In Vivo Biosensing: A Brief Review", Journal of Diabetes Science and Technology. 2013, vol. 7, No. 4, pp. 1030-1038.
Hermanides, J., et al., "Current Application of Continuous Glucose Monitoring in the Treatment of Diabetes", Diabetes Care, 2011, vol. 34, Suppl. 2, pp. S197-S201.
Hovorka, R., "Continuous glucose monitoring and closed-loop systems", Diabetic Medicine, 2005, vol. 23, pp. 1-12.
Insert Molding, 1996, retrieved from https://www.mddionline.com/equipment/insert-molding, 4 pages.
International Diabetes Device 2022 Blue Book, Seagrove Partners, 142 pages.
Joseph, J. I., et al., "Glucose Sensing in the Subcutaneous Tissue: Attempting to Correlate the Immune Response with Continuous Glucose Monitoring Accuracy", Diabetes Technology & Therapeutics, 2018, vol. 20, No. 5, pp. 321-324.
Lomas, P., "Dexcom G7 Release: The Most Exciting New Features", 2024, retrieved from https://notjustapatch.com/dexcom-g7-features/, 13 pages.
Lovett, L., "What's next for Dexcom? CEO, CTO talk G6 for inpatient use, expanding CGMs for patients without diabetes", 2020, retrieved from https://www.mobihealthnews.com/news/whats-next-dexcom-ceo-cto-talk-g6-inpatient-use-expanding-cgms-patients-without-diabetes, 6 pages.
Medtronic Enlite Serter User Guide, 2014, 26 pages.
Medtronic MiniMed iPro2 User Guide, 2010, pp. 1-99.
Meltsner, M A, et al., "Observations on rotating needle insertions using a brachytherapy robot", Phys. Med. Biol., 2007, vol. 52, pp. 6027-6037.
Nichols, S. P., et al., "Biocompatible Materials for Continuous Glucose Monitoring Devices", Chem Rev., 2013, vol. 113, No. 4, pp. 2528-2549.
Ólafsdottir, A. F., et al., "A Clinical Trial of the Accuracy and Treatment Experience of the Flash Glucose Monitor FreeStyle Libre in Adults with Type 1 Diabetes", Diabetes Technology & Therapeutics, 2017, vol. 19, No. 3, pp. 164-172.
"Periphery", Cambridge Dictionary of American English, 2000, p. 631.
"Product Review: Abbott FreeStyle Libre Flash Glucose Monitor", DiabetesMine Team, 2021, retrieved from https://www.healthline.com/diabetesmine/abbott-freestyle-libre-review#bottom-line, 6 pages.
"Real-World Data Show Abbott's Freestyle LibreR Systems And GLP-1 Medicines Work Better Together For People With Type 2 Diabetes", 2024, PRNewswire, 2 pages.
Rice, M. J., et al., "Continuous Measurement of Glucose: Facts and Challenges", Anesthesiology, 2012, vol. 116, No. 1, pp. 199-204.
Rigo, R. S., et al., "Cutaneous Reactions to Continuous Glucose Monitoring and Continuous Subcutaneous Insulin Infusion Devices in Type 1 Diabetes Mellitus", Journal of Diabetes Science and Technology, 2021, vol. 15, No. 4, pp. 786-791.

(56) References Cited

OTHER PUBLICATIONS

Rocchitta, G., et al., "Enzyme Biosensors for Biomedical Applications: Strategies for Safeguarding Analytical Performances in Biological Fields", Sensors, 2016. vol. 16, No. 6, 21 pages.
Sclater, N., et al., eds., Mechanisms and Mechanical Devices Sourcebook, Fourth Edition, 2007, Chapter 12—Shaft Couplings and Connections, pp. 290-307.
"Transcutaneous", Webster's Third New International Dictionary, 2002, p. 2426.
Tsumura, R., et al., "Histological Evaluation of Tissue Damage Caused by Rotational Needle Insertion", Proceedings of the Annual International Conference of the IEEE Engineering in Medicine and Biology Society, 2016, pp. 5120-5123.
Van Den Boom, L., et al., "Changes in the utilization of blood glucose test strips among patients using intermittent-scanning continuous glucose monitoring in Germany", Diabetes, Obesity and Metabolism, 2020, vol. 22, pp. 922-928.
Watkin, J., "An Introduction to Flash Glucose Monitoring", 2013, 14 pages.
Xu, J., et al., "Anti-Biofouling Strategies for Long-Term Continuous Use of Implantable Sensors", Chemosensors, 2020, vol. 20 No. 3, 29 pages.
CA, 3,050,721 Examiner's Report, Nov. 8, 2024.
EP, 19151577.4 Examination Report, Oct. 7, 2024.
EP, 20177712.5 Summons to Attend Oral Proceedings, Oct. 1, 2024.
EP, 20177712.5 Response to Summons to Attend Oral Proceedings, Aug. 30, 2024.
EP, 20195922.8 Grounds of Appeal, Sep. 6, 2024.
EP, 21211041.5 Response to Summons to Attend Oral Proceedings Dexcom, Nov. 12, 2024.
EP, 21211041.5 Response to Summons to Attend Oral Proceedings, Nov. 12, 2024.
EP, 21211041.5 Summons to Attend Oral Proceedings, Sep. 23, 2024.
EP, 23166498.8 Examination Report, Sep. 2, 2024.
EP, 24152079.0 Extended Search Report, Sep. 4, 2024.
EP, 24183336.7 Extended Search Report, Oct. 11, 2024.
EP, 24187206.8 Extended Search Report, Oct. 9, 2024.
MX, MX/a/2021/007294 Office Action, Aug. 20, 2024.
US Declaration of Karl R. Leinsing, MSME, PE, IPR No. 2023-01409, Jul. 19, 2024.
US, Patent Owner's Response, IPR No. 2023-01409, Jul. 19, 2024.
US, Deposition of Gary Fletcher, Ph.D., IPR No. 2023-01409, Jun. 26, 2024.
US, Reexamination U.S. Appl. No. 90/019,329 Ex Parte Reexamination Certificate, Oct. 30, 2024.
US, Reexamination U.S. Appl. No. 90/019,329 Notice of Intent to Issue Ex Parte Reexamination Certificate, Oct. 8, 2024.
US, Reexamination U.S. Appl. No. 90/019,329 Decision on Petition Under 37 C.F.R. § 1.59, Sep. 16, 2024.
US, Reexamination U.S. Appl. No. 90/019,329 Statutory disclaimer per Manual of Patent Examining Procedure (MPEP) 1490, Sep. 3, 2024.
US, Reexamination U.S. Appl. No. 90/019,329 Petition Under 37 C.F.R. § 1.182 to Seal Document Versions Filed via IDS and Substitute Redacted Document Versions Therfor, Aug. 1, 2024.
US, Reexamination No. U.S. Appl. No. 90/019,329 Petition Under 37 CFR § 1.59 to Expunge Application Papers, Aug. 1, 2024.
US, Reexamination No. U.S. Appl. No. 90/019,329 Ex Parte Reexamination Interview Summary, Jul. 25, 2024.
US, Reexamination U.S. Appl. No. 90/019,329 Decision on Petition Under 37 C.F.R. § 1.59, Jul. 22, 2024.
US, Reexamination U.S. Appl. No. 90/019,329 Decision Sua Sponte Vacating Notice of Intent to Issue Ex Parte Reexamination Certificate, Jul. 3, 2024.
US, Reexamination U.S. Appl. No. 90/019,329 Petition Under 37 CFR § 1.59 to Expunge Application Papers, Jun. 12, 2024.
US, Reexamination U.S. Appl. No. 90/019,331 Ex Parte Reexamination Certificate, Nov. 14, 2024.
US, Reexamination U.S. Appl. No. 90/019,331 Notice of Intent to Issue Ex Parte Reexamination Certificate, Oct. 15, 2024.
US, Reexamination U.S. Appl. No. 90/019,331 Decision on Petition Under 37 C.F.R. § 1.59, Sep. 16, 2024.
US, Reexamination U.S. Appl. No. 90/019,331 Decision Granting Petition, Aug. 26, 2024.
US, Reexamination U.S. Appl. No. 90/019,331 Petition Under 37 C.F.R. § 1.182 to Seal Document Versions Filed via IDS and Substitute Redacted Document Versions Therfor, Aug. 1, 2024.
US, Reexamination U.S. Appl. No. 90/019,331 Petition Under 37 CFR § 1.59 to Expunge Application Papers Aug. 1, 2024.
US, Reexamination U.S. Appl. No. 90/019,331 Petition to Withdraw From Issue and Reopen the Proceeding, Jul. 26, 2024.
US, Reexamination U.S. Appl. No. 90/019,331 Decision on Petition Under 37 C.F.R. § 1.59, Jul. 16, 2024.
US, Reexamination U.S. Appl. No. 90/019,331 Petition Under 37 CFR § 1.59 to Expunge Application Papers, Jun. 12, 2024.
US, Reexamination U.S. Appl. No. 90/019,307 Petition Under 37 CFR § 1.181 to Terminate, Aug. 15, 2024.
US, Reexamination U.S. Appl. No. 90/019,307 Decision on Petitions, Aug. 7, 2024.
US, Reexamination U.S. Appl. No. 90/019,307 Petition Under 37 CFR § 1.59 to Expunge Application Papers, Aug. 1, 2024.
US, Reexamination U.S. Appl. No. 90/019,307 Petition Under 37 CFR § 1.59 to Expunge Application Papers, Jun. 12, 2024.
US, Reexamination U.S. Appl. No. 90/019,307 Notification of Concurrent Proceedings, May 15, 2024.
US, Reexamination U.S. Appl. No. 90/019,307 Petition Under 37 CFR §§ 1.182 and/or § 1.183 to Allow Filing and Consideration of Response to Patent Owner's Extraordinary Petition to Suspend, Mar. 19, 2024.
US, Reexamination U.S. Appl. No. 90/019,307 Petition Under 37 CFR § 1.181 and/or § 1.183 to Suspend, Mar. 1, 2024.
US, Ex Parte Reexamination Certificate of U.S. Pat. No. 10,959,654, Nov. 5, 2024.
US, Reexamination U.S. Appl. No. 90/019,330 Notice of Intent to Issue Ex Parte Reexamination Certificate, Oct. 7, 2024.
US, Reexamination U.S. Appl. No. 90/019,330 Decision on Petition Under 37 C.F.R. § 1.59, Sep. 16, 2024.
US, Reexamination U.S. Appl. No. 90/019,330 Decision Granting Petition and Vacating a Reexamination Certificate, Aug. 26, 2024.
US, Ex Parte Reexamination Certificate of U.S. Pat. No. 10,959,654, Aug. 5, 2024.
US, Reexamination U.S. Appl. No. 90/019,330 Petition Under 37 C.F.R. § 1.182 to Seal Document Versions Filed via IDS and Substitute Redacted Document Versions Therfor, Aug. 1, 2024.
US, Reexamination U.S. Appl. No. 90/019,330 Petition Under 37 CFR § 1.59 to Expunge Application Papers, Aug. 1, 2024.
US, Reexamination U.S. Appl. No. 90/019,330 Petition to Withdraw From Issue and Reopen the Proceeding, Jul. 26, 2024.
US, Reexamination U.S. Appl. No. 90/019,330 Decision on Petition Under 37 C.F.R. § 1.59, Jul. 16, 2024.
US, Reexamination U.S. Appl. No. 90/019,330 Notice of Intent to Issue Ex Parte Reexamination Certificate of U.S. Pat. No. 10,959,654, Jul. 1, 2024.
US, Reexamination U.S. Appl. No. 90/019,330 Petition Under 37 CFR § 1.59 to Expunge Application Papers, Jun. 12, 2024.
WO, PCT/US24/16127 ISR and Written Opinion, Sep. 11, 2024.
ACCU-CHEK® Softclix Lancet Device retrieved from file:///C:/Users/afredericks/Downloads/softclix-user-manual.pdf, 2007, 2 pages.
Using your ACCU-CHEK® Multiclix Lancet Device, 2005, retrieved from https://www.northcoastmed.com/wp-content/uploads/2023/03/multiclix_userguide.pdf, 2 pages.
American National Standard, Ansi/Aami HE75:2009, Human factors engineering—Design of medical devices, 2010, 465 pages.
Automated Retractable VanishPoint Syringe 510(k) Safety and Effectiveness Summary, 1998, 5 pages.
"Bluetooth rival unveiled by Nokia", 2006, retrieved from news.bbc.co.uk/1/hi/technology/5403564.stm, 2 pages.
Breton, M., et al., "Fully Integrated Artificial Pancreas in Type 1 Diabetes: Modular Closed-Loop Glucose Control Maintains Near Normoglycemia", Diabetes, 2012, vol. 61, No. 9, pp. 2230-2237.
Dexcom G5 Mobile System User Guide, 2015, pp. 1-260.

(56) References Cited

OTHER PUBLICATIONS

Dexcom G6 Continuous Glucose Monitoring (CGM) System Section 510(k) Approval, 2022, 7 pages.
Freckmann, G., et al., "Performance Evaluation of Three Continuous Glucose Monitoring Systems: Comparison of Six Sensors per Subject in Parallel", Journal of Diabetes Science and Technology, 2013, vol. 7, No. 4, pp. 842-853.
FreeStyle Libre 2 HCP Pulse Report, 2021, 13 pages.
"FreeStyle Libre 2—Zucker messen ohne stechen per Sensor und App", German Innovation Awards Gold Winner, 2020, retrieved from https://www.german-innovation-award.de/preistraeger/preis/gewinner/freestyle-libre-2-zucker-messen-ohne-stechen-per-sensor-und-app/# :~:text=Beschreibung%20Die%20kontinuierliche%20Glukosemessung%20mit, um%20die%20Glukosewerte%20kontinuierlich%20aufzuzeichnen, 1 page.
International Standard, IEC 62366, Medical devices—Application of usability engineering to medical devices, 2007, 214 pages.
Kaye, R., et al., "Medical Device Use-Safety: Incorporating Human Factors Engineering into Risk Management", 2000, retrieved from https://www.qualysinnova.com/download/files/MD-Use-Safety.pdf, pp. 1-33.
Medtronic MiniMed Paradigm® 512 and 712 Insulin Pumps User Guide, 2005, pp. 1-136.
Microlet® 2 Lancing Device, 2008, retrieved from https://image.tigermedical.com/Manuals/BAY6606-20141216010820833.pdf, 1 page.
AU, 2019404908 Examiner's Report, Feb. 17, 2025.
CA, 3,228,738 Examiner's Report, May 8, 2025.
CN, 202180063087.5 First Office Action, Aug. 14, 2025.
CN, 202211091194.1 Notification of Filing Divisional Application, Mar. 27, 2025.
EP, 17182379.2 Written Submissions, Aug. 6, 2025.
EP, 17182379.2 Summons to Attend Oral Proceedings, Jul. 4, 2025.
EP, 17182379.2 Reply to Reply to Opposition, May 16, 2025.
EP, 17182379.2 Reply to Opposition, Feb. 27, 2025.
EP, 18741791.0 Examination Report, Sep. 12, 2025.
EP, 19151577.4 Examination Report, Sep. 3, 2025.
EP, 19900891.3 Examination Report, May 8, 2025.
EP, 20177703.4 Response to Withdrawals, Jan. 7, 2025.
EP, 20177703.4 Withdrawal of Intervention, Dec. 27, 2024.
EP, 20177703.4 Withdrawal of Opposition, Dec. 27, 2024.
EP, 20177703.4 Written Submissions Dexcom, Nov. 22, 2024.
EP, 20177712.5 Written Submissions Gulde, Aug. 21, 2025.
EP, 20177712.5 Response to Summons to Attend Oral Proceedings, Aug. 21, 2025.
EP, 20195922.8 Withdrawal of Intervention, Dec. 27, 2024.
EP, 20195922.8 Withdrawal of Opposition, Dec. 27, 2024.
EP, 21192910.4 Notice of Opposition Stolmar, Sep. 10, 2025.
EP, 21192910.4 Notice of Opposition Strawman, Sep. 10, 2025.
EP, 21211041.5 Grounds of Appeal, Apr. 23, 2025.
EP, 21211041.5 Withdrawal of Opposition, Dec. 27, 2024.
EP, 21211041.5 Notice of Appeal, Dec. 17, 2024.
EP, 21211041.5 Minutes of Oral Proceedings, Dec. 13, 2024.
EP, 23190032.5 Examination Report, May 19, 2025.
EP, 24152079.0 Examination Report, Dec. 2, 2024.
EP, 24194029.5 Examination Report, Aug. 26, 2025.
EP, 24194029.5 Extended Search Report, Nov. 18, 2024.
EP, 24201435.5 Extended Search Report, Jan. 27, 2025.
EP, 24218309.3 Extended Search Report, Jul. 9, 2025.
EP, 24220160.6 Extended Search Report, Jun. 17, 2025.
JP, 2023-514023 Final Office Action, Aug. 20, 2025.
JP, 2023-514023 Office Action, Apr. 16, 2025.
JP, 2023-514024 Office Action, Apr. 30, 2025.
JP, 2023-516522 Office Action, Mar. 5, 2025.
JP, 2023-532327 Office Action,
JP, 2024-31538 Office Action, Oct. 16, 2024.
JP, 2025-026588 Office Action, Aug. 27, 2025.
MX, MX/a/2021/007294 Second Office Action, Feb. 19, 2025.
MY, PI2021003022 Examination Report, Mar. 5, 2025.
MY, PI2022002786 Examination Report, Jan. 8, 2025.

UP, Second Expert Opinion of Dr Michael Schoemaker in Litigation of EP 3977921, Nov. 8, 2024.
US, Decision Denying Institution of Inter Partes Review, IPR No. 2024-00860, Nov. 20, 2024.
US, Patent Owner's Response To Petitioner's Explanation Of Parallel Petitions Challenging U.S. Pat. No. 11,510,325, IPR No. 2024-00860, Aug. 23, 2024.
US, Patent Owner Preliminary Response Pursuant to 37 C.F.R. § 42.107, IPR No. 2024-00860, Aug. 23, 2024.
US, Declaration of Julia Castellano, IPR No. 2024-00860, Aug. 21, 2024.
US, Declaration of Scott E. Davis, IPR No. 2024-00860, Jun. 5, 2024.
US, Petitioner's Explanation Of Parallel Petitions Challenging U.S. Pat. No. 11,510,325, IPR No. 2024-00860, May 9, 2024.
US, Termination Due to Settlement After Institution of Trial, IPR No. 2023-01409, Jan. 7, 2025.
US, Joint Motion to Treat Settlement Agreement as Business Confidential Information. IPR No. 2023-01409, Jan. 3, 2025.
US, Joint Motion to Terminate Proceeding Under 35 U.S.C. § 317(a), IPR No. 2023-01409, Jan. 3, 2025.
US, Order Setting Oral Argument, IPR No. 2023-01409, Dec. 11, 2024.
US, Patent Owner's Sur-Reply, IPR No. 2023-01409, Dec. 10, 2024.
US, Deposition of Gary D. Fletcher, Ph.D., IPR No. 2023-01409, Dec. 4, 2024.
US, Patent Owner's Request For Oral Argument, IPR No. 2023-01409, Dec. 3, 2024.
US, Petitioner's Request For Oral Argument, IPR No. 2023-01409, Dec. 3, 2024.
US, Patent Owner's Objections to Petitioner's Exhibits Submitted With Its Reply, IPR No. 2023-01409With Its Reply, IPR No. 2023-01409, Nov. 1, 2024.
US, Petitioner's Updated Exhibit List, IPR No. 2023-01409, Oct. 25, 2024.
US, Second Declaration of Gary Fletcher, Ph.D., IPR No. 2023-01409, Oct. 25, 2024.
US, Petitioner's Reply to Patent Owner's Response, IPR No. 2023-01409, Oct. 25, 2024.
US, Deposition of Karl R. Leinsing, MSME, PE, IPR No. 2023-01409, Oct. 17, 2024.
US, Conference Call Before The Patent Trial And Appeal Board. Before Judge Cynthia Hardman, IPR No. 2023-01409, Oct. 17, 2024.
US, Notice of Joint Stipulation to Modify Schedule, IPR No. 2023-01409, Sep. 26, 2024.
US, Decision Denying Patent Owner's Request on Rehearing of Decision Denying Institution, IPR No. 2023-01396, Aug. 9, 2024.
US, Reexamination U.S. Appl. No. 90/019,307 Final Office Action, Jul. 8, 2025.
US, Reexamination U.S. Appl. No. 90/019,307 Office Action, Mar. 18, 2025.
US Reexamination U.S. Appl. No. 90/019,307 Decision on Petition, Feb. 13, 2025.
US, Reexamination U.S. Appl. No. 90/019,329 Decision on Petition Under 37 C.F.R. § 1.181, Mar. 18, 2025.
WO, PCT/US25/13698 ISR and Written Opinion, Jun. 5, 2025.
WO, PCT/US25/13698 Invitation to Pay Additional Fees, Apr. 15, 2025.
WO, PCT/US25/27260 ISR and Written Opinion, Sep. 16, 2025.
WO, PCT/US25/27260 Invitation to Pay Additional Fees, Jul. 24, 2025.
Abbott Patent Marking Diabetes, 2024, retrieved from https://www.abbott.com/patents/diabetes-patents.html, 6 pages.
"The Advantages of the Cleo® 90 Infusion Set Are Clear", 2019, retrieved from https://web.archive.org/web/20220816002119/https://smiths-medical.com/-/media/M/Smiths-medical_com//Files/Import-Files/Product-Literature/IN193873GB-092019_LR.pdf, 2 pages.
Burge, M. R., et al., "Continuous Glucose Monitoring: The Future of Diabetes Management", Diabetes Spectrum, 2008, vol. 21, No. 2, pp. 112-119.

(56)         References Cited

OTHER PUBLICATIONS

Clancy, N. T., et al., "A new device for assessing changes in skin viscoelasticity using indentation and optical measurement", Skin Research and Technology, 2010, vol. 16, pp. 210-228.

Cleo® 90 Infusion Set 510(k) Premarket Notification, 2004, 1 page.

Dexcom STS Continuous Monitors FDA Premarket Approval (PMA), 2006, 2 pages.

Freestyle Navigator Answers to Frequently Asked Questions, 2007, retrieved from https://web.archive.org/web/20080917183534/http:/www.freestylenavigator.com/ab_nav/url/content/en_US/3 0.10.10:1 O/general_content/General_ContenL0000004.htm, 2 pages.

"The Future is Bright for Veteran-centric Rehabilitation Research Publications", Journal of Rehabilitation Research & Development (JRRD), 2013, retrieved from https://www.rehab.research.va.gov/jrrd/index.html, 2 pages.

Mazze, R. S., et al., "Evaluating the Accuracy, Reliability, and Clinical Applicability of Continuous Glucose Monitoring (CGM): Is CGM Ready for Real Time?", Diabetes Technology & Therapeutics, 2009, vol. 11, No. 1., pp. 11-18.

Medtronic MiniMed Guardian® REAL-Time Components, 2007, retrieved from https://web.archive.org/20071013095335/http:/www.medtronicdiabetes.com/products/guardia n/components.html, 2 pages.

Medtronic MiniMed Guardian® REAL-Time Features, 2007, retrieved from https://web.archive.org/20071025084715/http:/www.medtronicdiabetes.com/products/guardia n/features.html, 2 pages.

Piper, H. G., et al., "Real-Time Continuous Glucose Monitoring in Pediatric Patients During and After Cardiac Surgery", Pediatrics, 2006, vol. 118, No. 3, pp. 1176-1184.

Rabiee, A., et al., "Numerical and Clinical Accuracy of a Continuous Glucose Monitoring System during Intravenous Insulin Therapy in the Surgical and Burn Intensive Care Units", Journal of Diabetes Science and Technology, 2009, vol. 3, No. 4, pp. 951-959.

Sacks, A. H., et al., "Skin blood flow changes and tissue deformations produced by cylindrical indentors", Journal of Rehabilitation Research and Development, 1985, vol. 22, No. 3, pp. 1-6.

Schneider, M., et al., "Evaluating the use of the Cleo® 90 infusion set for patients on a palliative care unit", International Journal of Palliative Nursing, 2009, vol. 15,. No. 8, pp. 372-376.

* cited by examiner

704

1402   1418
1410   1416
       1414
       1412
1446

1420
704
1422
1436
1426
1424   1434
1428

706

2102

706

Proximal

Distal

150

702

710

1102

1104

802

704

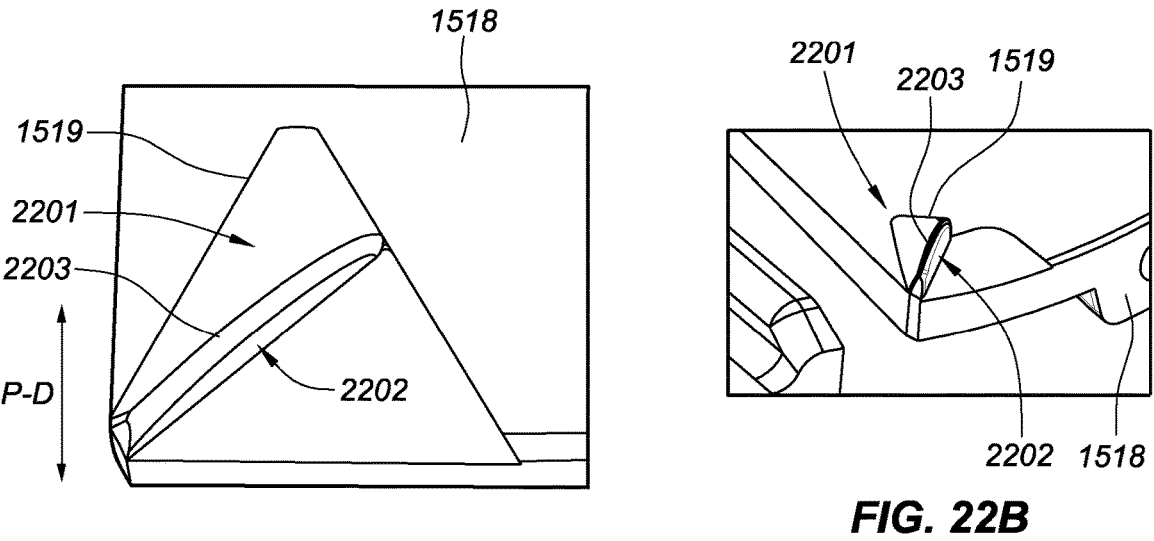
FIG. 22A
FIG. 22B
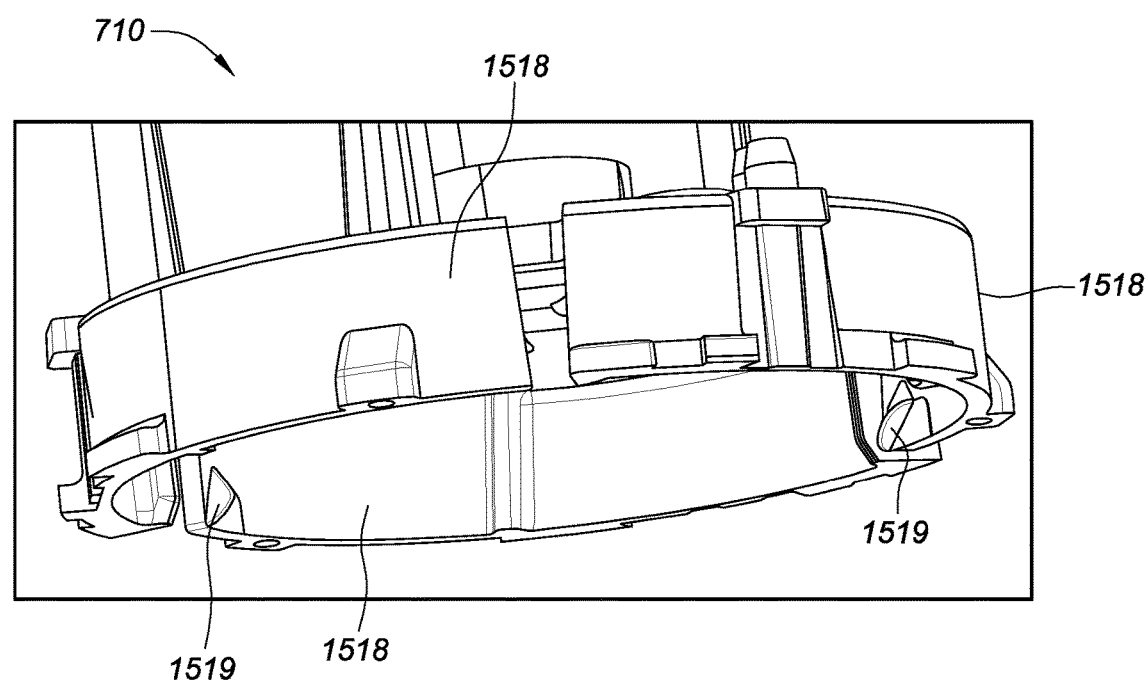
FIG. 22C

SYSTEMS, DEVICES, AND METHODS FOR ASSEMBLING AN APPLICATOR AND SENSOR CONTROL DEVICE

CROSS-REFERENCE TO RELATED APPLICATIONS

This application is a continuation of U.S. application Ser. No. 15/154,329, filed May 13, 2016, which claims priority to and the benefit of U.S. Provisional Application Ser. No. 62/161,778, filed May 14, 2015, U.S. Provisional Application Ser. No. 62/199,912, filed Jul. 31, 2015, and U.S. Provisional Application Ser. No. 62/203,565, filed Aug. 11, 2015, all of which are incorporated by reference herein in their entireties for all purposes.

FIELD

The subject matter described herein relates generally to systems, devices, and methods for assembling an applicator and sensor control device for use in an in vivo analyte monitoring system.

BACKGROUND

Diabetes is a metabolic disease which relates to high blood sugar levels in the body and can be a result of the pancreas failing to produce enough insulin or cells in the body responding improperly to insulin produced. Numerous complications can arise if symptoms of diabetes are not carefully monitored and treated include diabetic ketoacidosis, nonketotick hypersmolar coma, cardiovascular disease, stroke, kindey failure, foot ulcers, eye damage and others. Traditionally, monitoring has involved an individual pricking a finger to draw blood and testing the blood for glucose levels. More recent advancements have allowed for long-term monitoring of blood glucose using sensors which are maintained in the body for periods of days, weeks, or longer.

Long-term monitoring of analytes in bodily fluid can be accomplished when a user assembles a sterile sensor control device with an applicator or insertion mechanism and inserts a sensor of the device into contact with a bodily fluid. While current sensors can be convenient for users, they can suffer from user errors which cause malfunctions. These malfunctions can be caused by improper use due to accidents, lack of education, poor coordination, complicated procedures and other issues. Some prior art systems suffer by relying too much on the precision assembly of a sensor control device and an applicator by the user, prior to actually deploying the sensor control device on the user's body.

Thus, needs exist for more reliable sensor application devices that are easy to use by the patient.

SUMMARY

Provided herein are example embodiments of systems, devices and methods for assembling an applicator and a sensor control device. An applicator can be provided to the user in a sterile package with an electronics housing of the sensor control device contained therein. A structure separate from the applicator, such as a container, can also be provided to the user as a sterile package with a sensor module and a sharp module contained therein. The user can couple the sensor module to the electronics housing and can couple the sharp to the applicator with an assembly process that involves insertion of the applicator into the container in a specified manner. The embodiments provided herein are improved to prevent or reduce the negative impact of the applicator tilting with respect to the container during a sensor assembly process. Other improvements and advantages are provided as well. The embodiments described herein can make the assembly process more reliable and easier to complete by the user. After assembly, the applicator can be used to position the sensor control device on a human body with a sensor in contact with the wearer's bodily fluid (e.g., interstitial fluid, dermal fluid, blood, etc.). The various configurations of these devices and variations to the assembly methods are described in detail by way of the embodiments which are only examples.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIG. 22A is a close-up side view of a portion of an example embodiment of an electronics housing carrier.

FIG. 22B is a close-up perspective view of a portion of an example embodiment of an electronics housing carrier.

FIG. 22C is a perspective view another example embodiment of an electronics housing carrier.

DETAILED DESCRIPTION

This disclosure is not limited to the particular embodiments described, as such may, of course, vary. The terminology used herein is for the purpose of describing particular embodiments only, and is not intended to be limiting, since the scope of the present disclosure will be limited only by the appended claims.

Figure 1:
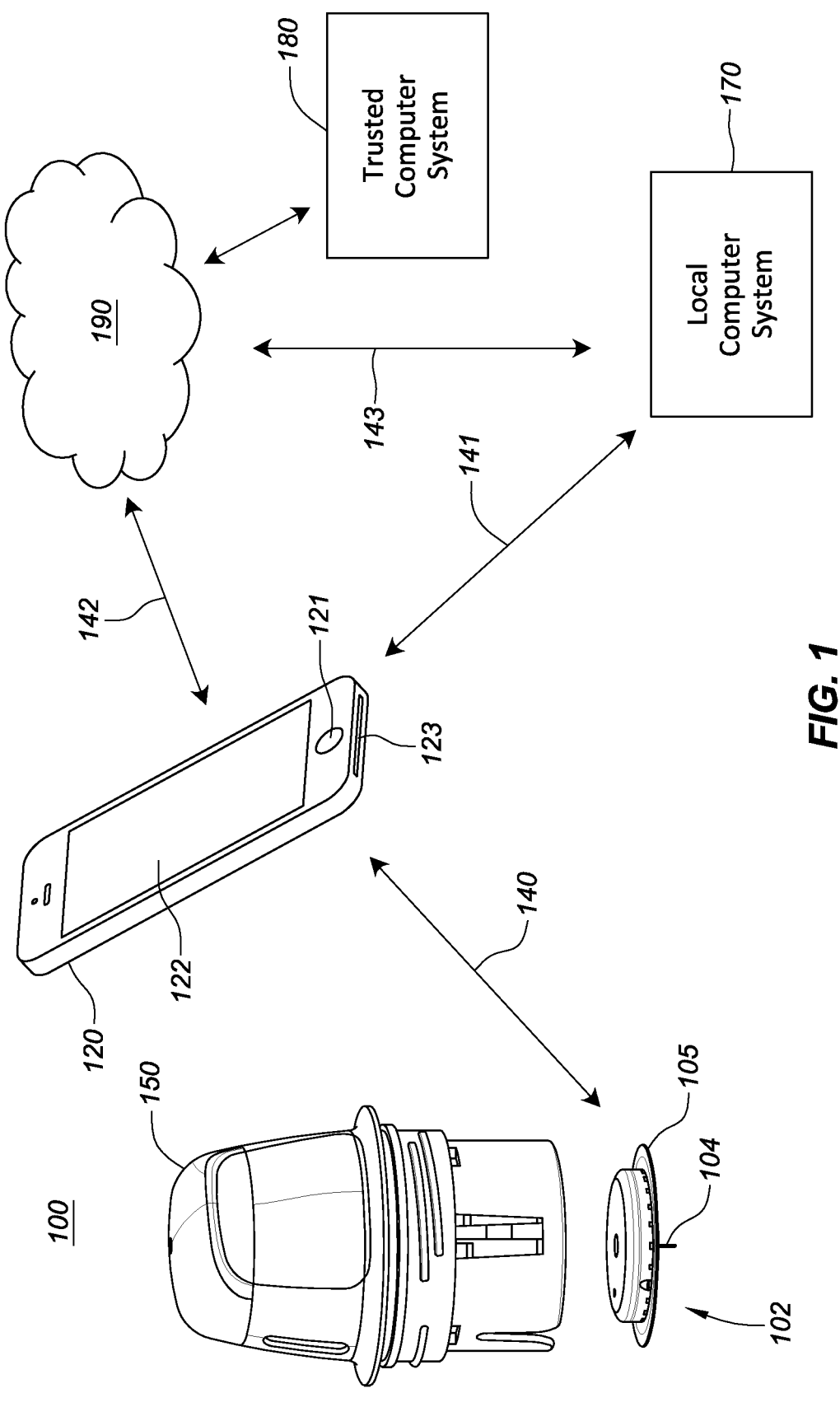
FIG. 1 is a system overview of a sensor applicator, reader device, monitoring system, network and remote system.

FIG. 1 is a conceptual diagram depicting an example embodiment of an analyte monitoring system 100 that includes a sensor applicator 150, a sensor control device 102, and a reader device 120. Here, sensor applicator 150 can be used to deliver sensor control device 102 to a monitoring location on a user's skin where a sensor 104 is maintained in position for a period of time by an adhesive patch 105. Sensor control device 102 is further described in FIG. 2B and can communicate with reader device 120 via a communication path 140 using a wired or wireless technique. Example wireless protocols include Bluetooth, Bluetooth Low Energy (BLE, BTLE, Bluetooth SMART, etc.), Near Field Communication (NFC) and others. Users can monitor applications installed in memory on reader device 120 using screen 122 and input 121 and the device battery can be recharged using power port 123. More detail about reader device 120 is set forth with respect to FIG. 2A below. Reader device 120 can communicate with local computer system 170 via a communication path 141 using a wired or wireless technique. Local computer system 170 can include one or more of a laptop, desktop, tablet, phablet, smartphone, set-top box, video game console, or other computing device and wireless communication can include any of a number of applicable wireless networking protocols including Bluetooth, Bluetooth Low Energy (BTLE), Wi-Fi or others. Local computer system 170 can communicate via communications path 143 with a network 190 similar to how reader device 120 can communicate via a communications path 142 with network 190, by wired or wireless technique as described previously. Network 190 can be any of a number of networks, such as private networks and public networks, local area or wide area networks, and so forth. A trusted computer system 180 can include a server and can provide authentication services and secured data storage and can communicate via communications path 144 with network 190 by wired or wireless technique.

Figure 2A:
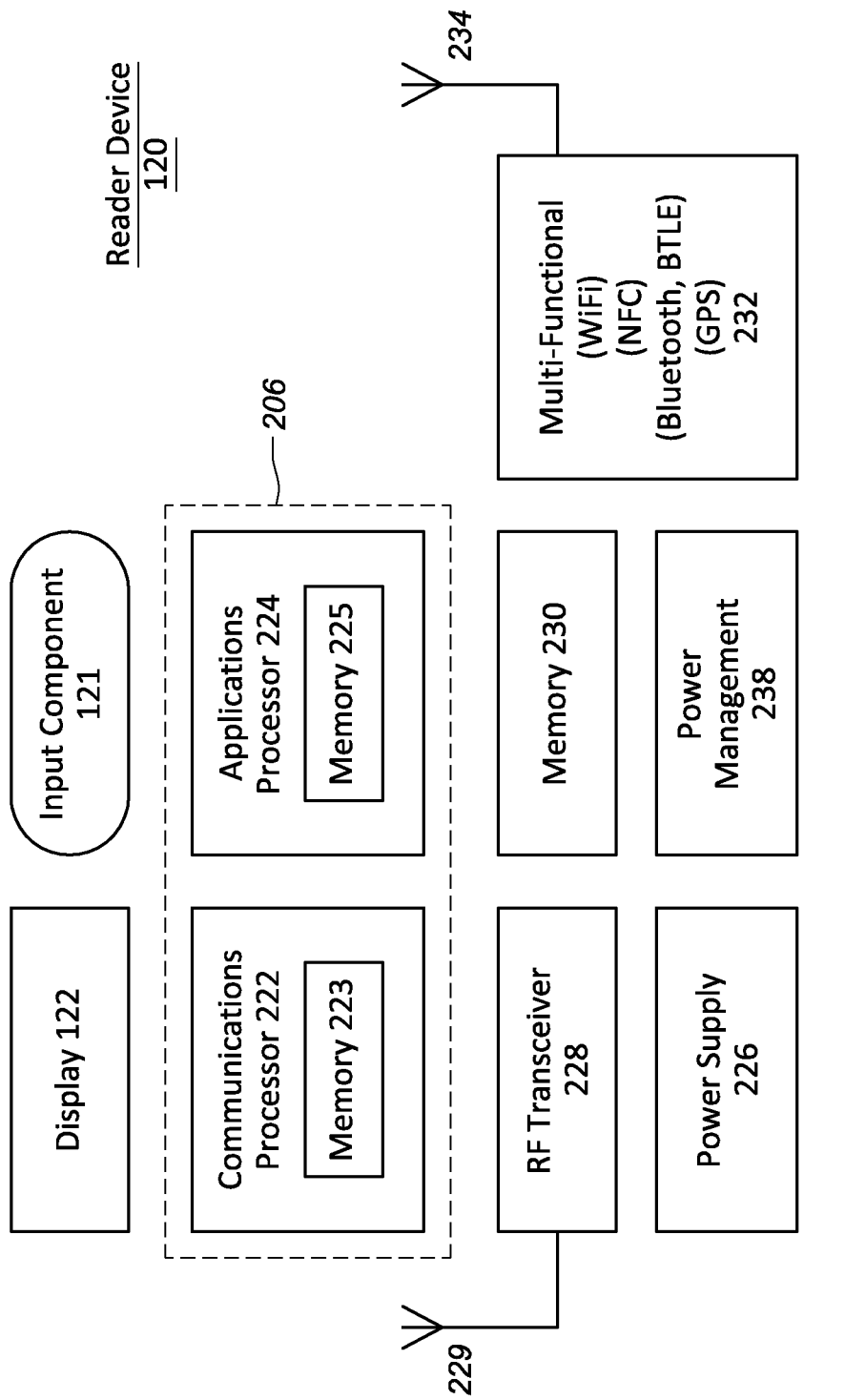
FIG. 2A is a block diagram depicting an example embodiment of a reader device.

FIG. 2A is a block diagram depicting an example embodiment of a reader device configured as a smartphone. Here, reader device 120 can include a display 122, input component 121, and a processing core 206 including a communications processor 222 coupled with memory 223 and an applications processor 224 coupled with memory 225. Also included can be separate memory 230, RF transceiver 228 with antenna 229, and power supply 226 with power management module 238. Also included can be a multi-functional transceiver 232 which can communicate over Wi-Fi, NFC, Bluetooth, BTLE, and GPS with an antenna 234. As understood by one of skill in the art, these components are electrically and communicatively coupled in an appropriate manner to make a functional device.

Figure 2B:
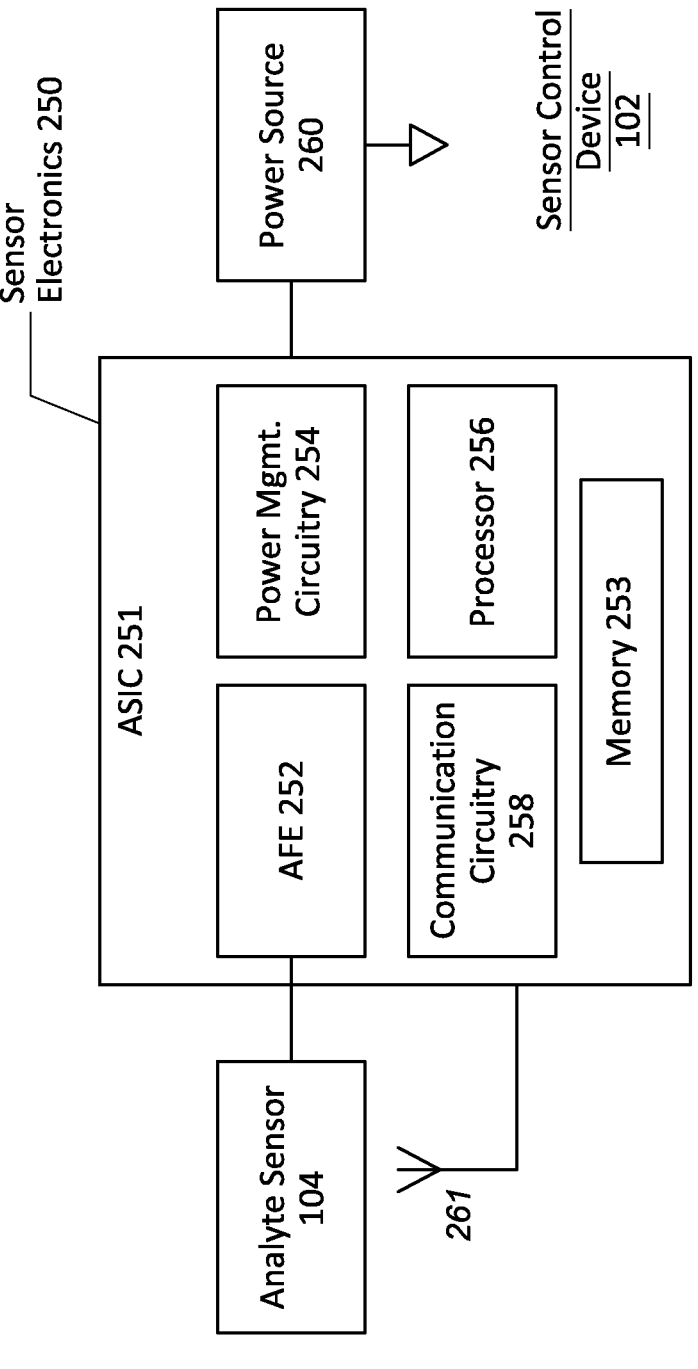
FIG. 2B is a block diagram depicting an example embodiment of a sensor control device.

FIG. 2B is a block diagram depicting an example embodiment of a sensor control device 102. Here, sensor device 120 can include an analyte sensor 104 coupled with an application specific integrated circuit (ASIC) 251, which is also coupled with an antenna 261 and power source 260. ASIC 251 can further include an analog front-end (AFE) 252, power management circuitry 254, communication circuitry 258, a processor 256 and memory 253. All elements are electrically and communicatively coupled as would be understood by one of skill in the art.

Figures 3A, 3B, 3C, 3D, 3E, 3F:
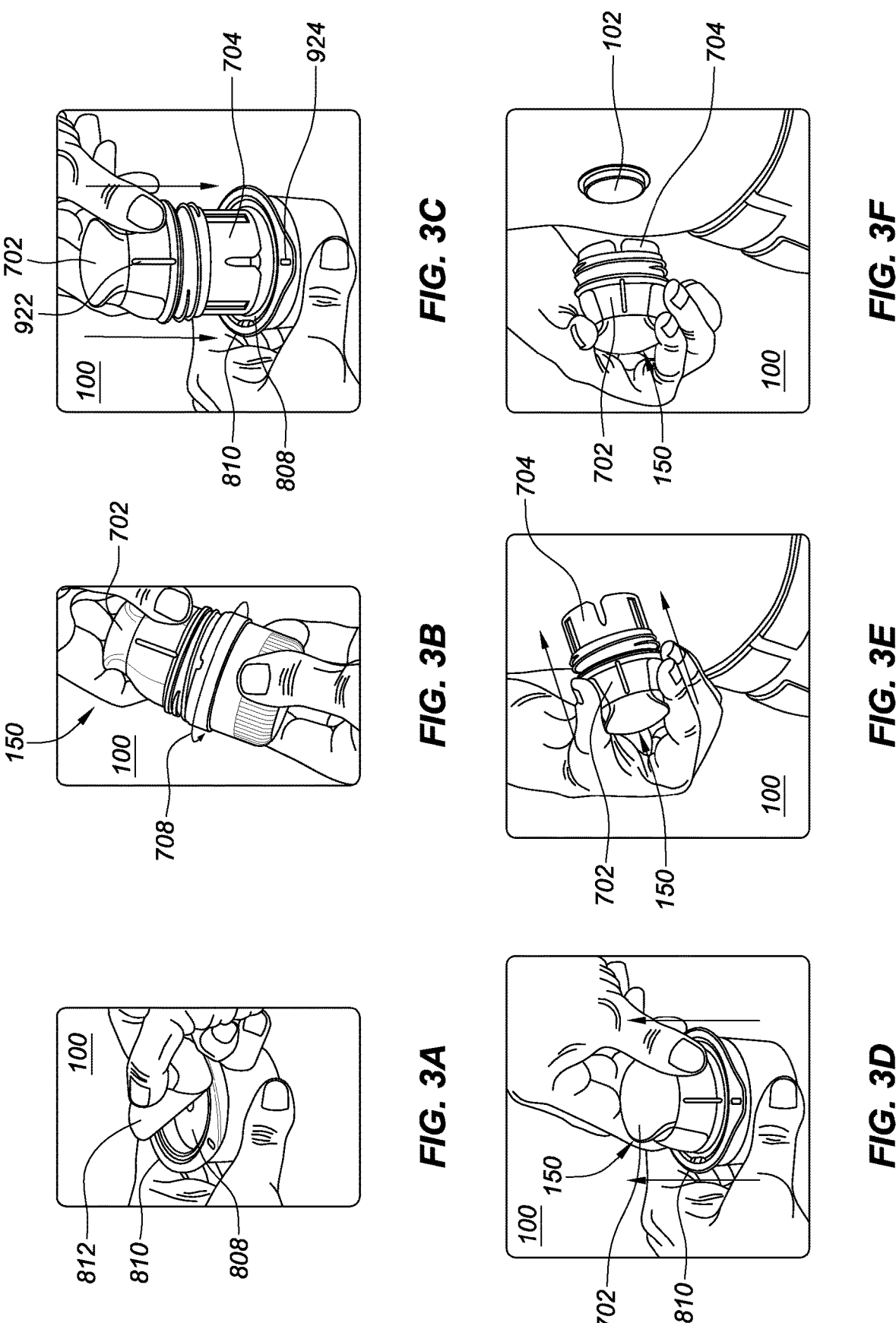
FIG. 3A is a proximal perspective view depicting an example embodiment of a user preparing a tray for an assembly.
FIG. 3B is a side view depicting an example embodiment of a user preparing an applicator device for an assembly.
FIG. 3C is a proximal perspective view depicting an example embodiment of a user inserting an applicator device into a tray during an assembly.
FIG. 3D is a proximal perspective view depicting an example embodiment of a user removing an applicator device from a tray during an assembly.
FIG. 3E is a proximal perspective view depicting an example embodiment of a patient applying a sensor using an applicator device.
FIG. 3F is a proximal perspective view depicting an example embodiment of a patient with an applied sensor and a used applicator device.

The components of sensor control device 102 can be acquired by a user in multiple packages requiring final assembly by the user before delivery to an appropriate user location. FIGS. 3A-3D depict an example embodiment of an assembly process for sensor control device 102 by a user, including preparation of separate components before coupling the components in order to ready the sensor for delivery. FIGS. 3E-3F depict an example embodiment of delivery of sensor control device 102 to an appropriate user location by selecting the appropriate delivery location and applying device 102 to the location.

FIG. 3A is a proximal perspective view depicting an example embodiment of a user preparing a container 810, configured here as a tray (although other packages can be used), for an assembly process. The user can accomplish this preparation by removing lid 812 from tray 810 to expose platform 808, for instance by peeling a non-adhered portion of lid 812 away from tray 810 such that adhered portions of lid 812 are removed. Removal of lid 812 can be appropriate in various embodiments so long as platform 808 is adequately exposed within tray 810. Lid 812 can then be placed aside.

FIG. 3B is a side view depicting an example embodiment of a user preparing an applicator device 150 for assembly. Applicator device 150 can be provided in a sterile package sealed by a cap 708. Preparation of applicator device 150 can include uncoupling housing 702 from cap 708 to expose sheath 704 (FIG. 3C). This can be accomplished by unscrewing (or otherwise uncoupling) cap 708 from housing 702. Cap 708 can then be placed aside.

FIG. 3C is a proximal perspective view depicting an example embodiment of a user inserting an applicator device 150 into a tray 810 during an assembly. Initially, the user can insert sheath 704 into platform 808 inside tray 810 after aligning housing orienting feature 922 (or slot or recess) and tray orienting feature 924 (an abutment or detent). Inserting sheath 704 into platform 808 temporarily unlocks sheath 704 relative to housing 702 and also temporarily unlocks platform 808 relative to tray 810. At this stage, removal of applicator device 150 from tray 810 will result in the same state prior to initial insertion of applicator device 150 into tray 810 (i.e., the process can be reversed or aborted at this point and then repeated without consequence).

Sheath 704 can maintain position within platform 808 with respect to housing 702 while housing 702 is distally advanced, coupling with platform 808 to distally advance platform 808 with respect to tray 810. This step unlocks and collapses platform 808 within tray 810. Sheath 704 can contact and disengage locking features (not shown) within tray 810 that unlock sheath 704 with respect to housing 702 and prevent sheath 704 from moving (relatively) while housing 702 continues to distally advance platform 808. At the end of advancement of housing 702 and platform 808, sheath 704 is permanently unlocked relative to housing 702. A sharp and sensor (not shown) within tray 810 can be coupled with an electronics housing (not shown) within housing 702 at the end of the distal advancement of housing 702. Operation and interaction of the applicator device 150 and tray 810 are further described below.

FIG. 3D is a proximal perspective view depicting an example embodiment of a user removing an applicator device 150 from a tray 810 during an assembly. A user can remove applicator 150 from tray 810 by proximally advancing housing 702 with respect to tray 810 or other motions having the same end effect of uncoupling applicator 150 and tray 810. The applicator device 150 is removed with sensor control device 102 (not shown) fully assembled (sharp, sensor, electronics) therein and position for delivery.

FIG. 3E is a proximal perspective view depicting an example embodiment of a patient applying sensor control device 102 using applicator device 150 to a target area of skin, for instance on an abdomen or other appropriate location. Advancing housing 702 distally collapses sheath 704 within housing 702 and applies the sensor to the target location such that an adhesive layer on the bottom side of device 102 adheres to the skin. The sharp is automatically retracted when housing 702 is fully advanced, while the sensor (not shown) is left in position to measure analyte levels.

FIG. 3F is a proximal perspective view depicting an example embodiment of a patient with sensor control device 102 in an applied position. The user can then remove applicator 150 from the application site.

Figures 4A, 4B, 4C:
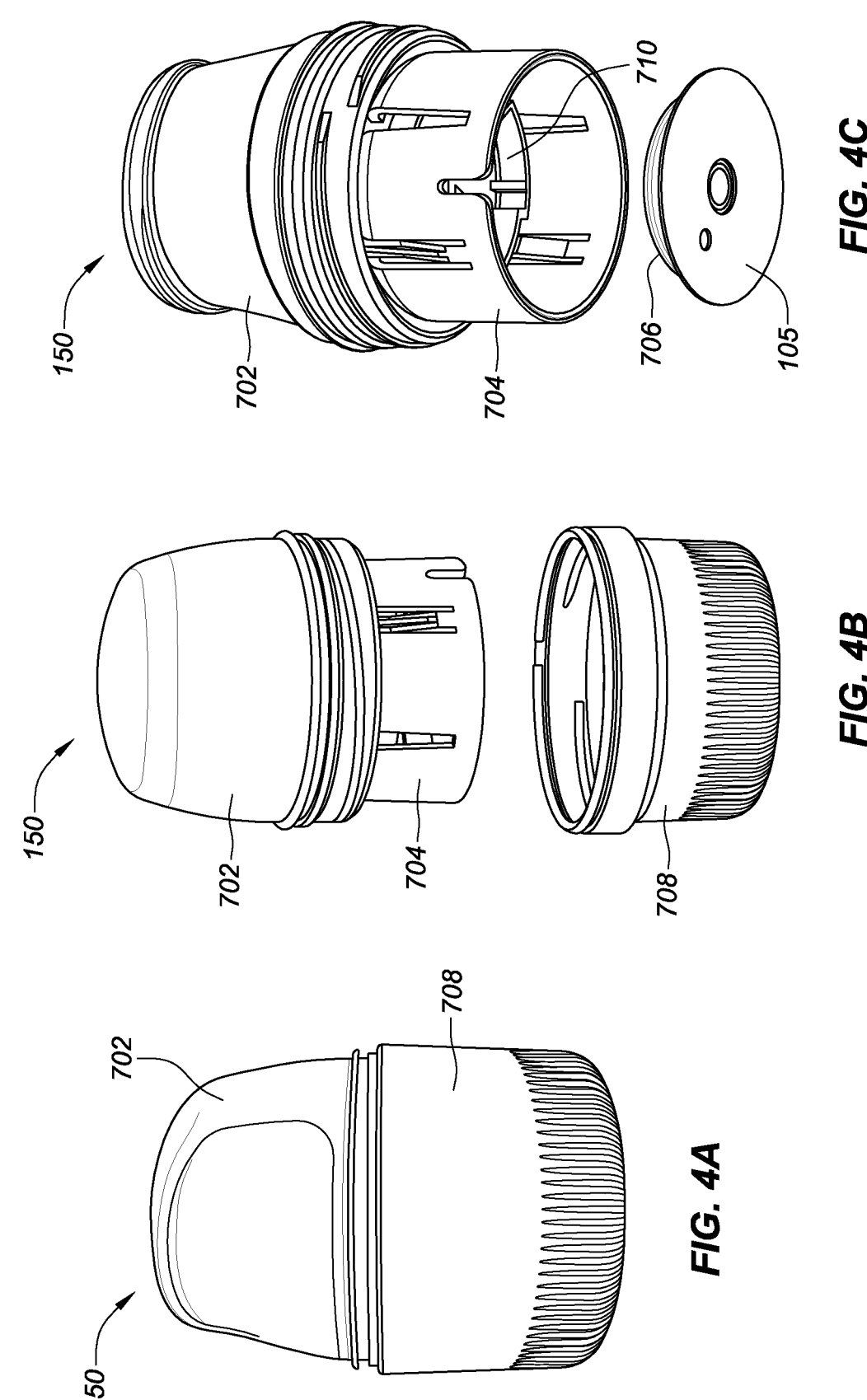
FIG. 4A is a side view depicting an example embodiment of an applicator device coupled with a cap.
FIG. 4B is a side perspective view depicting an example embodiment of an applicator device and cap decoupled.
FIG. 4C is a perspective view depicting an example embodiment of a distal end of an applicator device and electronics housing.

System 100, described with respect to FIGS. 3A-3F and elsewhere herein, can provide a reduced or eliminated chance of accidental breakage, permanent deformation, or incorrect assembly of applicator components compared to prior art systems. Since applicator housing 702 directly engages platform 808 while sheath 708 unlocks, rather than indirect engagement via sheath 708, relative angularity between sheath 708 and housing 702 will not result in breakage or permanent deformation of the arms or other components. The potential for relatively high forces (such as in conventional devices) during assembly will be reduced, which in turn reduces the chance of unsuccessful user assembly FIG. 4A is a side view depicting an example embodiment of an applicator device 150 coupled with screw cap 708. This is an example of how applicator 150 is shipped to and received by a user, prior to assembly by the user with a sensor. FIG. 4B is a side perspective view depicting applicator 150 and cap 708 after being decoupled. FIG. 4C is a perspective view depicting an example embodiment of a distal end of an applicator device 150 with electronics housing 706 and adhesive patch 105 removed from the position they would have retained within sheath 104 when cap 708 is in place.

Figure 5A:
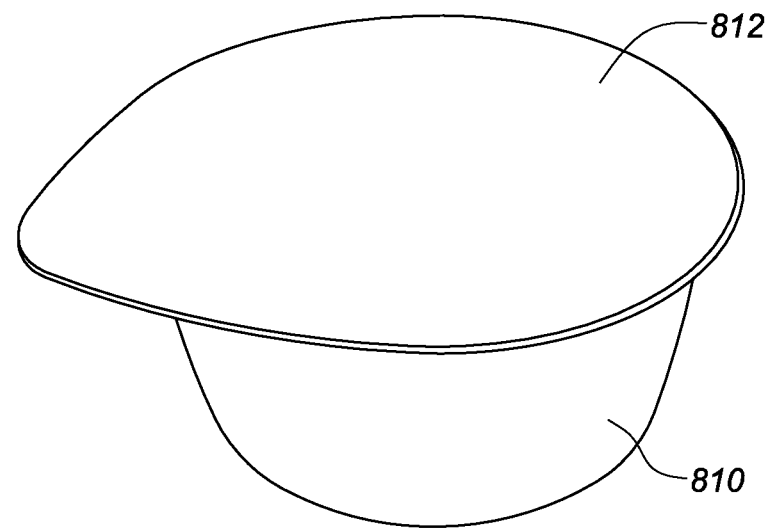
FIG. 5A is a proximal perspective view depicting an example embodiment of a tray with sterilization lid coupled.

FIG. 5A is a proximal perspective view depicting an example embodiment of a tray 810 with sterilization lid 812 removably coupled thereto, which may be representative of how the package is shipped to and received by a user prior to assembly.

Figure 5B:
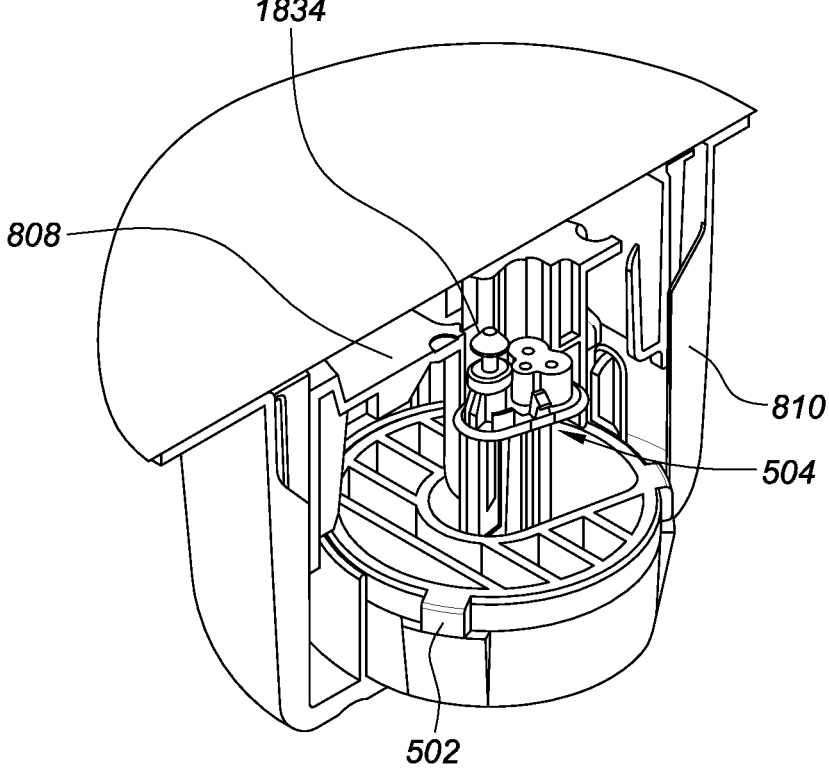
FIG. 5B is a proximal perspective cutaway view depicting an example embodiment of a tray with sensor delivery components.

FIG. 5B is a proximal perspective cutaway view depicting sensor delivery components within tray 810. Platform 808 is slidably coupled within tray 810. Desiccant 502 is stationary with respect to tray 810. Sensor module 504 is mounted within tray 810.

Figure 5C:
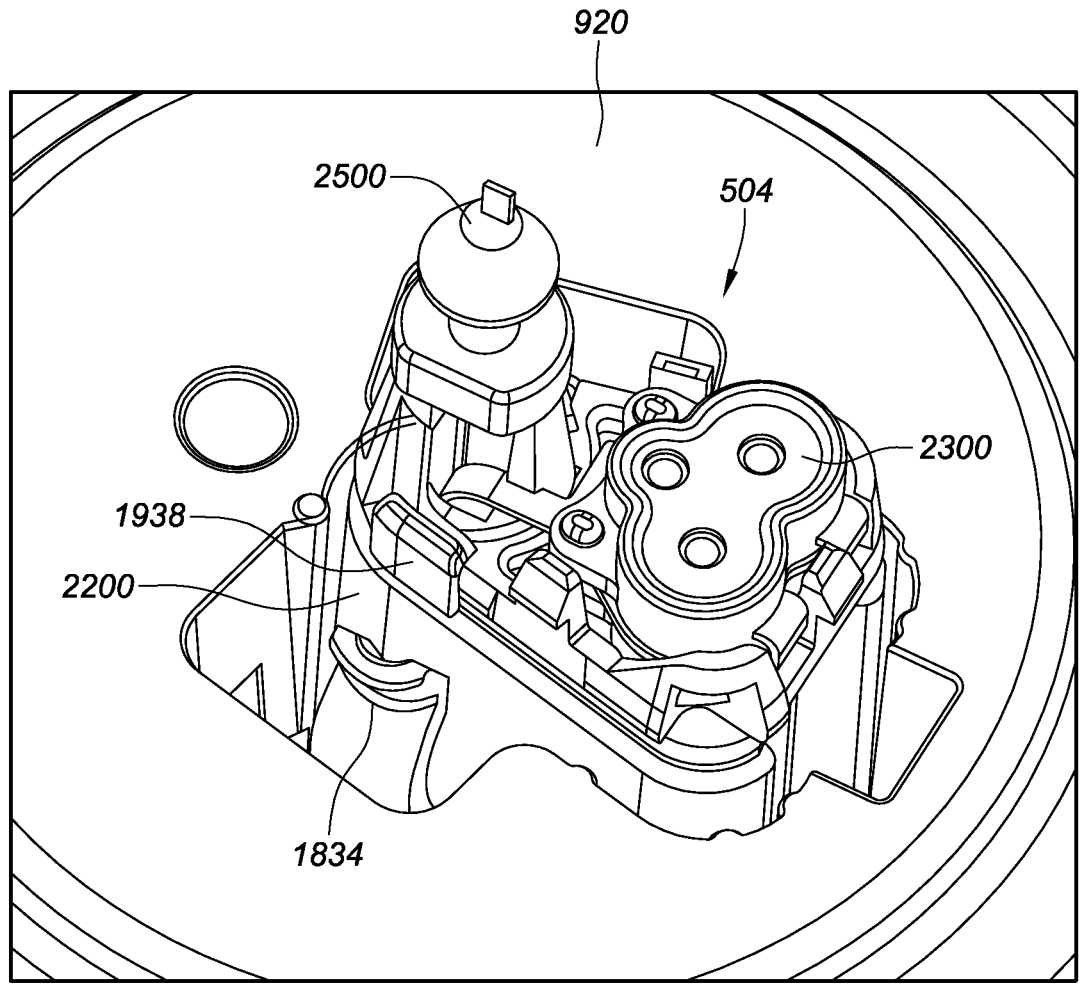
FIG. 5C is a proximal perspective view depicting sensor delivery components.

FIG. 5C is a proximal perspective view depicting sensor module 504 in greater detail. Here, retention arm extensions 1834 of platform 808 releasably secure sensor module 504 in position. Module 2200 is coupled with connector 2300, sharp module 2500 and sensor (not shown) such that during assembly they can be removed together as sensor module 504.

FIGS. 6A-H are now referenced in describing multiple example embodiments of systems, devices, and methods for assembling sensor control device 102 (e.g., for mating electronics housing 706 with sensor module 504) and for attaching sharp module 2500 to applicator device 150. In these embodiments, the process is performed by insertion of applicator device 150 a predetermined distance into tray 810 by a user. These embodiments will make reference to numerous components of system 100 that are shown and described with respect to FIGS. 7A-21D. The full descriptions of those components will therefore follow.

Figure 6A:
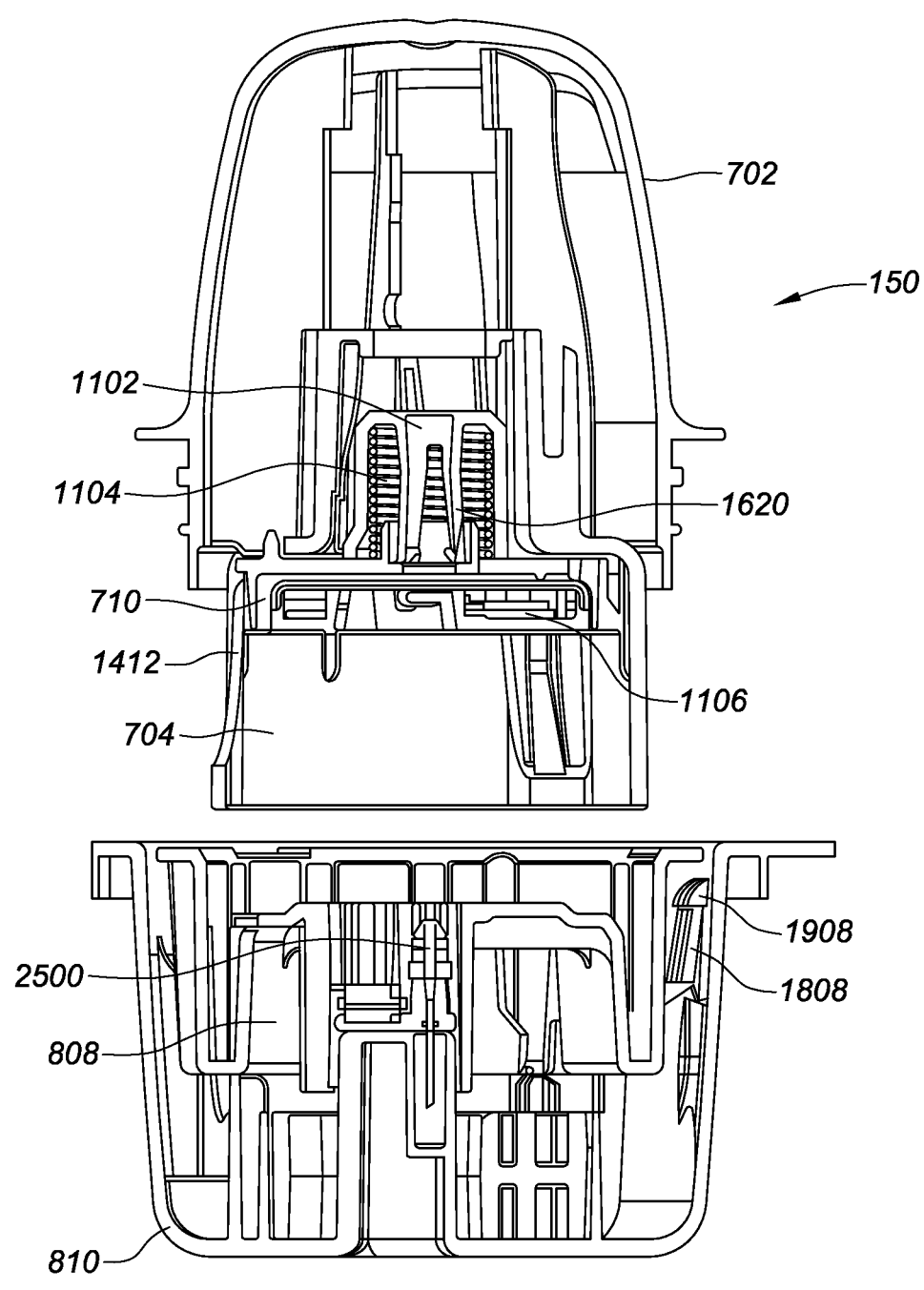
FIG. 6A is a side cross-section depicting an example embodiment of an applicator device and a tray.

FIG. 6A is a side cross-section depicting an example embodiment of an applicator device 150 and a tray 810. Here, tray 810 provides support and protection for components held inside platform 808. Platform 808 is slidably coupled within tray 810. In the initial position, one or more outer deflectable arms (or structures) 1808 of platform 808 are positioned between platform 808 and tray 810 (see also FIG. 12A) and are locked within a surface contour of tray

8

810. Here, the surface contour includes an anti-removal feature 1910 (see also FIG. 13A) and a platform initial lock ledge 1904 of a sloped detent 1912 (see FIG. 13B) of tray 810. Here, outer deflectable arms 1808 are configured as detent snaps 1808 and cooperate with feature 1910 to secure platform 808 in its initial position with respect to tray 810.

Sharp module 2500 can be coupled with tray 810 and/or sensor module 504. As described previously, applicator 150 includes exterior housing 702 slidably coupled with sheath 704. Housing 702 is coupled with electronics housing carrier 710 which engages spring 1104 and sharp module carrier 1102.

Figure 6B:
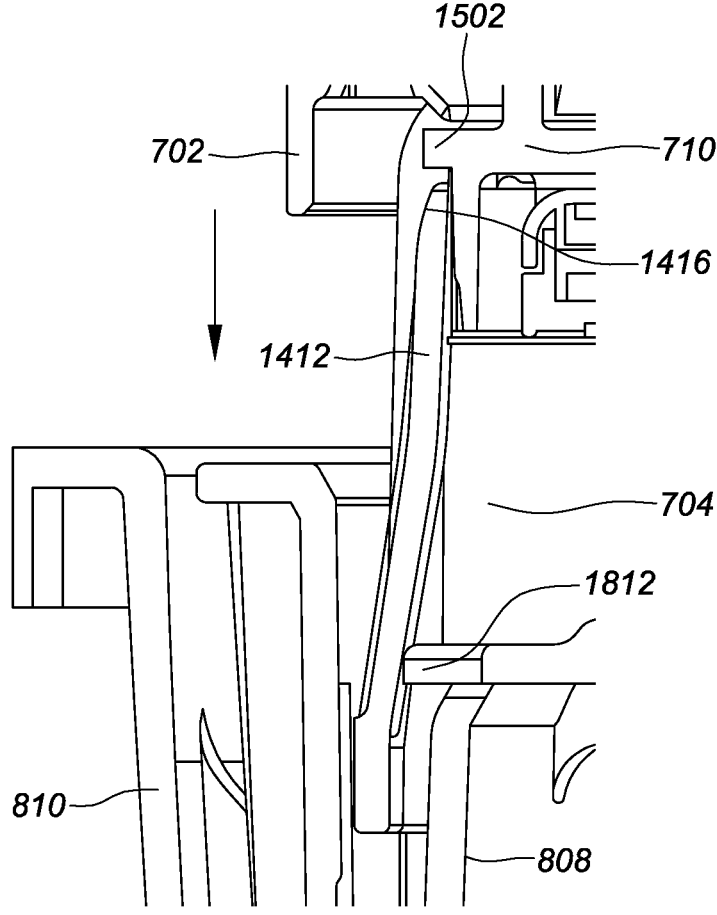
FIG. 6B is a side cross-section depicting an example embodiment of an applicator device and a tray showing a first interaction between components.

FIG. 6B is a side cross-section depicting an initial orientation of components when the user aligns sheath 704 and commences insertion of sheath 704 into platform 808 (see FIG. 3C) and tray 810. Sheath 704 includes deflectable locking arms (or structures) 1412 that have a proximally facing surface 1416 (a lock arms interface) which abuts an opposing surface 1502 (an opposing lock interface) on an outwardly extending ledge of electronics housing carrier 710. Lock arms interface 1416 of lock arms 1412 can be engaged with lock interface 1502 of electronics housing carrier 710 in an initial locked configuration prior to insertion of sheath 704 into platform 808. This configuration keeps sheath 704 in a locked position with respect to housing 702 and prevents sheath 704 from being retracted into housing 702. Platform 808 includes sheath unlock abutments, or ribs, 1812 that contact and push against the angled orientation or sloped surface of lock arms 1412 as sheath 704 is advanced distally.

Figure 6C:
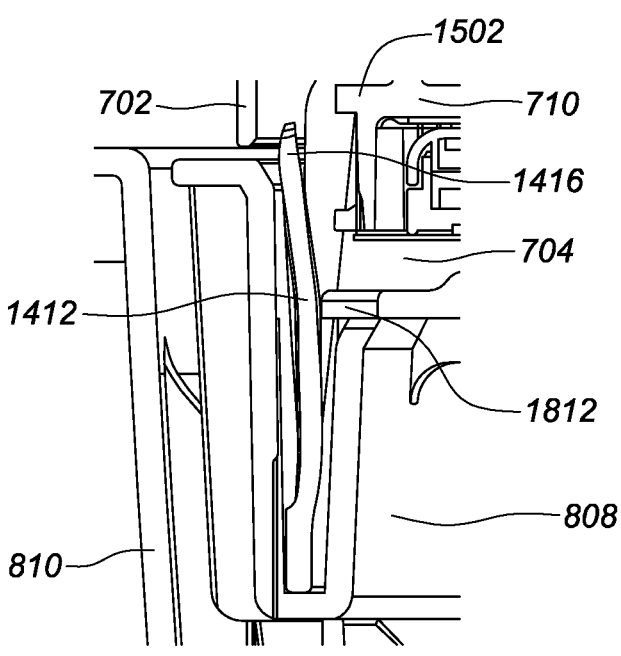
FIG. 6C is a side cross-section depicting an example embodiment of an applicator device and tray showing a subsequent interaction between components.
Figure 12A:
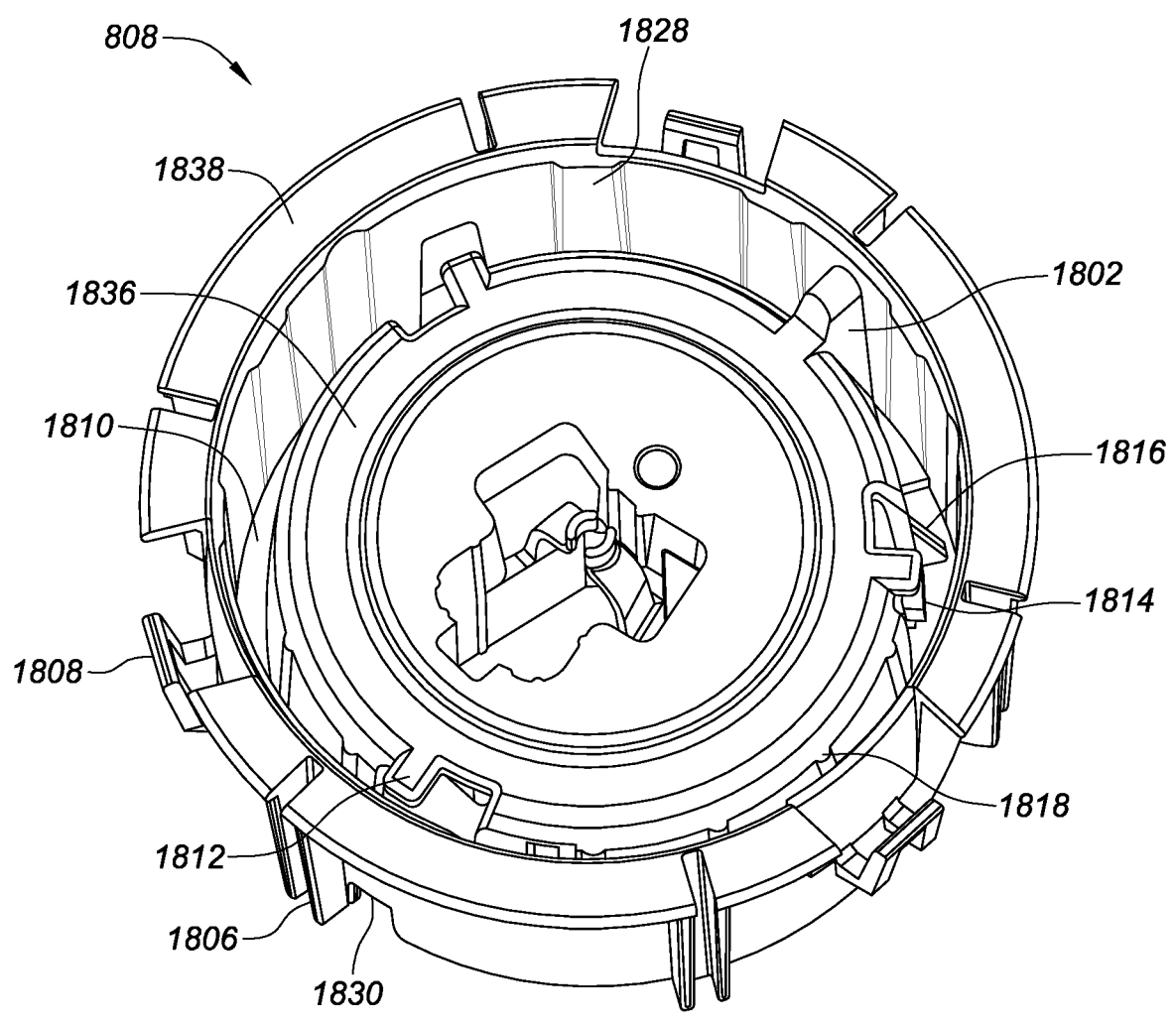
FIG. 12A is a proximal perspective view depicting an example embodiment of a platform.
Figure 12B:
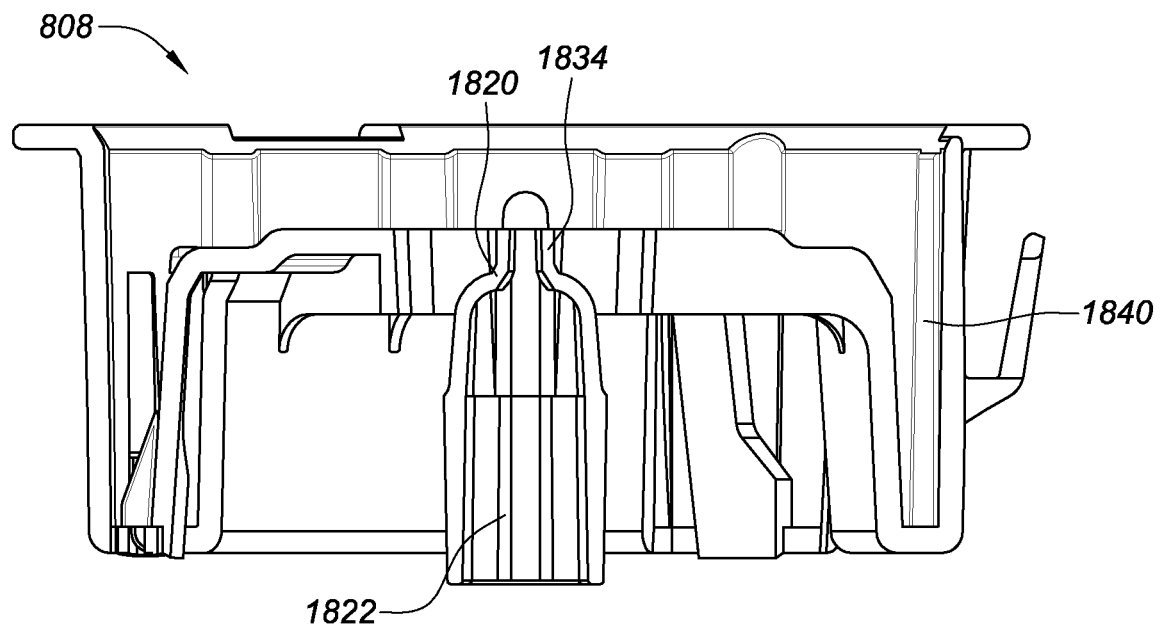
FIG. 12B is a side cross-section depicting an example embodiment of a platform.
Figure 12C:
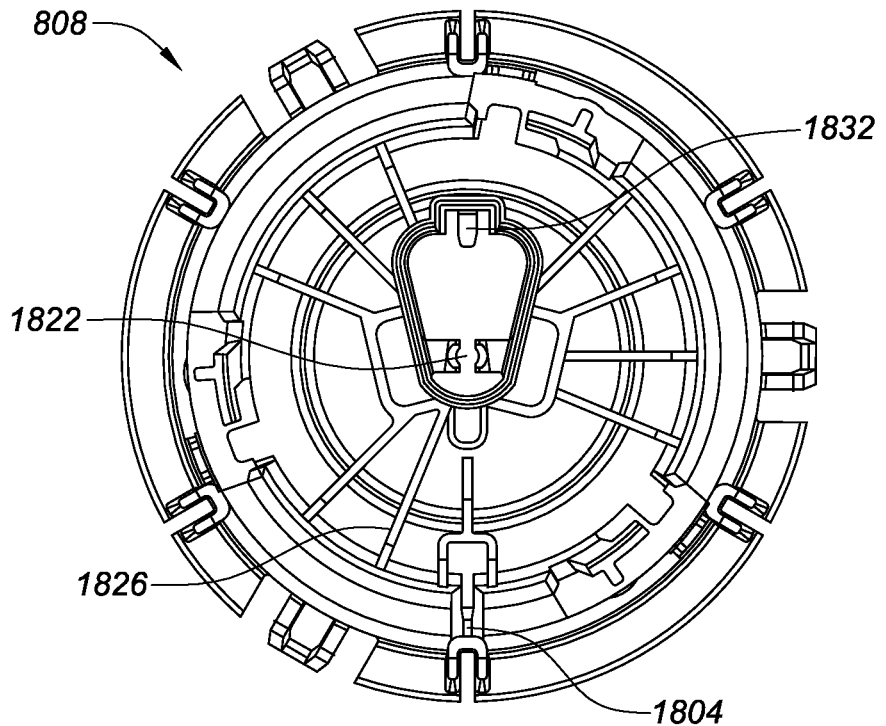
FIG. 12C is an end view depicting an example embodiment of a distal end of a platform.
Figure 12D:
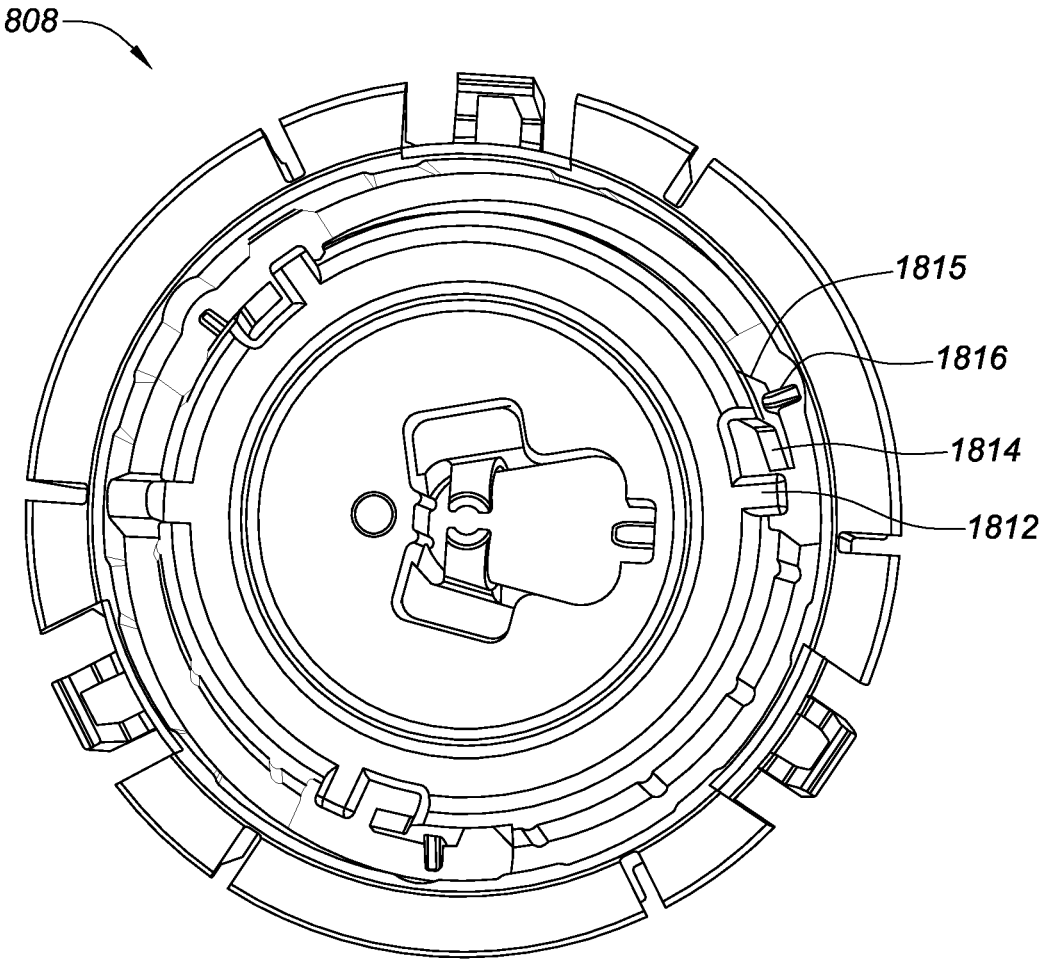
FIG. 12D is a proximal view depicting an example embodiment of a rib feature of a platform.
Figure 12E:
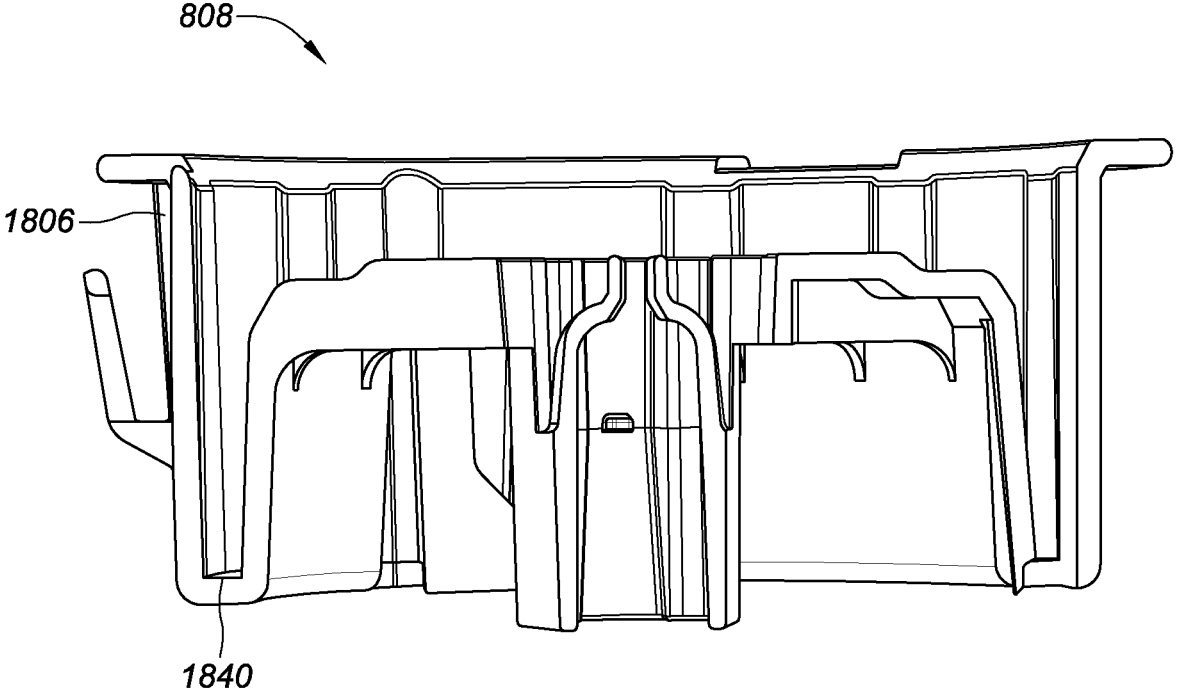
FIG. 12E is a side cross-section depicting an example embodiment of a sheath push surface of a platform.

In FIG. 6C, housing 702 has been advanced distally with sheath 704 moving in unison and a distal surface or edge of sheath 704 (for example, sheath push surface 1446 shown in FIG. 8A) can optionally engage a proximal surface of platform 808 (e.g., at the bottom of sheath receiving channel 1840 shown in FIG. 12E). The advancement of sheath 704 distally causes sheath unlock ribs 1812 to slidably engage and push against lock arms 1412 and force them away from their resting position (i.e., against their direction of bias).

Here, ribs 1812 push or move lock arms 1412 in a direction that is laterally outward from an interior of sheath 704, for example, generally in the direction from right-to-left as shown in FIG. 6C. In this embodiment, lock arms 1412 are moved outwardly while no force is applied against a distal surface or edge of sheath 704. For example, sheath push surface 1446 is not in contact with a nonmoving surface within container 810 that can resist the downward (proximal-to-distal) movement of applicator 150. As such, lock arms 1412 are disengaged while no significant or substantial load is applied to sheath 704 in a distal-to-proximal direction.

Once lock arms 1412 are moved such that proximally facing surface 1416 no longer contacts opposing surface 1502, sheath 704 is no longer locked in place with respect to housing 702 (e.g., sheath 704 and housing 702 transition from a state that resists sliding to a state where sheath 704 and housing 702 become relatively more slidable with respect to each other), although sheath 704 is still releasably maintained in position with respect to housing 702 by deflectable positioning arms (or structures) 1402 as described below. At the position of FIG. 6C, if the user ceases to apply force in a distal direction, i.e., stops pushing on housing 702, and removes applicator 150 from platform 808 (and tray 810), then lock arms 1412 will automatically return to their resting position where proximally facing surface 1416 contacts opposing surface 1502, again locking sheath 704 with respect to housing 702. Thus the assembly process can be aborted at this stage and initiated again later (without consequence) if necessary.

Figure 6D:
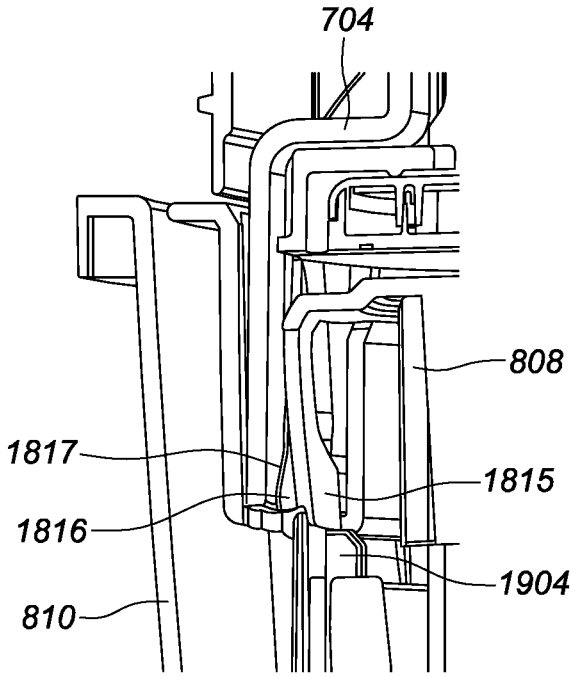
FIG. 6D is a side cross-section depicting an example embodiment of an applicator device and tray showing a further interaction between components.

Turning to FIG. 6D, platform 808 can include one or more inner deflectable lock arms (or structures) 1815, each of which can include an unlock rib 1816 having a sloped surface 1817. The advancement of sheath 704 also causes sheath push surface 1446 (FIG. 8A) to contact sloped surface 1817 of a platform unlock rib 1816 and displace inner platform lock arm 1815 from engagement with a platform initial ledge lock 1904 of tray 810 (see also FIG. 13C). The advancement of sheath 704 has already caused lock arms interface 1416 to disengage from lock interface 1502, and this can occur before the release of inner platform lock arm 1815, substantially simultaneously with the release of inner platform lock arm 1815, or after the release of inner platform lock arm 1815. Like with lock arms 1412, if the user ceases to apply force in a distal direction, i.e., stops pushing on housing 702, and removes applicator 150 from platform 808 (and tray 810), then lock arms 1815 will automatically return to their resting position where they were contacting platform initial ledge lock 1904, again locking platform 808 with respect to tray 810. Thus the assembly process can be aborted at this stage and initiated again later (without consequence) if necessary.

Figure 6E:
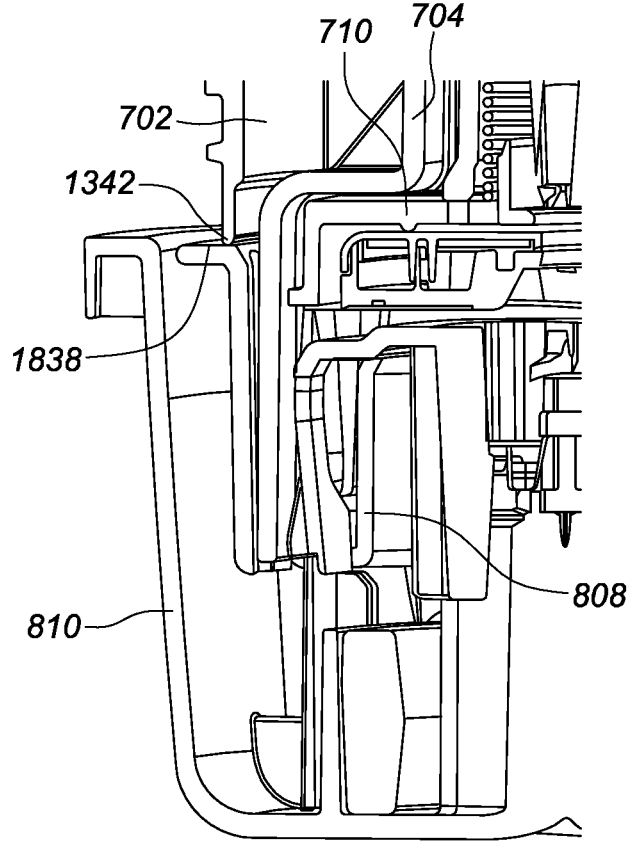
FIG. 6E is a side cross-section depicting an example embodiment of an applicator device and tray showing yet another interaction between components.
Figure 6F:
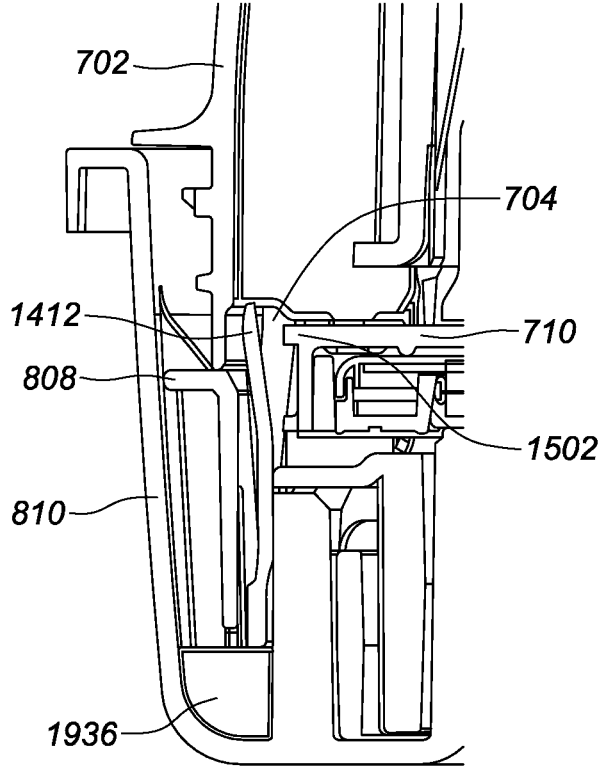
FIG. 6F is a side cross-section depicting an example embodiment of an applicator device and tray showing additional component interaction.

FIG. 6E shows the system after release of both platform lock arms 1815 and sheath lock arms 1412. Here, platform collapse surface 1342 of housing 702 contacts or engages platform collapse surface 1838 of platform 808. This is also shown in FIG. 6F. In these embodiments, platform 808 is advanced distally by housing 702 and not sheath 704. In other words, in these embodiments, after housing platform collapse surface 1342 contacts platform collapse surface 1838, sheath 704 no longer transfers force from the user's pushing motion to platform 808. That function is performed directly by housing 702.

Figure 13A:
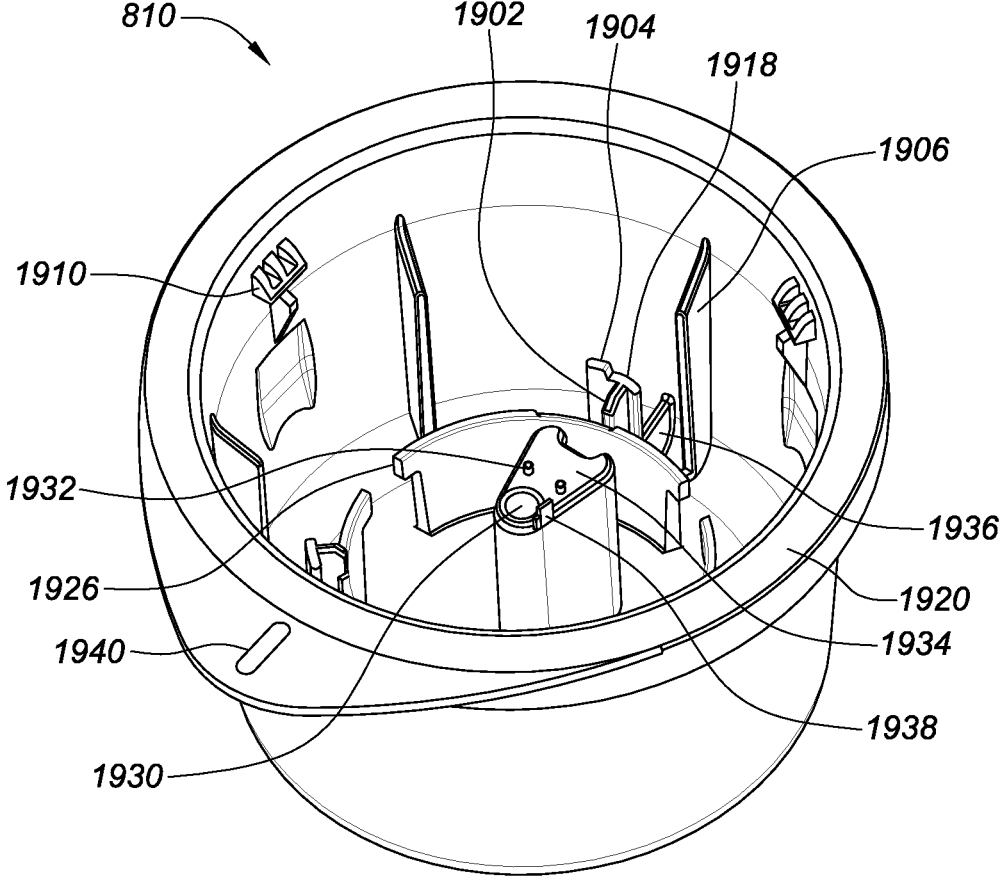
FIG. 13A is a proximal perspective view depicting an example embodiment of a tray.
Figure 13B:
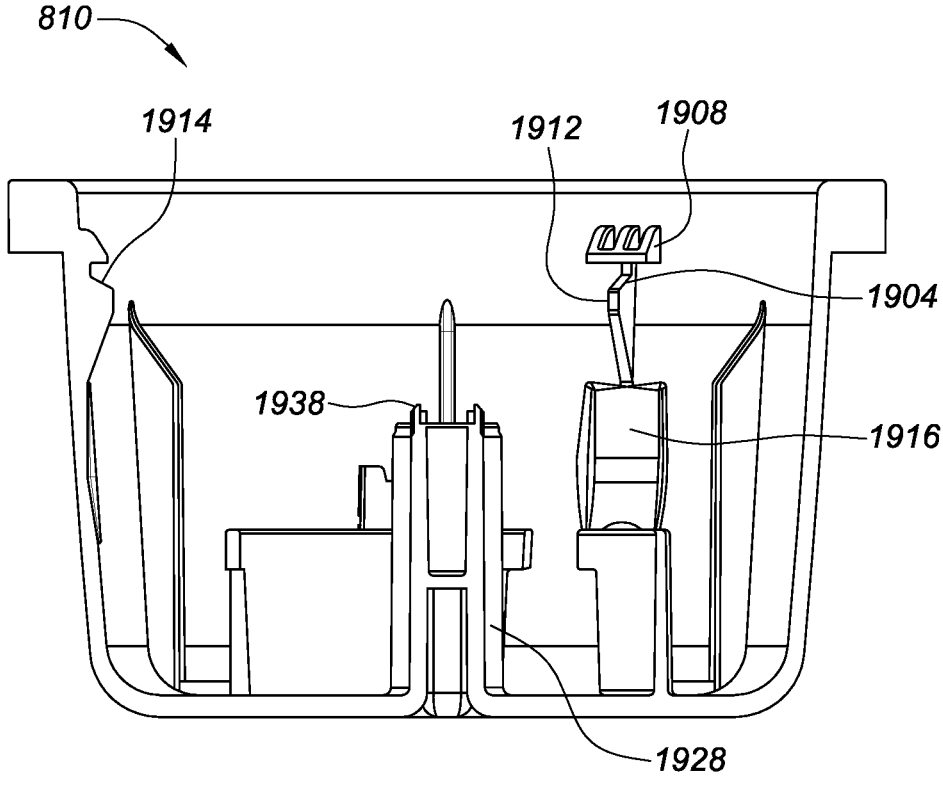
FIG. 13B is a side cross-section depicting an example embodiment of a tray.

The force applied by the user to housing 702 against platform 808 should be sufficient to cause detent snap 1808 to move (deflect radially inwardly) from platform initial lock ledge 1904 and over detent 1912 (see FIG. 13B). This releases platform 808 with respect to tray 810 and allows platform 808 to slide distally within tray 810 from the position of FIG. 6E to that of FIG. 6F.

During advancement of housing 702 against platform 808, sheath 704 remains engaged with housing 702 and moves in unison with housing 702. As described with respect to FIG. 8C, sheath 704 can include one or more deflectable positioning arms 1402, configured here as detent snaps 1402 (although other configurations can be used), where each snap 1402 includes a bridge section 1408. Initially, a bridge section 1408 of each snap 1402 can rest in a locked groove 1332 of housing 702 (see FIG. 7C). Bridge section 1408 can be moved from groove 1332 to groove 1334 with sufficient force applied by the user. Thus, sheath 704 is releasably maintained in position by the interaction of bridge section 1408 and the various grooves, indentations, or contours on locking rib 1340. In certain embodiments, movement of bridge section 1408 along locking rib 1340 towards the proximal end of housing 702 is only permitted once lock arms 1412 have been deflected and unlocked by moving proximally facing surface 1416 out of contact with opposing surface 1502 as shown in FIG. 6C.

Turning to FIG. 6F, as platform 808 moves distally, sheath 704 comes into contact with a sheath unlock rib 1936 that impedes further distal movement of sheath 704. The surface of sheath 704 the contacts sheath unlock rib 1936 can be any distal or distally-facing surface or edge, including the distal-most edge of sheath 704, which is sheath push surface 1446.

Figure 6G:
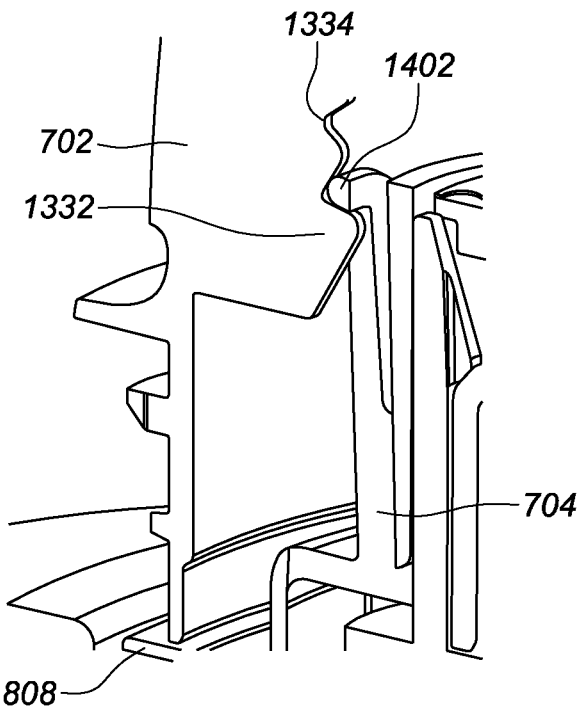
FIGS. 6G-H are side cross-section depictions of an example embodiment of an applicator device showing changes in sheath and housing orientation.
Figure 6H:
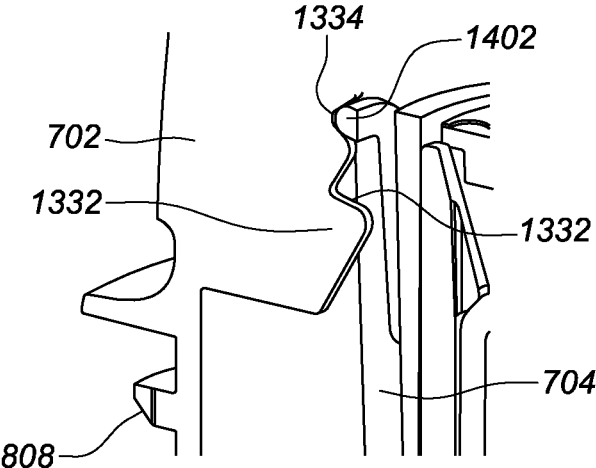

As housing 702 is advanced distally and sheath 704 is prevented from advancing by sheath unlock rib 1936 as shown in FIG. 6F (e.g., further advancement of applicator 150 in the proximal-to-distal direction causes a force to be exerted by the nonmoving sheath unlock rib 1936 against sheath 704), detent snaps 1402 move from locked groove 1332, as shown in FIG. 6G, over a detent or outwardly extending ridge to un-locked groove 1334 as shown in FIG. 6H. The user can sense the movement of sheath 704 from groove 1332 to 1334 and this, as well as the cessation of movement of platform 808, can serve as tactile feedback that the sensor assembly process is complete. FIG. 6F also shows that proximally facing surface 1416 of lock arms 1412 have moved past opposing surface 1502 of carrier 710 and cannot return to the locked position because sheath 704 has moved proximally with respect to carrier 710 and carrier 710 now holds lock arms 1412 in the unlocked position.

Referring back to FIG. 5B, in the initial position, sensor module 504 is beneath one or more retention arm extensions 1834 of platform 808. As platform 808 is moved distally, retention arm extensions 1834 are pushed against sensor module 504 and move radially outward to expose sensor module 504. In the embodiment depicted in FIGS. 12A-D, there are two retention arm extensions 1834 that are positioned opposite to each other. FIG. 5C depicts one of these arm extensions after having been deflected outward by passage over sensor module 504. The distal movement of platform 808 has exposed sharp module 2500 and module snaps 2202 (see also FIG. 16A) of module 2200 as shown in FIG. 5C.

The profile of sensor module 504 can match or be shaped in complementary fashion to the sensor module receptacle 2002 at the base of electronics housing 706 (see FIGS. 14A-B and 21A-D). Receptacle 2002 includes module snap ledges 2010 (see FIG. 14B) that interface and lock with module snaps 2202.

As housing 702 pushes against platform 808 it exposes sharp module 2500 and module snaps 2202. Although not shown here, at the stage of advancement depicted in FIG. 6G, module snaps 2202 have moved into receptacle 2002 and hub 2516 of sharp module 2500 (FIG. 19) is in close proximity with sharp assembly lead-in surface 1624 of sharp retention clip 1620 (FIG. 10B). Further movement of housing 702 towards the position depicted in FIG. 6H causes sensor module 504 to connect with (e.g., snap into) electronics housing 706 as module snaps 2202 slide past module snap ledges 2010 and then deflect outwardly towards their position of normal bias (the position of FIG. 16B). At substantially the same time, the sloped surface of hub 2516 of sharp module 2500 contacts and slides against a complementary sloped lead-in surface 1624 at the base of each retention clip 1620, which pushes clips 1620 radially outwardly away from their position of normal bias until hub 2516 passes the base of each retention clip 1620 and those clips 1620 deflect back towards their positon of normal bias. A stop surface 1627 at the distal terminus of each arm 1618 can be a planar face perpendicular to the direction of advancement. This stop surface 1627 can contact a proximal planar face of hub push cylinder 2508 (FIG. 19) and stop the axial advancement of sharp carrier 1102 with respect to sharp module 2500. This stop surface 1627 can also act as the backstop for sharp module 2500 during the sharp insertion process.

Thus, in one embodiment, just before detent snap 1402 passes into unlocked recess 1334 as depicted in FIG. 6H or, in another embodiment, at substantially the same time as detent snap 1402 passes into unlocked recess 1334 as depicted in FIG. 6H, retention clips 1620 capture sharp hub 2516 and lock (or secure) sharp module 2500 to applicator 150, and module snaps 2202 enter into a locked relationship with electronics housing 706 and lock (or secure) sensor module 504 to housing 706, forming a complete sensor control device 102. This position is also depicted in FIG. 3D. At this point applicator 150 can be withdrawn from tray 810 in the direction of the arrows of FIG. 3D and used in the sensor control device delivery process as shown in FIGS. 3E-F and also described with respect to FIGS. 20A-E.

Figure 7A:
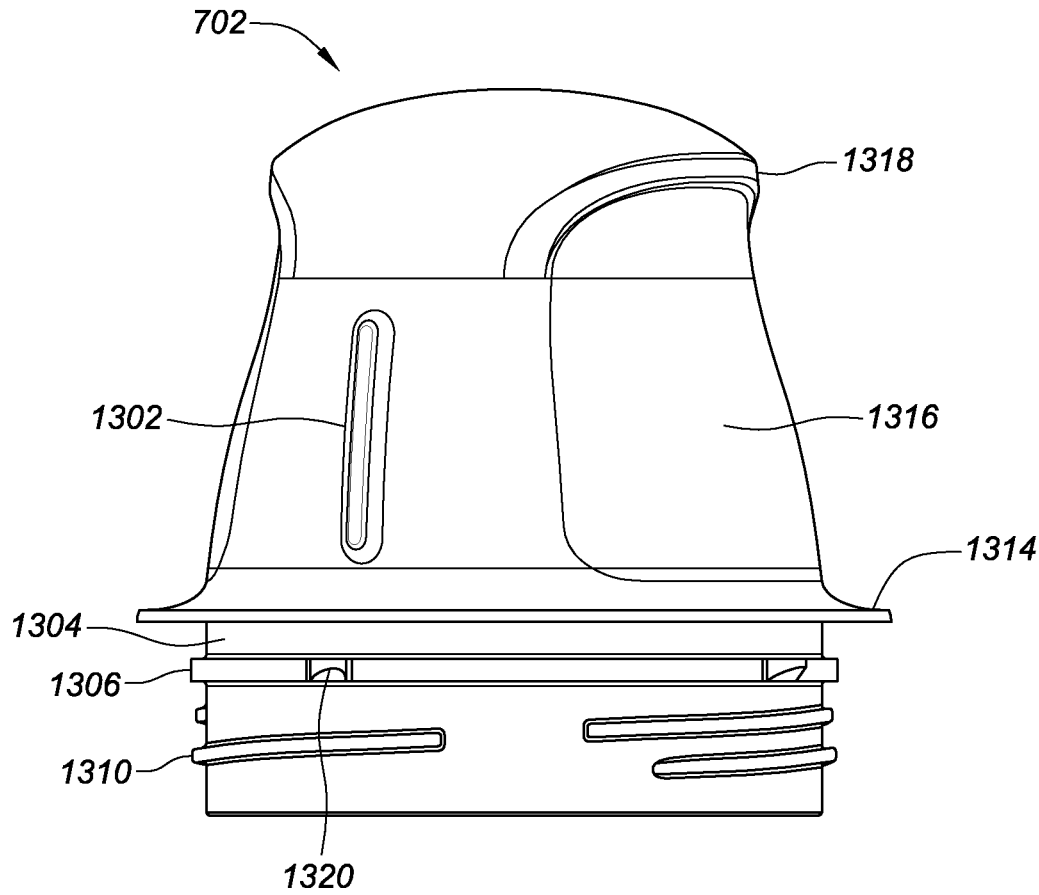
FIG. 7A is side view depicting an example embodiment of a housing.

Turning now to a detailed description of various components of system 100, FIG. 7A is side view depicting an example embodiment of housing 702 that can include an internal cavity with support structures for applicator function. A user can push housing 702 in a distal direct to activate the applicator assembly process and then also to cause delivery of sensor control device 102, after which the cavity of housing 702 can act as a receptacle for a sharp. In the example embodiment various features are shown including housing orienting feature 1302 for orienting the device during assembly and use. Tamper ring groove 1304 can be a recess located around an outer circumference of housing 702, distal to a tamper ring protector 1314 and proximal to a tamper ring retainer 1306. Tamper ring groove 1304 can retain a tamper ring so users can identify whether the device has been tampered with or otherwise used. Housing threads 1310 can secure housing 702 to cap 708 by aligning with complimentary cap threads 1708 as shown in FIG. 11A and rotating in a clockwise or counterclockwise direction. A side grip zone 1316 of housing 702 can provide an exterior surface location where a user can grip housing 702 in order to use it. Grip overhang 1318 is a slightly raised ridge with respect to side grip zone 1316 which can aid in ease of removal of housing 702 from cap 708. A shark tooth 1320 can be a raised section with a flat side located on a clockwise edge to shear off a tamper ring 1702 and hold tamper ring 1702 in place after a user has unscrewed cap 708 and housing 702. In the example embodiment four shark teeth 1320 are shown although more or less can be used as desired.

Figure 7B:
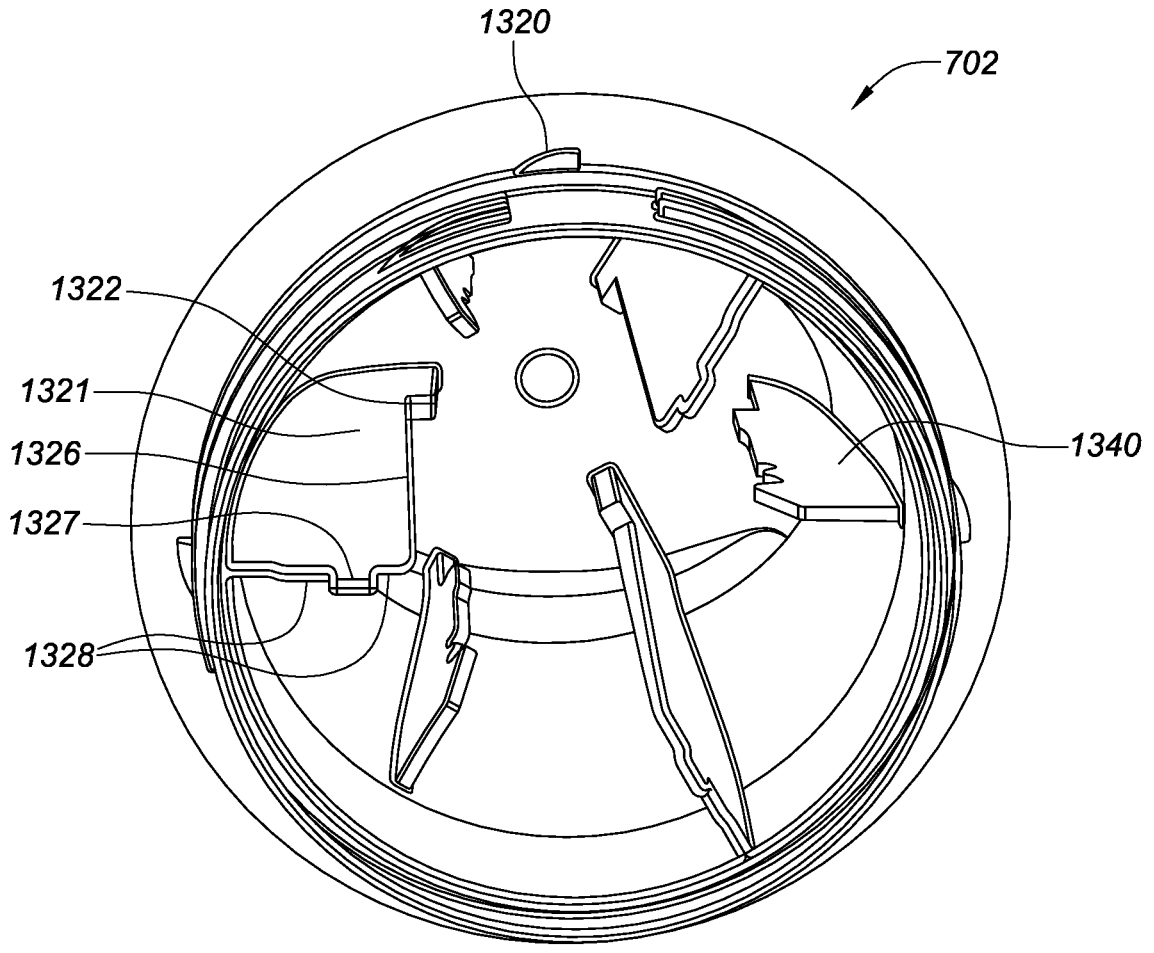
FIG. 7B is a perspective view depicting an example embodiment of a distal end of a housing.

FIG. 7B is a perspective view depicting a distal end of housing 702. Here, three housing guide structures 1321 are located at 120 degree angles with respect to each other and at 60 degree angles with respect to locking structures 1340, of which there are also three at 120 degree angles with respect to each other. Other angular orientations, either symmetric or asymmetric, can be used, as well as any number of one or more structures 1321 and 1340. Here, each structure 1321 and 1340 is configured as a planar rib, although other shapes can be used. Each guide rib 1321 includes a guide edge 1326 that can pass along a surface of sheath 704 (e.g., guide rail 1418 described with respect to FIG. 8A). An insertion hard stop 1322 can be a flat, distally facing surface of housing guide rib 1321 located near a proximal end of housing guide rib 1321. Insertion hard stop 1322 provides a surface for a sensor electronics carrier travel limiter face 1420 of a sheath 704 (FIG. 8B) to abut during use, preventing sensor electronics carrier travel limiter face 1420 from moving any further in a proximal direction. A carrier interface post 1327 passes through an aperture 1510 (FIG. 9A) of housing carrier 710 during an assembly. A sensor electronics carrier interface 1328 can be a rounded, distally facing surface of housing guide ribs 1321 which interfaces with electronics housing carrier 710.

Figure 7C:
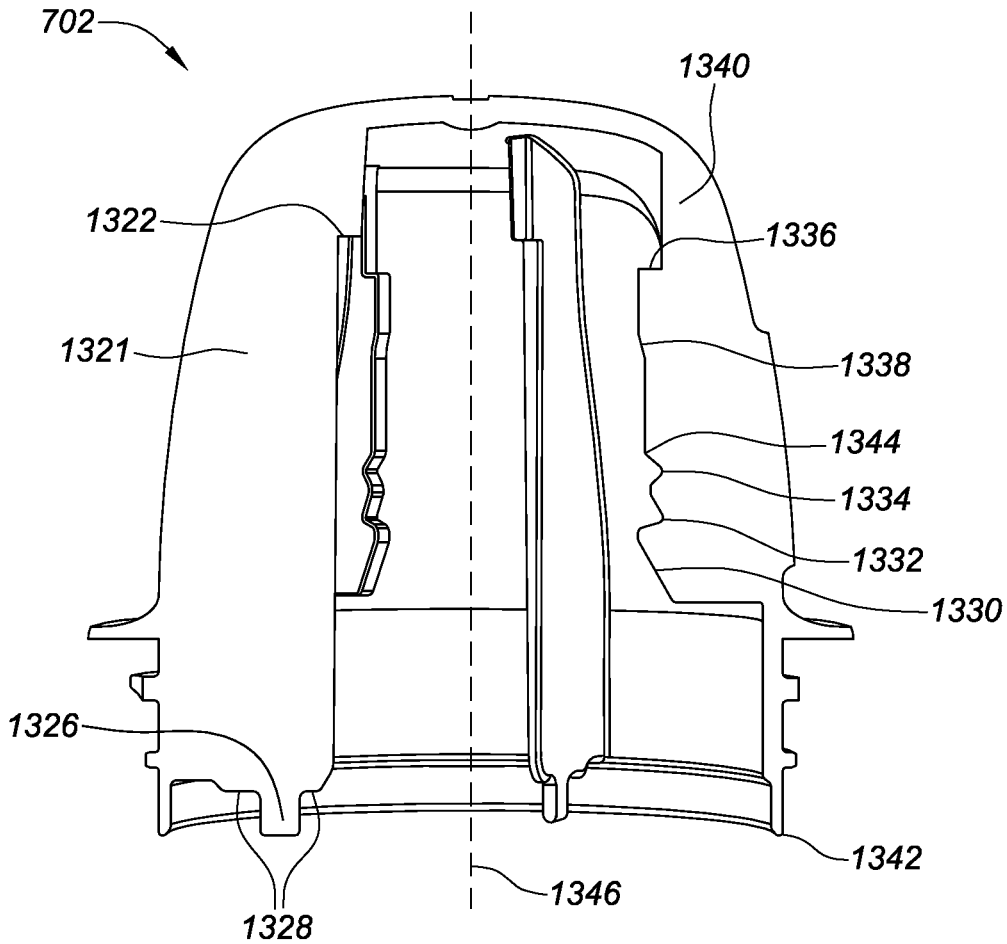
FIG. 7C is a side cross-section depicting an example embodiment of a housing.

FIG. 7C is a side cross-section depicting an example embodiment of a housing. In the example embodiment side cross sectional profiles of housing guide rib 1321 and locking rib 1340 are shown. Locking rib 1340 includes sheath snap lead-in feature 1330 near a distal end of locking rib 1340 which flares outward from central axis 1346 of housing 702 distally. Each sheath snap lead-in feature 1330 causes detent snap round 1404 of detent snap 1402 of sheath 704 as shown in FIG. 8C to bend inward toward central axis 1346 as sheath 704 moves into housing 702. Once past a distal point of sheath snap lead-in feature 1330, detent snap 1402 of sheath 704 is locked into place in locked groove 1332. As such, detent snap 1402 cannot be easily moved in a distal direction due to a surface with a near perpendicular plane to central axis 1346, shown as detent snap flat 1406 in FIG. 8C.

When housing 702 has been moved further distally with respect to sheath 704 to shift detent snaps 1402 into the un-locked grooves 1334, applicator 150 is in an "armed" position, ready for use. Thus, when a user applies distal pressure to housing 702 while sheath 704 is pressed against the skin, detent snap 1402 passes over firing detent 1344. This begins a firing sequence (as described with respect to FIGS. 20A-C) due to release of stored energy in the deflected detent snaps 1402 and detent snap 1402 travels proximally toward sheath stopping ramp 1338 which is slightly flared outward with respect to central axis 1346 and slows sheath 704 movement during the firing sequence. The next groove encountered by detent snap 1402 after un-locked groove 1334 is final lockout groove 1336 which detent snap 1402 enters at the end of the stroke or pushing sequence performed by the user. Final lockout recess 1336 can be proximal to a surface oriented perpendicular to central axis 1346 which, after detent snap 1402 passes, engages a detent snap flat 1406 and prevents reuse of the device by securely holding sheath 704 in place with respect to housing 702.

Housing platform collapse surface 1342 is a distal surface of housing 702 which a user uses to engage a platform collapse surface 1838 of platform 808 as shown in FIG. 12A. Insertion hard stop 1322 prevents sheath 704 from advancing proximally with respect to housing 702 by engaging sensor electronics carrier travel limiter face 1420.

Figure 8A:
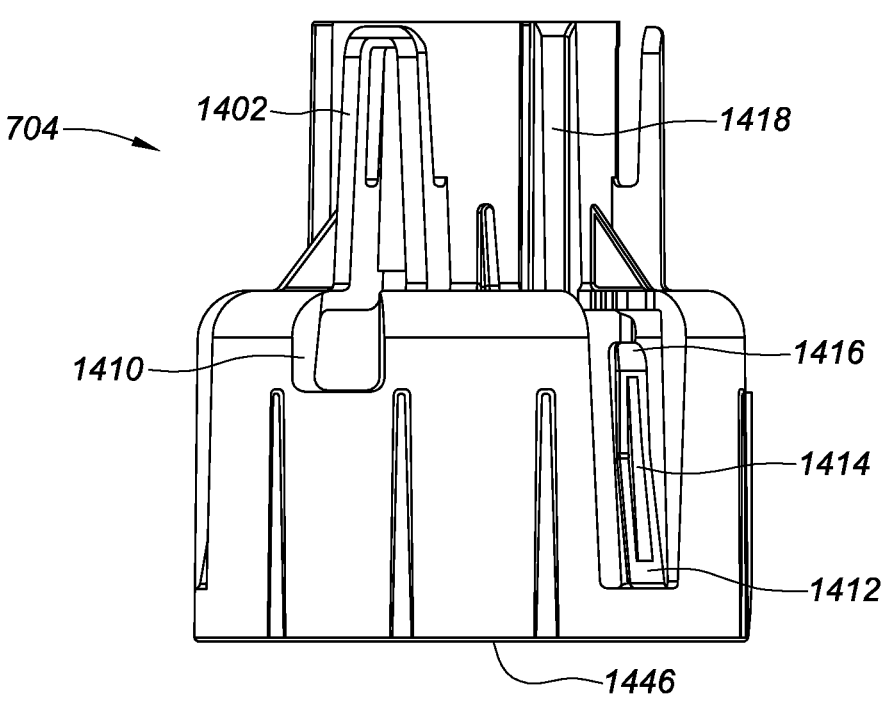
FIG. 8A is a side view depicting an example embodiment of a sheath.
Figure 8B:
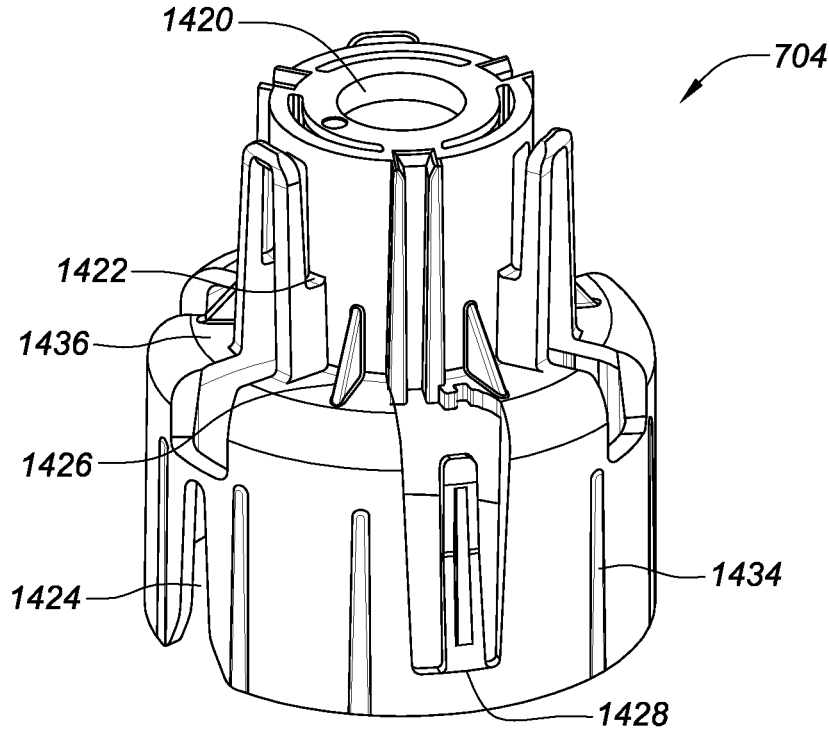
FIG. 8B is a perspective view depicting an example embodiment of a proximal end of a sheath.
Figure 8C:
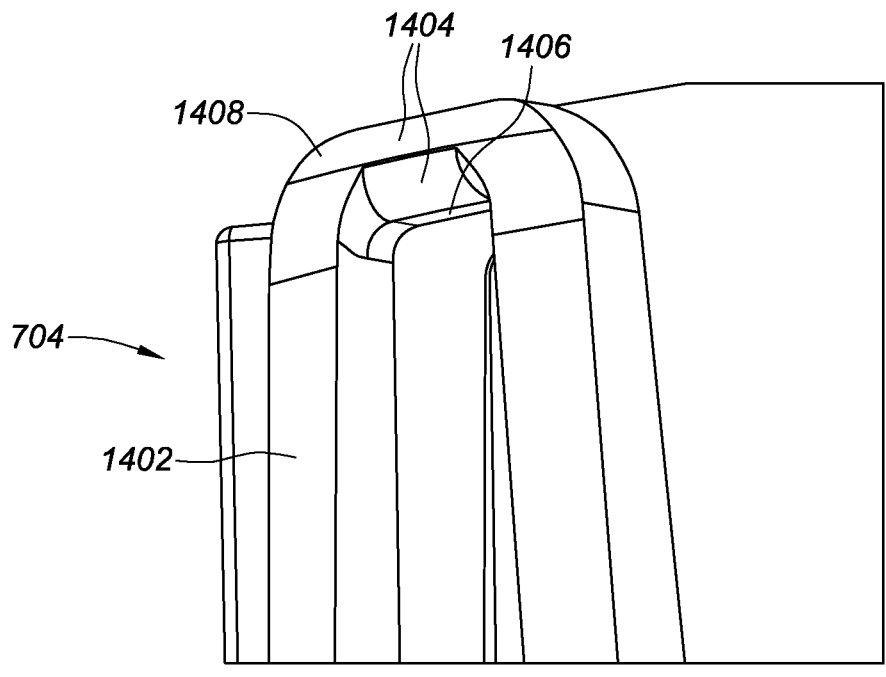
FIG. 8C is a close-up perspective view depicting an example embodiment of a distal side of a detent snap of a sheath.

FIGS. 8A and 8B are a side view and perspective view, respectively, depicting an example embodiment of sheath 704. In this example embodiment, sheath 704 can stage sensor control device 102 above a user's skin surface prior to application. Sheath 704 can also contain features that help retain a sharp in a position for proper application of a sensor, determine the force required for sensor application, and guide sheath 704 relative to housing 702 during application. Detent snaps 1402 are near a proximal end of sheath 704, described further with respect to FIG. 8C below. Sheath 704 can have a generally cylindrical cross section with a first radius in a proximal section (closer to top of figure) that is shorter than a second radius in a distal section (closer to bottom of figure). Also shown are a plurality of detent clearances 1410, three in the example embodiment. Sheath 704 can include one or more detent clearances 1410, each of which can be a cutout with room for sheath snap lead-in feature 1330 to pass distally into until a distal surface of locking rib 1340 contacts a proximal surface of detent clearance 1410.

Guide rails 1418 are disposed between a sensor electronics carrier traveler limiter face 1420 at a proximal end of sheath 704 and a cutout around lock arms 1412. Each guide rail 1418 can be a channel between two ridges where the guide edge 1326 of housing guide rib 1321 can slide distally with respect to sheath 704.

Lock arms 1412 are disposed near a distal end of sheath 704 and can include an attached distal end and a free proximal end, which can be lock arm interface 1416. Lock arms 1412 can lock sensor electronics carrier 710 to sheath 704 when lock arm interface 1416 of lock arms 1412 engage lock interface 1502 of sensor electronics carrier 710. Lock arm strengthening ribs 1414 can be disposed near a central location of each lock arm 1412 and can act as a strengthening point for an otherwise weak point of each lock arm 1412 to prevent lock arm 1412 from bending excessively or breaking.

Detent snap stiffening features 1422 can be located along the distal section of detent snaps 1402 and can provide reinforcement to detent snaps 1402. Alignment notch 1424 can be a cutout near the distal end of sheath 704, which provides an opening for user alignment with sheath orientation feature of platform 808. Stiffening ribs 1426 can include buttresses, that are triangularly shaped here, which provide support for detent base 1436. Housing guide rail clearance 1428 can be a cutout for a distal surface of housing guide rib 1321 to slide during use.

FIG. 8C is a close-up perspective view depicting an example embodiment of a distal side of a detent snap 1402 of sheath 704. Detent snap 1402 can include a detent snap bridge 1408 located near or at its proximal end. Detent snap 1402 can have a proximal feature which includes a detent snap flat 1406 on a distal side of detent snap bridge 1408. A proximal surface and outer surface of detent snap bridge 1408 can be detent snap rounds which are rounded surfaces, allowing for easier movement of detent snap bridge 1408 across some interior surfaces of housing 702.

Figure 8D:
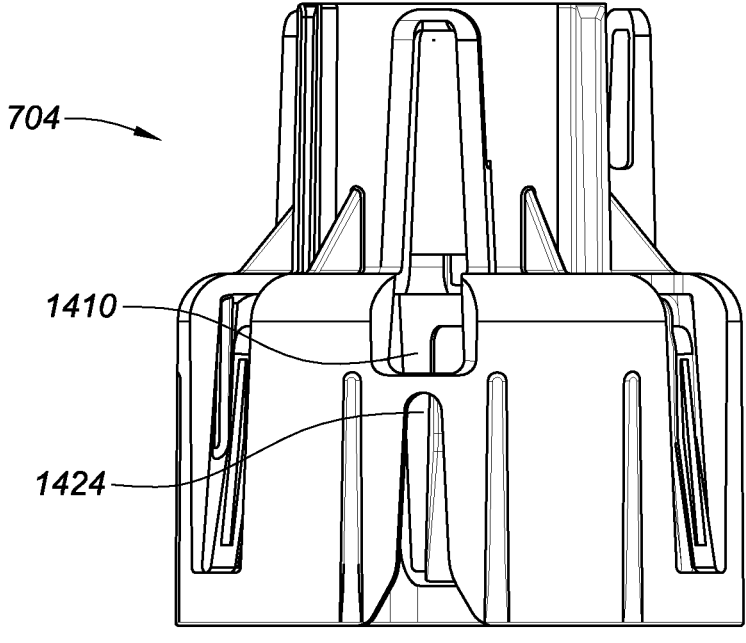
FIG. 8D is a side view depicting an example embodiment of features of a sheath.

FIG. 8D is a side view depicting an example embodiment of sheath 704. Here, alignment notch 1424 can be relatively close to detent clearance 1410. Detent clearance 1410 is in a relatively proximal location on distal portion of sheath 704. Additionally, a distal portion of sheath 704 can be relatively short enough so that sheath 704 does not contact a platform or at least is not the primary advancement surface of an applicator but rather housing 702 in order to prevent alignment issues.

Figure 8E:
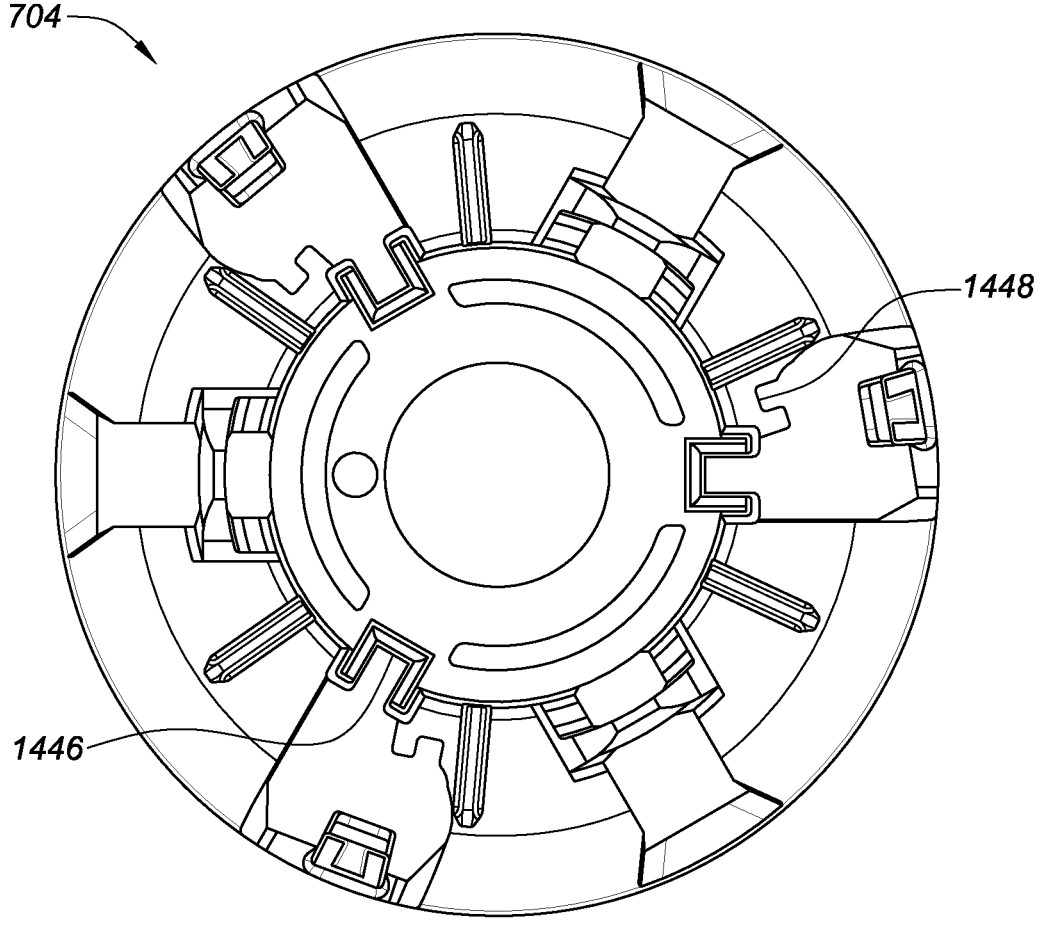
FIG. 8E is an end view depicting an example embodiment of a proximal end of a sheath.

FIG. 8E is an end view depicting an example embodiment of a proximal end of sheath 704. Here, a back wall for guide rails 1446 can provide a channel for housing guide rib 1321 of housing 702 to slidable couple with. Sheath rotation limiter 1448 can be notches which reduce or prevent rotation of the sheath 704.

Figure 9A:
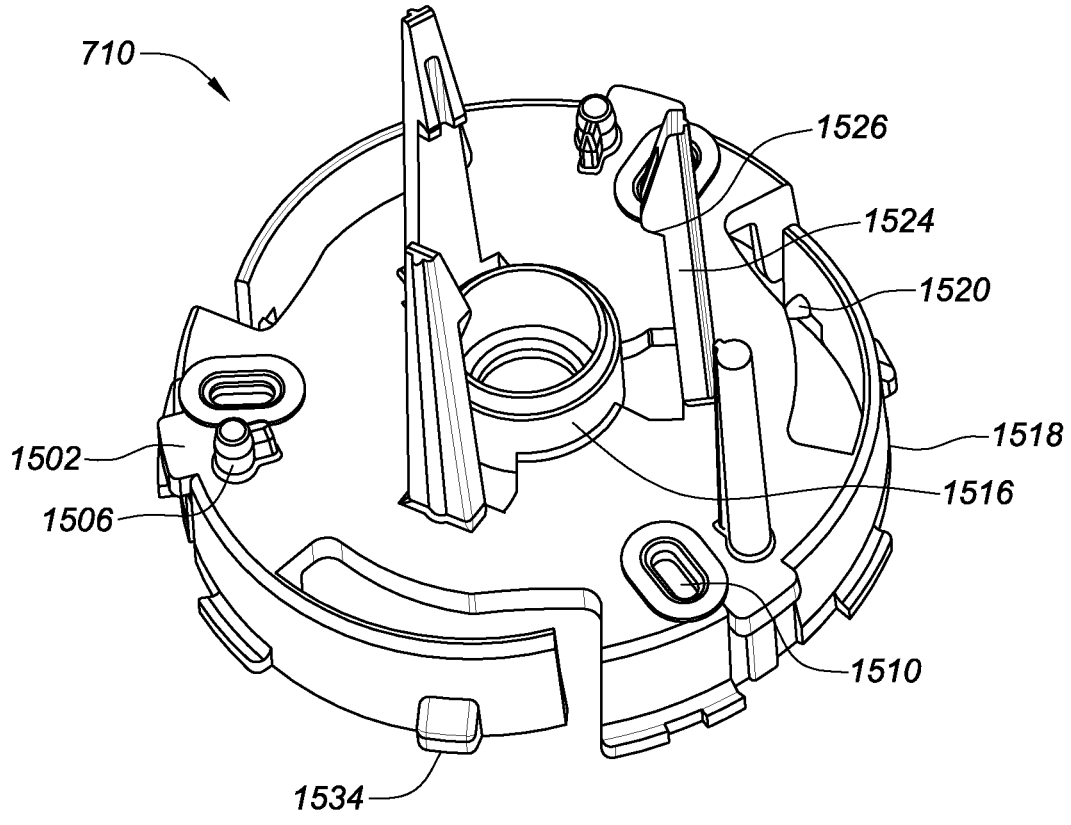
FIG. 9A is a proximal perspective view depicting an example embodiment of a sensor electronics carrier.

FIG. 9A is a proximal perspective view depicting an example embodiment of sensor electronics carrier 710 that can retain sensor electronics within applicator 150. It can also retain introducer carrier 1102 with sharp module 2500. In this example embodiment sensor electronics carrier 710 generally has a hollow round flat cylindrical shape, and can include one or more deflectable introducer carrier lock arms (or structures) 1524 (e.g., three) extending proximally from a proximal surface surrounding a centrally located spring alignment ridge 1516 (for maintaining alignment of spring 1104 as seen in FIG. 6A). Each lock arm 1524 has a detent or retention feature 1526 located at or near its proximal end. Shock lock 1534 can be a tab located on an outer circumference of sensor electronics carrier 710 extending outward and can lock sensor electronics carrier 710 for added safety prior to firing. Rotation limiter 1506 can be a proximally extending relatively short protrusion on a proximal surface of sensor electronics carrier 710 which limits rotation of carrier 710. Introducer carrier lock arms 1524 can interface with carrier 1102 as described with reference to FIGS. 10A-10B below.

Figure 9B:
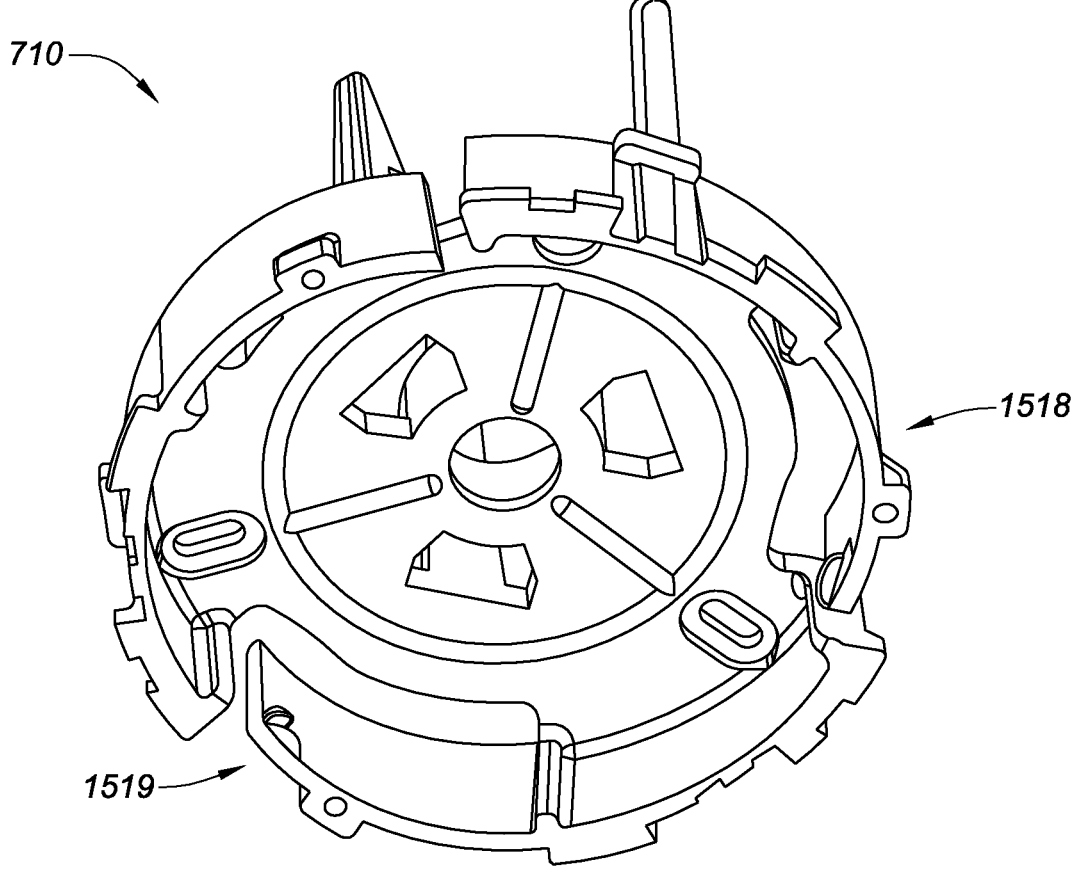
FIG. 9B is a distal perspective view depicting an example embodiment of a sensor electronics carrier.

FIG. 9B is a distal perspective view of sensor electronics carrier 710. Here, one or more sensor electronics retention spring arms (or structures) 1518 (e.g., three) are normally biased towards the position shown and include a detent 1519 that can pass over the distal surface of electronics housing 706 of device 102 when housed within recess or cavity 1521. In certain embodiments, after sensor control device 102 has been adhered to the skin with applicator 150, the user pulls applicator 150 proximally away from the skin. The adhesive force retains sensor control device 102 on the skin and overcomes the lateral force applied by spring arms 1518. As a result, spring arms 1518 deflect radially outwardly and disengage detents 1519 from sensor control device 102 thereby releasing sensor control device 102 from applicator 150.

Figure 10A:
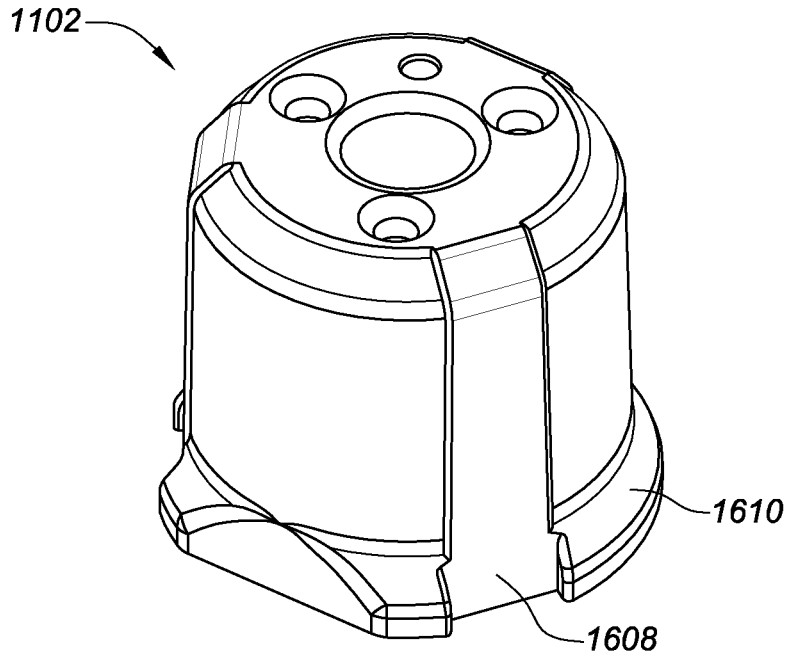
FIG. 10A is a proximal perspective view depicting an example embodiment of a sharp carrier.
Figure 10B:
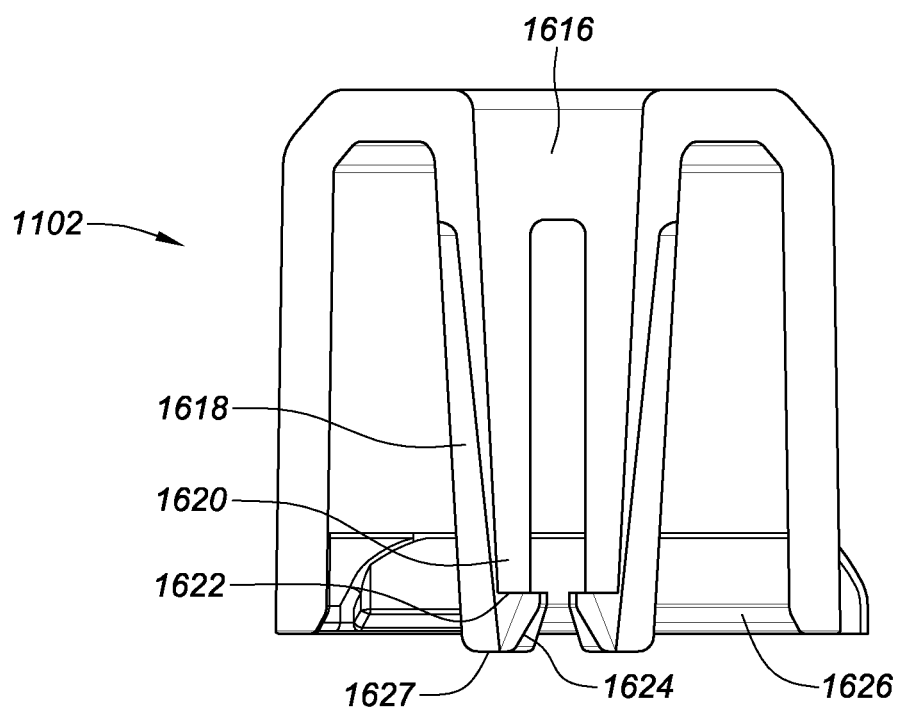
FIG. 10B is a side cross-section depicting an example embodiment of a sharp carrier.

FIGS. 10A and 10B are a proximal perspective view and side cross-section view, respectively, depicting an example embodiment of sharp carrier 1102. Sharp carrier 1102 can grasp and retain sharp module 2500 within applicator 150. It can also automatically retract as a result of a spring changing from a compressed to an extended state during an insertion process, as described with respect to FIG. 20D. Near a distal end of sharp carrier 1102 can be anti-rotation slots 1608 which prevent sharp carrier 1102 from rotating when located within a central area of introducer carrier lock arms 1524. Anti-rotation slots 1608 can be located between sections of sharp carrier base chamfer 1610 which can ensure full retraction of sharp carrier 1102 through sheath 704 upon retraction of sharp carrier 1102 at the end of the deployment procedure.

Figure 19:
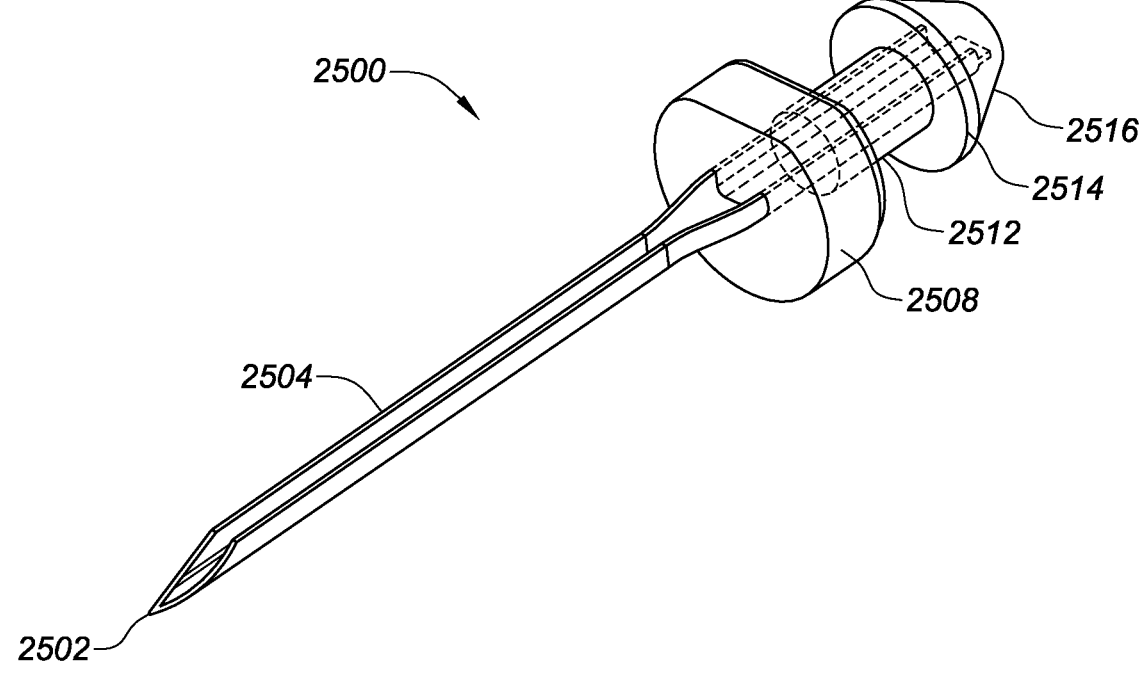
FIG. 19 is a perspective view depicting an example embodiment of a sharp.

Sharp retention arms (or structures) 1618 can be located in an interior of sharp carrier 1102 about a central axis and can include a sharp retention clip 1620 at a distal end of each arm 1618. Sharp retention clips 1620 can have a proximal surface which can be nearly perpendicular to the central axis and can abut a distally facing surface of sharp hub 2516 (FIG. 19).

Figure 11:
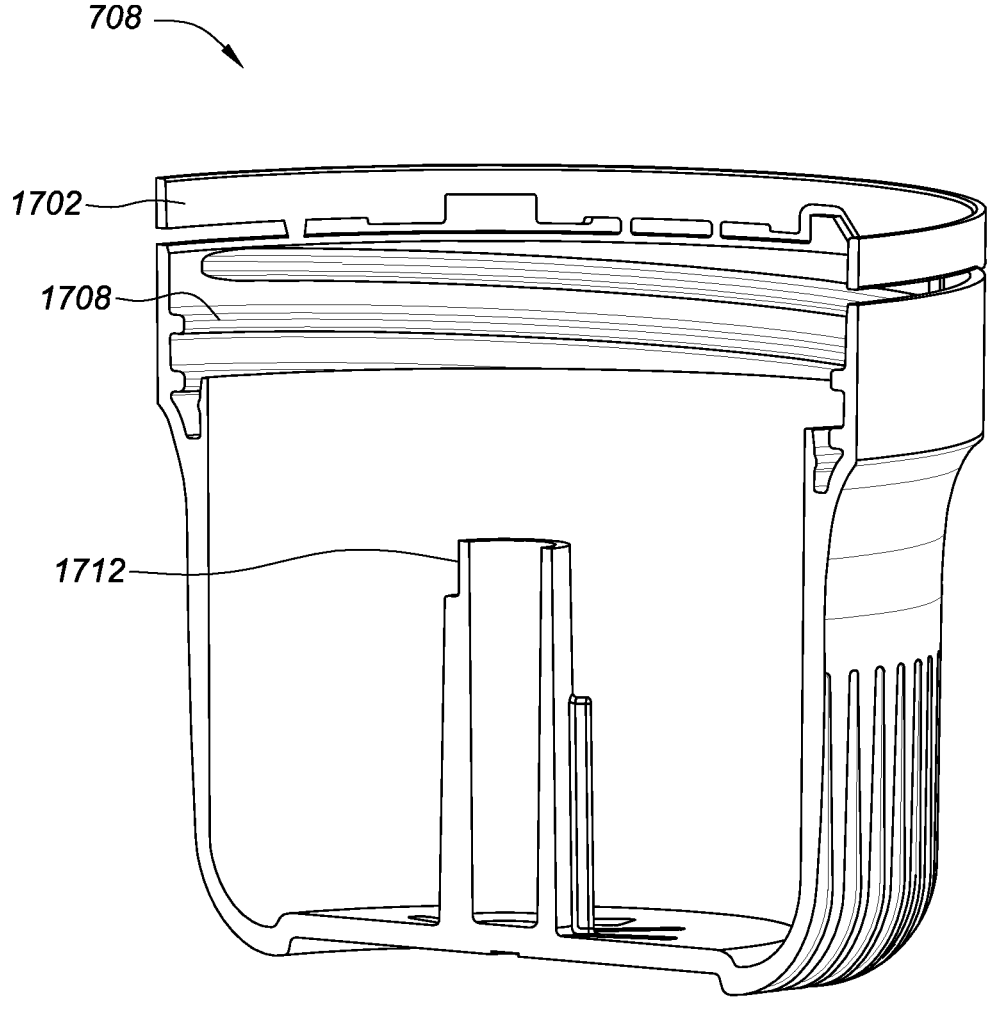
FIG. 11 is a perspective cross-section view depicting an example embodiment of a cap.

FIG. 11 is a perspective cross-section view depicting an example embodiment of cap 708, which, when coupled with housing 702 via threads 1708 can create a sterile or at least dust-free environment during shipping and storage and can protect electronics housing 706 and prevent adhesive layer 105 from becoming dirty. Tamper ring 1702 can be at a distal end of cap 708. A sensor electronics support 1712 can support electronics housing 706 while retained within carrier 710.

FIGS. 12A and 12B are a proximal perspective view and side cross-sectional view, respectively, depicting an example embodiment of platform 808 that can retain and protect sharp module 2500 and sensor module 504 within a loader assembly such as tray 810. Platform 808 can have various features to engage sheath 704. These can include a platform collapse surface 1838, which can engage housing platform collapse surface 1342. A sheath push surface 1810 can provide a proximal surface for distal sheath push surface 1446. One or more sheath unlock members or ribs 1812 of platform 808 can extend radially outward from a central region or surface of platform 808 into sheath receiving channel 1840 to engage lock arms 1412 of sheath 704. In other embodiments, the orientation of the parts can be reversed such that ribs 1812 can extend radially inward from the platform sidewall and lock arms 1412 deflect inwardly into a free space to unlock sheath 704. In all embodiments, ribs 1812 can have any desired structure and/or shape that functions to oppose the sloped surface of lock arms 1412 and cause them to deflect away from their resting position (i.e., the position to which they are biased).

One or more tilt reducing members or ribs 1828 and one or more outside diameter members or ribs 1818 can reduce the likelihood of sheath 704 tilting within sheath receiving channel 1840 due to a thickness which is greater than a standard wall thickness of platform 808. Sheath orientation feature (e.g., a ridge) 1802 can interface with alignment notch 1424 of sheath 704. A cutout or space 1830 can provide a clearance for sheath unlock rib 1936 (FIG. 13A) in a distal surface of platform 808.

Platform 808 can also have various features to engage tray 810. One or more detent arms or snaps 1808 can maintain a platform orientation and engagement within tray by interfacing with platform assembly lead in 1908, platform initial lock ledge 1904, and detent rib 1912 of tray 810. A motion guide member 1822 can maintain alignment with a tray 810 during use. One or more introducer retention arms 1820 each with a retention arm extension 1834 can maintain a position of sharp module 2500 within tray 810.

FIG. 12C is a bottom up view depicting a distal end of platform 808. An orientation feature core out 1804 can ensure that sheath orientation feature 1802 does not interfere with alignment and distal pushing of sheath 704 when performing a sharp capture operation. A deflectable tab 1832 can maintain a module assembly in place for drop and shock robustness. Clearance 1822 for introducer retention features 1820 allows retention features to swing clear during distal movement of platform 808. As such, clearance 1822 provides room for a sensor module to be captured by an applicator during assembly. FIG. 12D is a top down view depicting a proximal end of platform 808, showing sheath unlock ribs 1812, platform unlock ribs 1816, and lock snaps 1814, the functions of which were described with respect to FIGS. 6A-H.

FIG. 12E is a side cross-section of platform 808. Alignment and orientation surfaces 1806 can be located at regular or irregular intervals around an exterior circumference of sheath 808. These are typically channels with walls extending from a proximal to a distal end of sheath 808 and open at the distal end and proximal end. The alignment and orientation features 1806 can engage guide ribs 1906 of tray 810.

Figure 12F:
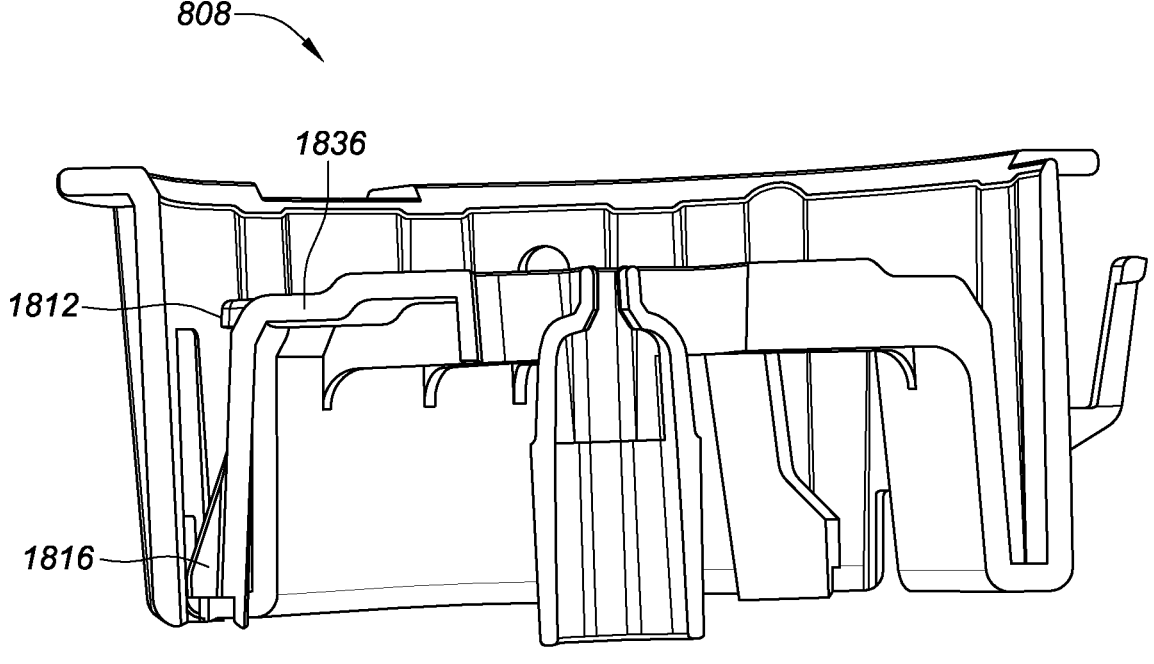
FIG. 12F is a side cross-section depicting an example embodiment of a platform unlock rib of a platform.

FIG. 12F is a side cross-sectional view depicting platform 808. In certain embodiments, a stepped down surface can serve as a patch clearance feature 1836 that can provide clearance for an adhesive patch to ensure it does not become adhered to this proximal surface or face of platform 808 during the assembly process. Similarly, platform unlock ribs 1816 can be set further distally in order to delay a contact between sheath 704 and platform unlock ribs.

Figure 12G:
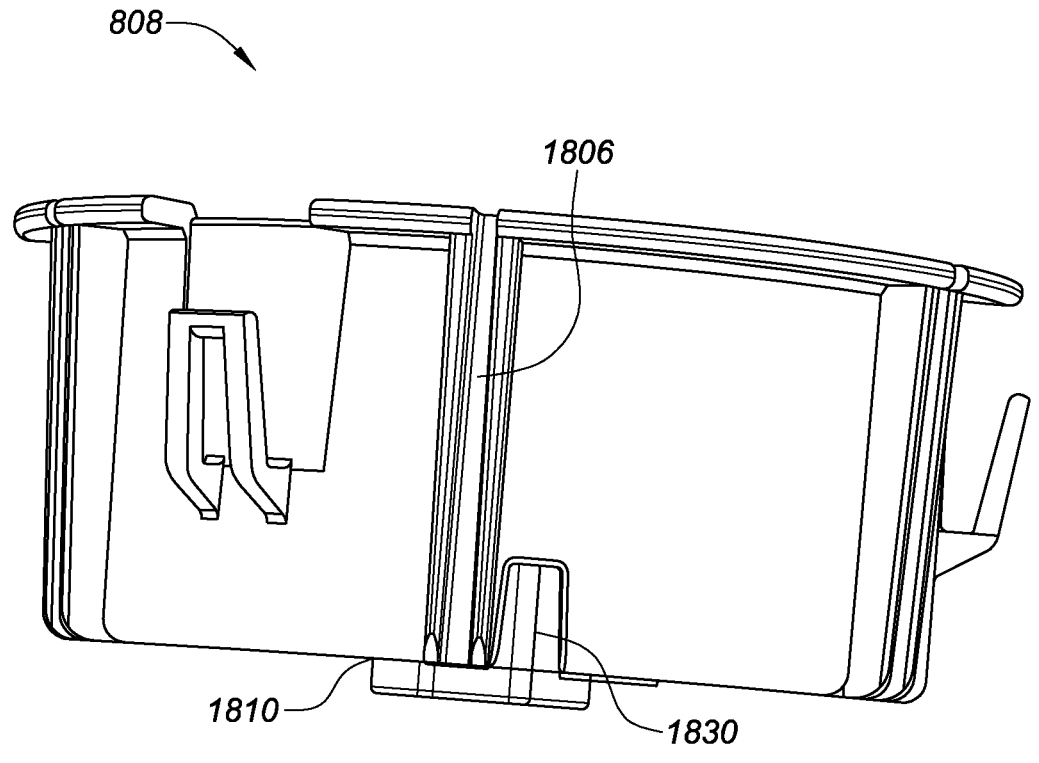
FIG. 12G is a side view depicting an example embodiment of a sheath clearance unlock feature of a platform.

FIG. 12G is a side view depicting platform 808. Here, one or more clearances or cutouts 1830 for sheath unlock ribs 1836 can be extended further distally than prior designs. This can provide additional clearance for sheath 704 since upon reaching this area sheath 704 is no longer a pushing surface for platform 808 yet unlocking of sheath 704 is desirable for proper applicator use.

FIG. 13A is a proximal perspective view depicting an example embodiment of tray or container 810. Tray 810 and lid 812 can create a sterile environment for a sensor and sharp. Here, a foil seal surface 1920 can be a proximal surface that seals with lid 812 using a standard adhesive or a heat-activated adhesive for sterilization purposes. Lock ribs 1902 can contain geometry allowing a platform 808 to lock into a pre-use position. A platform initial lock ledge 1904 can be flat and interact with platform 808 to lock platform 808 from accidental collapse prior to assembly of applicator to loader. Guide ribs 1906 can be ribs that act to orient and guide platform 808 prior and during assembly of applicator and loader. Anti-removal feature 1910 can prevent removal of platform 808 from tray 810 after it has been initially installed. Sheath unlock rib (platform) clearance ledge 1918 can clear sheath unlock ribs on platform 808 when platform 808 is in a collapsed state within tray 810. Desiccant engaging rib 1926 can flex out to allow for desiccant assembly and ensure that desiccant stays in place during drop, shock or vibration. Sharp clearance hole 1930 can be a hole which provides clearance for sharp tip 2502 (FIG. 19) so that the tip is not damaged during shipping or other movement. Module locating post 1932 can be a post that locates sensor module 504 within tray 810. Module support 1934 can set the height of sensor module 504 and sharp module 2500 within tray 810. Alignment mark 1940 can aid a user in aligning an applicator to a container during assembly.

One or more transition features 1938 can be included that extend proximally from module support 1934. These features 1938 can also be seen in FIGS. 5C and 13B. Transition features 1938 can have various shapes. Here there are two that are configured as projections with inner sidewalls that can lie flush against sensor module 504 and provide added support and resistance to tilting or lateral motion. Projections 1938 can have a sloped or rounded outed surface and can be positioned directly beneath retention arm extensions 1834 when in the resting position of FIG. 12B. As platform 808 moves distally, retention arm extensions 1834 come into contact with and slide over the rounded or sloped outer surface of transition features 1938. The rounded or sloped surfaces help retention arm extensions 1834 deflect and transition over sensor module 504 and onto tray 810 without disrupting or adjusting the position of module 504.

FIG. 13B is a side cross-sectional view depicting tray 810. Platform assembly lead-in 1908 can be a lead-in chamfer to aid in assembly of platform 808 to tray 810. Detent rib 1912 can be a rib or member that includes curved surface 1914. Surface 1914 can allow platform 808 to build a predetermined force prior to distal movement during assembly of the applicator and sensor control device 102. Friction reducing undercut surface 1916 can be an undercut that lowers the total friction seen by platform 808 as it collapses during assembly of the applicator to the loader. Platform motion guide surface 1928 can be a running surface that guides motion of platform 808 with respect to tray 810 during assembly of loader to applicator.

Figure 13C:
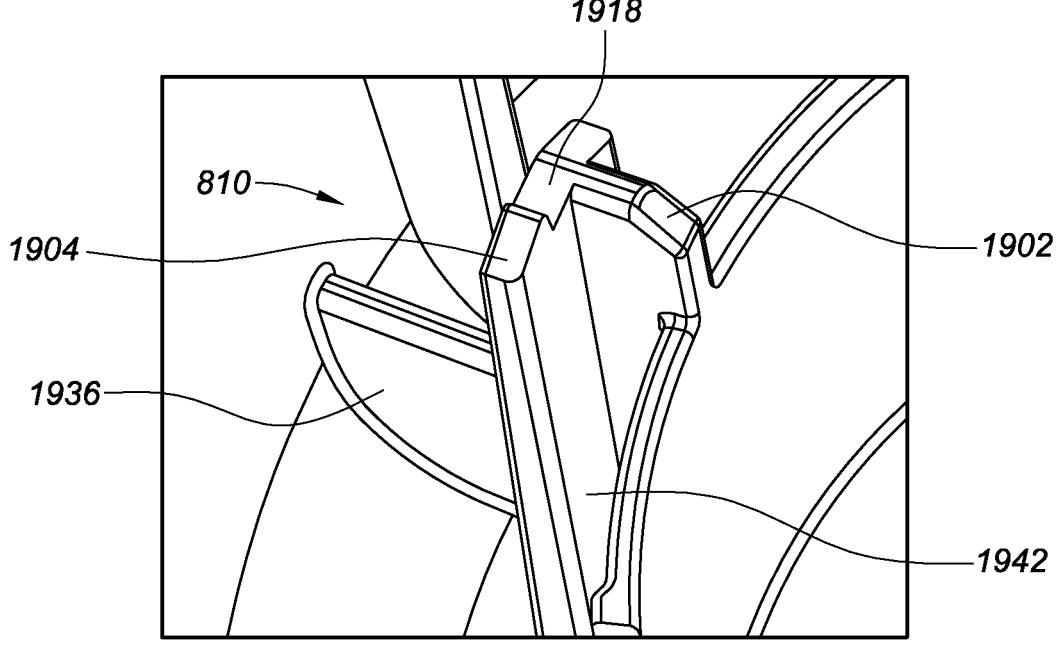
FIG. 13C is a close-up view depicting an example embodiment of a cutout and rib feature of a tray.

FIG. 13C is a close-up view depicting an example embodiment of sheath unlock rib 1936 of tray 810. Unlock rib 1936 can have any desired shape and/or structure that functions as a rigid stop for the advancement of sheath 704, e.g., an abutment formed in or extending from the base or bottom of tray 810.

A platform initial lock ledge 1904 can support platform 808 and ensure it is not accidentally pushed or collapsed distally. Sheath unlock rib (platform) clearance feature 1918 can be short as not to impact unlock ribs 1812 of platform 808 early during a distal advancement by a user. Likewise, a lock rib 1902 can be relatively short. If a user were to proximally retreat housing 702 and its coupled components, lock arms 1412 would re-engage lock interface 1502 as in the primary configuration shown in FIG. 6A. This feature can prevent misfiring of the applicator by dropping or incorrectly aligning when re-assembling applicator with cap. A cutout 1942 can allow clearance for lock arms 1815 of platform 808.

Figure 14A:
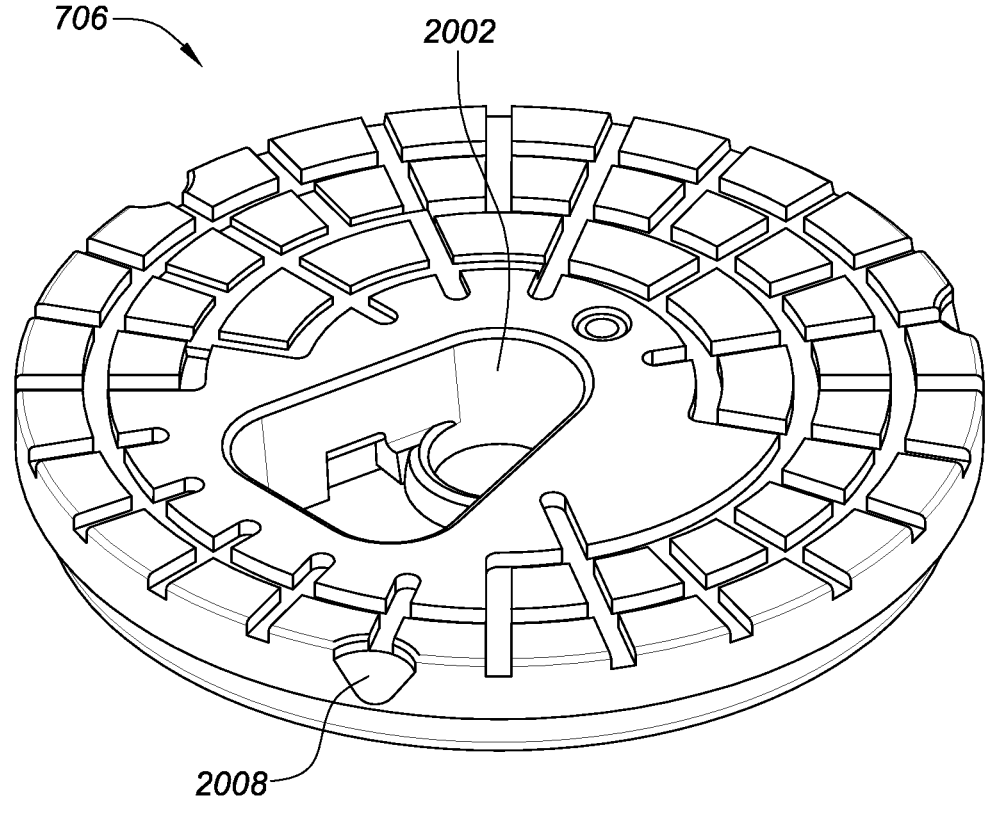
FIG. 14A is a distal perspective view depicting an example embodiment of a mount.
Figure 14B:
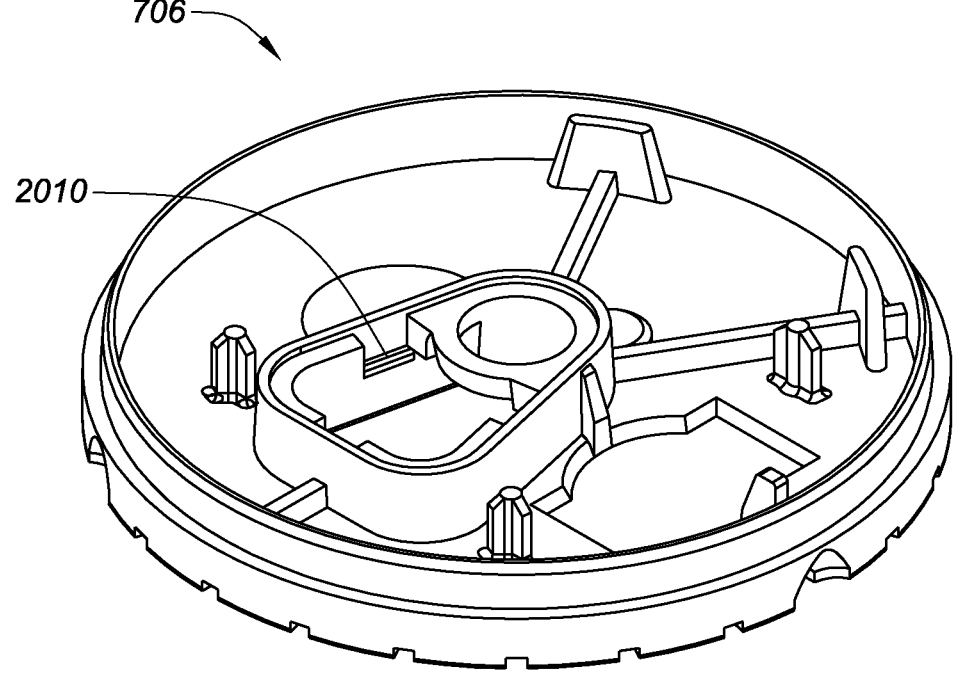
FIG. 14B is a proximal perspective view depicting an example embodiment of a mount.

FIGS. 14A and 14B are a distal perspective view and a proximal perspective view, respectively, depicting an example embodiment of a distal portion of electronics housing 706. Shown here is a receptacle 2002 for receiving sensor module 504. One or more carrier grips or recesses 2008 can interface with retention detents 1519 of carrier 710 for coupling housing 706 to carrier 710. One or more module snap ledges 2010 can engage deflectable module arms or snaps 2202 (FIG. 16A).

Figure 15A:
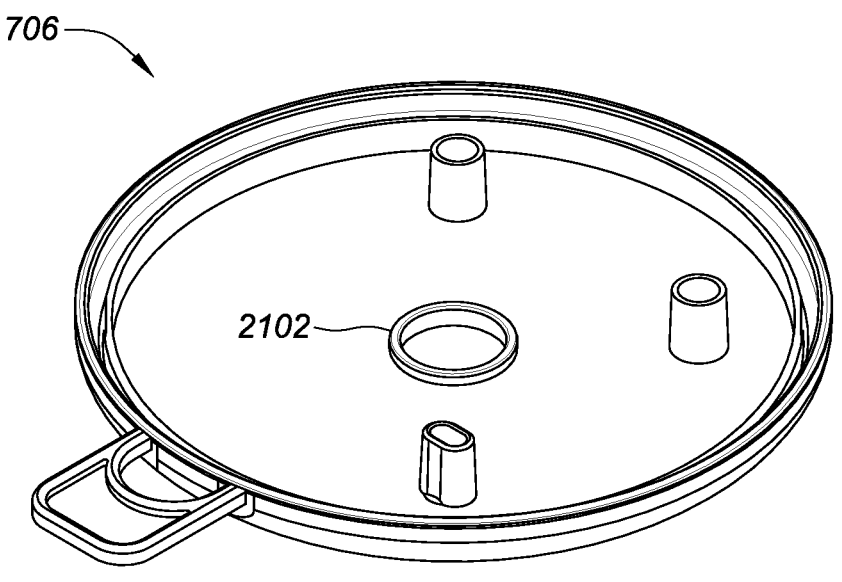
FIG. 15A is a distal perspective view depicting an example embodiment of a shell.
Figure 15B:
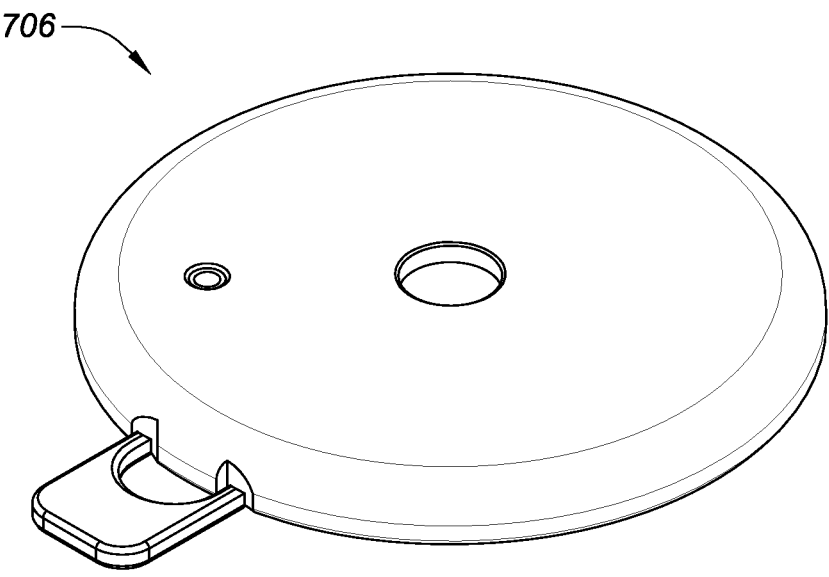
FIG. 15B is a proximal perspective view depicting an example embodiment of a shell.

FIGS. 15A and 15B are a distal perspective view and a proximal perspective view, respectively, depicting an example embodiment of a proximal portion of housing 706 that can be securely coupled with the distal portion of housing 706 depicted in FIGS. 14A-B. An aperture 2102 is present through which distal tip 2502 of the sharp can pass through during assembly of applicator 150 and retraction of sharp after insertion of the sensor.

Figure 16A:
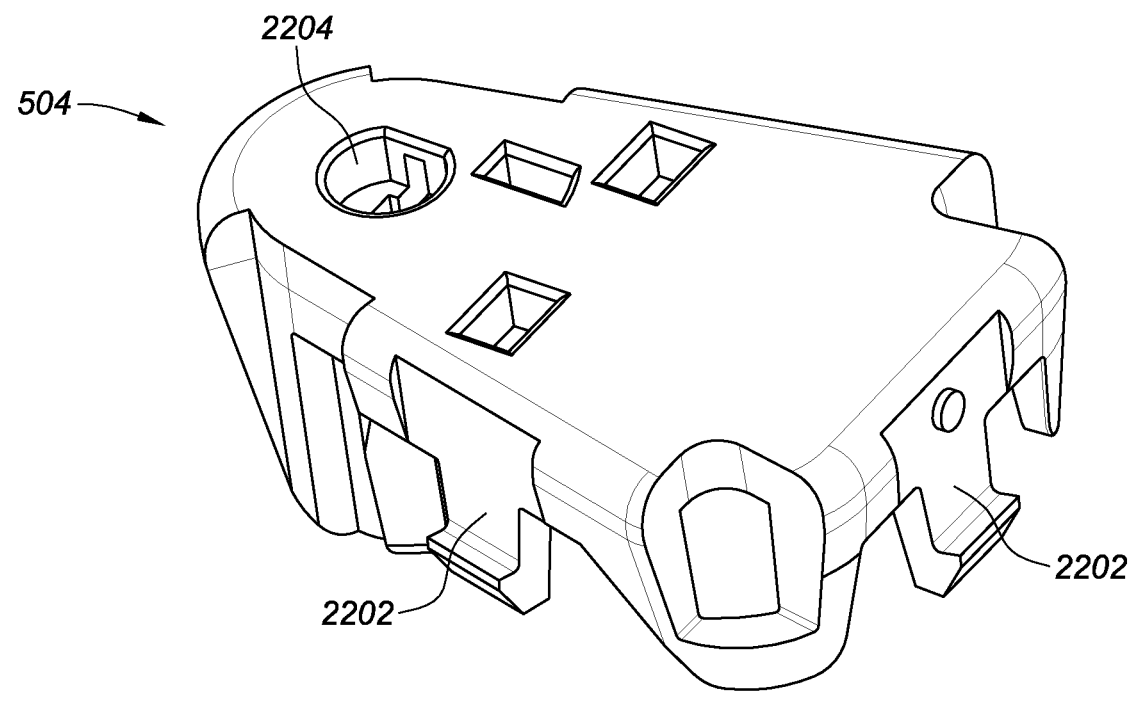
FIG. 16A is a top perspective view depicting an example embodiment of a module.
Figure 16B:
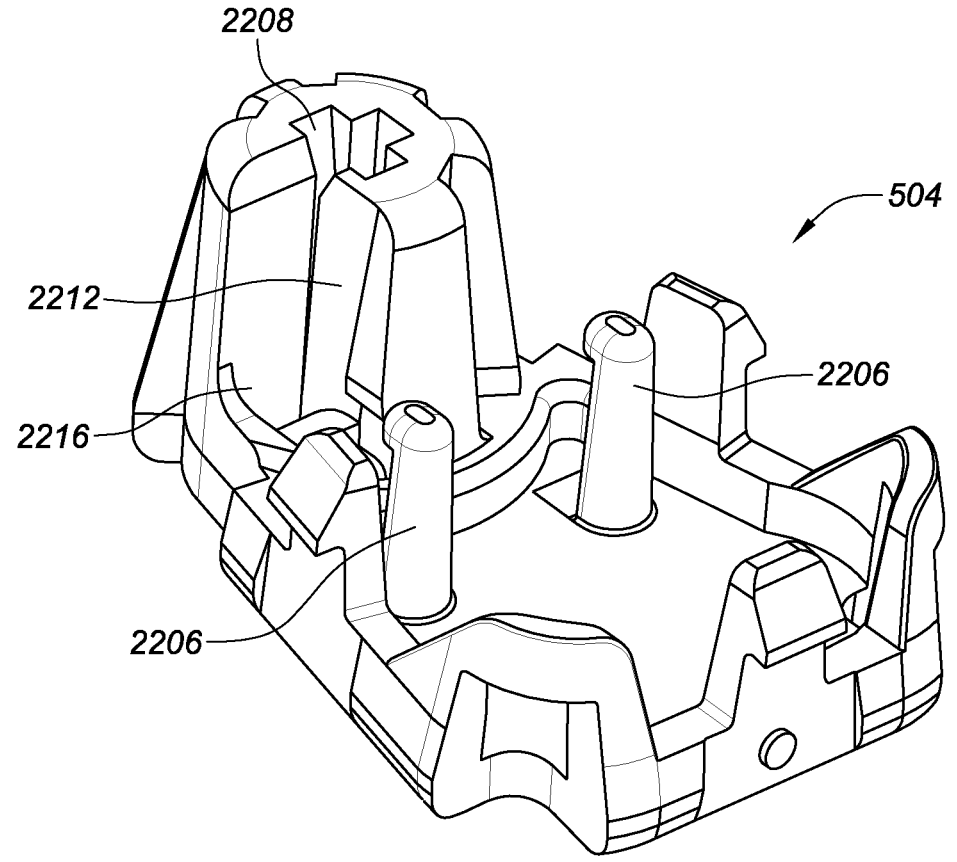
FIG. 16B is a bottom perspective view depicting an example embodiment of a module.

FIGS. 16A and 16B are a top perspective view and a bottom perspective view, respectively, depicting an example embodiment of sensor module 504. Module 504 can hold a connector 2300 (FIGS. 17A-B) and a sensor 104 (FIG. 18). Module 504 is capable of being securely coupled with electronics housing 706. One or more deflectable arms or module snaps 2202 can snap into the corresponding features 2010 of housing 706. A sharp slot 2208 can provide a location for sharp tip 2502 to pass through and sharp shaft 2504 to temporarily reside. A sensor ledge 2212 can define a sensor position in a horizontal plane, prevent a sensor from lifting connector 2300 off of posts and maintain sensor 104 parallel to a plane of connector seals. It can also define sensor bend geometry and minimum bend radius. It can limit sensor travel in a vertical direction and prevent a tower from protruding above an electronics housing surface and define a sensor tail length below a patch surface. A sensor wall 2216 can constrain a sensor and define a sensor bend geometry and minimum bend radius.

Figure 17A:
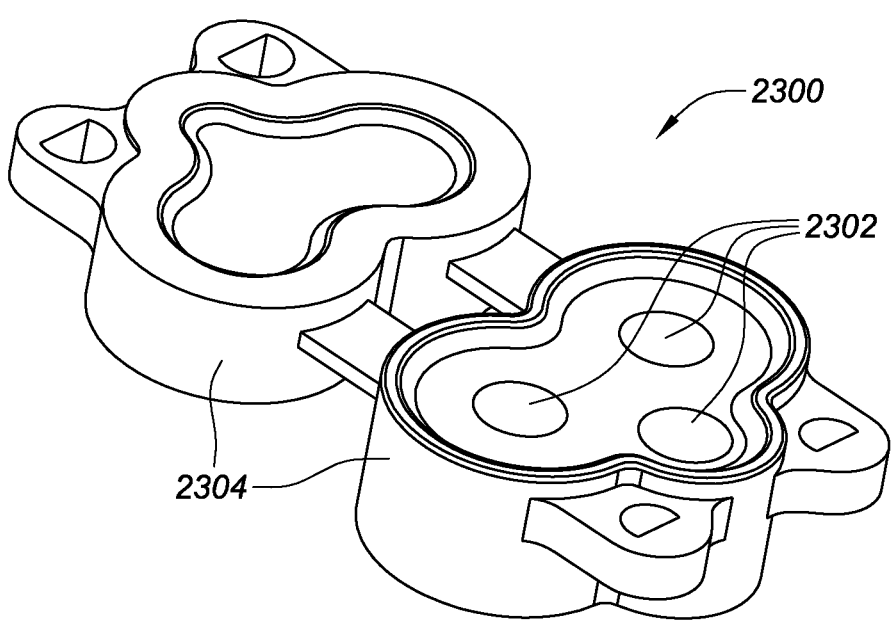
FIG. 17A is a perspective view depicting an example embodiment of a connector.
Figure 17B:
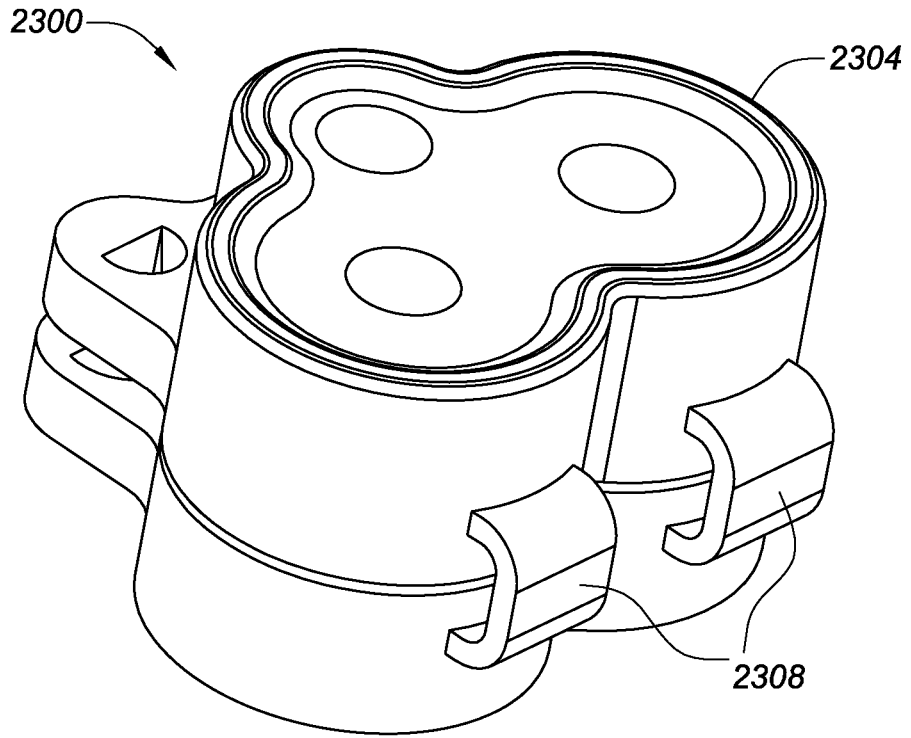
FIG. 17B is a compressed view depicting an example embodiment of a connector.
Figure 18:
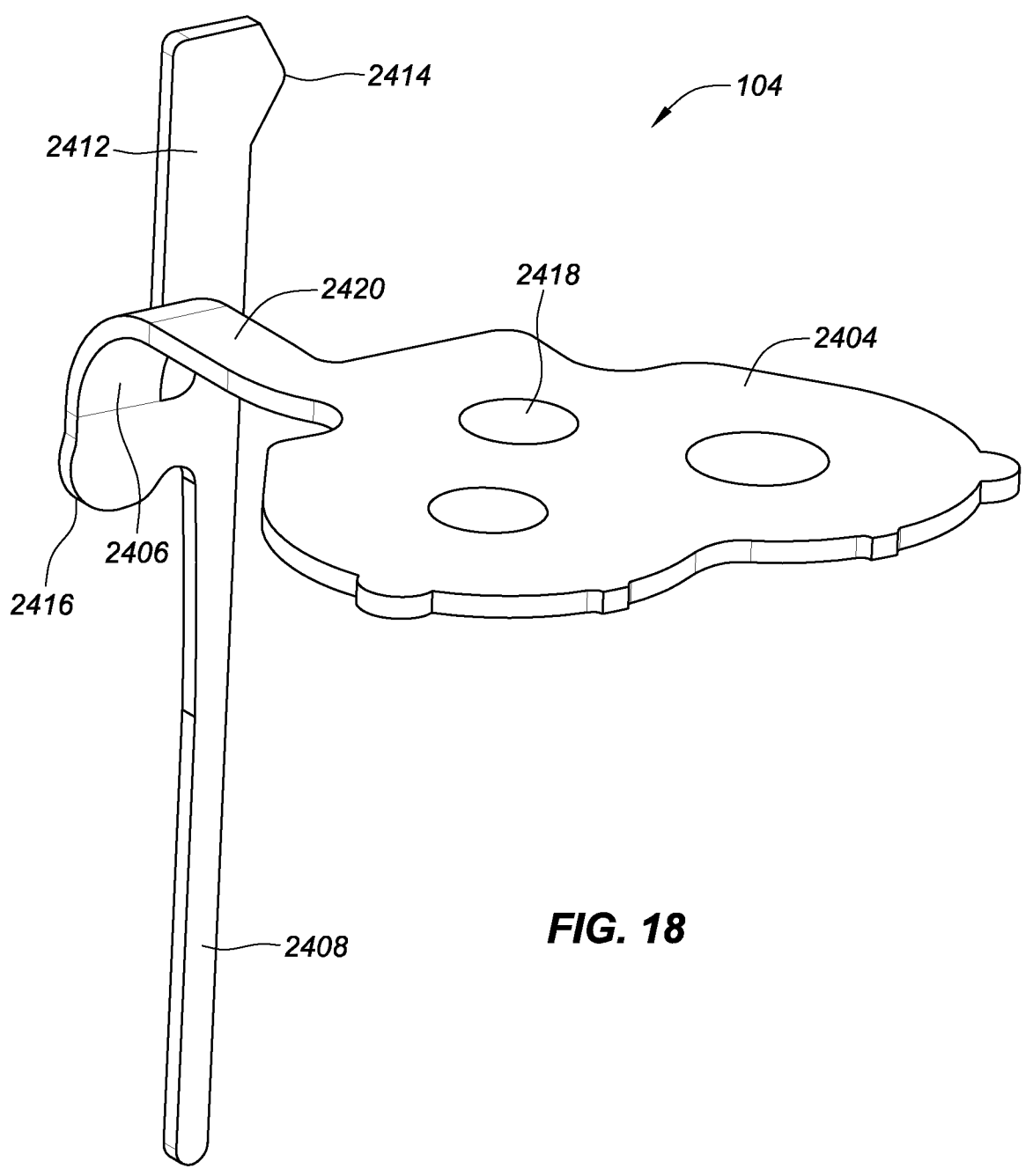
FIG. 18 is a perspective view depicting an example embodiment of a sensor.

FIGS. 17A and 17B are perspective views depicting an example embodiment of connector 2300 in an open state and a closed state, respectively. Connector 2300 can be made of silicone rubber that encapsulates compliant carbon impregnated polymer modules that serve as electrical conductive contacts 2302 between sensor 104 and electrical circuitry contacts for the electronics within housing 706. The connector can also serve as a moisture barrier for sensor 104 when assembled in a compressed state after transfer from a container to an applicator and after application to a user's skin. A plurality of seal surfaces 2304 can provide a watertight seal for electrical contacts and sensor contacts. One or more hinges 2208 can connect two distal and proximal portions of connector 2300.

FIG. 18 is a perspective view depicting an example embodiment of sensor 104. A neck 2406 can be a zone which allows folding of the sensor, for example ninety degrees. A membrane on tail 2408 can cover an active analyte sensing element of the sensor 104. Tail 2408 can be the portion of sensor 104 that resides under a user's skin after insertion. A flag 2404 can contain contacts and a sealing surface. A biasing tower 2412 can be a tab that biases the tail 2408 into sharp slot 2208. A bias fulcrum 2414 can be an offshoot of biasing tower 2412 that contacts an inner surface of a needle to bias a tail into a slot. A bias adjuster 2416 can reduce a localized bending of a tail connection and prevent sensor trace damage. Contacts 2418 can electrically couple the active portion of the sensor to connector 2300. A service loop 2420 can translate an electrical path from a vertical direction ninety degrees and engage with sensor ledge 2212 (FIG. 16B).

FIG. 19 is a perspective view depicting an example embodiment of sharp module 2500. A sharp tip 2502 can penetrate the skin while carrying sensor tail 2408 in a hollow or recess of shaft 2504 to put the active surface into contact with bodily fluid. A hub push cylinder 2508 can provide a surface for a sharp carrier to push during insertion. A hub small cylinder 2512 can provide a space for the extension of sharp hub contact faces 1622 (FIG. 10B). A hub snap pawl locating cylinder 2514 can provide a cylindrical surface of a snap pawl for faces 1622 to abut. A hub snap pawl 2514 can be a conical surface that opens clip 1620 during installation of sharp module 2500.

Figure 20A:
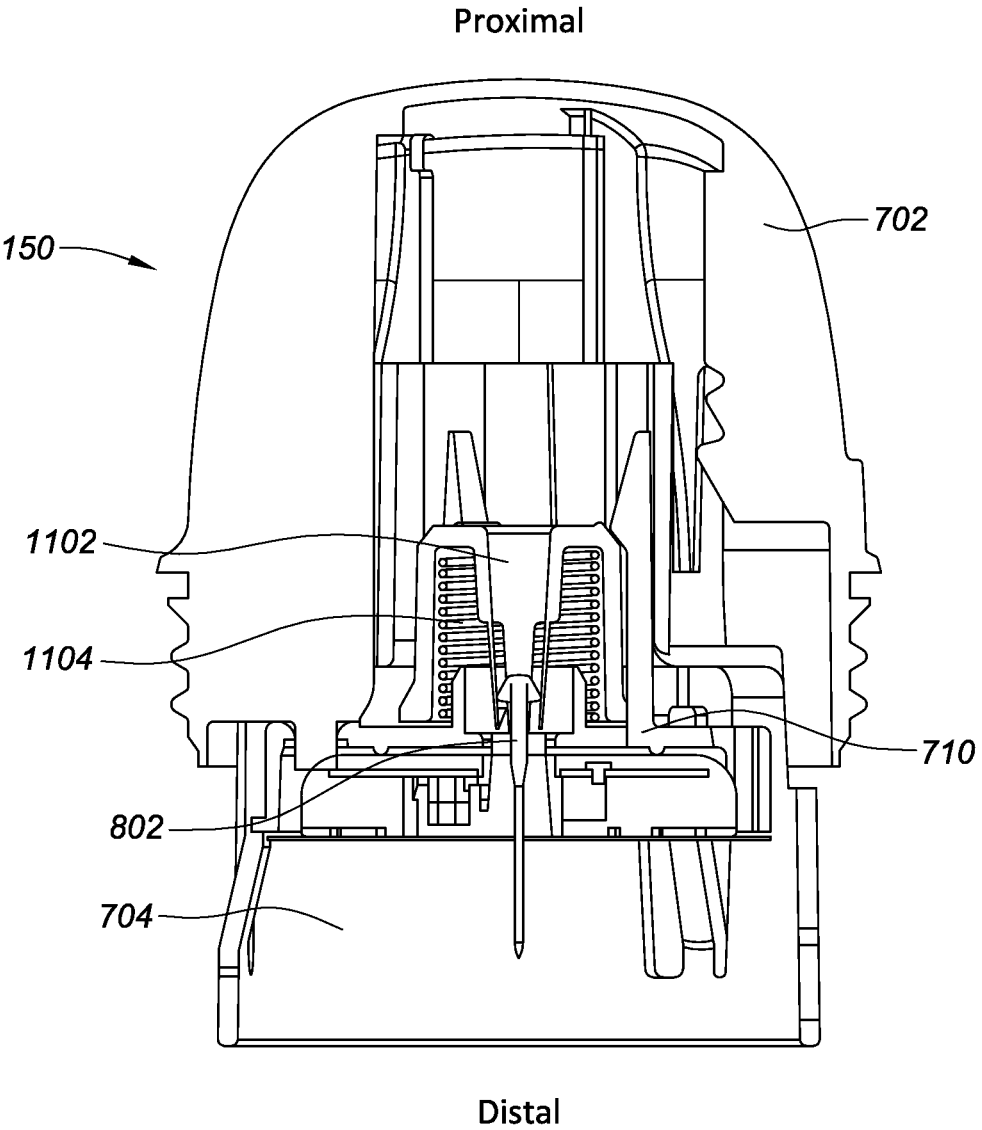
FIG. 20A is a side cross-section depicting an example embodiment of an applicator device.
Figure 20B:
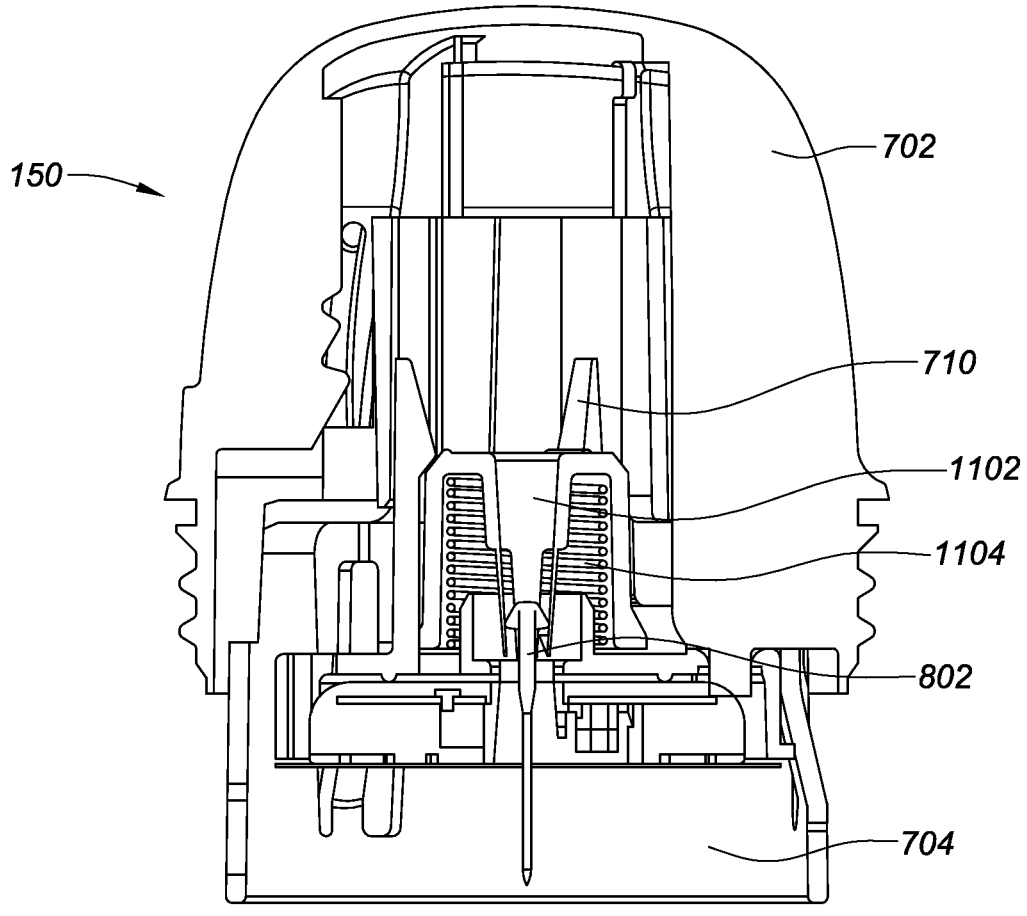
FIG. 20B is a side cross-section depicting an example embodiment of an applicator device during an initial sensor delivery step.
Figure 20C:
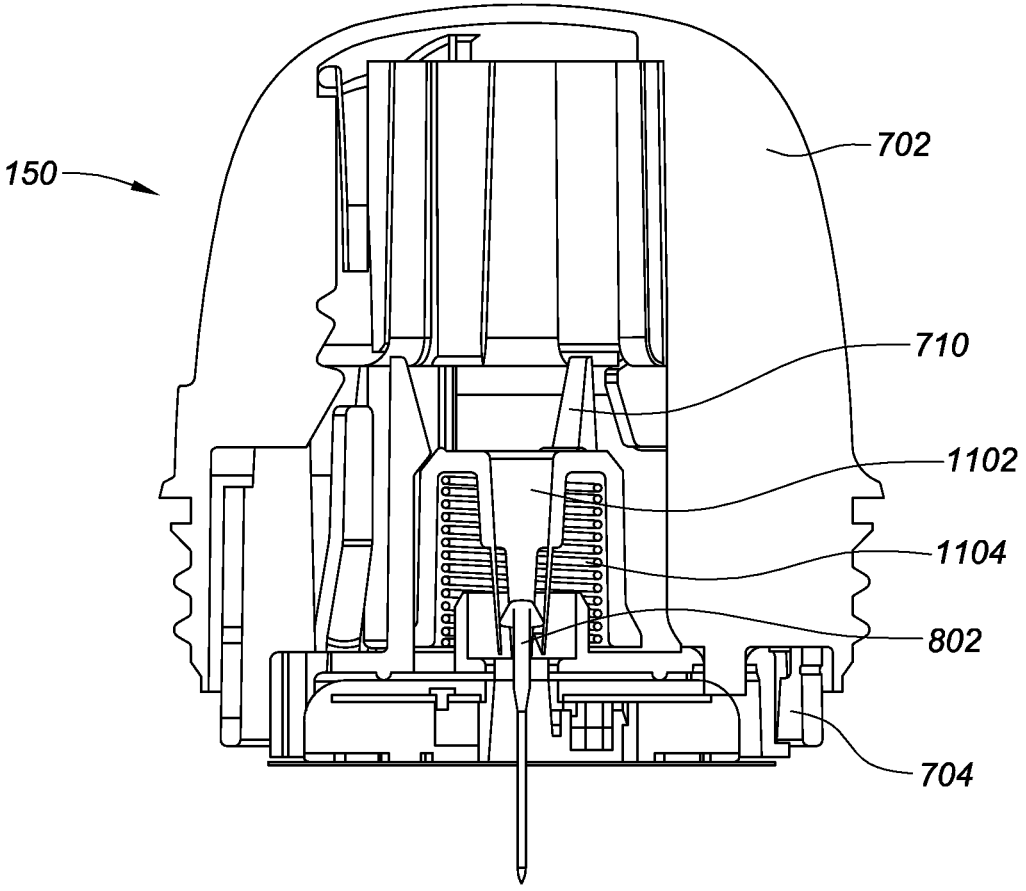
FIG. 20C is a side cross-section depicting an example embodiment of an applicator device during a subsequent sensor delivery step.
Figure 20D:
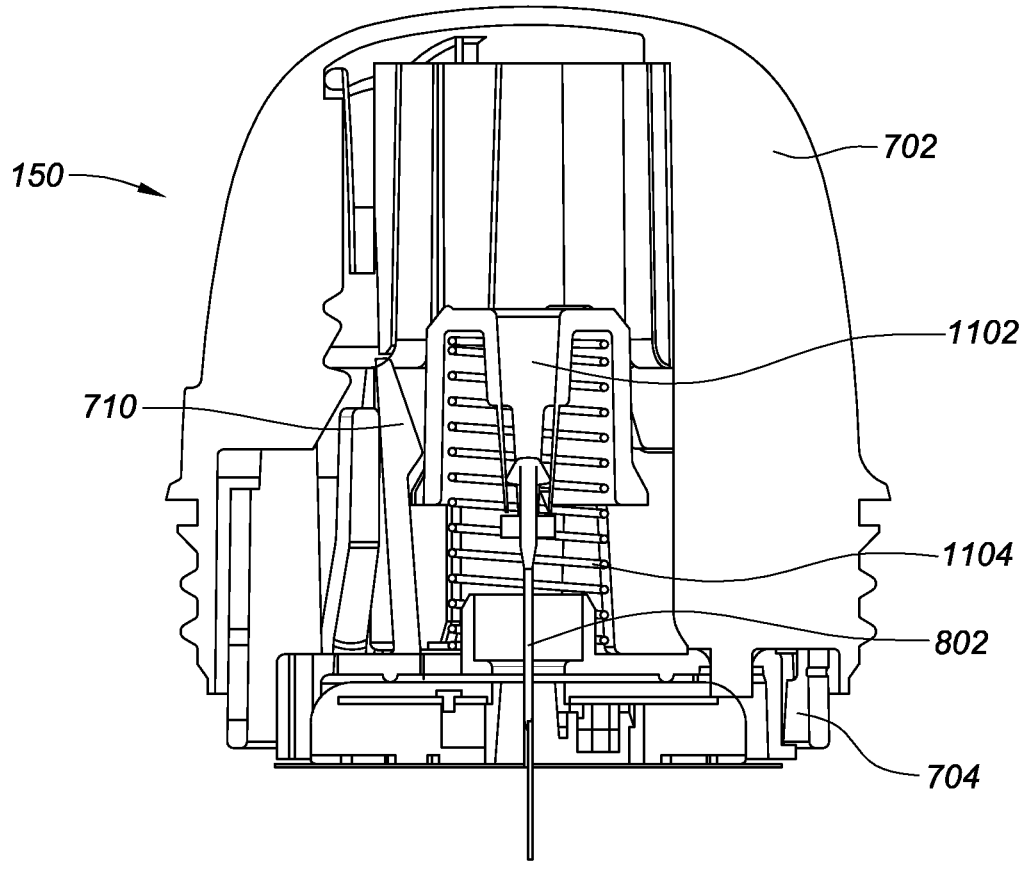
FIG. 20D is a side cross-section depicting an example embodiment of an applicator device during a subsequent sensor delivery step, with a sharp disengaging.

FIGS. 20A-20E are side cross-sectional views depicting an example embodiment of an applicator 150 during deployment of sensor control device 102. FIG. 20A shows applicator 150 in a state ready to be positioned against a user's skin. In FIG. 20B, housing 702 has been advanced with respect to sheath 704 but the sharp has not yet exited applicator 150. Here, the housing has been advanced in a proximal-to-distal direction along a longitudinal axis of applicator 150. In FIG. 20C, housing 702 has been fully advanced by the user's manual push force, and the sharp and sensor are extending their maximum distance from the distal end of sheath 704. Also, the introducer carrier retention features 1526 of arms 1524 have cleared an inner diameter of sheath 704 and are free to move as shown in FIG. 20D.

In FIG. 20D, sharp carrier 1102 is no longer constrained by electronics housing carrier arms 1524. Thus, spring 1104 is free to expand from its compressed orientation in a proximal direction and push the proximal end of electronics housing carrier arms 1524 radially outward as it expands. This causes sharp module 2500 to retract from the user's skin and into a central area of spring 1104 within housing 702.

Figure 20E:
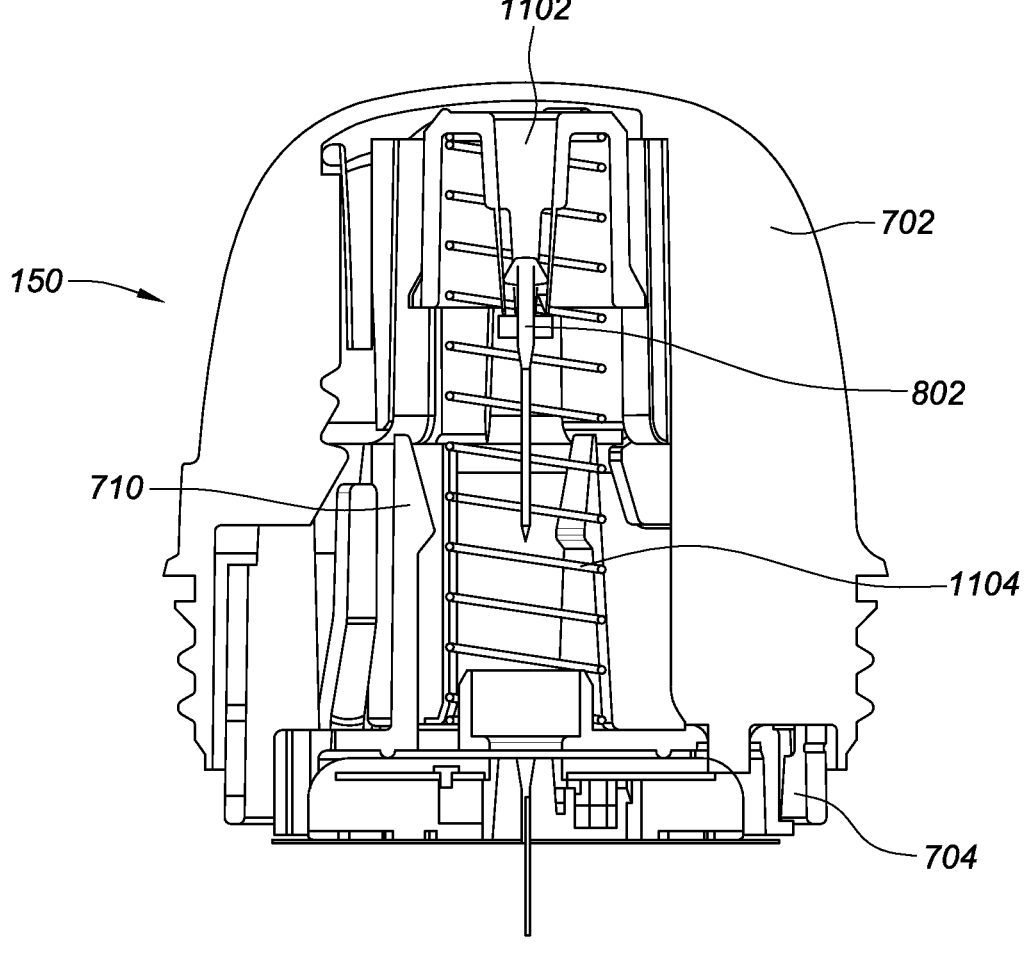
FIG. 20E is a side cross-section depicting an example embodiment of an applicator device in a post-sensor delivery process configuration.

In FIG. 20E, spring 1104 has expanded until a proximal end of sharp carrier 1102 reaches a distal surface of sheath 704 and thus the whole device is locked in position. An adhesive on distal surface of an electronics housing causes it to remain on the user's skin with the sensor in the skin when the user proximally removes the device from the skin.

FIGS. 21A-D are distal perspective, proximal perspective, side, and distal end views, respectively, depicting an additional example embodiment of electronics housing 706. Here, receptacle 2002 can be seen where sensor module 504 can be received during assembly. Adhesive 2102 is present on adhesive layer 105. Outer seal 2028 can protect the electronics in the interior of electronics housing 706.

FIG. 22A is a close-up side view of an example embodiment of a retention detent 1519 on the interior surface of a retention spring arm 1518 of electronics housing carrier 710. FIG. 22B is a close-up perspective view of this example embodiment and FIG. 22C is a perspective view of an example embodiment of carrier 710 with three arms 1518 and retention detents 1519 visible on the interior of two of the three arms 1518 (the third is obscured).

In these embodiments, retention detents 1519 each have a partially conical (projecting) proximal (or upper) surface 2201 and a distal (or lower or underside) surface 2202. Partially conical upper surface 2201 slopes away from the interior surface of each arm 1518 such that the proximal terminus of surface 2201 is closer to the interior surface of arm 1518 than a point along the distal edge of surface 2201. After sensor control device 102 is adhered to the surface of the body, this sloped or tapered surface 2201 slides along a similarly shaped but complementary (recessed) surface of carrier grip 2008 (FIG. 21C) and causes the respective arm 1518 to deflect radially outwards (against its bias), thereby releasing sensor control device 102.

The distal edge 2203 of proximal surface 2201 (at the transition to distal surface 2202) is not perpendicular to the direction of axial movement of sensor control device 102 with respect to carrier 1102 (i.e., the proximal-distal direction P-D shown in FIG. 22A) but is rather transverse or at an angle to the proximal-distal direction. Here, the angle is approximately 45 degrees, although greater and lesser angles can be used (e.g., 30 degrees, 60 degrees, etc.).

Figures 21A, 21B, 21C, 21D:
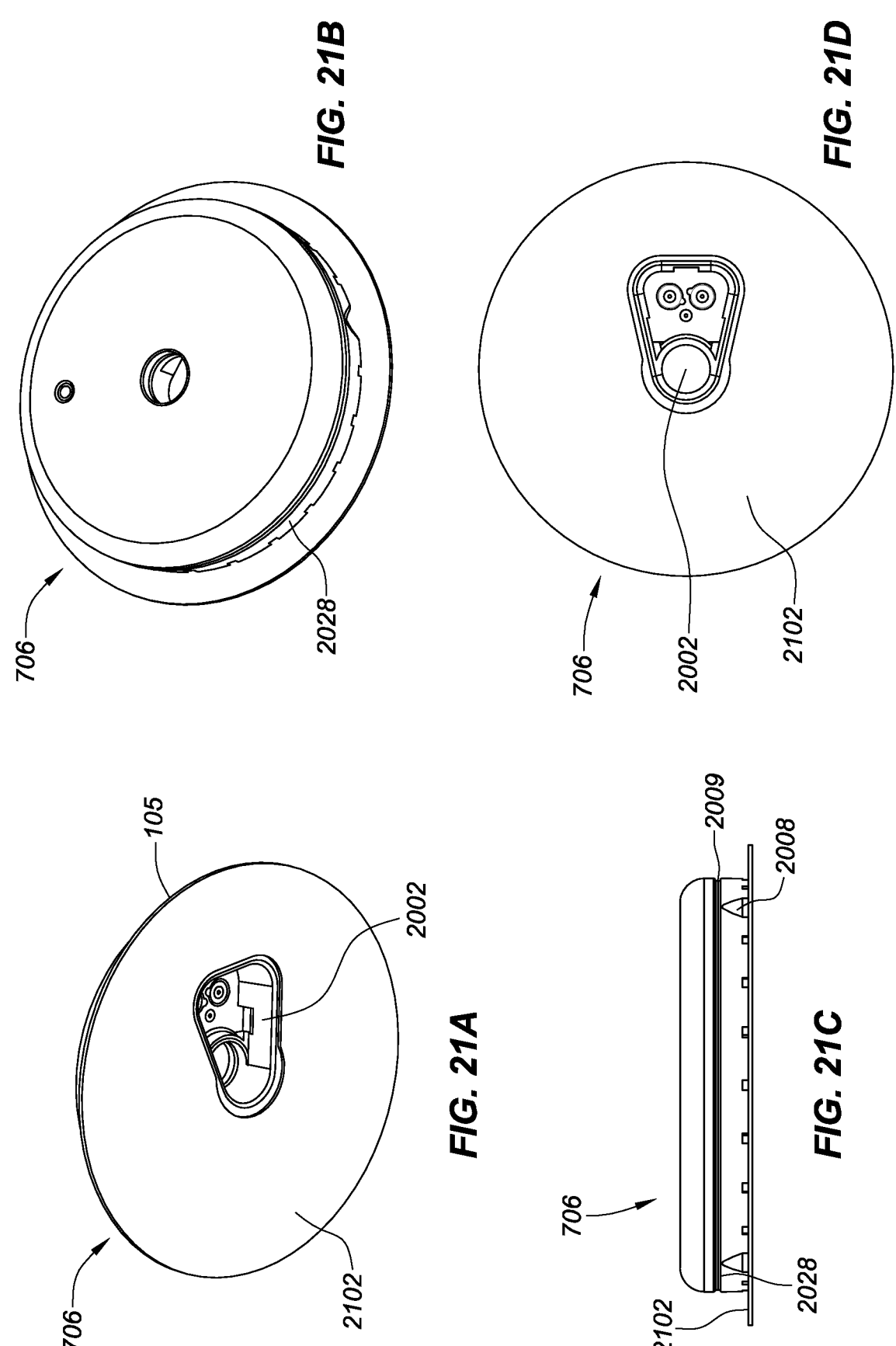
FIG. 21A is a perspective view depicting an example embodiment of a distal end of an assembled electronics housing.
FIG. 21B is a perspective view depicting an example embodiment of a proximal end of an assembled electronics housing.
FIG. 21C is a side view depicting an example embodiment of an assembled electronics housing.
FIG. 21D is a proximal view depicting an example embodiment of an assembled electronics housing.

This angling reduces the chance that edge 2203 will catch on a portion of sensor control device 102 after adhesive attachment to the skin, such as gap or groove 2009 shown in FIG. 21C, which may be a seam or interface between a distal portion of electronics housing 706 (as depicted in FIGS. 14A-B) and a proximal portion of electronics housing 706 (as depicted in FIGS. 15A-B) and can be perpendicular or otherwise transverse to direction P-D. Edge 2203 is preferably transverse to a longitudinal axis of an elongate gap, groove, seam, or interface on sensor control device that is proximal to carrier grip 2008. Catching of edge 2203 on sensor control device 102 could adversely remove sensor control device 102 from the skin when applicator 150 is removed. There is no similarly angled groove or edge on sensor control device 102 that can catch edge 2203 when angled as shown. Distal surface 2202 is planar or substantially planar, here, although other shapes or contours can be used so long as edge 2203 remains angled.

In another example embodiment, the configurations just described can be reversed such that retention detents 1519 with the partially conical surface and the complementary carrier grips 2008 can be reversed such that the retention detents 1519 are present on sensor control device 102 and the complementary grips 2008 are present on applicator 150, such as on arms 1518. In such an embodiment, the orientation of detents 1519 and grips 2008 are inverted (turned upside down) to allow proper deflection of arms 1518 upon withdrawal of applicator 150.

A number of deflectable structures are described herein, including but not limited to deflectable positioning arms 1402, deflectable locking arms 1412, introducer carrier lock arms 1524, sharp retention arms 1618, outer deflectable arms 1808, inner deflectable lock arms 1815, retention arm extensions 1834, and module snaps 2202. These deflectable structures are composed of a resilient material such as plastic or metal (or others) and operate in a manner well known to those of ordinary skill in the art. The deflectable structures each has a resting state or position that the resilient material is biased towards. If a force is applied that causes the structure to deflect or move from this resting state or position, then the bias of the resilient material will cause the structure to return to the resting state or position once the force is removed (or lessened). In many instances these structures are configured as arms with detents, or snaps, but other structures or configurations can be used that retain the same characteristics of deflectability and ability to return to a resting positon, including but not limited to a leg, a clip, a catch, an abutment on a deflectable member, and the like.

As used herein and in the appended claims, the singular forms "a", "an", and "the" include plural referents unless the context clearly dictates otherwise.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. An in vivo analyte monitoring system, comprising:
a sensor control device configured to monitor an in vivo analyte level of a user, the sensor control device comprising:
a first engagement member;
an in vivo analyte sensor, a distal portion of which is configured to be positioned under a skin surface of the user and in contact with a bodily fluid of the user;
an electronics housing; and
sensor electronics disposed within the electronics housing and electrically coupled with a proximal portion of the in vivo analyte sensor; and
an applicator configured to apply the sensor control device to the body of the user, the applicator comprising:
a deflectable arm having a second engagement member configured to engage with the first engagement member,
wherein one of the first and second engagement members comprises an at least partially conical projecting surface,
wherein the at least partially conical projecting surface comprises a distal edge, and
wherein the distal edge is not perpendicular to a direction of axial movement of the sensor control device with respect to the applicator.

2. The system of claim 1, wherein the second engagement member comprises the at least partially conical projecting surface and the first engagement member comprises a complementary recess.

3. The system of claim 2, wherein the at least partially conical projecting surface slopes away from an interior surface of the deflectable arm such that a proximal terminus of the at least partially conical projecting surface is closer to the interior surface than a point along the distal edge of the at least partially conical projecting surface, wherein the proximal terminus is relatively farther from a body attachment surface of the sensor control device than the distal edge.

4. The system of claim 2, wherein the sensor control device comprises a gap or groove proximal to the complementary recess.

5. The system of claim 4, wherein the distal edge is not perpendicular with a longitudinal axis of the gap or groove.

6. The system of claim 5, wherein the distal edge is configured to slide across the gap or groove without catching the gap or groove as the applicator is withdrawn from the body of the user.

7. The system of claim 1, wherein the direction of axial movement is between a proximal location and a distal location.

8. The system of claim 1, wherein the deflectable arm is a first deflectable arm, wherein the applicator further comprises a plurality of deflectable arms including the first deflectable arm, wherein each deflectable arm of the plurality of deflectable arms comprises a corresponding engagement member that comprises a corresponding at least partially conical projecting surface, and wherein the sensor control device comprises a plurality of complementary recesses, wherein each complementary recess of the plurality of complementary recesses is configured to engage with a corresponding engagement member of the corresponding engagement members.

9. The system of claim 1, wherein an angle between the distal edge and the direction of axial movement of the sensor control device with respect to the applicator is approximately 45 degrees.

10. The system of claim 1, wherein an angle between the distal edge and the direction of axial movement of the sensor control device with respect to the applicator is less than 90 degrees.

11. The system of claim 1, wherein the in vivo analyte monitoring system is a glucose monitoring system, and wherein the in vivo analyte level of the user is a glucose level of the user.

12. The system of claim 1, wherein the applicator further comprises an electronics housing carrier having a plurality of deflectable arms, and wherein the deflectable arm is a first deflectable arm of the plurality of deflectable arms.

13. The system of claim 1, wherein the sensor control device is configured to be advanced from a proximal position entirely within the applicator to a distal position in the direction of axial movement.

14. The system of claim 1, wherein the sensor control device is further configured to communicate with a reader device over a wireless communication path according to a wireless communication protocol.

15. The system of claim 1, wherein the in-vivo analyte sensor is coupled with an application specific integrated circuit.

* * * * *